US008378085B2

(12) United States Patent
Andries et al.

(10) Patent No.: US 8,378,085 B2
(45) Date of Patent: Feb. 19, 2013

(54) BACTERIAL ATP SYNTHASE BINDING DOMAIN

(75) Inventors: Koenraad Jozef Lodewijk Marcel Andries, Beerse (BE); Hinrich Wilhelm Helmut Gohlmann, s-Hertogenbosch (NL); Jean-Marc Edmond Fernand Marie Neefs, Lier (BE); Peter Karel Maria Verhasselt, Herent (BE); Johann Winkler, Brasschaat (BE); Marc Rene De Jonge, Tilburg (NL); Lucien Maria Henricus Koymans, Retie (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 13/306,255

(22) Filed: Nov. 29, 2011

(65) Prior Publication Data

US 2012/0219964 A1 Aug. 30, 2012

Related U.S. Application Data

(62) Division of application No. 11/576,023, filed as application No. PCT/EP2005/054893 on Sep. 28, 2005, now Pat. No. 8,088,891.

(60) Provisional application No. 60/620,500, filed on Oct. 20, 2004.

(30) Foreign Application Priority Data

Sep. 28, 2004 (EP) .................................... 04104720

(51) Int. Cl.
*C07H 21/04* (2006.01)
*C12Q 1/00* (2006.01)

(52) U.S. Cl. .......................................... 536/23.1; 435/4

(58) Field of Classification Search ........................ None
See application file for complete search history.

(56) References Cited

U.S. PATENT DOCUMENTS 6,583,266 B1 * 6/2003 Smith et al. ................... 530/350
7,067,512 B2 6/2006 Lu et al.

FOREIGN PATENT DOCUMENTS

| WO | 93/09103 A1 | 5/1993 |
| WO | 02/077183 A2 | 10/2002 |
| WO | WO 02/077183 | * 10/2002 |
| WO | 2004/011436 A1 | 2/2004 |

OTHER PUBLICATIONS

Andries, et al., "A Diarylquinoline Drug Active on the ATP Synthase of Mycobacterium Tuberculosis", Science, vol. 307, pp. 223-227 (2005).
Bacon, et al., "Docking by Least-Squares Fitting of Molecular Surface Patterns", J. Mol. Biol., vol. 225, pp. 849-858, (1992).
Batlett, et al., "CAVEAT: A Program to Facilitate the Structure-Derived Design of Biologically Active Molecules." In Molecular Recognition in Chemical and Biological Problems, Special Pub., Royal Chem. Soc., 78, pp. 82-196 (1989).
Berendsen, et al. "GROMACS: A Message-Passing Parallel Molecular Dynamics Implementation", Computer Physics Communications, vol. 91, pp. 43-56, (1995).
Bohm, "The Computer Program LUDI: A New Method for the De Novo Design of Enzyme Inhibitors", Journal of Computer-Aided Molecular Design, vol. 6, pp. 61-78 (1992).
Brusilow, et al., "Synthesis and Assembly of the $F_0$ Genes Cloned into Bacteriophage and Integrated into the *Escherichia coli* Chromosome", The Journal of Biological Chemistry, vol. 269, No. 10, pp. 7285-7289, (1994).
Brutlag, et al., "Improved Sensitivity of Biological Sequence Database Searches", Comp. App. Biosci., vol. 6, No. 3, pp. 237-245 (1990).
Claxton, et al., "A Systematic Review of the Associations between Dose Regimens and Medication Compliance", Clinical Therapeutics, vol. 23, No. 8, pp. 1296-1310, (2001).
Cohen, et al., "Molecular Modeling Software and Methods for Medicinal Chemistry", J. of Medicinal Chemistry, vol. 33, No. 3, pp. 883-894 (1990).
Corbett, et al., "The Growing Burden of Tuberculosis", Arch. Intern. Med., vol. 163, pp. 1009-1021, (2003).
Garuti, et al. Synthesis and Antiproliferative Activity of Some Benzimidazole-4,7-dione Derivatives, Bioorganic & Medicinal Chemistry Letters 10, pp. 2193-2195, (2000).
Gibbons, et al., "The Structure of the Central Stalk in Bovine $F_1$-ATPase at 2.4 A Resolution", Nature Structural Biology, vol. 7, No. 11, pp. 1055-1061 (2000).
Ginsburg, et al., "Fluoroquinolones, Tuberculosis and Resistance", The Lancet Infectious Diseases, vol. 3, p. 432-442 (2003).
Goodford, "A Computational Procedure for Determining Energetically Favorable Binding Sites on Biologically Important Macromolecules," J. Med. Chem., vol. 28, pp. 849-857 (1985).
Goodsell, et al., "Automated Docking of Substrates to Proteins by Simulated Annealing", Proteins: Structure. Function, and Genetics, vol. 8, pp. 195-202 (1990).
Halgren, Merck Molecular Force Field. I. Basis, Form, Scope, Parameterization, and Performance of MMFF94*, Journal of Computational Chemistry, vol. 17, Nos. 5&6, pp. 490-516, (1996).
Jain, et al., "Substituted 4-Methylquinolines as a New Class of Anti-Tuberculosis Agents", Bioorganic & Medicinal Chemistry Letters, vol. 13, pp. 1051-1054, (2003).
Kunin, et al., "Antimicrobial Activities of Mefloquine and a Series of Related Compounds", Antimicrobial Agents and Chemotherapy, vol. 44, No. 4, pp. 848-852, (2000).
Kuntz, et al., "A Geometric Approach to Macromolecule-Ligand Interactions", Journal of Molelcular Biology, vol. 161, pp. 269-288, (1982).

(Continued)

*Primary Examiner* — Suzanne M Noakes
(74) *Attorney, Agent, or Firm* — Andrea Jo Kamage

(57) ABSTRACT

This invention provides an isolated mutant atpE protein and departing from said mutant atpE protein the identification of an ATPase binding domain. This invention also provides related nucleic acids, vectors, host cells, pharmaceutical compositions and articles of manufacture. This invention further provides methods for determining whether a test compound interacts with an atpE protein, i.e. with the ATPase binding domain of the present invention, as well as pharmaceuticals compositions comprising said test compound, in particular as antimicrobials, more particular as antimycobacterial agent, even more particular for treating tuberculosis in a subject.

5 Claims, 2 Drawing Sheets

OTHER PUBLICATIONS

Lindahl, et al., "Gromacs 3.0: a Package for Molecular Simulation and Trajectory Analysis", J. Mol. Model, vol. 7, pp. 306-317 (2001).
Lounis, et al., "Effectiveness of Once-Weekly Rifapentine and Moxifloxacin Regimens Against Mycobacterium Tuberculosis in Mice", Antimicrobial Agents and Chemotheraphy, vol. 45, No. 12, pp. 3482-3486, (2001).
Martin, et al., "3D Database Searching in Drug Design", Journal of Medicinal Chemistry, vol. 35, No. 12, pp. 2145-2154, (1992).
Meng, et al., "Automated Docking with Grid-Based Energy Evaluation", Journal of Computational Chemistry, vol. 13, No. 4, pp. 505-524, (1992).
Miranker, et al., "Functionality Maps of Binding Sites: A Multiple Copy Simultaneous Search Method", Proteins: Structure, Function and Genetics, vol. 11, pp. 29-34, (1991).
Navia, et al., "Use of Structural Information in Drug Design," Current Opinion in Structural Biology, vol. 2, pp. 202-210 (1992).
Nishibata, et al., "Automatic Creation of Drug Candidate Structures Based on Receptor Structure. Starting Point for Artificial Lead Generation", Tetrahedron, vol. 47, No. 43, pp. 8985-8990, (1991).
O'Brien, "The Need for New Drugs Against Tuberculosis, Obstacles, Opportunities, and Next Steps", Am. J. Respir. Crit. Care Med., vol. 163, pp. 1055-1058, (2001).
Ponder, et al., "An Efficient Newton-like Method for Molecular Mechanics Energy Minimization of Large Molecules", Journal of Computational Chemistry, vol. 8, No. 7, pp. 1016-1024, (1987).
Rastogi, et al., "Structural Changes Linked to Proton Translocation by Subunit C of the ATP Synthase" Nature, vol. 402, pp. 263-268, (1999).
Rotstein, et al., GroupBuild: A Fragment-Based Method for De Novo Drug Design, J. Med. Chem., vol. 36, pp. 1700-1710, (1993).
Sebald, et al., "N,N'-Dicyclohexylcarbodiimide Binds Specifically to a Single Glutamyl Residue of the Proteolipid Subunit of the Mitochondrial Adenosinetriphosphatases from Neurosporta Crassa and *Saccharamyces cerevisia*", Proc. Natl. Acad. Sci USA, vol. 77, No. 2, pp. 785-789, (1980).
Stover, et al., "A Small-Molecule Nitroimidazopyran Drug Candidate for the Treatment of Tuberculosis", Nature, vol. 405, pp. 962-966 (2000).
Vangapandu, et al., "Ring-Substituted Quinolines as Potential Anti-Tuberculosis Agents", Bioorganic & Medicinal Chemistry vol. 12, pp. 2501-2508, (2004).
Global Alliance for TB Drug Development, Developing a faster TB cure (2004; http://www.tballiance.org).
UNAIDS, AIDS epidemic update 2003 (2003; www.unaids.org/Unaids/EN/Resources).
World Health Organization, Tuberculosis (2004; http://www.who.int/health_topics/tuberculosis/en/).
World Health Organization, Tuberculosis Fact Sheet No 104 (2004; http://www.who.int/mediacentre/factsheets/fs104/en/).
XP-0023669646—Database Geneseq 'Online! "Protein encoded by Prokaryotic essential gene #22134" (2003).
XP-002369647—Database Geneseq 'Online! "Protein encoded by Prokaryotic essential gene #20429" (2003).
XP-002369648—Database Geneseq 'Online! "Protein encoded by Prokaryotic essential gene #21419" (2003).
XP-002369649—Database Geneseq 'Online! Protein encoded by Prokaryotic essential gene #19799 (2003).

* cited by examiner

US 8,378,085 B2

BACTERIAL ATP SYNTHASE BINDING DOMAIN

CROSS REFERENCE TO RELATED APPLICATIONS

This application is a divisional application of U.S. Ser. No. 11/576,023, filed Mar. 26, 2007, which is a national stage application of Patent Application No. PCT/EP2005/054893, filed Sep. 28, 2005, which application claims priority from U.S. Patent Application No. 60/620,500, filed Oct. 20, 2004 and EPO Patent Application No. 04104720.0, filed Sep. 28, 2004, all of which are hereby incorporated by reference in their entirety.

This invention provides an isolated mutant atpE protein and departing from said mutant atpE protein the identification of an ATPase binding domain. This invention also provides related nucleic acids, vectors, host cells, pharmaceutical compositions and articles of manufacture. This invention further provides methods for determining whether a test compound interacts with an atpE protein, i.e. with the ATPase binding domain of the present invention, as well as pharmaceuticals compositions comprising said test compound, in particular as antimicrobials, more particular as antimycobacterial agent, even more particular for treating tuberculosis in a subject.

BACKGROUND OF THE INVENTION

After AIDS, tuberculosis (TB) is the leading cause of adult mortality (2-3 million deaths per year) in the world and is a critical impediment to alleviating global poverty and suffering (1). Factors contributing to the resurgence of the disease include difficulties in implementing anti-TB programs in many countries, the dramatic increase in the number of immunosuppressed individuals—due mainly to HIV infection—and the movement of people through and from areas where TB is endemic. The TB and HIV epidemics fuel one another in co-infected people—currently 11 million adults—increasing both morbidity and mortality (2, 3). In addition, TB is the leading cause of death in HIV-infected people (4).

Although first-line anti-TB drug regimens can achieve more than 90% efficacy rates, their complexity can lead to poor compliance when adequate medical support and TB treatment programs are not available and, in turn, to the emergence of resistance (5). Multidrug-resistant (MDR) strains of TB complicate treatment substantially (6). The Global Alliance for TB Drug Development has recommended that any new treatment should offer at least one of the following three advantages over existing therapies: shortening or simplifying effective treatment of TB; increasing efficacy against MDR-TB; and improving treatment of the latent form of TB infection. Such a new drug would greatly improve patient compliance, thereby reducing the cost of TB treatment programs like the World Health Organization (WHO)'s Directly Observed Treatment Short-course (DOTs) strategy (7).

Newer anti-TB candidates currently in preclinical and clinical development tend to be either from existing families of drugs (such as moxifloxacin), or analogs of first-line drugs such as MJH-98-1-81 (from isoniazid), the oxazolidinones, and rifapentine (a close analog of rifampin) (8). Although these new drugs may be potent, analog compounds provide only temporary solutions to resistance (9), as they rely on the same mechanism of action as the existing families of drugs.

Antibiotics in general usually inhibit bacterial replication by inhibiting bacterial metabolism though a specific mechanism. For example, isoniazid interferes with the enzymatic machinery that synthesizes mycolic acids, necessary components of the cell wall, while rifampicin interferes with the bacterial machinery for transcribing RNA from DNA. It is accordingly of interest to explore novel methods to identify anti-TB compounds that target different mycobacterial specific aspects of cell growth and replication compared to the known agents.

SUMMARY OF THE INVENTION

This invention provides for isolated mutant atpE proteins, in particular encoded by the amino acid sequences selected from (SEQ ID No. 1), (SEQ ID No. 2), (SEQ ID No. 3), (SEQ ID No. 4) and (SEQ ID No. 5), an isolated nucleic acid encoding said mutant atpE proteins, in particular selected from the group consisting of (SEQ ID No. 6), (SEQ ID No. 7), (SEQ ID No. 8), (SEQ ID No. 9) and (SEQ ID No. 10) and a vector comprising the instant nucleic acid. In a particular embodiment the mutant atpE protein is encoded by SEQ ID No. 2 and the isolated nucleic acid sequence encoding said protein consists of SEQ ID No. 7.

This invention further provides a host-vector system comprising a host cell having therein the instant expression vector.

This invention further provides an isolated cell comprising a mutant atpE protein, wherein said protein induces anti-microbial resistance in the cell.

This invention further provides a method for identifying an anti-microbial compound said method comprising the steps of
(a) contacting a cell expressing an atpE protein with a test compound under physiological conditions;
(b) determining whether the test compound interacts with the atpE protein.

This invention further provides a method for evaluating the potential of a test compound to interact with an atpE protein said method comprising;
(a) using molecular modeling techniques to generate a three-dimensional structure of the atpE protein;
(b) employing computational means to perform a fitting operation between the test compound and the three-dimensional structure of the atpE protein; and
(c) analyzing the results of said fitting operation to quantify the association of the test compound with the three dimensional structure of the atpE protein.

It is also an object of the present invention to provide a binding site of an $F_0$ part of an ATPase comprising at least the amino acids $Ala^{24}$, $Gly^{27}$, $Phe^{53}$, $Val^{57}$, $Gly^{58}$, $Glu^{61}$, $Tyr^{64}$ and $Phe^{65}$ of one C subunit; the amino acids $Ser^{132}$, $Leu^{183}$, $Ser^{184}$, $Leu^{185}$, and $Arg^{186}$ of one A subunit and said amino acids having the atomic coordinates of any of Tables 3, 4 or 5.

In a further object, the present invention provides the use of the aforementioned binding domain in a method to identify compounds that interact with the $F_0$ part of an ATPase and to their potential as anti-microbial compounds, in particular in a method to identify anti-mycobacterial compounds.

It is accordingly, an object of the present invention to provide a method of treating a subject with a microbially-based infection, comprising administering to the subject a compound that interacts with the $F_0$ part of an ATPase, in particular with an atpE protein at the resistance-conferring mutation sites or with the binding site of the present invention. This invention further provides a method for treating a subject afflicted with tuberculosis comprising administering to the subject an agent that interacts with an atpE protein using any of the aforementioned screening methods. In the methods of treatment comprising the use of a compound that interacts with the $F_0$ part of an ATPase, in particular with an atpE protein, compounds previously known to interact with the F$_O$ part of an ATPase, and in particular with an atpE protein are to be excluded. More in particular the use of the DARQ J compounds described in (11) in any of the disclosed method of treatments is to be excluded.

This invention further provides for a pharmaceutical composition comprising an agent that interacts with an atpE protein in a cell, and a pharmaceutically acceptable carrier. Finally, this invention provides for an article of manufacture comprising a packaging and a pharmaceutical agent, wherein (a) the pharmaceutical agent interacts with an atpE protein in a cell, and (b) the packaging comprises a label indicating the use of the agent for treating a bacterial infection in a subject. In a particular embodiment the present invention provides the use of DARQ J in the manufacture of an anti-microbial medicine.

This and further aspects of the present invention will be discussed in more detail hereinafter.

BRIEF DESCRIPTION OF THE DRAWING

Table. 1 The minimum inhibitory concentrations (MICs) of the lead DARQ compound (J), that inhibited 90% of the growth of different mycobacterial species. the number of strains tested were n=1, unless otherwise indicated.

Table. 2 The amino acids surrounding the binding site for the DARQ J compound.

Figures 1, 2:
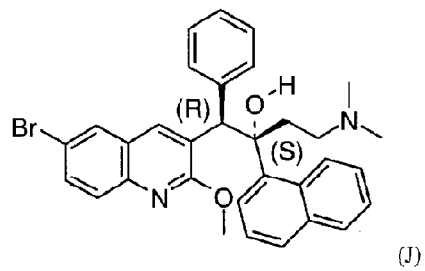

Table. 3 The atomic coordinates for the amino acids surrounding the binding site for the DARQ J compound derived from both the wild type and DARQ J mutant *M. tuberculosis* strain.

Table 4. The atomic coordinates for the binding site for the DARQ J compound in the wild type *M. tuberculosis*.

Table 5. The atomic coordinates for the binding site for the DARQ J compound in the DARQ J mutant *M. tuberculosis* strain.

Table 6. The atomic coordinates for the mutant atpE protein (SEQ ID No. 2) of *M. tuberculosis.*

Table 7. The atomic coordinates for the wild type atpE protein (SEQ ID No. 1) of *M. tuberculosis.*

FIG. 1 Absolute configuration of R207910, hereinafter also referred to as J or DARQ J.

FIG. 2 atpE protein sequence alignments for *M. tuberculosis* and *M. smegmatis* mutants. Mtb_S: drug-sensitive strain of *M. tuberculosis* H37Rv, atpE (1-81). Accession number: Swiss-Prot Q10598 (SEQ ID No. 1). Mtb_R: drug-resistant strain of *M. tuberculosis* BK12, atpE (1-81) (SEQ ID No. 2). Msm_S: drug-sensitive strain of *M. smegmatis*, atpE (1-86). Sequence obtained by the Institute for Genome Research (SEQ ID No. 3). Msm_R09 (SEQ ID No. 4) and R10 (SEQ ID No. 5): drug-resistant strains of *M. smegmatis* atpE (1-86). Sequences obtained in-house. Human: *Homo sapiens*, ATP5G3 (66-142). Accession number: Ensembl ENSP00000284727. Top numbering: *M. tuberculosis* and *M. smegmatis* atpE. Bottom numbering: H sapiens ATP5G3 (66-142) Shading indicates amino acid similarity using BLOSUM62 matrix (black=high, grey=medium). Arrows indicate the positions of the point mutations observed in the resistant strains.

FIG. 3 Total cellular ATP-measurement of *M. tuberculosis* in presence of DARQ J, Isoniazid & DCCD. Relative Luminescence Units of Oxyluciferin measured at 526 nm, both in wild type *M. tuberculosis* and DARQ J mutant *M. tuberculosis.*

FIG. 4. Ribbon representation of the three C-subunits (A Chain, K Chain and L Chain) and the A subunit (M chain) which form together the binding site for the DARQ J compound.

DETAILED DESCRIPTION

Definitions

As used in this application, except as otherwise expressly provided herein, each of the following terms shall have the meaning set forth below.

"atpE protein" shall mean the C chain of the $F_0$ subunit of ATPase complex as represented by SwissProt entry Q10598 for *M. tuberculosis*, or a protein having at least 70, 80, 90, 95, 97 or 99% sequence identity to said *M. tuberculosis* sequence.

"$F_1F_0$ ATPase" also referred to as ATPase, ATP synthase or $F_0F_1$ ATP ase shall mean a large-multisubunit complex that catalyses the synthesis or hydrolysis of ATP. $F_0F_1$ ATPases are composed of two domains: an $F_1$ part, which is extrinsic to the membrane and contains the catalytic sites and an $F_0$ part which spans the bilayer and contains a proton pore. The ATP ases are found in the plasma membrane of bacteria, the thylakoid membrane of chloroplasts, and the inner membrane of mitochondria where they use the energy of a proton electrochemical gradient to drive ATP synthesis.

"Administering" shall mean delivering in a manner, which is effected or performed using any of the various methods and delivery systems known to those skilled in the art. Administering can be performed, for example, topically, intravenously, pericardially, orally, via implant, transmucosally, transdermally, intramuscularly, subcutaneously, intraperitoneally, intrathecally, intralymphatically, intralesionally, or epidurally. Administering can also be performed, for example, once, a plurality of times, and/or over one or more extended periods.

"Host cells" include, but are not limited to, bacterial cells, yeast cells, fungal cells, insect cells, and mammalian cells. Bacterial cells can be transfected by methods well-known in the art such as calcium phosphate precipitation, electroporation and microinjection.

"Isolated", with respect to atpE protein, shall mean an atpE protein-containing membrane fragment preparation or other suitable preparation wherein atpE retains its natural function and is free from some or all of the other proteins in its native milieu. It is meant to include membrane preparations comprising the $F_0$ part of an $F_0F_1$ ATPase, in particular an $F_0$ part comprising the mutant atpE proteins of the present invention.

"Bacterial cell" shall mean any bacterial cell. Bacterial cells include, without limitation, cells which are normal, abnormal and transformed, and are exemplified by mycobacteria, in particular *Mycobacterium tuberculosis* and *Mycobacterium smegmatis*, corynebacteria, nocardia, gram-positive bacteria such as for example streptococcus, staphylococcus and enterococcus or gram negative bacteria such as for example *Escherichia coli, Heamophilus influenzae* and *Helicobacter pylori.*

The terms "nucleic acid" and "polynucleotide" are used interchangeably herein, and each refers to a polymer of deoxyribonucleotides and/or ribonucleotides. The deoxyribonucleotides and ribonucleotides can be naturally occurring or synthetic analogues thereof.

The term "physiological conditions" shall mean, with respect to a given cell, such conditions, which would normally constitute the cell's biochemical milieu. The cell's biochemical milieu includes, without limitation some or all the proteases to which the cell is normally exposed. Such conditions include, but are not limited, to in vivo conditions.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

"Subject" shall mean any animal, such as a mammal or a bird, including, without limitation, a cow, a horse, a sheep, a pig, a dog, a cat, a rodent such as a mouse or rat, a turkey, a chicken and a primate. In the preferred embodiment, the subject is a human being.

"Treating" shall include, without limitation, eliminating, reversing the course of, slowing the progression of, reducing the symptoms of, or otherwise ameliorating, a disease in a subject.

"Vector" shall mean any nucleic acid vector known in the art. Such vectors include, but are not limited to, plasmid vectors, cosmid vectors, and bacteriophage vectors.

The terms "Candidate substance" and "Test compound" are used interchangeably and refer to a substance that is believed to interact with another moiety, i.e. the atpE protein, as a biological response modifier. For example a representative candidate substance is believed to interact with an atpE protein and is believed to modify the ATPase activity. Exemplary candidate substances that can be investigated using the methods of the present invention include, but are not restricted to, peptides, enzymes, enzyme substrates, co-factors, sugars, oligonucleotides, chemical compounds small molecules and monoclonal antibodies.

"Modulate" shall mean an increase, decrease or other alteration of any or all chemical and biological activities or properties of a wild type or mutant atpE protein.

"Interact" shall mean detectable interactions between molecules, including "binding" interactions between molecules. Interactions can, for example, be protein-protein or protein-nucleic acid in nature. Such interactions can be detected using art know procedures, for example, yeast two-hybrid assay, immunoprecipitation, SPA-assay or filter binding assays.

As used herein, the term "atomic coordinates" or "structure coordinates" refers to mathematical coordinates that describe the positions of atoms in Protein Data Bank (PDB) format, including X, Y, Z and B for each atom. Those of skilled in the art understand that a set of structure coordinates determined by X-ray crystallography is not without standard error. For the purpose of this invention, any set of structure coordinates for ATPsynthase from any source having a root mean square deviation of non-hydrogen atoms of less than 1.5 Å when superimposed on the non-hydrogen atom position of the corresponding atomic coordinates of Tables 3, 4, 5, 6 or 7 are considered substantially identical or homologous. In a more preferred embodiment, any set of structure coordinates for ATPsynthase from any source having a root mean square deviation of non-hydrogen atoms of less than 0.75 Å when superimposed on the non-hydrogen atom position of the corresponding atomic coordinates of Tables 3, 4, 5, 6 or 7 are considered substantially identical.

Embodiments of the Invention

Mutant atpE Proteins

This invention provides for isolated mutant atpE proteins, in particular bacterial atpE proteins, more particular mycobacterial atpE proteins, even more particular *M. tuberculosis* or *M. smegmatis* atpE proteins. The mutation is selected from single point mutations, insertions or deletions. In one embodiment of the invention the mutation consist of at least one point mutation located in any one of amino acids 20 to 40, in particular 30 to 40, preferable in amino acid 34 or of amino acids 60 to 75, in particular 62 to 73, preferably in amino acid 69 as shown in the sequence alignment of FIG. 2. In a further embodiment the isolated mutant atpE proteins are selected from Mtb_R (SEQ ID No. 2), Msm_R09 (SEQ ID No. 4) and Msm_R10 (SEQ ID No. 5) as shown in FIG. 2 or of an amino acid sequence having at least 70, 80, 90, 95, 97 or 98% sequence identity to any of the aforementioned amino acid sequences.

This invention further provides an isolated nucleic acid encoding said mutant atpE proteins. In one embodiment said nucleic acid sequence consists of all genes that encode an $F_0$ part, such as for example described in *J. Biol. Chem.,* 1994, Vol. 269(10), p. 7285-7289, wherein said genes are transcribed from a single promoter and comprise the nucleic acid sequence encoding the mutant atpE protein of the present invention. The nucleic acid can be DNA or RNA, and preferably DNA and are in a further embodiment selected from the nucleic acid sequences encoding Mtb_R (SEQ ID No. 7) Msm_R09 (SEQ ID No. 9), Msm_R10 (SEQ ID No. 10) or a nucleic acid sequence having at least 70, 80, 90, 95, 97 or 98% sequence identity to any of the aforementioned nucleic acid sequences.

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI-BLAST, which may be used with default parameters.

The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4.

Another method for determining the best overall match between a nucleic acid sequence or a portion thereof, and a query sequence is the use of the FASTDB computer program based on the algorithm of Brutlag et al (Comp. App. Biosci., 6; 237-245 (1990)). The program provides a global sequence alignment. The result of said global sequence alignment is in percent identity. Suitable parameters used in a FASTDB search of a DNA sequence to calculate percent identity are: Matrix=Unitary, k-tuple=4, Mismatch penalty=1, Joining Penalty=30, Randomization Group Length=0, Cutoff Score=1, Gap Penalty=5, Gap Size Penalty=0.05, and Window Size=500 or query sequence length in nucleotide bases, whichever is shorter. Suitable parameters to calculate percent identity and similarity of an amino acid alignment are: Matrix=PAM 150, k-tuple=2, Mismatch Penalty=1, Joining Penalty=20, Randomization Group Length=0, Cutoff Score=1, Gap Penalty=5, Gap Size Penalty=0.05, and Window Size=500 or query sequence length in nucleotide bases, whichever is shorter.

This invention further provides a vector comprising the instant nucleic acid. In one embodiment the vector is a plasmid vector.

This invention further provides a host-vector system comprising a host cell having therein the instant plasmid vector. The cell can be prokaryotic or eukaryotic, in one embodiment the host cell is a bacterial cell, in particular a mycobacterial cell such as for example *M. tuberculosis* or *M. smegmatis.*

This invention further provides an isolated cell comprising a mutant atpE protein, which protein induces anti-microbial resistance in the cell. In one embodiment the isolated cell consists of a *M. smegmatis* cell transformed with a mutant mycobacterial atpE protein, in particular transformed with a mutant mycobacterial atpE protein wherein the mutation consist of at least one point mutation located in any one of amino acids 20 to 40, in particular 30 to 40, preferable in amino acid 34 or of amino acids 60 to 75, in particular 62 to 73, preferably in amino acid 69 as shown in the sequence alignment of FIG. 2.

Screening Methods

This invention further provides a method for identifying an anti-microbial compound said method comprising the steps of (a) contacting a cell expressing an atpE protein with a test compound under physiological conditions;
(b) determining whether the test compound interacts with the atpE protein.

In one embodiment the atpE protein used in the aforementioned method, consist of a bacterial atpE protein, in particular a mycobacterial protein and is meant to include both the wild type atpE proteins as well as the mutant atpE proteins as described hereinbefore. In a further embodiment of the present invention, the mycobacterial atpE protein used in the aforementioned method consists of a mutant mycobacterial atpE protein according to the invention. In a particular embodiment of the aforementioned assay a host cell transformed with a mutant atpE protein of the invention is used and the interaction of the test compound with said atpE protein is assessed by determining the possible inhibition of the enzymatic activity of the $F_1F_0$-ATPase comprising said mutant atpE protein. Inhibition of the $F_1F_0$-ATPase activity is determined using art known procedures, such as for example by adding the substance to a system comprising the $F_1F_0$-ATPase and ATP as a substrate, with detection of the enzymatic activity by coupling the production of ADP to the oxidation of NADH via pyruvate kinase and lactate hydrogenase reactions.

In one embodiment of the assay, the atpE protein may be employed in a binding assay. Binding assays may be competitive or non-competitive. Such an assay can accommodate the rapid screening of a large number of compounds to determine which compounds, if any, are capable of binding to the polypeptides.

Within this context, the present invention provides a method to identify whether a test compound binds to an isolated atpE protein of the present invention, and is thus a potential anti-microbial compound, said method comprising;

a) contacting cells expressing the atpE protein wherein such cells do not normally express said atpE protein, with the test compound in the presence and absence of a compound known to bind the atpE protein,
b) determine the binding of the test compound to the atpE protein using the compound known to bind to the atpE protein as a reference.

Binding of the test compound or of the compound known to bind to the atpE protein, hereinafter also referred to as reference compound, is assessed using art-known methods for the study of protein-ligand interactions. For example, such binding can be measured by employing a labeled substance or reference compound. The test compound or reference compound, in particular compound J (FIG. 1) can be labeled in any convenient manner known in the art, e.g. radioactively, fluorescently or enzymatically. In a particular embodiment of the aforementioned method, the compound known to bind to the atpE protein, also known as the reference compound is detectably labeled, and said label is used to determine the binding of the test compound to the atpE protein. Said reference compound being labeled using a radiolabel, a fluorescent label or an enzymatic label, more preferably a radiolabel.

In an alternative embodiment of the present invention, the aforementioned binding assays are performed on a cellular composition, i.e a cellular extract, a cell fraction or cell organels comprising an atpE protein as defined hereinbefore. More in particular, the aforementioned binding assays are performed on a cellular composition, i.e. a membrane preparation comprising an atpE protein as defined hereinbefore, wherein said cellular composition, i.e. membrane preparation is obtained from a *M. smegmatis* cell transformed with a mutant mycobacterial atpE protein, in particular transformed with a mutant mycobacterial atpE protein wherein the mutation consist of at least one point mutation located in any one of amino acids 20 to 40, in particular 30 to 40, preferable in amino acid 34 or of amino acids 60 to 75, in particular 62 to 73, preferably in amino acid 69 as shown in the sequence alignment of FIG. 2. Taking the numbering of Mtb_S (SEQ ID No. 1) or of Mtb_R (SEQ ID No. 2) as a reference, the aforementioned regions correspond to amino acids 14 to 34, in particular 24 to 34, preferably in amino acid 28 or to amino acids 54 to 69, in particular 56 to 67, preferably to amino acid 63.

In one embodiment the binding assays are performed using membrane preparations. These membrane preparations can be used in conventional filter-binding assays (eg. Using Brandel filter assay equipment) or in high throughput Scintillation Proximity type binding assays (SPA and Cytostar-T flashplate technology; Amersham Pharmacia Biotech) to detect binding of radio-labelled atpE ligands (including $^3$H labelled DARQs) and displacement of such radio-ligands by competitors for the binding site. Radioactivity can be measured with Packard Topcount, or similar instrumentation, capable of making rapid measurements from 96-, 384-, 1536-microtitre well formats. SPA/Cytostar-T technology is particularly amenable to high throughput screening and therefore this technology is suitable to use as a screen for compounds able to displace standard ligands.

Another approach to study binding of ligands to atpE protein in an environment approximating the native situation makes use of a surface plasmon resonance effect exploited by the Biacore instrument (Biacore). atpE protein in membrane preparations or whole cells could be attached to the biosensor chip of a Biacore and binding of ligands examined in the presence and absence of compounds to identify competitors of the binding site.

Molecular Modeling

This invention further provides a method for evaluating the potential of a test compound to interact with an atpE protein said method comprising;

(a) using molecular modeling techniques to formulate a three dimensional structure of the atpE protein;
(b) employing computational means to perform a fitting operation between the test compound and the three-dimensional structure of the atpE protein; and
(c) analyzing the results of said fitting operation to quantify the association of the test compound with the three dimensional structure of the atpE protein.

Molecular modeling techniques are known in the art, including both hardware and software appropriate for creating and utilizing models of receptors and enzyme conformations.

Numerous computer programs are available and suitable for the processes of computer modeling, model building and computationally identifying, selecting and evaluating potential atpE interacting compounds in the methods described herein. These include for example, GRID (available from Oxford University, UK), MCSS (available from Accelrys, Inc., San Diego, Calif.), AUTODOCK (available from Oxford Molecular Group), FLEX X (available form Tripos, St. Louis. MO), DOCK (available from University of California, San Francisco, Calif.), CAVEAT (available from University of California, Berkeley), HOOK (available from Accelrys, Inc., San Diego, Calif.) and 3D database systems such as MACCS-3D (available from MDL Information Systems, San Leandro, Calif.), UNITY (available from Tripos, St. Louis, Mo.) and CATALYST (available from Accelrys, Inc., San Diego, Calif.). Potential candidate substances may also be computationally designed "de novo" using software packages as LUDI (available from Biosym Technologies, San Diego, Calif.), LEGEND (available from Accelrys, Inc, San Diego, Calif.) and LEAPFROG (available from Tripos, St. Louis, Mo.). Compound deformation energy and electrostatic repulsion, may be analysed using programs such as GAUSSIAN 92, AMBER, QUANTA/CHARMM and INSIGHT II/DISCOVER. These computer evaluation and modeling techniques may be performed on any suitable hardware including for example, workstations available from Silicon Graphics, Sun Microsystems and others. These modeling techniques, methods, hardware and software packages are representative and are not intended to be a comprehensive listing. Other modeling techniques known in the art may also be employed in accordance with this invention. See for example, N. C. Cohen, *Molecular Modeling in Drug Design*, Academic Press (1996).

In one embodiment of the present invention, the three-dimensional structure of the atpE protein is generated using the atomic coordinates of the $Ile^{28}$, $Glu^{61}$ and $Ile^{63}$ of *E. coli* (Protein Database 1Q01)+/−a root mean square deviation of the backbone atoms of said amino acids of not more that 10 Å, preferably not more that 5 Å.

As provided in the examples hereinafter, it has been an object of the present invention to provide the three-dimensional structure of the atpE protein. Tables 6 and 7 provide the atomic coordinates for the mutant and wild type atpE protein with SEQ ID No. 2 and SEQ ID No. 1. Thus, in one embodiment the three-dimensional structure of the atpE protein is generated using the atomic coordinates of Tables 6 or 7. In a particular embodiment the three-dimensional structure of the atpE protein is generated using the atomic coordinates of Table 7. The DARQ J compound inhibits the interaction of $Arg^{186}$ of the A subunit with $Glu^{61}$ of the C-subunit in its deprotonated from. It is accordingly an object of the present invention to provide the use of the atomic coordinates of Tables 6 or 7 in a method to evaluate the potential of a test compound to interact with an atpE protein.

Binding Site

In another embodiment the present invention provides the characterization of a binding site in the $F_0$ part of an ATPase. This binding site, identified as being capable of binding the DARQ J compound, was found to coincide with the regions identified hereinbefore, as the resistance-conferring mutation sites in the atpE proteins of *M. tuberculosis* and *M. smegmatis* (17). Hence, the present invention provides a binding site in the $F_0$ part of an ATPase characterised in that it comprises the resistance-conferring mutation sites of an atpE protein. The resistance-conferring mutation sites as used herein refer to amino acids 14 to 34, in particular 24 to 34 and to amino acids 53 to 69, in particular 56 to 67 of an atpE protein, taking the numbering of Mtb_S (SEQ ID No. 1) or of Mtb_R (SEQ ID No. 2) as a reference.

In a further embodiment the binding site comprises at least the amino acids $Ala^{24}$, $Gly^{27}$, $Phe^{53}$, $Val^{57}$, $Gly^{58}$, $Glu^{61}$, $Tyr^{64}$ and $Phe^{65}$ of one C subunit and the amino acids $Ser^{182}$, $Leu^{183}$, $Leu^{85}$, and $Arg^{186}$ of one A subunit (having for the A subunit, the codes Ser 206-Leu 207-Leu 209 and Arg 210 in Tables 3, 4 and 5), wherein said amino acids have the atomic coordinates of any of Tables 3, 4 or 5 or homologous structure coordinates comprising a root mean square deviation of non-hydrogen atoms of less than about 1.5 Å, preferably not more that 0.75 Å, when superimposed on the non-hydrogen atom positions of the corresponding atomic coordinates of Tables 3, 4 or 5. In a particular embodiment the binding site comprises amino acids $Ala^{21}$, $Gly^{25}$ of a first C subunit; amino acids $Ala^{24}$, $Gly^{27}$, $Phe^{53}$, $Phe^{54}$, $Val^{57}$, $Gly^{58}$, $Glu^{61}$, $Tyr^{64}$, $Phe^{65}$ of a second C subunit; amino acids $Met^{17}$, $Gly^{19}$, $Gly^{20}$, $Ala^{21}$, $Ile^{22}$, $Gly^{23}$, $Ala^{24}$, $Gly^{25}$, $Ile^{26}$, $Gly^{27}$, $Asp^{28}$, $Gly^{29}$, $Ala^{31}$, $Phe^{53}$, $Thr^{56}$, $Val^{57}$, $Gly^{58}$, $Leu^{59}$, $Val^{60}$, $Glu^{61}$, $Ala^{62}$, $Ala^{63}/Pro^{63}$, $Tyr^{64}$, $Phe^{65}$ of a third C subunit and amino acids $Leu^{183}$, $Leu^{185}$ and $Arg^{186}$ of an A subunit; wherein said amino acids have the atomic coordinates of any of Tables 3, 4 or 5 or homologous structure coordinates comprising a root mean square deviation of non-hydrogen atoms of less than about 1.5 Å, preferably not more that 0.75 Å, when superimposed on the non-hydrogen atom positions of the corresponding atomic coordinates of Tables 3, 4 or 5. In an even more particular embodiment the binding site consists of the amino acids $Ala^{21}$, $Gly^{25}$ of a first C subunit; amino acids $Ala^{24}$, $Gly^{27}$, $Phe^{53}$, $Phe^{54}$, $Val^{57}$, $Gly^{58}$, $Glu^{61}$, $Tyr^{64}$, $Phe^{65}$ of a second C subunit; amino acids $Met^{17}$, $Gly^{19}$, $Gly^{20}$, $Ala^{21}$, $Ile^{22}$, $Gly^{23}$, $Ala^{24}$, $Gly^{25}$, $Ile^{26}$, $Gly^{27}$, $Asp^{28}$, $Gly^{29}$, $Ala^{31}$, $Phe^{53}$, $Thr^{56}$, $Val^{57}$, $Gly^{58}$, $Leu^{59}$, $Val^{60}$, $Glu^{61}$, $Ala^{62}$, $Ala^{63}/Pro^{63}$, $Tyr^{64}$, $Phe^{65}$ of a third C subunit and amino acids $Leu^{183}$, $Leu^{185}$, and $Arg^{186}$ of an A subunit; wherein said amino acids have the atomic coordinates of any of Tables 3, 4 or 5. In a most particular embodiment the binding site consists of the amino acids $Ala^{21}$, $Gly^{25}$ of a first C subunit; amino acids $Ala^{24}$, $Gly^{27}$, $Phe^{53}$, $Phe^{54}$, $Val^{57}$, $Gly^{58}$, $Glu^{61}$, $Tyr^{64}$, $Phe^{65}$ of a second C subunit; amino acids $Met^{17}$, $Gly^{19}$, $Gly^{20}$, $Ala^{21}$, $Ile^{22}$, $Gly^{23}$, $Ala^{24}$, $Gly^{25}$, $Ile^{26}$, $Gly^{27}$, $Asp^{28}$, $Gly^{29}$, $Ala^{31}$, $Phe^{53}$, $Thr^{56}$, $Val^{57}$, $Gly^{58}$, $Leu^{59}$, $Val^{60}$, $Glu^{61}$, $Ala^{62}$, $Ala^{63}/Pro^{63}$, $Tyr^{64}$, $Phe^{65}$ of a third C subunit and amino acids $Leu^{183}$, $Leu^{185}$ and $Arg^{186}$ of an A subunit; wherein said amino acids have the atomic coordinates of Table 3.

It is accordingly an object of the present invention to evaluate the potential of a test compound to interact with an atpE protein using the atomic coordinates as outlined above, in computational screening programs. In one embodiment, the present invention provides a method to evaluate the potential of a test compound to interact with an atpE protein, said method comprising; -molecular modeling techniques to generate the three-dimensional structure of a binding site of an $F_0$ part of an ATPase; -employing computational means to perform a fitting operation between the test compound and the three-dimensional structure of the binding site; and -analyzing the results of said fitting operation to quantify the association of the test compound with the three-dimensional structure of the binding site. In an further embodiment of the present invention, the three-dimensional structure of the binding site is generated using the atomic coordinates of Tables 3, 4 or 5 or homologous structure coordinates comprising a root mean square deviation of non-hydrogen atoms of less than about 1.5 Å, preferably not more that 0.75 Å, when superimposed on the non-hydrogen atom positions of the corresponding atomic coordinates of Tables 3, 4 or 5. In a particular embodiment the three-dimensional structure is generated using the atomic coordinates of the amino acids $Ala^{21}$, $Gly^{25}$ of the A Chain of any of Tables 3, 4 or 5; the amino acids $Ala^{24}$, $Gly^{27}$, $Phe^{53}$, $Phe^{54}$, $Val^{57}$, $Gly^{58}$, $Tyr^{64}$, $Phe^{65}$, $Glu^{61}$, of the K Chain of any of Tables 3, 4 or 5; the amino acids $Met^{17}$, $Gly^{19}$, $Gly^{20}$, $Ala^{21}$, $Ile^{22}$, $Gly^{23}$, $Ala^{24}$, $Gly^{25}$, $Ile^{26}$, $Gly^{27}$, $Asp^{28}$, $Gly^{29}$, $Ala^{31}$, $Phe^{53}$, $Thr^{56}$, $Val^{57}$, $Gly^{58}$, $Leu^{59}$, $Val^{69}$, $Glu^{61}$, $Ala^{62}$, $Ala^{63}/Pro^{63}$, $Tyr^{64}$, $Phe^{65}$ of the L Chain of any of Tables 3, 4 or 5; and the amino acids $Ser^{206}$, $Leu^{207}$, $Leu^{207}$, and $Arg^{210}$ of the M Chain of any of Tables 3, 4 or 5.

In this screening, the quality of fit of such compounds to the binding site may be judged either by shape complementarity or by estimated interaction energy (Meng, E. C. et al., J. Coma. Chem 13:505-524 (1992)).

Use of Binding Site

The design of compounds that bind to, promote or inhibit the functional activity of atpE according to this invention generally involves consideration of two factors. First, the compound must be capable of physically and structurally associating with atpE. Non-covalent molecular interactions important in the association of atpE with the compound, include hydrogen bonding, van der Waals and hydrophobic interactions. Second, the compound must be able to assume a conformation that allows it to associate with atpE. Although certain portions of the compound may not directly participate in the association with atpE, those portions may still influence the overall conformation of the molecule. This, in turn, may have a significant impact on binding affinities, therapeutic efficacy, drug-like qualities and potency. Such conformational requirements include the overall three-dimensional structure and orientation of the chemical entity or compound in relation to all or a portion of the active site or other region of atpE or the spacing between functional groups of a compound comprising several chemical entities that directly interact with atpE.

The potential, predicted, inhibitory agonist, antagonist or binding effect of a ligand or other compound on atpE may be analyzed prior to its actual synthesis and testing by the use of computer modeling techniques. If the theoretical structure of the given compound suggests insufficient interaction and association between it and atpE, synthesis and testing of the compound may be obviated. However, if computer modeling indicates a strong interaction, the molecule may then be synthesized and tested for its ability to interact with atpE. In this manner, synthesis of inoperative compounds may be avoided. In some cases, inactive compounds are synthesized predicted on modeling and then tested to develop a SAR (structure-activity relationship) for compounds interacting with a specific region of atpE. One skilled in the art may use one of several methods to screen chemical entities fragments, compounds, or agents for their ability to associate with atpE and more particularly with the individual binding pockets or active sites of atpE. This process may begin by visual inspection of, for example, the active site on the computer screen based on the atomic coordinates of atpE or atpE complexed with a ligand. Selected chemical entities, compounds, or agents may then be positioned in a variety of orientations, or docked within an individual binding pocket of atpE. Docking may be accomplished using software such as Quanta and Sybyl, followed by energy minimization and molecular dynamics with standard molecular mechanics forcefields, such as CHARMM and AMBER.

Specialized computer programs may also assist in the process of selecting chemical entities. These include but are not limited to: GRID (Goodford, P. J., "A Computational Procedure for Determining Energetically Favorable Binding Sites on Biologically Important Macromolecules," J. Med. Chem. 28:849-857 (1985), available from Oxford University, Oxford, UK); MCSS (Miranker, A. and M. Karplus, "Functionality Maps of Binding Sites: A Multiple Copy Simultaneous Search Method." Proteins: Structure, Function and Genetics 11: 29-34 (1991), available from Molecular Simulations, Burlington, Mass.); AUTODOCK (Goodsell, D. S, and A. J. Olsen, "Automated Docking of Substrates to Proteins by Simulated Annealing" Proteins: Structure. Function, and Genetics 8:195-202 (1990), available from Scripps Research Institute, La Jolla, Calif.); and DOCK (Kuntz, I. D. et al., "A Geometric Approach to Macromolecule-Ligand Interactions," J.-Mol. Biol. 161:269-288 (1982), available from University of California, San Francisco, Calif.).

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand binding site and suggest ligands with complementary steric properties.

Once suitable chemical entities, compounds, or agents have been selected, they can be assembled into a single ligand or compound or inhibitor or activator. Assembly may proceed by visual inspection of the relationship of the fragments to each other on the three-dimensional image. This may be followed by manual model building using software such as Quanta or Sybyl.

Useful programs to aid in connecting the individual chemical entities, compounds, or agents include but are not limited to: CAVEAT (Bartlett, P. A. et al., "CAVEAT: A Program to Facilitate the Structure-Derived Design of Biologically Active Molecules." In Molecular Recognition in Chemical and Biological Problems, Special Pub., Royal Chem. Soc., 78, pp. 82-196 (1989)); 3D Database systems such as MACCS-3D (MDL Information Systems, San Leandro, Calif. and Martin, Y. C., "3D Database Searching in Drug Design", J. Med. Chem. 35: 2145-2154 (1992); and HOOK (available from Molecular Simulations, Burlington, Mass.).

Several methodologies for searching three-dimensional databases to test pharmacophore hypotheses and select compounds for screening are available. These include the program CAVEAT (Bacon et al., J. Mol. Biol. 225:849-858 (1992)). For instance, CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding. Instead of proceeding to build an inhibitor activator, agonist or antagonist of atpE in a step-wise fashion one chemical entity at a time as described above, such compounds may be designed as a whole or "de novo" using either an empty active site or optionally including some portion(s) of a known molecules. These methods include: LUDI (Bohm, H.-J., "The Computer Program LUDI: A New Method for the De Novo Design of Enzyme Inhibitors", J. ComR. Aid. Molec. Design, 6, pp. 61-78 (1992), available from Biosym Technologies, San Diego, Calif.); LEGEND (Nishibata, Y. and A. Itai, Tetrahedron 47:8985 (1991), available from Molecular Simulations, Burlington, Mass.); and LeapFrog (available from Tripos Associates, St. Louis, Mo.). For instance, the program LUDI can determine a list of interaction sites into which to place both hydrogen bonding and hydrophobic fragments. LUDI then uses a library of linkers to connect up to four different interaction sites into fragments. Then smaller "bridging" groups such as —$CH_2$— and —COO— are used to connect these fragments. For example, for the enzyme DHFR, the placements of key functional groups in the well-known inhibitor methotrexate were reproduced by LUDI. See also, Rotstein and Murcko, J. Med. Chem. 36: 1700-1710 (1992).

Other molecular modeling techniques may also be employed in accordance with this invention. See, e.g., Cohen, N. C. et al., "Molecular Modeling Software and Methods for Medicinal Chemistry, *J. Med. Chem.* 33:883-894 (1990). See also, Navia, M. A. and M. A. Murcko, "The Use of Structural Information in Drug Design," Current Opinions in Structural Biology, 2, pp. 202-210 (1992).

Once a compound has been designed or selected by the above methods, the affinity with which that compound may bind or associate with atpE may be tested and optimized by computational evaluation and/or by testing biological activity after synthesizing the compound. Inhibitors or compounds may interact with the atpE in more than one conformation that is similar in overall binding energy. In those cases, the deformation energy of binding is taken to be the difference between the energy of the free compound and the average energy of the conformations observed when the compound binds to atpE.

A compound designed or selected as binding or associating with atpE may be further computationally optimized so that in its bound state it would preferably lack repulsive electrostatic interaction with atpE. Such non-complementary (e.g., electrostatic) interactions include repulsive charge-charge, dipole-dipole and charge-dipole interactions. Specifically, the sum of all electrostatic interactions between the inhibitor and atpE when the inhibitor is bound, preferably make a neutral or favorable contribution to the enthalpy of binding. Weak binding compounds will also be designed by these methods so as to determine SAR. See, for example, U.S. Appl. Nos. 60/275,629; 60/331,235; 60/379,617; and, Ser. No. 10/097,249.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., COPYRGT 1992); AMBER, version 4.0 (P. A. Kollman, University of California at San Francisco, COPYRGT 1994); QUANTA/CHARMM (Molecular Simulations, Inc., Burlington, Mass. COPYRGT 1994); and Insight II/Discover (Biosysm Technologies Inc., San Diego, Calif. COPYRGT 1994). Other hardware systems and software packages will be known to those skilled in the art.

Once a compound that associates with atpE has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted chemical compounds may then be analyzed for efficiency of fit to atpE by the same computer methods described in detail, above.

The present invention further provides systems, particularly computer-based systems, which contain the sequence and/or structure coordinates described herein. Such systems are designed to do structure determination and rational drug design for atpE or for the binding site in the $F_0$ part of the ATPase. The computer-based systems refer to the hardware means, software means and data storage means used to analyze the sequence and/or structure coordinates of the present invention in any of the computer methods described in detail, above. The minimum hardware means of the computer-based system of the present invention comprises a central processing unit (CPU), input means, output means and data storage means. A skilled person can readily appreciate which of the currently available computer-based systems are suitable for use in the present invention.

It is accordingly an object of the present invention to provide computer readable data storage medium containing the structure coordinates described herein. As used herein, "computer readable data storage medium" refers to any medium which can be read or accessed directly by a computer. Such media include, but are not limited to: magnetic storage media, such as floppy disks, hard disc storage media and magnetic tape; optical storage media such as optical discs or CD-ROM; electrical storage media such as RAM and ROM; and hybrids of these categories such as magnetical/optical storage media.

Methods of Treatment

As already mentioned hereinbefore, it is also an object of the present invention to provide the use of compounds identified using any of the aforementioned screening methods in a method of treating a subject with a microbially-based infection. In general, bacterial pathogens may be classified as either gram-positive or gram-negative pathogens. Antimicrobial compounds with activity against both gram-positive and gram-negative pathogens are generally regarded as having a broad spectrum of activity. The compounds of the present invention are regarded as active against gram-positive and/or gram-negative bacterial pathogens. In particular, the present compounds are active against at least one gram-positive bacterium, preferably against several gram-positive bacteria, more preferably against one or more gram-positive bacteria and/or one or more gram-negative bacteria.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogens*; Bacilli, for example *Bacillus subtilis; Listeria*, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against those bacteria of which the viability depends on proper functioning of $F_1F_0$ ATP synthase. Without being bound to any theory, it is taught that the activity of the present compounds lies in inhibition of the $F_1F_0$ ATP synthase, in particular the inhibition of the $F_0$ complex of the $F_1F_0$ ATP synthase, more in particular the inhibition of the proton transfer from $Arg^{186}$ of the A subunit to $Glu^{61}$ of the C subunit of the $F_0$ complex of the $F_1F_0$ ATP synthase, leading to killing of the bacteria by depletion of the cellular ATP levels of the bacteria. The compounds identified using any of the aforementioned screening methods are particularly active against Gram-positive bacteria, more particular mycobacteria, and most particular against infections caused by *M. africanum, M. avium, M. bovis, M. bovis*-BCG, *M. chelonae, M. fortuitum, M. gordonae, M. intracellulare, M. kansasii, M. microti, M. scrofulaceum, M. paratuberculosis, M. leprea, M. tuberculosis, M. ulcerans* and *M. ranae.*

Whenever used hereinbefore or hereinafter, that the compounds can treat a bacterial infection it is meant that the compounds can treat an infection with one or more bacterial strains. When used however, in relation to the use of DARQ J as an anti-microbial compound, anti-microbial is meant to be a compound that can treat an infection with one or more bacterial strains, provided that said bacterial strains are other than mycobacteria.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

This invention further provides a method for treating a subject afflicted with tuberculosis comprising administering to the subject an agent that interacts with an atpE protein.

Pharmaceutical Compositions

This invention further provides for a pharmaceutical composition comprising an agent that interacts with an atpE protein in a cell, and a pharmaceutically acceptable carrier.

Such agents may be formulated into compositions comprising an agent together with a pharmaceutically acceptable carrier or diluent. The agent may in the form of a physiologically functional derivative, such as an ester or a salt, such as an acid addition salt or basic metal salt, or an N or S oxide. Compositions may be formulated for any suitable route and means of administration. Pharmaceutically acceptable carriers or diluents include those used in formulations suitable for oral, rectal, nasal, inhalable, topical (including buccal and sublingual), vaginal or parenteral (including subcutaneous, intramuscular, intravenous, intradermal, intrathecal and epidural) administration. The choice of carrier or diluent will of course depend on the proposed route of administration, which, may depend on the agent and its therapeutic purpose. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Gennaro et al., Remington's Pharmaceutical Sciences, Mack Publishing Company, Easton, Pa., 18th Edition, 1990.

The composition or formulation to be administered will, in any event, contain a quantity of the active compound(s) in an amount effective to alleviate the symptoms of the subject being treated.

The exact dosage and frequency of administration of the present compounds depends on the particular compound used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

Dosage forms or compositions containing active ingredient in the range of 0.25 to 95% with the balance made up from non-toxic carrier may be prepared. Depending on the mode of administration, the pharmaceutical composition will preferably comprise from 0.05 to 99% by weight, more preferably from 0.1 to 70% by weight of the active ingredients, and, from 1 to 99.95% by weight, more preferably from 30 to 99.9 weight % of a pharmaceutically acceptable carrier, all percentages being based on the total composition.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Finally, this invention provides for an article of manufacture comprising a packaging and a pharmaceutical agent, wherein (a) the pharmaceutical agent interacts with an atpE protein in a cell, and (b) the packaging comprises a label indicating the use of the agent for treating a bacterial infection in a subject. In particular as an anti-mycobacterial medicine.

Throughout this description the terms "standard methods", "standard protocols" and "standard procedures", when used in the context of molecular biology techniques, are to be understood as protocols and procedures found in an ordinary laboratory manual such as: Current Protocols in Molecular Biology, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXPERIMENTAL

Using *Mycobacterium smegmatis* as a surrogate, we discovered a series of DARQs with potent in vitro activity against several mycobacteria (11). To date, 20 molecules of the DARQ series have a minimal inhibitory concentration (MIC) below 0.5 μg/ml against *Mycobacterium tuberculosis* H37Rv, and for three of these the anti-mycobacterial activity was confirmed in the in vivo mouse model.

Structurally and mechanistically, DARQs are very different from both fluoroquinolones (including methoxyquinolones) and other quinoline classes, including mefloquine and its analogs, 4-methylquinolines and 4-quinolylhydrazones (12-16). One of the major structural differences between DARQs and other quinolone or quinoline classes is the specificity of the functionalized lateral (3') chain borne by the DARQ class. In addition, the lack of mycobacterial cross-resistance with existing chemical classes points to a different mechanism of action.

The lead compound of the DARQs, hereinafter referred to as J or DARQ J (FIG. 1), was found to have an unique spectrum of potent and selective anti-mycobacterial activity in vitro (Table 1). The median MIC, obtained for the laboratory strain H37Rv and six fully susceptible isolates was 0.060 μg/ml, versus 1.00 μg/ml for rifampin. J demonstrated similar in vitro efficacy against *M. tuberculosis* clinical isolates resistant to the first-line TB agents rifampin, streptomycin, ethambutol and pyrazinamide; and the second-line TB agent moxifloxacin. For eight clinical isolates resistant to isoniazid, the median MIC was 0.010 μg/ml. The lack of cross-resistance with currently used anti-TB agents suggested that J may retain activity against MDR-TB strains. Indeed, using the BACTEC™ culture system, a clear concentration-dependent inhibition of bacterial growth was seen when MDR-TB strains were exposed to fixed concentrations of J. Out of the 30 isolates of MDR-TB, 13 (43%) were found to be susceptible to 0.100 μg/ml of J and 17 (57%) were susceptible to 0.010 μg/ml of J. A similar high degree of susceptibility (MIC below 0.010 μg/ml) was seen for only one of 10 additional fully drug-susceptible strains, when tested using the BACTEC™ system, while all strains were susceptible to 0.100 μg/ml of J.

Potent activity was also demonstrated against other mycobacterial species including *Mycobacterium bovis* and *Mycobacterium kansasii*, as well as species naturally resistant to many other anti-TB agents and involved in opportunistic infections, such as *Mycobacterium avium* complex (MAC), *Mycobacterium abcessus*, *Mycobacterium fortuitum* and *Mycobacterium marinum* (Table 1).

Surprisingly, the activity of J appeared to be specific for mycobacteria. J was barely active against species close to mycobacteria such as *Corynebacterium* (MIC 4.00 μg/ml) and *Nocardia* (MIC >4.00 μg/ml) and not active against other organisms including Gram positive *Streptococcus pneumoniae*, *Staphylococcus aureus*—including methicillin-resistant strains (MIC >32 μg/ml)—and *Enterococcus faecalis*, or Gram negative *Escherichia coli*, *Haemophilus influenzae*, and *Helicobacter pylori*. Exposure of *M. tuberculosis* in log-phase growth to concentrations of J at 100×MIC resulted in a $10^3$ log reduction in bacterial counts after 12 days, indicating that J has bactericidal activity in vitro. The effect of J on stationary phase tubercle bacilli has not yet been studied.

Isolation of Mutants, Cross-Resistance and Postulated Drug Target

By investigating mycobacterial resistance, we aimed to identify the molecular drug target and propose a mechanism of action. Resistant mutants of *M. tuberculosis* and *M. smegmatis* were derived by in vitro selection at inhibitory concentrations of J, in order to:

quantify the proportion of resistant mutants in mycobacteria (with rifampin as a control)

assess the resistance pattern of resistant mutants (including cross-/non-cross-resistance to quinolones)

investigate the mechanism of action.

From selection experiments, the proportion of mutants with reduced sensitivity to J was $5 \times 10^{-7}$ and $2 \times 10^{-8}$ at MIC× 4, and $5 \times 10^{-8}$ and $1 \times 10^{-8}$ at MIC×8 for *M. tuberculosis* and *M. smegmatis*, respectively (supporting online text). In the case of *M. tuberculosis*, these proportions were comparable to those of mutants resistant to rifampin ($10^{-7}$ to $10^{-8}$) and indicates that naturally-occurring resistance to J is rare. In addition, the sensitivity of the *M. tuberculosis* strains resistant to J remained unchanged to the anti-TB agents isoniazid, rifampin, streptomycin, amikacin, ethambutol and moxifloxacin. Further analysis of *M. tuberculosis* and *M. smegmatis* mutants with a reduced susceptibility to J showed that there were no mutations in the DNA gyrase regions gyrA and gyrB, sequences in which quinolone resistance typically develops. This confirms that the molecular target for J is different from that of the fluoroquinolones.

One approach to determining the molecular target for J and inferring a mechanism of action is to identify and compare resistance-conferring mutations in sensitive and resistant strains of *M. tuberculosis* and *M. smegmatis*. The genomes of the resistant *M. tuberculosis* strain BK12 and the two resistant *M. smegmatis* strains R09 and R10, as well as the parental *M. smegmatis*, were sequenced to near completion. We identified resistance-conferring mutations by comparative analysis of the genome sequences of sensitive and resistant strains of *M. tuberculosis* and *M. smegmatis* (FIG. 2). We showed that the only gene affected in all three independent mutants versus corresponding parental wild-type encodes for atpE, a part of the $F_0$ subunit of ATP synthase. This suggests that atpE is responsible for resistance to J in the mutant strains, indicating that J inhibits a new *M. tuberculosis* target, the proton pump of ATP synthase.

Complementation studies were performed to show that the mutant atpE gene is responsible for resistance to J and by direct inference that the atpE gene product is the target of J in mycobacteria. Given the fact that it is known that all genes of the ATP synthase operon have to be expressed in a coordinated way, i.e. all genes that encode the $F_0$ part have to expressed from the same location, we amplified the $F_0$ part of the operon from the resistant *M. smegmatis* strain (D32V) and selected clones that did not acquire additional mutations through the PCR process. Wild-type *M. smegmatis* was transformed with a plasmid containing the thus selected mutant $F_0$ fragment. This rendered the cells resistant to J with a MIC practically identical to that of the resistant strain *M. smegmatis* R09 (D32V). In addition, when the plasmid was re-isolated from these transformants and the atpE gene was sequenced, it was shown to have remained the mutant allele (D32V).

The actual effect of DARQ J on ATP production in *M. tuberculosis* was further demonstrated by measuring the effect of J on the total cellular ATP present in the mycobacteria using the ATP Bioluminescence Luciferase Assay Kit HS II of Roche. This assay is based on the ATP driven conversion of D-Luciferin to Oxyluciferin that can be measured at 526 nm.

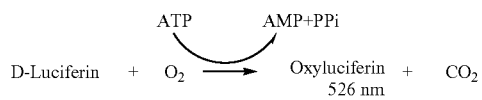

Briefly, the effect of DARQ J on total ATP was tested in both wild type *M. tuberculosis* and the mutant strain. DCCD which is a well known inhibitor of ATP synthase was used as a positive control and isoniazid which is an inhibitor for biosynthesis of certain cell wall components, but has no effect on ATP production, was used as a negative control.

Figure 3:
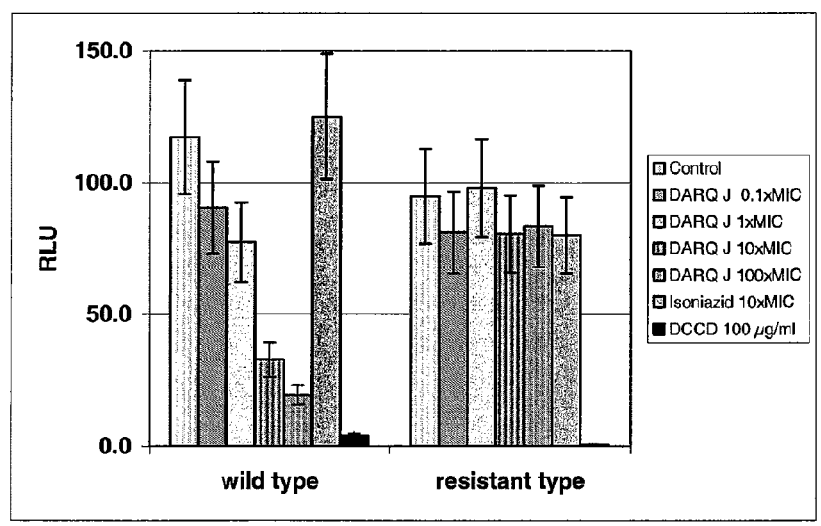
Figure 4:
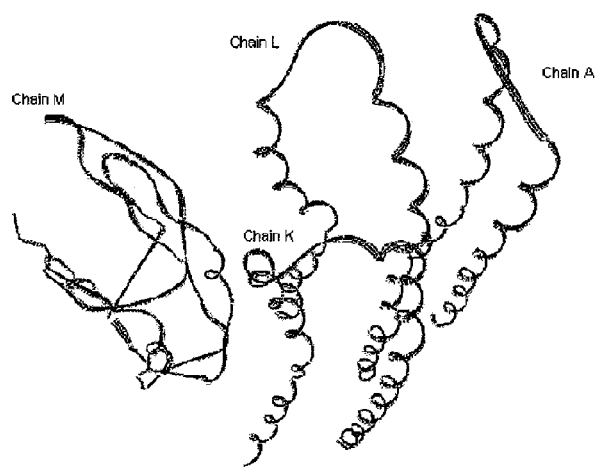

As can be seen in FIG. 3, treatment of the wild type *M. tuberculosis* with DARQ J, leads to dose dependent decrease in ATP production in these bacteria. In contrast isoniazid has no effect on ATP production. As already described hereinbefore, exposing these bacteria to high concentration of the DARQ J raised the diarylquinolines resistant mutants of *M. tuberculosis*. When these resistant *M. tuberculosis* were treated with DARQ J these bacteria did not show any decrease in the ATP production even at 100 times the Minimal Inhibitory Concentration (MIC) of this compound. In contrast DCCD was able to block the ATP production in these bacilli suggesting that DARQ J and DCCD have different binding pockets in ATP synthases.

Computer Modeling and Identification of the DARQ J Binding Region

To further investigate the different mode of action of DCCD and DARQ J, a computer generated 3D model of the ATP synthase for both the wild type and DARQ J mutant *M. tuberculosis* were generated. The atomic coordinates provided in Tables 4 and 5 were computed by preparing a model of the 3D structure of the published amino acid sequences P63691 and AJ865377. The actual DARQ J binding site was found to be located at the contact area of the A and C subunits, more in particular around Amino Acid 'Arg 210' of the A subunit and 'Glu 61' of the C subunit, as referred to in tables 3, 4 or 5. This fits nicely with the results seen for the screening of resistance-conferring mutations in sensitive and resistant strains of *M. tuberculosis* and *M. smegmatis*, described above.

The model is based on optimization of the relative placement of the A- and C helices of the ATPase structure and the orientation of the amino acids back-bone and side-chain towards minimal computed internal strain. The geometry was obtained by means of a number of molecular dynamics simulation cycles and molecular mechanics relaxations starting from previously published general helix geometry of a different organism [E-Coli PDB entry code 1C17—V. K. Rastogi and M. E. Girvin, Nature, 402, 263-268 (1999)]. Molecular dynamics and geometry relaxation were both performed with a forcefield parameterization based on MMFF94s [Halgren, T. A. (1996), J. Comput. Chem., 17, 490-519], but any state of the art molecular dynamics software could be employed [Berendsen, H. J. C., van der Spoel, D. and van Drunen, R., Comp. Phys. Comm. 91 (1995), 43-56; Lindahl, E., Hess, B. and van der Spoel, D., J. Mol. Mod. 7 (2001) 306-317.] followed by a suitable geometry optimization [J. W. Ponder and F. M. Richards, J. Comput. Chem., 8, 1016-1024 (1987)].

The computed coordinates in the tables 3, 4 and 5 comprise the part (with 30 Angstrom radius volume) of the predicted structure of the region considered relevant for inhibition of the MTB ATPase activity in these enzymes, based on the proposed mode of inhibition and on the occurrence of resistance inducing point mutations in biological assays.

DISCUSSION

The DARQ J is a member of a new chemical class of anti-TB agents with an MIC equal to or lower than that of reference compounds. Its spectrum is unique in its specificity to mycobacteria, including atypical species important in humans; MAC, *M. kansasii* and the fast growers *M. fortuitum* and *M. abscessus*. This anti-mycobacterial-specific spectrum differs from that of isoniazid, which has no activity against MAC. The clinical use of J will be highly targeted to the treatment of TB and mycobacterial infections. The inability of J to inhibit non-mycobacteria should translate into less selective pressure and a lower risk of resistance developing in other bacterial species, when compared with antibiotics with broader spectra (9).

The target and mechanism of action of J is different from that of other anti-TB agents. A comparison of the sequences of ATP synthases of different bacteria and of eukaryotic ATP synthase, and in particular of the C chain of the $F_0$ subunit of the ATPase complex, together with the 3D modelling of the ATP synthases of the wild type and mutant *M. tuberculosis*, provides a rationale for the specificity of the antibacterial spectrum and, to a lesser extent, the safety profile.

The dynamics study performed on the constructed Mycobacterium ATPase models show that in these structures a cavity (the binding site according to the atomic coordinates of Table 3) exists on the contact area of the A and C subunits (around Amino Acid 'Arg 210' of the A subunit and 'Glu 61' of the C subunit). The tables 4 and 5 provide the coordinates of two studied variants of the atoms surrounding this site, and their average position. The DARQ J inhibitor is able to interfere with the normal proton transfer step involving these two amino acids by prohibiting these two amino-acids to interact. The stereospecifity of DARQ J can be understood from the asymmetry of the predicted binding site; the active chiral enantiomer accommodates this cavity optimally, other forms of the compound and variants of ATPase are less well matched.

The binding site we have derived here is on an entirely different part of the ATPase system than DCCD (DARQs are in the membrane part of the enzyme, DCCD binding occurs approximately 90 Angstrom away inside the cell; based on the PDB structure of a Bovine ATPase crystal "1E79"—published in C. Gibbons, M. G. Montgomery, A. G. W. Leslie, J. E. Walker, Nat. Struct. Biol., 7,1055 (2000). Therefore the atoms that could potentially be involved with DCCD type inhibition of MTB ATPAse are not in the region listed in the coordinate tables of the binding site (which only just spans the membrane portion of the enzyme) and, reciprocally, this part of the enzyme involved in the DARQ J mode of inhibition is not present in the published "1E79" structure (which only shows the intracellular part). This difference in binding site may explain the different response of *M. tuberculosis* observed in the in vitro ATP production assay.

Notwithstanding the above, older studies with DCCD on mitochondrial ATPases suggest another binding site located around an acidic amino-acid in a lipophyllic environment of the $F_0$ region of the enzyme e.g. by Sebald W, Machleidt W, Wachter E., Proc Natl Acad Sci USA. 1980 February; 77(2): 785-789. This binding position on mitochondrial ATPases can be considered analogous to the one described for the *Mycobacterium* species here.

At the same time, targeting a new mechanism ensures that currently circulating TB strains with resistance mutations to available treatments are not cross-resistant to J. It is obvious from our in vitro studies that J has at least as high anti-bacterial effect against MDR-TB isolates, even against those with a broad four-drug resistance, as against normal wild type pan-susceptible strains of *M. tuberculosis*. This observation is important since it clearly demonstrates that there is no cross-resistance with existing anti-TB drugs. Given the further identification of the binding pocket in the membrane part of the ATPase, the results of this study will allow further development of new anti-bacterial compounds, in particular anti-mycobacterial compounds targeting ATP synthesis in these organisms.

REFERENCES

1. Global Alliance for TB Drug Development, *Developing a faster TB cure* (2004; http://www.tballiance.org).
2. E. L. Corbett et al., *Arch. Intern. Med.* 163, 1009 (2003).
3. UNAIDS, *AIDS epidemic update* 2003 (2003; www.unaids.org/Unaids/EN/Resources).
4. World Health Organization, *Tuberculosis* (2004; http://www.who.int/health topics/tuberculosis/en/).
5. R. J. O'Brien, P. P. Nunn, *Am. J. Respir. Crit. Care Med.* 163, 1055 (2001).
6. World Health Organization, *Tuberculosis Fact Sheet No* 104 (2004; http://www.who.int/mediacentre/factsheets/fs104/en/).
7. A. J. Claxton, J. Cramer, C. Pierce, *Clin. Ther.* 23, 1296 (2001).
8. N. Lounis et al., *Antimicrob. Agents Chemother.* 45, 3482 (2001).
9. A. S. Ginsburg, J. H. Grosset, W. R. Bishai, *Lancet Infect. Dis.* 3, 432 (2003).
10. C. K. Stover et al., *Nature* 405, 962 (2000).
11. Guillemont J, Emile G, Patent (International Publication Number. WO 2004/011436. International Publication Date Feb. 5, 2004).
12. Barbachyn M R, Brickner S J, Patent (International Publication Number: WO 93/09103, International Publication Date: 13 May 1993, International Application Number: PCT/US92/08267, International Filing Date: 1992).
13. R. Jain, B. Vaitilingam, A. Nayyar, P. B. Palde, *Bioorg. Med. Chem. Lett.* 13, 1051 (2003).
14. C. M. Kunin, W. Y. Ellis, *Antimicrob. Agents Chemother.* 44, 848 (2000).
15. L. Savini, L. Chiasserini, A. Gaeta, C. Pellerano, *Bioorg. Med. Chem* 10, 2193 (2002).
16. S. Vangapandu, M. Jain, R. Jain, S. Kaur, P. P. Singh, *Bioorg. Med. Chem.* 12, 2501 (2004).
17. K. Andries et al., *Science* 307, 223 (2005).

TABLE 1

| Mycobacterial species | MIC (μg/ml) Median values |
|---|---|
| *M. tuberculosis*, H37Rv | 0.030 |
| *M. tuberculosis*, fully susceptible clinical isolates, 6 strains | 0.060 |
| *M. tuberculosis* resistant to isoniazid, 8 strains | 0.010 |
| *M. tuberculosis* resistant to rifampin | 0.030 |
| *M. tuberculosis* resistant to isoniazid and rifampin, 2 strains | 0.030 |
| *M. tuberculosis* resistant to isoniazid and streptomycin | 0.010 |
| *M. tuberculosis* resistant to ethambutol | 0.010 |
| *M. tuberculosis* resistant to pyrazinamide | 0.030 |
| *M. tuberculosis* resistant to moxifloxacin, 2 strains | 0.090 |
| *M. bovis* | 0.003 |
| *M. avium* complex, 7 strains | 0.010 |
| *M. kansasii* | 0.003 |
| *M. marinum* | 0.003 |
| *M. fortuitum*, 3 strains | 0.010 |
| *M. fortuitum* resistant to fluoroquinolone, 2 strains | 0.010 |
| *M. abscessus* | 0.250 |
| *M. smegmatis*, 7 strains | 0.007 |

TABLE 2

Sequence P63691 = SEQ ID No.1 = MYCTUB C-subunit, wt
Sequence AJ865377 = SEQ ID No.2 = MYCTUB C-subunit, mutant
Sequence P63654 = SEQ ID No.11 = MYCTUB A-subunit, wt and mutant
Amino acids surrounding the binding site based on the atomic coordinates of Table 3
C-subunit 1 ## - A chain
$Ala^{21}$, $Gly^{25}$
C-subunit 2 ## - K chain
$Ala^{24}$, $Gly^{27}$, $Phe^{53}$, $Phe^{54}$, $Val^{57}$, $Gly^{58}$, $Glu^{61}$, $Tyr^{64}$, $Phe^{65}$
C-subunit 3 ## - L chain
$Met^{17}$, $Gly^{19}$, $Gly^{20}$, $Ala^{21}$, $Ile^{22}$, $Gly^{23}$, $Ala^{24}$, $Gly^{25}$, $Ile^{26}$, $Gly^{27}$, $Asp^{28}$, $Gly^{29}$, $Ala^{31}$, $Phe^{53}$, $Thr^{56}$, $Val^{57}$, $Gly^{58}$, $Leu^{59}$, $Val^{60}$, $Glu^{61}$, $Ala^{62}$, $Ala^{63}$/$Pro^{63}$, $Tyr^{64}$, $Phe^{65}$.
A subunit ## - M chain
$Ser^{182}$, $Leu^{183}$, $Leu^{185}$, $Arg^{186}$ (having the codes Ser 206 - Leu 207 - Leu 209
and Arg 210 in Tables 3)

TABLE 3

| | | | | | | | | | | | |
|---|---|---|---|---|---|---|---|---|---|---|---|
| ATOM | 1 | N | ALA | A | 21 | 6.113 | −13.437 | −0.893 | 1.00 | 0.00 | N |
| ATOM | 2 | CA | ALA | A | 21 | 5.269 | −13.569 | 0.293 | 1.00 | 0.00 | C |
| ATOM | 3 | C | ALA | A | 21 | 3.954 | −12.807 | 0.141 | 1.00 | 0.00 | C |
| ATOM | 4 | O | ALA | A | 21 | 2.885 | −13.379 | 0.316 | 1.00 | 0.00 | O |
| ATOM | 5 | CB | ALA | A | 21 | 5.986 | −13.138 | 1.571 | 1.00 | 0.00 | C |
| ATOM | 6 | N | GLY | A | 25 | −0.067 | −14.118 | −0.399 | 1.00 | 0.00 | N |
| ATOM | 7 | CA | GLY | A | 25 | −1.020 | −13.780 | 0.640 | 1.00 | 0.00 | C |
| ATOM | 8 | C | GLY | A | 25 | −2.283 | −13.168 | 0.073 | 1.00 | 0.00 | C |
| ATOM | 9 | O | GLY | A | 25 | −3.376 | −13.689 | 0.241 | 1.00 | 0.00 | O |
| ATOM | 10 | N | ALA | K | 24 | −1.077 | −5.399 | 11.361 | 1.00 | 0.00 | N |
| ATOM | 11 | CA | ALA | K | 24 | −1.976 | −5.787 | 12.444 | 1.00 | 0.00 | C |
| ATOM | 12 | C | ALA | K | 24 | −3.305 | −5.041 | 12.351 | 1.00 | 0.00 | C |
| ATOM | 13 | O | ALA | K | 24 | −4.356 | −5.642 | 12.491 | 1.00 | 0.00 | O |
| ATOM | 14 | CB | ALA | K | 24 | −1.345 | −5.577 | 13.818 | 1.00 | 0.00 | C |
| ATOM | 15 | N | GLY | K | 27 | −5.452 | −6.238 | 9.570 | 1.00 | 0.00 | N |

TABLE 3-continued

| | | | | | | | | | | |
|---|---|---|---|---|---|---|---|---|---|---|
| ATOM | 16 | CA | GLY | K | 27 | −5.851 | −7.589 | 9.928 | 1.00 | 0.00 | C |
| ATOM | 17 | C | GLY | K | 27 | −7.090 | −7.620 | 10.800 | 1.00 | 0.00 | C |
| ATOM | 18 | O | GLY | K | 27 | −8.059 | −8.290 | 10.473 | 1.00 | 0.00 | O |
| ATOM | 19 | N | PHE | K | 53 | −11.017 | −14.602 | 19.149 | 1.00 | 0.00 | N |
| ATOM | 20 | CA | PHE | K | 53 | −9.784 | −15.282 | 18.770 | 1.00 | 0.00 | C |
| ATOM | 21 | C | PHE | K | 53 | −9.069 | −14.469 | 17.700 | 1.00 | 0.00 | C |
| ATOM | 22 | O | PHE | K | 53 | −7.894 | −14.188 | 17.837 | 1.00 | 0.00 | O |
| ATOM | 23 | CB | PHE | K | 53 | −10.007 | −16.732 | 18.330 | 1.00 | 0.00 | C |
| ATOM | 24 | CG | PHE | K | 53 | −8.712 | −17.498 | 18.270 | 1.00 | 0.00 | C |
| ATOM | 25 | CD1 | PHE | K | 53 | −7.970 | −17.568 | 17.070 | 1.00 | 0.00 | C |
| ATOM | 26 | CD2 | PHE | K | 53 | −8.215 | −18.156 | 19.416 | 1.00 | 0.00 | C |
| ATOM | 27 | CE1 | PHE | K | 53 | −6.755 | −18.266 | 17.025 | 1.00 | 0.00 | C |
| ATOM | 28 | CE2 | PHE | K | 53 | −7.002 | −18.858 | 19.365 | 1.00 | 0.00 | C |
| ATOM | 29 | CZ | PHE | K | 53 | −6.270 | −18.911 | 18.171 | 1.00 | 0.00 | C |
| ATOM | 30 | N | PHE | K | 54 | −9.831 | −14.105 | 16.597 | 1.00 | 0.00 | N |
| ATOM | 31 | CA | PHE | K | 54 | −9.260 | −13.364 | 15.476 | 1.00 | 0.00 | C |
| ATOM | 32 | C | PHE | K | 54 | −8.595 | −12.097 | 15.996 | 1.00 | 0.00 | C |
| ATOM | 33 | O | PHE | K | 54 | −7.423 | −11.868 | 15.755 | 1.00 | 0.00 | O |
| ATOM | 34 | CB | PHE | K | 54 | −10.281 | −12.983 | 14.388 | 1.00 | 0.00 | C |
| ATOM | 35 | CG | PHE | K | 54 | −10.604 | −14.066 | 13.398 | 1.00 | 0.00 | C |
| ATOM | 36 | CD1 | PHE | K | 54 | −9.957 | −14.298 | 12.312 | 1.00 | 0.00 | C |
| ATOM | 37 | CD2 | PHE | K | 54 | −11.580 | −14.820 | 13.486 | 1.00 | 0.00 | C |
| ATOM | 38 | CE1 | PHE | K | 54 | −10.285 | −15.248 | 11.337 | 1.00 | 0.00 | C |
| ATOM | 39 | CE2 | PHE | K | 54 | −11.905 | −15.767 | 12.506 | 1.00 | 0.00 | C |
| ATOM | 40 | CZ | PHE | K | 54 | −11.260 | −15.979 | 11.430 | 1.00 | 0.00 | C |
| ATOM | 41 | N | VAL | K | 57 | −5.533 | −12.244 | 18.563 | 1.00 | 0.00 | N |
| ATOM | 42 | CA | VAL | K | 57 | −4.302 | −12.645 | 17.888 | 1.00 | 0.00 | C |
| ATOM | 43 | C | VAL | K | 57 | −3.748 | −11.428 | 17.142 | 1.00 | 0.00 | C |
| ATOM | 44 | O | VAL | K | 57 | −2.561 | −11.155 | 17.226 | 1.00 | 0.00 | O |
| ATOM | 45 | CB | VAL | K | 57 | −4.472 | −13.892 | 16.988 | 1.00 | 0.00 | C |
| ATOM | 46 | CG1 | VAL | K | 57 | −3.247 | −14.150 | 16.128 | 1.00 | 0.00 | C |
| ATOM | 47 | CG2 | VAL | K | 57 | −4.733 | −15.142 | 17.831 | 1.00 | 0.00 | C |
| ATOM | 48 | N | GLY | K | 58 | −4.660 | −10.700 | 16.389 | 1.00 | 0.00 | N |
| ATOM | 49 | CA | GLY | K | 58 | −4.292 | −9.496 | 15.662 | 1.00 | 0.00 | C |
| ATOM | 50 | C | GLY | K | 58 | −3.574 | −8.479 | 16.534 | 1.00 | 0.00 | C |
| ATOM | 51 | O | GLY | K | 58 | −2.502 | −8.003 | 16.192 | 1.00 | 0.00 | O |
| ATOM | 52 | N | GLU | K | 61 | −0.207 | −9.648 | 18.102 | 1.00 | 0.00 | N |
| ATOM | 53 | CA | GLU | K | 61 | 0.806 | −9.654 | 17.043 | 1.00 | 0.00 | C |
| ATOM | 54 | C | GLU | K | 61 | 1.665 | −8.402 | 17.132 | 1.00 | 0.00 | C |
| ATOM | 55 | O | GLU | K | 61 | 2.877 | −8.491 | 17.077 | 1.00 | 0.00 | O |
| ATOM | 56 | CB | GLU | K | 61 | 0.193 | −9.817 | 15.646 | 1.00 | 0.00 | C |
| ATOM | 57 | CG | GLU | K | 61 | 1.204 | −9.858 | 14.524 | 1.00 | 0.00 | C |
| ATOM | 58 | CD | GLU | K | 61 | 0.555 | −10.023 | 13.178 | 1.00 | 0.00 | C |
| ATOM | 59 | OE1 | GLU | K | 61 | −0.140 | −9.444 | 12.697 | 1.00 | 0.00 | O |
| ATOM | 60 | OE2 | GLU | K | 61 | 0.829 | −10.852 | 12.555 | 1.00 | 0.00 | O |
| ATOM | 61 | N | TYR | K | 64 | 4.232 | −8.387 | 19.897 | 1.00 | 0.00 | N |
| ATOM | 62 | CA | TYR | K | 64 | 5.349 | −9.298 | 19.625 | 1.00 | 0.00 | C |
| ATOM | 63 | C | TYR | K | 64 | 6.441 | −8.615 | 18.816 | 1.00 | 0.00 | C |
| ATOM | 64 | O | TYR | K | 64 | 7.607 | −8.776 | 19.118 | 1.00 | 0.00 | O |
| ATOM | 65 | CB | TYR | K | 64 | 4.964 | −10.610 | 18.922 | 1.00 | 0.00 | C |
| ATOM | 66 | CG | TYR | K | 64 | 4.033 | −11.512 | 19.656 | 1.00 | 0.00 | C |
| ATOM | 67 | CD1 | TYR | K | 64 | 4.038 | −11.638 | 21.058 | 1.00 | 0.00 | C |
| ATOM | 68 | CD2 | TYR | K | 64 | 3.155 | −12.305 | 18.914 | 1.00 | 0.00 | C |
| ATOM | 69 | CE1 | TYR | K | 64 | 3.176 | −12.505 | 21.695 | 1.00 | 0.00 | C |
| ATOM | 70 | CE2 | TYR | K | 64 | 2.306 | −13.187 | 19.542 | 1.00 | 0.00 | C |
| ATOM | 71 | CZ | TYR | K | 64 | 2.318 | −13.274 | 20.937 | 1.00 | 0.00 | C |
| ATOM | 72 | OH | TYR | K | 64 | 1.474 | −14.099 | 21.599 | 1.00 | 0.00 | O |
| ATOM | 73 | N | PHE | K | 65 | 6.031 | −7.871 | 17.720 | 1.00 | 0.00 | N |
| ATOM | 74 | CA | PHE | K | 65 | 6.997 | −7.165 | 16.873 | 1.00 | 0.00 | C |
| ATOM | 75 | C | PHE | K | 65 | 7.762 | −6.104 | 17.631 | 1.00 | 0.00 | C |
| ATOM | 76 | O | PHE | K | 65 | 8.941 | −5.932 | 17.396 | 1.00 | 0.00 | O |
| ATOM | 77 | CB | PHE | K | 65 | 6.392 | −6.543 | 15.630 | 1.00 | 0.00 | C |
| ATOM | 78 | CG | PHE | K | 65 | 5.963 | −7.560 | 14.648 | 1.00 | 0.00 | C |
| ATOM | 79 | CD1 | PHE | K | 65 | 5.824 | −7.882 | 14.293 | 1.00 | 0.00 | C |
| ATOM | 80 | CE1 | PHE | K | 65 | 5.429 | −8.819 | 13.385 | 1.00 | 0.00 | C |
| ATOM | 81 | CZ | PHE | K | 65 | 5.167 | −9.448 | 12.818 | 1.00 | 0.00 | C |
| ATOM | 82 | CE2 | PHE | K | 65 | 5.302 | −9.137 | 13.148 | 1.00 | 0.00 | C |
| ATOM | 83 | CD2 | PHE | K | 65 | 5.697 | −8.196 | 14.053 | 1.00 | 0.00 | C |
| ATOM | 84 | N | MET | L | 17 | 11.107 | −10.632 | 7.686 | 1.00 | 0.00 | N |
| ATOM | 85 | CA | MET | L | 17 | 10.139 | −10.826 | 8.764 | 1.00 | 0.00 | C |
| ATOM | 86 | C | MET | L | 17 | 8.887 | 9.997 | 8.526 | 1.00 | 0.00 | C |
| ATOM | 87 | O | MET | L | 17 | 7.804 | −10.514 | 8.641 | 1.00 | 0.00 | O |
| ATOM | 88 | CB | MET | L | 17 | 10.705 | −10.543 | 10.163 | 1.00 | 0.00 | C |
| ATOM | 89 | CG | MET | L | 17 | 11.688 | −11.601 | 10.657 | 1.00 | 0.00 | C |
| ATOM | 90 | SD | MET | L | 17 | 10.846 | −13.177 | 10.983 | 1.00 | 0.00 | S |
| ATOM | 91 | CE | MET | L | 17 | 11.507 | −14.142 | 9.610 | 1.00 | 0.00 | C |
| ATOM | 92 | N | GLY | L | 19 | 7.665 | −8.503 | 5.731 | 1.00 | 0.00 | N |
| ATOM | 93 | CA | GLY | L | 19 | 6.955 | −8.955 | 4.577 | 1.00 | 0.00 | C |
| ATOM | 94 | C | GLY | L | 19 | 6.222 | −10.215 | 4.817 | 1.00 | 0.00 | C |
| ATOM | 95 | O | GLY | L | 19 | 5.027 | −10.326 | 4.589 | 1.00 | 0.00 | O |

TABLE 3-continued

| ATOM | 96 | N | GLY | L | 20 | 7.028 | −11.189 | 5.274 | 1.00 | 0.00 | N |
|---|---|---|---|---|---|---|---|---|---|---|---|
| ATOM | 97 | CA | GLY | L | 20 | 6.545 | −12.472 | 5.462 | 1.00 | 0.00 | C |
| ATOM | 98 | C | GLY | L | 20 | 5.400 | −12.516 | 6.352 | 1.00 | 0.00 | C |
| ATOM | 99 | O | GLY | L | 20 | 4.328 | −12.921 | 5.962 | 1.00 | 0.00 | O |
| ATOM | 100 | N | ALA | L | 21 | 5.696 | −12.094 | 7.607 | 1.00 | 0.00 | N |
| ATOM | 101 | CA | ALA | L | 21 | 4.773 | −12.247 | 8.668 | 1.00 | 0.00 | C |
| ATOM | 102 | C | ALA | L | 21 | 3.441 | −11.568 | 8.418 | 1.00 | 0.00 | C |
| ATOM | 103 | O | ALA | L | 21 | 2.401 | −12.101 | 8.724 | 1.00 | 0.00 | O |
| ATOM | 104 | CB | ALA | L | 21 | 5.365 | −11.795 | 9.953 | 1.00 | 0.00 | C |
| ATOM | 105 | N | ILE | L | 22 | 3.503 | −10.313 | 7.908 | 1.00 | 0.00 | N |
| ATOM | 106 | CA | ILE | L | 22 | 2.293 | −9.551 | 7.618 | 1.00 | 0.00 | C |
| ATOM | 107 | C | ILE | L | 22 | 1.551 | −10.212 | 6.464 | 1.00 | 0.00 | C |
| ATOM | 108 | O | ILE | L | 22 | 0.349 | −10.406 | 6.550 | 1.00 | 0.00 | O |
| ATOM | 109 | CB | ILE | L | 22 | 2.557 | −8.055 | 7.417 | 1.00 | 0.00 | C |
| ATOM | 110 | CG1 | ILE | L | 22 | 2.757 | −7.350 | 8.740 | 1.00 | 0.00 | C |
| ATOM | 111 | CG2 | ILE | L | 22 | 1.424 | −7.339 | 6.679 | 1.00 | 0.00 | C |
| ATOM | 112 | CD1 | ILE | L | 22 | 3.979 | −7.733 | 9.410 | 1.00 | 0.00 | C |
| ATOM | 113 | N | GLY | L | 23 | 2.307 | −10.532 | 5.345 | 1.00 | 0.00 | N |
| ATOM | 114 | CA | GLY | L | 23 | 1.730 | −11.131 | 4.153 | 1.00 | 0.00 | C |
| ATOM | 115 | C | GLY | L | 23 | 0.953 | −12.395 | 4.473 | 1.00 | 0.00 | C |
| ATOM | 116 | O | GLY | L | 23 | −0.212 | −12.517 | 4.150 | 1.00 | 0.00 | O |
| ATOM | 117 | N | ALA | L | 24 | 1.683 | −13.360 | 5.127 | 1.00 | 0.00 | N |
| ATOM | 118 | CA | ALA | L | 24 | 1.102 | −14.632 | 5.548 | 1.00 | 0.00 | C |
| ATOM | 119 | C | ALA | L | 24 | −0.076 | −14.444 | 6.468 | 1.00 | 0.00 | C |
| ATOM | 120 | O | ALA | L | 24 | −1.054 | −15.158 | 6.348 | 1.00 | 0.00 | O |
| ATOM | 121 | CB | ALA | L | 24 | 2.105 | −15.541 | 6.198 | 1.00 | 0.00 | C |
| ATOM | 122 | N | GLY | L | 25 | 0.067 | −13.469 | 7.438 | 1.00 | 0.00 | N |
| ATOM | 123 | CA | GLY | L | 25 | −0.962 | −13.170 | 8.392 | 1.00 | 0.00 | C |
| ATOM | 124 | C | GLY | L | 25 | −2.268 | −12.811 | 7.747 | 1.00 | 0.00 | C |
| ATOM | 125 | O | GLY | L | 25 | −3.300 | −13.370 | 8.064 | 1.00 | 0.00 | O |
| ATOM | 126 | N | ILE | L | 26 | −2.180 | −11.796 | 6.833 | 1.00 | 0.00 | N |
| ATOM | 127 | CA | ILE | L | 26 | −3.331 | −11.306 | 6.108 | 1.00 | 0.00 | C |
| ATOM | 128 | C | ILE | L | 26 | −3.969 | −12.476 | 5.367 | 1.00 | 0.00 | C |
| ATOM | 129 | O | ILE | L | 26 | −5.165 | −12.691 | 5.457 | 1.00 | 0.00 | O |
| ATOM | 130 | CB | ILE | L | 26 | −2.991 | −10.132 | 5.190 | 1.00 | 0.00 | C |
| ATOM | 131 | CG1 | ILE | L | 26 | −2.576 | −8.894 | 5.997 | 1.00 | 0.00 | C |
| ATOM | 132 | CG2 | ILE | L | 26 | −4.165 | −9.810 | 4.293 | 1.00 | 0.00 | C |
| ATOM | 133 | CD1 | ILE | L | 26 | −1.882 | −7.842 | 5.205 | 1.00 | 0.00 | C |
| ATOM | 134 | N | GLY | L | 27 | −3.109 | −13.215 | 4.602 | 1.00 | 0.00 | N |
| ATOM | 135 | CA | GLY | L | 27 | −3.538 | −14.338 | 3.799 | 1.00 | 0.00 | C |
| ATOM | 136 | C | GLY | L | 27 | −4.376 | −15.318 | 4.569 | 1.00 | 0.00 | C |
| ATOM | 137 | O | GLY | L | 27 | −5.486 | −15.649 | 4.182 | 1.00 | 0.00 | O |
| ATOM | 138 | N | ASP | L | 28 | −3.765 | −15.784 | 5.701 | 1.00 | 0.00 | N |
| ATOM | 139 | CA | ASP | L | 28 | −4.384 | −16.736 | 6.597 | 1.00 | 0.00 | C |
| ATOM | 140 | C | ASP | L | 28 | −5.751 | −16.267 | 7.012 | 1.00 | 0.00 | C |
| ATOM | 141 | O | ASP | L | 28 | −6.700 | −17.036 | 6.990 | 1.00 | 0.00 | O |
| ATOM | 142 | CB | ASP | L | 28 | −3.509 | −17.005 | 7.806 | 1.00 | 0.00 | C |
| ATOM | 143 | CG | ASP | L | 28 | −4.194 | −17.916 | 8.775 | 1.00 | 0.00 | C |
| ATOM | 144 | OD1 | ASP | L | 28 | −4.748 | −17.548 | 9.761 | 1.00 | 0.00 | O |
| ATOM | 145 | OD2 | ASP | L | 28 | −4.162 | −19.199 | 8.388 | 1.00 | 0.00 | O |
| ATOM | 146 | N | GLY | L | 29 | −5.813 | −14.962 | 7.433 | 1.00 | 0.00 | N |
| ATOM | 147 | CA | GLY | L | 29 | −7.031 | −14.368 | 7.892 | 1.00 | 0.00 | C |
| ATOM | 148 | C | GLY | L | 29 | −8.136 | −14.525 | 6.883 | 1.00 | 0.00 | C |
| ATOM | 149 | O | GLY | L | 29 | −9.135 | −15.175 | 7.140 | 1.00 | 0.00 | O |
| ATOM | 150 | N | ALA | L | 31 | −8.315 | −16.031 | 3.866 | 1.00 | 0.00 | N |
| ATOM | 151 | CA | ALA | L | 31 | −8.577 | −17.400 | 3.418 | 1.00 | 0.00 | C |
| ATOM | 152 | C | ALA | L | 31 | −9.439 | −18.145 | 4.436 | 1.00 | 0.00 | C |
| ATOM | 153 | O | ALA | L | 31 | −10.328 | −18.897 | 4.067 | 1.00 | 0.00 | O |
| ATOM | 154 | CB | ALA | L | 31 | −7.301 | −18.191 | 3.147 | 1.00 | 0.00 | C |
| ATOM | 155 | N | PHE | L | 53 | −8.637 | −24.705 | 11.956 | 1.00 | 0.00 | N |
| ATOM | 156 | CA | PHE | L | 53 | −8.164 | −23.333 | 11.852 | 1.00 | 0.00 | C |
| ATOM | 157 | C | PHE | L | 53 | −6.980 | −23.146 | 12.776 | 1.00 | 0.00 | C |
| ATOM | 158 | O | PHE | L | 53 | −5.941 | −22.715 | 12.352 | 1.00 | 0.00 | O |
| ATOM | 159 | CB | PHE | L | 53 | −9.246 | −22.283 | 12.113 | 1.00 | 0.00 | C |
| ATOM | 160 | CG | PHE | L | 53 | −8.740 | −20.882 | 11.934 | 1.00 | 0.00 | C |
| ATOM | 161 | CD1 | PHE | L | 53 | −8.446 | −20.390 | 10.644 | 1.00 | 0.00 | C |
| ATOM | 162 | CD2 | PHE | L | 53 | −8.535 | −20.038 | 13.053 | 1.00 | 0.00 | C |
| ATOM | 163 | CE1 | PHE | L | 53 | −7.950 | −19.094 | 10.483 | 1.00 | 0.00 | C |
| ATOM | 164 | CE2 | PHE | L | 53 | −8.049 | −18.738 | 12.885 | 1.00 | 0.00 | C |
| ATOM | 165 | CZ | PHE | L | 53 | −7.751 | −18.269 | 11.601 | 1.00 | 0.00 | C |
| ATOM | 166 | N | THR | L | 56 | −3.737 | −24.941 | 11.832 | 1.00 | 0.00 | N |
| ATOM | 167 | CA | THR | L | 56 | −3.150 | −24.514 | 10.589 | 1.00 | 0.00 | C |
| ATOM | 168 | C | THR | L | 56 | −2.483 | −23.143 | 10.682 | 1.00 | 0.00 | C |
| ATOM | 169 | O | THR | L | 56 | −1.599 | −22.885 | 9.907 | 1.00 | 0.00 | O |
| ATOM | 170 | CB | THR | L | 56 | −4.089 | −24.659 | 9.379 | 1.00 | 0.00 | C |
| ATOM | 171 | OG1 | THR | L | 56 | −3.330 | −24.836 | 8.196 | 1.00 | 0.00 | O |
| ATOM | 172 | CG2 | THR | L | 56 | −5.044 | −23.506 | 9.164 | 1.00 | 0.00 | C |
| ATOM | 173 | N | VAL | L | 57 | −2.942 | −22.245 | 11.635 | 1.00 | 0.00 | N |
| ATOM | 174 | CA | VAL | L | 57 | −2.286 | −20.945 | 11.854 | 1.00 | 0.00 | C |
| ATOM | 175 | C | VAL | L | 57 | −0.799 | −21.212 | 12.078 | 1.00 | 0.00 | C |

TABLE 3-continued

| | | | | | | | | | | |
|---|---|---|---|---|---|---|---|---|---|---|
| ATOM | 176 | O | VAL | L | 57 | 0.047 | −20.684 | 11.375 | 1.00 | 0.00 | O |
| ATOM | 177 | CB | VAL | L | 57 | −2.896 | −20.104 | 13.004 | 1.00 | 0.00 | C |
| ATOM | 178 | CG1 | VAL | L | 57 | −2.085 | −18.841 | 13.259 | 1.00 | 0.00 | C |
| ATOM | 179 | CG2 | VAL | L | 57 | −4.335 | −19.696 | 12.714 | 1.00 | 0.00 | C |
| ATOM | 180 | N | GLY | L | 58 | −0.521 | −22.078 | 13.113 | 1.00 | 0.00 | N |
| ATOM | 181 | CA | GLY | L | 58 | 0.822 | −22.415 | 13.487 | 1.00 | 0.00 | C |
| ATOM | 182 | C | GLY | L | 58 | 1.623 | −22.917 | 12.328 | 1.00 | 0.00 | C |
| ATOM | 183 | O | GLY | L | 58 | 2.718 | −22.438 | 12.075 | 1.00 | 0.00 | O |
| ATOM | 184 | N | LEU | L | 59 | 1.030 | −23.955 | 11.641 | 1.00 | 0.00 | N |
| ATOM | 185 | CA | LEU | L | 59 | 1.708 | −24.654 | 10.580 | 1.00 | 0.00 | C |
| ATOM | 186 | C | LEU | L | 59 | 2.185 | −23.705 | 9.498 | 1.00 | 0.00 | C |
| ATOM | 187 | O | LEU | L | 59 | 3.300 | −23.786 | 9.049 | 1.00 | 0.00 | O |
| ATOM | 188 | CB | LEU | L | 59 | 0.855 | −25.774 | 9.958 | 1.00 | 0.00 | C |
| ATOM | 189 | CG | LEU | L | 59 | 0.528 | −26.940 | 10.883 | 1.00 | 0.00 | C |
| ATOM | 190 | CD1 | LEU | L | 59 | −0.499 | −27.867 | 10.248 | 1.00 | 0.00 | C |
| ATOM | 191 | CD2 | LEU | L | 59 | 1.757 | −27.717 | 11.236 | 1.00 | 0.00 | C |
| ATOM | 192 | N | VAL | L | 60 | 1.263 | −22.821 | 9.044 | 1.00 | 0.00 | N |
| ATOM | 193 | CA | VAL | L | 60 | 1.554 | −21.906 | 7.967 | 1.00 | 0.00 | C |
| ATOM | 194 | C | VAL | L | 60 | 2.691 | −20.965 | 8.356 | 1.00 | 0.00 | C |
| ATOM | 195 | O | VAL | L | 60 | 3.626 | −20.759 | 7.642 | 1.00 | 0.00 | O |
| ATOM | 196 | CB | VAL | L | 60 | 0.309 | −21.177 | 7.501 | 1.00 | 0.00 | C |
| ATOM | 197 | CG1 | VAL | L | 60 | 0.647 | −20.048 | 6.567 | 1.00 | 0.00 | C |
| ATOM | 198 | CG2 | VAL | L | 60 | −0.657 | −22.127 | 6.817 | 1.00 | 0.00 | C |
| ATOM | 199 | N | GLU | L | 61 | 2.551 | −20.346 | 9.512 | 1.00 | 0.00 | N |
| ATOM | 200 | CA | GLU | L | 61 | 3.536 | −19.393 | 9.934 | 1.00 | 0.00 | C |
| ATOM | 201 | C | GLU | L | 61 | 4.879 | −19.960 | 10.193 | 1.00 | 0.00 | C |
| ATOM | 202 | O | GLU | L | 61 | 5.880 | −19.269 | 10.118 | 1.00 | 0.00 | O |
| ATOM | 203 | CB | GLU | L | 61 | 3.063 | −18.660 | 11.104 | 1.00 | 0.00 | C |
| ATOM | 204 | CG | GLU | L | 61 | 1.925 | −17.819 | 10.799 | 1.00 | 0.00 | C |
| ATOM | 205 | CD | GLU | L | 61 | 1.586 | −17.006 | 11.921 | 1.00 | 0.00 | C |
| ATOM | 206 | OE1 | GLU | L | 61 | 0.975 | −17.516 | 12.864 | 1.00 | 0.00 | O |
| ATOM | 207 | OE2 | GLU | L | 61 | 1.964 | −15.931 | 11.778 | 1.00 | 0.00 | O |
| ATOM | 208 | N | ALA | L | 62 | 4.882 | −21.261 | 10.545 | 1.00 | 0.00 | N |
| ATOM | 209 | CA | ALA | L | 62 | 6.084 | −21.956 | 10.944 | 1.00 | 0.00 | C |
| ATOM | 210 | C | ALA | L | 62 | 7.286 | −21.785 | 10.048 | 1.00 | 0.00 | C |
| ATOM | 211 | O | ALA | L | 62 | 8.377 | −21.630 | 10.538 | 1.00 | 0.00 | O |
| ATOM | 212 | CB | ALA | L | 62 | 5.859 | −23.400 | 11.174 | 1.00 | 0.00 | C |
| ATOM | 213 | N | ALA | L | 63 | 7.092 | −21.848 | 8.706 | 1.00 | 0.00 | N |
| ATOM | 214 | CA | ALA | L | 63 | 8.178 | −21.680 | 7.793 | 1.00 | 0.00 | C |
| ATOM | 215 | C | ALA | L | 63 | 8.991 | −20.466 | 8.068 | 1.00 | 0.00 | C |
| ATOM | 216 | O | ALA | L | 63 | 10.208 | −20.527 | 8.043 | 1.00 | 0.00 | O |
| ATOM | 217 | CB | ALA | L | 63 | 7.615 | −21.644 | 6.413 | 1.00 | 0.00 | C |
| ATOM | 218 | N | TYR | L | 64 | 8.259 | −19.325 | 8.307 | 1.00 | 0.00 | N |
| ATOM | 219 | CA | TYR | L | 64 | 8.890 | −18.068 | 8.550 | 1.00 | 0.00 | C |
| ATOM | 220 | C | TYR | L | 64 | 9.659 | −18.103 | 9.830 | 1.00 | 0.00 | C |
| ATOM | 221 | O | TYR | L | 64 | 10.715 | −17.566 | 9.914 | 1.00 | 0.00 | O |
| ATOM | 222 | CB | TYR | L | 64 | 7.922 | −16.871 | 8.520 | 1.00 | 0.00 | C |
| ATOM | 223 | CG | TYR | L | 64 | 7.295 | −16.694 | 7.184 | 1.00 | 0.00 | C |
| ATOM | 224 | CD1 | TYR | L | 64 | 8.019 | −16.167 | 6.135 | 1.00 | 0.00 | C |
| ATOM | 225 | CD2 | TYR | L | 64 | 5.990 | −17.079 | 6.950 | 1.00 | 0.00 | C |
| ATOM | 226 | CE1 | TYR | L | 64 | 7.462 | −16.049 | 4.875 | 1.00 | 0.00 | C |
| ATOM | 227 | CE2 | TYR | L | 64 | 5.429 | −16.966 | 5.693 | 1.00 | 0.00 | C |
| ATOM | 228 | CZ | TYR | L | 64 | 6.164 | −16.453 | 4.661 | 1.00 | 0.00 | C |
| ATOM | 229 | OH | TYR | L | 64 | 5.574 | −16.357 | 3.438 | 1.00 | 0.00 | O |
| ATOM | 230 | N | PHE | L | 65 | 9.081 | −18.740 | 10.861 | 1.00 | 0.00 | N |
| ATOM | 231 | CA | PHE | L | 65 | 9.781 | −18.948 | 12.083 | 1.00 | 0.00 | C |
| ATOM | 232 | C | PHE | L | 65 | 11.125 | −19.657 | 11.874 | 1.00 | 0.00 | C |
| ATOM | 233 | O | PHE | L | 65 | 12.121 | −19.278 | 12.457 | 1.00 | 0.00 | O |
| ATOM | 234 | CB | PHE | L | 65 | 8.919 | −19.603 | 13.097 | 1.00 | 0.00 | C |
| ATOM | 235 | CG | PHE | L | 65 | 9.632 | −20.022 | 14.089 | 1.00 | 0.00 | C |
| ATOM | 236 | CD1 | PHE | L | 65 | 10.118 | −19.245 | 14.878 | 1.00 | 0.00 | C |
| ATOM | 237 | CE1 | PHE | L | 65 | 10.820 | −19.640 | 15.762 | 1.00 | 0.00 | C |
| ATOM | 238 | CZ | PHE | L | 65 | 11.035 | −20.813 | 15.882 | 1.00 | 0.00 | C |
| ATOM | 239 | CE2 | PHE | L | 65 | 10.543 | −21.593 | 15.120 | 1.00 | 0.00 | C |
| ATOM | 240 | CD2 | PHE | L | 65 | 9.847 | −21.203 | 14.227 | 1.00 | 0.00 | C |
| ATOM | 241 | N | SER | M | 206 | −1.016 | −25.619 | 19.505 | 1.00 | 0.00 | N |
| ATOM | 242 | CA | SER | M | 206 | −0.838 | −24.486 | 18.597 | 1.00 | 0.00 | C |
| ATOM | 243 | C | SER | M | 206 | −0.012 | −23.382 | 19.267 | 1.00 | 0.00 | C |
| ATOM | 244 | O | SER | M | 206 | 0.971 | −22.911 | 18.713 | 1.00 | 0.00 | O |
| ATOM | 245 | CB | SER | M | 206 | −2.188 | −23.963 | 18.088 | 1.00 | 0.00 | C |
| ATOM | 246 | OG | SER | M | 206 | −1.997 | −22.980 | 17.074 | 1.00 | 0.00 | O |
| ATOM | 247 | N | LEU | M | 207 | −0.489 | −22.952 | 20.499 | 1.00 | 0.00 | N |
| ATOM | 248 | CA | LEU | M | 207 | 0.102 | −21.823 | 21.215 | 1.00 | 0.00 | C |
| ATOM | 249 | C | LEU | M | 207 | 1.546 | −22.138 | 21.608 | 1.00 | 0.00 | C |
| ATOM | 250 | O | LEU | M | 207 | 2.423 | −21.302 | 21.441 | 1.00 | 0.00 | O |
| ATOM | 251 | CB | LEU | M | 207 | −0.714 | −21.400 | 22.455 | 1.00 | 0.00 | C |
| ATOM | 252 | CG | LEU | M | 207 | −1.865 | −20.400 | 22.201 | 1.00 | 0.00 | C |
| ATOM | 253 | CD1 | LEU | M | 207 | −1.340 | −19.000 | 21.895 | 1.00 | 0.00 | C |
| ATOM | 254 | CD2 | LEU | M | 207 | −2.853 | −20.839 | 21.125 | 1.00 | 0.00 | C |
| ATOM | 255 | N | LEU | M | 209 | 3.807 | −24.006 | 20.342 | 1.00 | 0.00 | N |

TABLE 3-continued

| ATOM | 256 | CA  | LEU | M | 209 | 4.747  | −24.049 | 19.229 | 1.00 | 0.00 | C |
| ATOM | 257 | C   | LEU | M | 209 | 5.571  | −22.762 | 19.135 | 1.00 | 0.00 | C |
| ATOM | 258 | O   | LEU | M | 209 | 6.785  | −22.821 | 18.999 | 1.00 | 0.00 | O |
| ATOM | 259 | CB  | LEU | M | 209 | 4.036  | −24.368 | 17.902 | 1.00 | 0.00 | C |
| ATOM | 260 | CG  | LEU | M | 209 | 4.958  | −24.569 | 16.686 | 1.00 | 0.00 | C |
| ATOM | 261 | CD1 | LEU | M | 209 | 5.927  | −25.732 | 16.873 | 1.00 | 0.00 | C |
| ATOM | 262 | CD2 | LEU | M | 209 | 4.109  | −24.811 | 15.444 | 1.00 | 0.00 | C |
| ATOM | 263 | N   | ARG | M | 210 | 4.854  | −21.566 | 19.167 | 1.00 | 0.00 | N |
| ATOM | 264 | CA  | ARG | M | 210 | 5.530  | −20.289 | 18.933 | 1.00 | 0.00 | C |
| ATOM | 265 | C   | ARG | M | 210 | 6.635  | −20.028 | 19.961 | 1.00 | 0.00 | C |
| ATOM | 266 | O   | ARG | M | 210 | 7.735  | −19.631 | 19.601 | 1.00 | 0.00 | O |
| ATOM | 267 | CB  | ARG | M | 210 | 4.594  | −19.094 | 18.716 | 1.00 | 0.00 | C |
| ATOM | 268 | CG  | ARG | M | 210 | 4.089  | −18.365 | 19.945 | 1.00 | 0.00 | C |
| ATOM | 269 | CD  | ARG | M | 210 | 2.763  | −18.019 | 20.020 | 1.00 | 0.00 | C |
| ATOM | 270 | NE  | ARG | M | 210 | 2.404  | −17.153 | 21.107 | 1.00 | 0.00 | N |
| ATOM | 271 | CZ  | ARG | M | 210 | 2.203  | −17.389 | 22.361 | 1.00 | 0.00 | C |
| ATOM | 272 | NH1 | ARG | M | 210 | 2.199  | −18.501 | 22.785 | 1.00 | 0.00 | N |
| ATOM | 273 | NH2 | ARG | M | 210 | 1.994  | −16.479 | 23.278 | 1.00 | 0.00 | N |

TABLE 4

| ATOM | 1  | N   | ALA | A | 21 | 6.345  | −14.031 | −0.384 | 1.00 | 0.00 | N |
| ATOM | 2  | CA  | ALA | A | 21 | 5.507  | −14.175 | 0.805  | 1.00 | 0.00 | C |
| ATOM | 3  | C   | ALA | A | 21 | 4.183  | −13.425 | 0.676  | 1.00 | 0.00 | C |
| ATOM | 4  | O   | ALA | A | 21 | 3.126  | −14.005 | 0.893  | 1.00 | 0.00 | O |
| ATOM | 5  | CB  | ALA | A | 21 | 6.228  | −13.751 | 2.081  | 1.00 | 0.00 | C |
| ATOM | 6  | N   | ILE | A | 22 | 4.282  | −12.074 | 0.350  | 1.00 | 0.00 | N |
| ATOM | 7  | CA  | ILE | A | 22 | 3.090  | −11.221 | 0.235  | 1.00 | 0.00 | C |
| ATOM | 8  | C   | ILE | A | 22 | 2.159  | −11.728 | −0.869 | 1.00 | 0.00 | C |
| ATOM | 9  | O   | ILE | A | 22 | 0.946  | −11.670 | −0.719 | 1.00 | 0.00 | O |
| ATOM | 10 | CB  | ILE | A | 22 | 3.362  | −9.687  | 0.133  | 1.00 | 0.00 | C |
| ATOM | 11 | CG1 | ILE | A | 22 | 4.114  | −9.223  | −1.134 | 1.00 | 0.00 | C |
| ATOM | 12 | CG2 | ILE | A | 22 | 4.108  | −9.189  | 1.374  | 1.00 | 0.00 | C |
| ATOM | 13 | CD1 | ILE | A | 22 | 3.187  | −8.776  | −2.254 | 1.00 | 0.00 | C |
| ATOM | 14 | N   | GLY | A | 23 | 2.782  | −12.213 | −2.016 | 1.00 | 0.00 | N |
| ATOM | 15 | CA  | GLY | A | 23 | 2.049  | −12.734 | −3.156 | 1.00 | 0.00 | C |
| ATOM | 16 | C   | GLY | A | 23 | 1.095  | −13.831 | −2.732 | 1.00 | 0.00 | C |
| ATOM | 17 | O   | GLY | A | 23 | −0.107 | −13.720 | −2.928 | 1.00 | 0.00 | O |
| ATOM | 18 | N   | ALA | A | 24 | 1.708  | −14.925 | −2.131 | 1.00 | 0.00 | N |
| ATOM | 19 | CA  | ALA | A | 24 | 0.944  | −16.088 | −1.682 | 1.00 | 0.00 | C |
| ATOM | 20 | C   | ALA | A | 24 | −0.144 | −15.660 | −0.712 | 1.00 | 0.00 | C |
| ATOM | 21 | O   | ALA | A | 24 | −1.298 | −16.015 | −0.897 | 1.00 | 0.00 | O |
| ATOM | 22 | CB  | ALA | A | 24 | 1.797  | −17.177 | −1.039 | 1.00 | 0.00 | C |
| ATOM | 23 | N   | GLY | A | 25 | 0.280  | −14.904 | 0.373  | 1.00 | 0.00 | N |
| ATOM | 24 | CA  | GLY | A | 25 | −0.589 | −14.587 | 1.491  | 1.00 | 0.00 | C |
| ATOM | 25 | C   | GLY | A | 25 | −1.877 | −13.947 | 1.018  | 1.00 | 0.00 | C |
| ATOM | 26 | O   | GLY | A | 25 | −2.953 | −14.520 | 1.129  | 1.00 | 0.00 | O |
| ATOM | 27 | N   | ILE | A | 26 | −1.699 | −12.685 | 0.473  | 1.00 | 0.00 | N |
| ATOM | 28 | CA  | ILE | A | 26 | −2.827 | −11.831 | 0.104  | 1.00 | 0.00 | C |
| ATOM | 29 | C   | ILE | A | 26 | −3.654 | −12.542 | −0.969 | 1.00 | 0.00 | C |
| ATOM | 30 | O   | ILE | A | 26 | −4.871 | −12.600 | −0.857 | 1.00 | 0.00 | O |
| ATOM | 31 | CB  | ILE | A | 26 | −2.401 | −10.397 | −0.323 | 1.00 | 0.00 | C |
| ATOM | 32 | CG1 | ILE | A | 26 | −1.597 | −9.649  | 0.770  | 1.00 | 0.00 | C |
| ATOM | 33 | CG2 | ILE | A | 26 | −3.603 | −9.553  | −0.763 | 1.00 | 0.00 | C |
| ATOM | 34 | CD1 | ILE | A | 26 | −2.318 | −9.454  | 2.099  | 1.00 | 0.00 | C |
| ATOM | 35 | N   | GLY | A | 27 | −2.942 | −13.062 | −2.046 | 1.00 | 0.00 | N |
| ATOM | 36 | CA  | GLY | A | 27 | −3.584 | −13.678 | −3.199 | 1.00 | 0.00 | C |
| ATOM | 37 | C   | GLY | A | 27 | −4.550 | −14.779 | −2.803 | 1.00 | 0.00 | C |
| ATOM | 38 | O   | GLY | A | 27 | −5.716 | −14.754 | −3.175 | 1.00 | 0.00 | O |
| ATOM | 39 | N   | ASP | A | 28 | −3.985 | −15.780 | −2.024 | 1.00 | 0.00 | N |
| ATOM | 40 | CA  | ASP | A | 28 | −4.732 | −16.946 | −1.539 | 1.00 | 0.00 | C |
| ATOM | 41 | C   | ASP | A | 28 | −5.998 | −16.489 | −0.825 | 1.00 | 0.00 | C |
| ATOM | 42 | O   | ASP | A | 28 | −7.077 | −17.007 | −1.083 | 1.00 | 0.00 | O |
| ATOM | 43 | CB  | ASP | A | 28 | −3.917 | −17.846 | −0.588 | 1.00 | 0.00 | C |
| ATOM | 44 | CG  | ASP | A | 28 | −2.860 | −18.655 | −1.307 | 1.00 | 0.00 | C |
| ATOM | 45 | OD1 | ASP | A | 28 | −2.422 | −18.431 | −2.426 | 1.00 | 0.00 | O |
| ATOM | 46 | OD2 | ASP | A | 28 | −2.415 | −19.668 | 0.523  | 1.00 | 0.00 | O |
| ATOM | 47 | N   | GLY | A | 29 | −5.802 | −15.500 | 0.131  | 1.00 | 0.00 | N |
| ATOM | 48 | CA  | GLY | A | 29 | −6.869 | −14.977 | 0.960  | 1.00 | 0.00 | C |
| ATOM | 49 | C   | GLY | A | 29 | −8.039 | −14.505 | 0.122  | 1.00 | 0.00 | C |
| ATOM | 50 | O   | GLY | A | 29 | −9.123 | −15.072 | 0.181  | 1.00 | 0.00 | O |
| ATOM | 51 | N   | LEU | A | 59 | 0.538  | −20.546 | −3.576 | 1.00 | 0.00 | N |
| ATOM | 52 | CA  | LEU | A | 59 | 1.616  | −21.013 | −2.702 | 1.00 | 0.00 | C |
| ATOM | 53 | C   | LEU | A | 59 | 2.837  | −21.443 | −3.522 | 1.00 | 0.00 | C |
| ATOM | 54 | O   | LEU | A | 59 | 3.955  | −21.055 | −3.213 | 1.00 | 0.00 | O |
| ATOM | 55 | CB  | LEU | A | 59 | 1.142  | −22.138 | −1.760 | 1.00 | 0.00 | C |
| ATOM | 56 | CG  | LEU | A | 59 | 2.189  | −22.609 | −0.730 | 1.00 | 0.00 | C |

TABLE 4-continued

| | | | | | | | | | | |
|---|---|---|---|---|---|---|---|---|---|---|
| ATOM | 57 | CD1 | LEU | A | 59 | 2.569 | −21.503 | 0.256 | 1.00 | 0.00 | C |
| ATOM | 58 | CD2 | LEU | A | 59 | 1.650 | −23.816 | 0.035 | 1.00 | 0.00 | C |
| ATOM | 59 | N | ILE | K | 16 | 10.658 | −2.962 | 11.070 | 1.00 | 0.00 | N |
| ATOM | 60 | CA | ILE | K | 16 | 9.857 | −4.034 | 11.671 | 1.00 | 0.00 | C |
| ATOM | 61 | C | ILE | K | 16 | 8.610 | −3.416 | 12.307 | 1.00 | 0.00 | C |
| ATOM | 62 | O | ILE | K | 16 | 7.498 | −3.841 | 12.023 | 1.00 | 0.00 | O |
| ATOM | 63 | CB | ILE | K | 16 | 10.670 | −4.907 | 12.676 | 1.00 | 0.00 | C |
| ATOM | 64 | CG1 | ILE | K | 16 | 11.731 | −5.750 | 11.933 | 1.00 | 0.00 | C |
| ATOM | 65 | CG2 | ILE | K | 16 | 9.763 | −5.838 | 13.492 | 1.00 | 0.00 | C |
| ATOM | 66 | CD1 | ILE | K | 16 | 12.834 | −6.259 | 12.850 | 1.00 | 0.00 | C |
| ATOM | 67 | N | GLY | K | 19 | 6.052 | −1.275 | 9.802 | 1.00 | 0.00 | N |
| ATOM | 68 | CA | GLY | K | 19 | 5.350 | −2.226 | 8.953 | 1.00 | 0.00 | C |
| ATOM | 69 | C | GLY | K | 19 | 4.316 | −2.998 | 9.750 | 1.00 | 0.00 | C |
| ATOM | 70 | O | GLY | K | 19 | 3.177 | −3.154 | 9.331 | 1.00 | 0.00 | O |
| ATOM | 71 | N | GLY | K | 20 | 4.790 | −3.509 | 10.947 | 1.00 | 0.00 | N |
| ATOM | 72 | CA | GLY | K | 20 | 3.964 | −4.243 | 11.882 | 1.00 | 0.00 | C |
| ATOM | 73 | C | GLY | K | 20 | 2.664 | −3.538 | 12.201 | 1.00 | 0.00 | C |
| ATOM | 74 | O | GLY | K | 20 | 1.605 | −4.149 | 12.169 | 1.00 | 0.00 | O |
| ATOM | 75 | N | ALA | K | 21 | 2.805 | −2.207 | 12.561 | 1.00 | 0.00 | N |
| ATOM | 76 | CA | ALA | K | 21 | 1.688 | −1.384 | 13.006 | 1.00 | 0.00 | C |
| ATOM | 77 | C | ALA | K | 21 | 0.546 | −1.397 | 12.001 | 1.00 | 0.00 | C |
| ATOM | 78 | O | ALA | K | 21 | −0.586 | −1.697 | 12.356 | 1.00 | 0.00 | O |
| ATOM | 79 | CB | ALA | K | 21 | 2.108 | 0.053 | 13.297 | 1.00 | 0.00 | C |
| ATOM | 80 | N | ILE | K | 22 | 0.886 | −1.005 | 10.709 | 1.00 | 0.00 | N |
| ATOM | 81 | CA | ILE | K | 22 | −0.140 | −0.867 | 9.671 | 1.00 | 0.00 | C |
| ATOM | 82 | C | ILE | K | 22 | −0.799 | −2.219 | 9.390 | 1.00 | 0.00 | C |
| ATOM | 83 | O | ILE | K | 22 | −2.005 | −2.285 | 9.195 | 1.00 | 0.00 | O |
| ATOM | 84 | CB | ILE | K | 22 | 0.297 | −0.092 | 8.393 | 1.00 | 0.00 | C |
| ATOM | 85 | CG1 | ILE | K | 22 | 1.377 | −0.768 | 7.521 | 1.00 | 0.00 | C |
| ATOM | 86 | CG2 | ILE | K | 22 | 0.768 | 1.314 | 8.779 | 1.00 | 0.00 | C |
| ATOM | 87 | CD1 | ILE | K | 22 | 0.806 | −1.667 | 6.434 | 1.00 | 0.00 | C |
| ATOM | 88 | N | GLY | K | 23 | 0.053 | −3.318 | 9.365 | 1.00 | 0.00 | N |
| ATOM | 89 | CA | GLY | K | 23 | −0.419 | −4.668 | 9.113 | 1.00 | 0.00 | C |
| ATOM | 90 | C | GLY | K | 23 | −1.487 | −5.090 | 10.101 | 1.00 | 0.00 | C |
| ATOM | 91 | O | GLY | K | 23 | −2.565 | −5.521 | 9.715 | 1.00 | 0.00 | O |
| ATOM | 92 | N | ALA | K | 24 | −1.109 | −4.970 | 11.431 | 1.00 | 0.00 | N |
| ATOM | 93 | CA | ALA | K | 24 | −1.982 | −5.345 | 12.540 | 1.00 | 0.00 | C |
| ATOM | 94 | C | ALA | K | 24 | −3.312 | −4.596 | 12.475 | 1.00 | 0.00 | C |
| ATOM | 95 | O | ALA | K | 24 | −4.357 | −5.184 | 12.715 | 1.00 | 0.00 | O |
| ATOM | 96 | CB | ALA | K | 24 | −1.317 | −5.133 | 13.898 | 1.00 | 0.00 | C |
| ATOM | 97 | N | GLY | K | 25 | −3.230 | −3.244 | 12.158 | 1.00 | 0.00 | N |
| ATOM | 98 | CA | GLY | K | 25 | −4.396 | −2.382 | 12.036 | 1.00 | 0.00 | C |
| ATOM | 99 | C | GLY | K | 25 | −5.442 | −2.961 | 11.101 | 1.00 | 0.00 | C |
| ATOM | 100 | O | GLY | K | 25 | −6.598 | −3.122 | 11.474 | 1.00 | 0.00 | O |
| ATOM | 101 | N | ILE | K | 26 | −4.967 | −3.257 | 9.828 | 1.00 | 0.00 | N |
| ATOM | 102 | CA | ILE | K | 26 | −5.823 | −3.841 | 8.789 | 1.00 | 0.00 | C |
| ATOM | 103 | C | ILE | K | 26 | −6.427 | −5.132 | 9.343 | 1.00 | 0.00 | C |
| ATOM | 104 | O | ILE | K | 26 | −7.637 | −5.300 | 9.305 | 1.00 | 0.00 | O |
| ATOM | 105 | CB | ILE | K | 26 | −5.098 | −4.071 | 7.428 | 1.00 | 0.00 | C |
| ATOM | 106 | CG1 | ILE | K | 26 | −4.568 | −2.767 | 6.788 | 1.00 | 0.00 | C |
| ATOM | 107 | CG2 | ILE | K | 26 | −5.980 | −4.825 | 6.426 | 1.00 | 0.00 | C |
| ATOM | 108 | CD1 | ILE | K | 26 | −5.622 | −1.714 | 6.477 | 1.00 | 0.00 | C |
| ATOM | 109 | N | GLY | K | 27 | −5.515 | −6.056 | 9.844 | 1.00 | 0.00 | N |
| ATOM | 110 | CA | GLY | K | 27 | −5.880 | −7.396 | 10.278 | 1.00 | 0.00 | C |
| ATOM | 111 | C | GLY | K | 27 | −7.077 | 7.409 | 11.210 | 1.00 | 0.00 | C |
| ATOM | 112 | O | GLY | K | 27 | −8.057 | −8.096 | 10.950 | 1.00 | 0.00 | O |
| ATOM | 113 | N | ASP | K | 28 | −6.936 | 6.610 | 12.341 | 1.00 | 0.00 | N |
| ATOM | 114 | CA | ASP | K | 28 | −7.969 | −6.501 | 13.377 | 1.00 | 0.00 | C |
| ATOM | 115 | C | ASP | K | 28 | −9.319 | −6.221 | 12.728 | 1.00 | 0.00 | C |
| ATOM | 116 | O | ASP | K | 28 | −10.281 | −6.940 | 12.967 | 1.00 | 0.00 | O |
| ATOM | 117 | CB | ASP | K | 28 | −7.684 | −5.409 | 14.428 | 1.00 | 0.00 | C |
| ATOM | 118 | CG | ASP | K | 28 | −6.719 | −5.887 | 15.482 | 1.00 | 0.00 | C |
| ATOM | 119 | OD1 | ASP | K | 28 | −5.501 | −5.869 | 15.384 | 1.00 | 0.00 | O |
| ATOM | 120 | OD2 | ASP | K | 28 | −7.384 | −6.394 | 16.550 | 1.00 | 0.00 | O |
| ATOM | 121 | N | GLY | K | 29 | −9.348 | −5.102 | 11.901 | 1.00 | 0.00 | N |
| ATOM | 122 | CA | GLY | K | 29 | −10.569 | −4.615 | 11.289 | 1.00 | 0.00 | C |
| ATOM | 123 | C | GLY | K | 29 | −11.212 | −5.698 | 10.448 | 1.00 | 0.00 | C |
| ATOM | 124 | O | GLY | K | 29 | −12.276 | −6.205 | 10.776 | 1.00 | 0.00 | O |
| ATOM | 125 | N | VAL | K | 30 | −10.501 | −6.027 | 9.303 | 1.00 | 0.00 | N |
| ATOM | 126 | CA | VAL | K | 30 | −11.107 | −6.819 | 8.230 | 1.00 | 0.00 | C |
| ATOM | 127 | C | VAL | K | 30 | −11.579 | −8.176 | 8.753 | 1.00 | 0.00 | C |
| ATOM | 128 | O | VAL | K | 30 | −12.714 | −8.565 | 8.512 | 1.00 | 0.00 | O |
| ATOM | 129 | CB | VAL | K | 30 | −10.270 | −6.937 | 6.923 | 1.00 | 0.00 | C |
| ATOM | 130 | CG1 | VAL | K | 30 | −−10.028 | −5.560 | 6.300 | 1.00 | 0.00 | C |
| ATOM | 131 | CG2 | VAL | K | 30 | −8.940 | −7.684 | 7.063 | 1.00 | 0.00 | C |
| ATOM | 132 | N | ALA | K | 31 | −10.636 | −8.920 | 9.451 | 1.00 | 0.00 | N |
| ATOM | 133 | CA | ALA | K | 31 | −10.883 | −10.314 | 9.808 | 1.00 | 0.00 | C |
| ATOM | 134 | C | ALA | K | 31 | −11.989 | −10.412 | 10.852 | 1.00 | 0.00 | C |
| ATOM | 135 | O | ALA | K | 31 | −12.931 | −11.178 | 10.696 | 1.00 | 0.00 | O |
| ATOM | 136 | CB | ALA | K | 31 | −9.624 | −11.033 | 10.283 | 1.00 | 0.00 | C |

TABLE 4-continued

| | | | | | | | | | | |
|---|---|---|---|---|---|---|---|---|---|---|
| ATOM | 137 | N | GLY | K | 32 | −11.816 | −9.610 | 11.974 | 1.00 | 0.00 | N |
| ATOM | 138 | CA | GLY | K | 32 | −12.719 | −9.669 | 13.109 | 1.00 | 0.00 | C |
| ATOM | 139 | C | GLY | K | 32 | −14.138 | −9.365 | 12.675 | 1.00 | 0.00 | C |
| ATOM | 140 | O | GLY | K | 32 | −15.039 | −10.185 | 12.801 | 1.00 | 0.00 | O |
| ATOM | 141 | N | PHE | K | 53 | −10.783 | −14.377 | 18.969 | 1.00 | 0.00 | N |
| ATOM | 142 | CA | PHE | K | 53 | −9.482 | −14.955 | 18.629 | 1.00 | 0.00 | C |
| ATOM | 143 | C | PHE | K | 53 | −8.723 | −14.019 | 17.685 | 1.00 | 0.00 | C |
| ATOM | 144 | O | PHE | K | 53 | −7.574 | −13.689 | 17.947 | 1.00 | 0.00 | O |
| ATOM | 145 | CB | PHE | K | 53 | −9.600 | −16.376 | 18.045 | 1.00 | 0.00 | C |
| ATOM | 146 | CG | PHE | K | 53 | −8.257 | −17.051 | 17.883 | 1.00 | 0.00 | C |
| ATOM | 147 | CD1 | PHE | K | 53 | −7.577 | −17.020 | 16.639 | 1.00 | 0.00 | C |
| ATOM | 148 | CD2 | PHE | K | 53 | −7.660 | −17.740 | 18.968 | 1.00 | 0.00 | C |
| ATOM | 149 | CE1 | PHE | K | 53 | −6.333 | −17.661 | 16.487 | 1.00 | 0.00 | C |
| ATOM | 150 | CE2 | PHE | K | 53 | −6.416 | −18.382 | 18.810 | 1.00 | 0.00 | C |
| ATOM | 151 | CZ | PHE | K | 53 | −5.753 | −18.344 | 17.571 | 1.00 | 0.00 | C |
| ATOM | 152 | N | PHE | K | 54 | −9.409 | −13.608 | 16.543 | 1.00 | 0.00 | N |
| ATOM | 153 | CA | PHE | K | 54 | −8.767 | −12.782 | 15.516 | 1.00 | 0.00 | C |
| ATOM | 154 | C | PHE | K | 54 | −8.164 | −11.541 | 16.176 | 1.00 | 0.00 | C |
| ATOM | 155 | O | PHE | K | 54 | −6.978 | −11.270 | 16.042 | 1.00 | 0.00 | O |
| ATOM | 156 | CB | PHE | K | 54 | −9.706 | −12.321 | 14.380 | 1.00 | 0.00 | C |
| ATOM | 157 | CG | PHE | K | 54 | −10.176 | −13.399 | 13.433 | 1.00 | 0.00 | C |
| ATOM | 158 | CD1 | PHE | K | 54 | −9.257 | −14.099 | 12.611 | 1.00 | 0.00 | C |
| ATOM | 159 | CD2 | PHE | K | 54 | −11.561 | −13.654 | 13.273 | 1.00 | 0.00 | C |
| ATOM | 160 | CE1 | PHE | K | 54 | −9.716 | −15.014 | 11.644 | 1.00 | 0.00 | C |
| ATOM | 161 | CE2 | PHE | K | 54 | −12.014 | −14.563 | 12.300 | 1.00 | 0.00 | C |
| ATOM | 162 | CZ | PHE | K | 54 | −11.094 | −15.240 | 11.482 | 1.00 | 0.00 | C |
| ATOM | 163 | N | ILE | K | 55 | −9.075 | −10.749 | 16.863 | 1.00 | 0.00 | N |
| ATOM | 164 | CA | ILE | K | 55 | −8.727 | −9.405 | 17.324 | 1.00 | 0.00 | C |
| ATOM | 165 | C | ILE | K | 55 | −7.693 | −9.410 | 18.450 | 1.00 | 0.00 | C |
| ATOM | 166 | O | ILE | K | 55 | −6.827 | −8.544 | 18.477 | 1.00 | 0.00 | O |
| ATOM | 167 | CB | ILE | K | 55 | −9.943 | −8.495 | 17.647 | 1.00 | 0.00 | C |
| ATOM | 168 | CG1 | ILE | K | 55 | −10.898 | −9.081 | 18.707 | 1.00 | 0.00 | C |
| ATOM | 169 | CG2 | ILE | K | 55 | −10.688 | −8.166 | 16.349 | 1.00 | 0.00 | C |
| ATOM | 170 | CD1 | ILE | K | 55 | −12.005 | −8.127 | 19.121 | 1.00 | 0.00 | C |
| ATOM | 171 | N | THR | K | 56 | −7.833 | −10.391 | 19.426 | 1.00 | 0.00 | N |
| ATOM | 172 | CA | THR | K | 56 | −6.922 | −10.464 | 20.567 | 1.00 | 0.00 | C |
| ATOM | 173 | C | THR | K | 56 | −5.505 | 10.773 | 20.080 | 1.00 | 0.00 | C |
| ATOM | 174 | O | THR | K | 56 | −4.555 | −10.147 | 20.530 | 1.00 | 0.00 | O |
| ATOM | 175 | CB | THR | K | 56 | −7.422 | −11.383 | 21.713 | 1.00 | 0.00 | C |
| ATOM | 176 | OG1 | THR | K | 56 | −6.750 | −11.036 | 22.925 | 1.00 | 0.00 | O |
| ATOM | 177 | CG2 | THR | K | 56 | −7.216 | −12.880 | 21.504 | 1.00 | 0.00 | C |
| ATOM | 178 | N | VAL | K | 57 | −5.382 | −11.788 | 19.134 | 1.00 | 0.00 | N |
| ATOM | 179 | CA | VAL | K | 57 | −4.079 | −12.161 | 18.578 | 1.00 | 0.00 | C |
| ATOM | 180 | C | VAL | K | 57 | −3.482 | −10.952 | 17.854 | 1.00 | 0.00 | C |
| ATOM | 181 | O | VAL | K | 57 | −2.287 | −10.725 | 17.957 | 1.00 | 0.00 | O |
| ATOM | 182 | CB | VAL | K | 57 | −4.122 | −13.438 | 17.699 | 1.00 | 0.00 | C |
| ATOM | 183 | CG1 | VAL | K | 57 | −2.785 | −13.707 | 17.001 | 1.00 | 0.00 | C |
| ATOM | 184 | CG2 | VAL | K | 57 | −4.464 | −14.666 | 18.551 | 1.00 | 0.00 | C |
| ATOM | 185 | N | GLY | K | 58 | −4.345 | −10.176 | 17.091 | 1.00 | 0.00 | N |
| ATOM | 186 | CA | GLY | K | 58 | −3.919 | −8.952 | 16.422 | 1.00 | 0.00 | C |
| ATOM | 187 | C | GLY | K | 58 | −3.232 | −7.958 | 17.352 | 1.00 | 0.00 | C |
| ATOM | 188 | O | GLY | K | 58 | −2.167 | −7.439 | 17.046 | 1.00 | 0.00 | O |
| ATOM | 189 | N | LEU | K | 59 | −3.928 | −7.669 | 18.517 | 1.00 | 0.00 | N |
| ATOM | 190 | CA | LEU | K | 59 | −3.421 | −6.732 | 19.526 | 1.00 | 0.00 | C |
| ATOM | 191 | C | LEU | K | 59 | −2.069 | −7.205 | 20.069 | 1.00 | 0.00 | C |
| ATOM | 192 | O | LEU | K | 59 | −1.126 | −6.432 | 20.181 | 1.00 | 0.00 | O |
| ATOM | 193 | CB | LEU | K | 59 | −4.441 | −6.520 | 20.664 | 1.00 | 0.00 | C |
| ATOM | 194 | CG | LEU | K | 59 | −4.043 | −5.453 | 21.703 | 1.00 | 0.00 | C |
| ATOM | 195 | CD1 | LEU | K | 59 | −3.930 | −4.059 | 21.088 | 1.00 | 0.00 | C |
| ATOM | 196 | CD2 | LEU | K | 59 | −5.062 | −5.428 | 22.840 | 1.00 | 0.00 | C |
| ATOM | 197 | N | VAL | K | 60 | −2.028 | −8.531 | 20.469 | 1.00 | 0.00 | N |
| ATOM | 198 | CA | VAL | K | 60 | −0.841 | −9.149 | 21.063 | 1.00 | 0.00 | C |
| ATOM | 199 | C | VAL | K | 60 | 0.332 | −9.119 | 20.061 | 1.00 | 0.00 | C |
| ATOM | 200 | O | VAL | K | 60 | 1.463 | −8.859 | 20.448 | 1.00 | 0.00 | O |
| ATOM | 201 | CB | VAL | K | 60 | −1.166 | −10.563 | 21.615 | 1.00 | 0.00 | C |
| ATOM | 202 | CG1 | VAL | K | 60 | 0.084 | −11.323 | 22.031 | 1.00 | 0.00 | C |
| ATOM | 203 | CG2 | VAL | K | 60 | −2.098 | −10.481 | 22.829 | 1.00 | 0.00 | C |
| ATOM | 204 | N | GLU | K | 61 | 0.026 | −9.421 | 18.739 | 1.00 | 0.00 | N |
| ATOM | 205 | CA | GLU | K | 61 | 0.996 | −9.380 | 17.639 | 1.00 | 0.00 | C |
| ATOM | 206 | C | GLU | K | 61 | 1.731 | −8.039 | 17.634 | 1.00 | 0.00 | C |
| ATOM | 207 | O | GLU | K | 61 | 2.948 | −8.006 | 17.511 | 1.00 | 0.00 | O |
| ATOM | 208 | CB | GLU | K | 61 | 0.337 | −9.677 | 16.274 | 1.00 | 0.00 | C |
| ATOM | 209 | CG | GLU | K | 61 | 1.291 | −9.513 | 15.092 | 1.00 | 0.00 | C |
| ATOM | 210 | CD | GLU | K | 61 | 0.631 | −9.807 | 13.767 | 1.00 | 0.00 | C |
| ATOM | 211 | OE1 | GLU | K | 61 | −0.550 | −9.630 | 13.503 | 1.00 | 0.00 | O |
| ATOM | 212 | OE2 | GLU | K | 61 | 1.553 | −10.205 | 12.854 | 1.00 | 0.00 | O |
| ATOM | 213 | N | ALA | K | 62 | 0.926 | −6.909 | 17.729 | 1.00 | 0.00 | N |
| ATOM | 214 | CA | ALA | K | 62 | 1.483 | −5.557 | 17.728 | 1.00 | 0.00 | C |
| ATOM | 215 | C | ALA | K | 62 | 2.586 | −5.411 | 18.775 | 1.00 | 0.00 | C |
| ATOM | 216 | O | ALA | K | 62 | 3.669 | −4.923 | 18.475 | 1.00 | 0.00 | O |

TABLE 4-continued

| | | | | | | | | | | |
|---|---|---|---|---|---|---|---|---|---|---|
| ATOM | 217 | CB | ALA | K | 62 | 0.419 | −4.487 | 17.928 | 1.00 | 0.00 | C |
| ATOM | 218 | N | ALA | K | 63 | 2.251 | −5.850 | 20.051 | 1.00 | 0.00 | N |
| ATOM | 219 | CA | ALA | K | 63 | 3.203 | −5.802 | 21.159 | 1.00 | 0.00 | C |
| ATOM | 220 | C | ALA | K | 63 | 4.484 | −6.563 | 20.818 | 1.00 | 0.00 | C |
| ATOM | 221 | O | ALA | K | 63 | 5.574 | −6.065 | 21.061 | 1.00 | 0.00 | O |
| ATOM | 222 | CB | ALA | K | 63 | 2.615 | −6.314 | 22.471 | 1.00 | 0.00 | C |
| ATOM | 223 | N | TYR | K | 64 | 4.320 | −7.827 | 20.262 | 1.00 | 0.00 | N |
| ATOM | 224 | CA | TYR | K | 64 | 5.460 | −8.695 | 19.951 | 1.00 | 0.00 | C |
| ATOM | 225 | C | TYR | K | 64 | 6.472 | −8.042 | 19.015 | 1.00 | 0.00 | C |
| ATOM | 226 | O | TYR | K | 64 | 7.665 | −8.258 | 19.180 | 1.00 | 0.00 | O |
| ATOM | 227 | CB | TYR | K | 64 | 5.069 | −10.062 | 19.359 | 1.00 | 0.00 | C |
| ATOM | 228 | CG | TYR | K | 64 | 4.322 | −11.015 | 20.266 | 1.00 | 0.00 | C |
| ATOM | 229 | CD1 | TYR | K | 64 | 4.486 | −11.028 | 21.679 | 1.00 | 0.00 | C |
| ATOM | 230 | CD2 | TYR | K | 64 | 3.483 | −11.993 | 19.678 | 1.00 | 0.00 | C |
| ATOM | 231 | CE1 | TYR | K | 64 | 3.829 | −11.984 | 22.471 | 1.00 | 0.00 | C |
| ATOM | 232 | CE2 | TYR | K | 64 | 2.857 | −12.979 | 20.459 | 1.00 | 0.00 | C |
| ATOM | 233 | CZ | TYR | K | 64 | 3.033 | −12.965 | 21.859 | 1.00 | 0.00 | C |
| ATOM | 234 | OH | TYR | K | 64 | 2.416 | −13.902 | 22.671 | 1.00 | 0.00 | O |
| ATOM | 235 | N | PHE | K | 65 | 5.971 | −7.269 | 17.972 | 1.00 | 0.00 | N |
| ATOM | 236 | CA | PHE | K | 65 | 6.881 | −6.566 | 17.058 | 1.00 | 0.00 | C |
| ATOM | 237 | C | PHE | K | 65 | 7.823 | −5.649 | 17.839 | 1.00 | 0.00 | C |
| ATOM | 238 | O | PHE | K | 65 | 9.014 | −5.614 | 17.560 | 1.00 | 0.00 | O |
| ATOM | 239 | CB | PHE | K | 65 | 6.180 | −5.739 | 15.966 | 1.00 | 0.00 | C |
| ATOM | 240 | CG | PHE | K | 65 | 5.527 | −6.570 | 14.890 | 1.00 | 0.00 | C |
| ATOM | 241 | CD1 | PHE | K | 65 | 4.136 | −6.471 | 14.655 | 1.00 | 0.00 | C |
| ATOM | 242 | CE1 | PHE | K | 65 | 3.536 | −7.174 | 13.596 | 1.00 | 0.00 | C |
| ATOM | 243 | CZ | PHE | K | 65 | 4.312 | −8.000 | 12.767 | 1.00 | 0.00 | C |
| ATOM | 244 | CE2 | PHE | K | 65 | 5.693 | −8.121 | 12.994 | 1.00 | 0.00 | C |
| ATOM | 245 | CD2 | PHE | K | 65 | 6.298 | −7.409 | 14.046 | 1.00 | 0.00 | C |
| ATOM | 246 | N | ASN | K | 67 | 8.600 | −5.837 | 21.135 | 1.00 | 0.00 | N |
| ATOM | 247 | CA | ASN | K | 67 | 9.499 | −6.640 | 21.975 | 1.00 | 0.00 | C |
| ATOM | 248 | C | ASN | K | 67 | 10.712 | −7.094 | 21.170 | 1.00 | 0.00 | C |
| ATOM | 249 | O | ASN | K | 67 | 11.841 | −6.910 | 21.603 | 1.00 | 0.00 | O |
| ATOM | 250 | CB | ASN | K | 67 | 8.840 | −7.875 | 22.619 | 1.00 | 0.00 | C |
| ATOM | 251 | CG | ASN | K | 67 | 7.877 | −7.498 | 23.726 | 1.00 | 0.00 | C |
| ATOM | 252 | OD1 | ASN | K | 67 | 6.675 | −7.388 | 23.534 | 1.00 | 0.00 | O |
| ATOM | 253 | ND2 | ASN | K | 67 | 8.480 | −7.263 | 24.941 | 1.00 | 0.00 | N |
| ATOM | 254 | N | LEU | K | 68 | 10.429 | −7.744 | 19.975 | 1.00 | 0.00 | N |
| ATOM | 255 | CA | LEU | K | 68 | 11.456 | −8.357 | 19.131 | 1.00 | 0.00 | C |
| ATOM | 256 | C | LEU | K | 68 | 12.495 | −7.303 | 18.752 | 1.00 | 0.00 | C |
| ATOM | 257 | O | LEU | K | 68 | 13.684 | −7.496 | 18.968 | 1.00 | 0.00 | O |
| ATOM | 258 | CB | LEU | K | 68 | 10.830 | −9.066 | 17.909 | 1.00 | 0.00 | C |
| ATOM | 259 | CG | LEU | K | 68 | 11.796 | −9.975 | 17.120 | 1.00 | 0.00 | C |
| ATOM | 260 | CD1 | LEU | K | 68 | 11.014 | −11.105 | 16.449 | 1.00 | 0.00 | C |
| ATOM | 261 | CD2 | LEU | K | 68 | 12.577 | −9.208 | 16.051 | 1.00 | 0.00 | C |
| ATOM | 262 | N | GLY | L | 14 | 14.989 | −7.715 | 8.662 | 1.00 | 0.00 | N |
| ATOM | 263 | CA | GLY | L | 14 | 13.793 | −6.924 | 8.905 | 1.00 | 0.00 | C |
| ATOM | 264 | C | GLY | L | 14 | 12.803 | −7.025 | 7.757 | 1.00 | 0.00 | C |
| ATOM | 265 | O | GLY | L | 14 | 11.628 | −7.291 | 7.964 | 1.00 | 0.00 | O |
| ATOM | 266 | N | ILE | L | 16 | 12.496 | −9.152 | 5.091 | 1.00 | 0.00 | N |
| ATOM | 267 | CA | ILE | L | 16 | 11.861 | −10.451 | 4.837 | 1.00 | 0.00 | C |
| ATOM | 268 | C | ILE | L | 16 | 10.744 | −10.700 | 5.848 | 1.00 | 0.00 | C |
| ATOM | 269 | O | ILE | L | 16 | 9.660 | −11.122 | 5.468 | 1.00 | 0.00 | O |
| ATOM | 270 | CB | ILE | L | 16 | 12.856 | −11.634 | 4.660 | 1.00 | 0.00 | C |
| ATOM | 271 | CG1 | ILE | L | 16 | 12.208 | −12.880 | 4.017 | 1.00 | 0.00 | C |
| ATOM | 272 | CG2 | ILE | L | 16 | 13.681 | −11.997 | 5.896 | 1.00 | 0.00 | C |
| ATOM | 273 | CD1 | ILE | L | 16 | 11.497 | −13.860 | 4.942 | 1.00 | 0.00 | C |
| ATOM | 274 | N | MET | L | 17 | 11.051 | −10.447 | 7.180 | 1.00 | 0.00 | N |
| ATOM | 275 | CA | MET | L | 17 | 10.081 | −10.700 | 8.246 | 1.00 | 0.00 | C |
| ATOM | 276 | C | MET | L | 17 | 8.818 | −9.866 | 8.100 | 1.00 | 0.00 | C |
| ATOM | 277 | O | MET | L | 17 | 7.742 | −10.352 | 8.419 | 1.00 | 0.00 | O |
| ATOM | 278 | CB | MET | L | 17 | 10.651 | −10.523 | 9.664 | 1.00 | 0.00 | C |
| ATOM | 279 | CG | MET | L | 17 | 11.609 | −11.637 | 10.084 | 1.00 | 0.00 | C |
| ATOM | 280 | SD | MET | L | 17 | 10.743 | −13.242 | 10.212 | 1.00 | 0.00 | S |
| ATOM | 281 | CE | MET | L | 17 | 11.465 | −14.067 | 8.772 | 1.00 | 0.00 | C |
| ATOM | 282 | N | ALA | L | 18 | 8.969 | −8.564 | 7.642 | 1.00 | 0.00 | N |
| ATOM | 283 | CA | ALA | L | 18 | 7.807 | −7.726 | 7.352 | 1.00 | 0.00 | C |
| ATOM | 284 | C | ALA | L | 18 | 6.915 | −8.420 | 6.322 | 1.00 | 0.00 | C |
| ATOM | 285 | O | ALA | L | 18 | 5.715 | −8.548 | 6.522 | 1.00 | 0.00 | O |
| ATOM | 286 | CB | ALA | L | 18 | 8.183 | −6.319 | 6.895 | 1.00 | 0.00 | C |
| ATOM | 287 | N | GLY | L | 19 | 7.564 | −8.879 | 5.182 | 1.00 | 0.00 | N |
| ATOM | 288 | CA | GLY | L | 19 | 6.870 | −9.586 | 4.117 | 1.00 | 0.00 | C |
| ATOM | 289 | C | GLY | L | 19 | 6.019 | −10.723 | 4.654 | 1.00 | 0.00 | C |
| ATOM | 290 | O | GLY | L | 19 | 4.826 | −10.794 | 4.389 | 1.00 | 0.00 | O |
| ATOM | 291 | N | GLY | L | 20 | 6.714 | −11.641 | 5.428 | 1.00 | 0.00 | N |
| ATOM | 292 | CA | GLY | L | 20 | 6.091 | −12.813 | 6.017 | 1.00 | 0.00 | C |
| ATOM | 293 | C | GLY | L | 20 | 4.924 | −12.424 | 6.902 | 1.00 | 0.00 | C |
| ATOM | 294 | O | GLY | L | 20 | 3.775 | −12.706 | 6.596 | 1.00 | 0.00 | O |
| ATOM | 295 | N | ALA | L | 21 | 5.288 | −11.749 | 8.053 | 1.00 | 0.00 | N |
| ATOM | 296 | CA | ALA | L | 21 | 4.370 | −11.537 | 9.169 | 1.00 | 0.00 | C |

TABLE 4-continued

| ATOM | 297 | C | ALA | L | 21 | 3.087 | −10.818 | 8.764 | 1.00 | 0.00 | C |
|---|---|---|---|---|---|---|---|---|---|---|---|
| ATOM | 298 | O | ALA | L | 21 | 2.008 | −11.206 | 9.192 | 1.00 | 0.00 | O |
| ATOM | 299 | CB | ALA | L | 21 | 5.030 | −10.783 | 10.317 | 1.00 | 0.00 | C |
| ATOM | 300 | N | ILE | L | 22 | 3.250 | −9.680 | 7.980 | 1.00 | 0.00 | N |
| ATOM | 301 | CA | ILE | L | 22 | 2.109 | −8.859 | 7.573 | 1.00 | 0.00 | C |
| ATOM | 302 | C | ILE | L | 22 | 1.336 | −9.638 | 6.508 | 1.00 | 0.00 | C |
| ATOM | 303 | O | ILE | L | 22 | 0.144 | −9.865 | 6.661 | 1.00 | 0.00 | O |
| ATOM | 304 | CB | ILE | L | 22 | 2.489 | −7.415 | 7.124 | 1.00 | 0.00 | C |
| ATOM | 305 | CG1 | ILE | L | 22 | 2.941 | −6.542 | 8.320 | 1.00 | 0.00 | C |
| ATOM | 306 | CG2 | ILE | L | 22 | 1.297 | −6.718 | 6.455 | 1.00 | 0.00 | C |
| ATOM | 307 | CD1 | ILE | L | 22 | 4.411 | −6.675 | 8.676 | 1.00 | 0.00 | C |
| ATOM | 308 | N | GLY | L | 23 | 2.058 | −10.000 | 5.378 | 1.00 | 0.00 | N |
| ATOM | 309 | CA | GLY | L | 23 | 1.420 | −10.535 | 4.184 | 1.00 | 0.00 | C |
| ATOM | 310 | C | GLY | L | 23 | 0.632 | −11.791 | 4.483 | 1.00 | 0.00 | C |
| ATOM | 311 | O | GLY | L | 23 | −0.575 | −11.846 | 4.285 | 1.00 | 0.00 | O |
| ATOM | 312 | N | ALA | L | 24 | 1.408 | −12.831 | 4.972 | 1.00 | 0.00 | N |
| ATOM | 313 | CA | ALA | L | 24 | 0.840 | −14.126 | 5.333 | 1.00 | 0.00 | C |
| ATOM | 314 | C | ALA | L | 24 | −0.200 | −13.997 | 6.437 | 1.00 | 0.00 | C |
| ATOM | 315 | O | ALA | L | 24 | −1.182 | −14.722 | 6.421 | 1.00 | 0.00 | O |
| ATOM | 316 | CB | ALA | L | 24 | 1.894 | −15.147 | 5.746 | 1.00 | 0.00 | C |
| ATOM | 317 | N | GLY | L | 25 | 0.065 | −13.074 | 7.441 | 1.00 | 0.00 | N |
| ATOM | 318 | CA | GLY | L | 25 | −0.835 | −12.872 | 8.565 | 1.00 | 0.00 | C |
| ATOM | 319 | C | GLY | L | 25 | −2.244 | −12.510 | 8.132 | 1.00 | 0.00 | C |
| ATOM | 320 | O | GLY | L | 25 | −3.203 | −13.173 | 8.505 | 1.00 | 0.00 | O |
| ATOM | 321 | N | ILE | L | 26 | −2.329 | −11.374 | 7.337 | 1.00 | 0.00 | N |
| ATOM | 322 | CA | ILE | L | 26 | −3.608 | −10.852 | 6.834 | 1.00 | 0.00 | C |
| ATOM | 323 | C | ILE | L | 26 | −4.264 | −11.948 | 5.991 | 1.00 | 0.00 | C |
| ATOM | 324 | O | ILE | L | 26 | −5.440 | −12.236 | 6.166 | 1.00 | 0.00 | O |
| ATOM | 325 | CB | ILE | L | 26 | −3.469 | −9.511 | 6.056 | 1.00 | 0.00 | C |
| ATOM | 326 | CG1 | ILE | L | 26 | −3.005 | −8.379 | 7.001 | 1.00 | 0.00 | C |
| ATOM | 327 | CG2 | ILE | L | 26 | −4.794 | −9.115 | 5.386 | 1.00 | 0.00 | C |
| ATOM | 328 | CD1 | ILE | L | 26 | −2.547 | −7.131 | 6.263 | 1.00 | 0.00 | C |
| ATOM | 329 | N | GLY | L | 27 | −3.444 | −12.534 | 5.034 | 1.00 | 0.00 | N |
| ATOM | 330 | CA | GLY | L | 27 | −3.895 | −13.566 | 4.116 | 1.00 | 0.00 | C |
| ATOM | 331 | C | GLY | L | 27 | −4.612 | −14.699 | 4.822 | 1.00 | 0.00 | C |
| ATOM | 332 | O | GLY | L | 27 | −5.743 | −15.030 | 4.495 | 1.00 | 0.00 | O |
| ATOM | 333 | N | ASP | L | 28 | −3.866 | −15.300 | 5.825 | 1.00 | 0.00 | N |
| ATOM | 334 | CA | ASP | L | 28 | −4.342 | −16.404 | 6.656 | 1.00 | 0.00 | C |
| ATOM | 335 | C | ASP | L | 28 | −5.678 | −16.044 | 7.295 | 1.00 | 0.00 | C |
| ATOM | 336 | O | ASP | L | 28 | −6.607 | −16.838 | 7.255 | 1.00 | 0.00 | O |
| ATOM | 337 | CB | ASP | L | 28 | −3.304 | −16.805 | 7.718 | 1.00 | 0.00 | C |
| ATOM | 338 | CG | ASP | L | 28 | −3.834 | −17.837 | 8.680 | 1.00 | 0.00 | C |
| ATOM | 339 | OD1 | ASP | L | 28 | −4.192 | −17.594 | 9.822 | 1.00 | 0.00 | O |
| ATOM | 340 | OD2 | ASP | L | 28 | −3.898 | −19.067 | 8.109 | 1.00 | 0.00 | O |
| ATOM | 341 | N | GLY | L | 29 | −5.735 | −14.805 | 7.918 | 1.00 | 0.00 | N |
| ATOM | 342 | CA | GLY | L | 29 | −6.922 | −14.317 | 8.598 | 1.00 | 0.00 | C |
| ATOM | 343 | C | GLY | L | 29 | −8.156 | −14.418 | 7.720 | 1.00 | 0.00 | C |
| ATOM | 344 | O | GLY | L | 29 | −9.113 | −15.099 | 8.061 | 1.00 | 0.00 | O |
| ATOM | 345 | N | VAL | L | 30 | −8.091 | −13.675 | 6.548 | 1.00 | 0.00 | N |
| ATOM | 346 | CA | VAL | L | 30 | −9.233 | −13.575 | 5.632 | 1.00 | 0.00 | C |
| ATOM | 347 | C | VAL | L | 30 | −9.587 | −14.913 | 4.961 | 1.00 | 0.00 | C |
| ATOM | 348 | O | VAL | L | 30 | −10.748 | −15.158 | 4.661 | 1.00 | 0.00 | O |
| ATOM | 349 | CB | VAL | L | 30 | −9.143 | −12.412 | 4.611 | 1.00 | 0.00 | C |
| ATOM | 350 | CG1 | VAL | L | 30 | −9.013 | −11.058 | 5.310 | 1.00 | 0.00 | C |
| ATOM | 351 | CG2 | VAL | L | 30 | −8.035 | −12.576 | 3.573 | 1.00 | 0.00 | C |
| ATOM | 352 | N | ALA | L | 31 | −8.539 | −15.791 | 4.710 | 1.00 | 0.00 | N |
| ATOM | 353 | CA | ALA | L | 31 | −8.767 | −17.161 | 4.238 | 1.00 | 0.00 | C |
| ATOM | 354 | C | ALA | L | 31 | −9.633 | −17.938 | 5.230 | 1.00 | 0.00 | C |
| ATOM | 355 | O | ALA | L | 31 | −10.516 | −18.686 | 4.834 | 1.00 | 0.00 | O |
| ATOM | 356 | CB | ALA | L | 31 | −7.472 | −17.928 | 3.981 | 1.00 | 0.00 | C |
| ATOM | 357 | N | GLY | L | 32 | −9.321 | −17.746 | 6.570 | 1.00 | 0.00 | N |
| ATOM | 358 | CA | GLY | L | 32 | −10.106 | −18.295 | 7.661 | 1.00 | 0.00 | C |
| ATOM | 359 | C | GLY | L | 32 | −11.567 | −17.924 | 7.538 | 1.00 | 0.00 | C |
| ATOM | 360 | O | GLY | L | 32 | −12.428 | −18.788 | 7.620 | 1.00 | 0.00 | O |
| ATOM | 361 | N | THR | L | 51 | −11.764 | −26.332 | 14.771 | 1.00 | 0.00 | N |
| ATOM | 362 | CA | THR | L | 51 | −10.467 | −26.987 | 14.935 | 1.00 | 0.00 | C |
| ATOM | 363 | C | THR | L | 51 | −9.452 | −26.599 | 13.848 | 1.00 | 0.00 | C |
| ATOM | 364 | O | THR | L | 51 | −8.351 | −26.190 | 14.199 | 1.00 | 0.00 | O |
| ATOM | 365 | CB | THR | L | 51 | −10.589 | −28.519 | 15.109 | 1.00 | 0.00 | C |
| ATOM | 366 | OG1 | THR | L | 51 | −11.578 | −28.792 | 16.105 | 1.00 | 0.00 | O |
| ATOM | 367 | CG2 | THR | L | 51 | −9.288 | −29.157 | 15.580 | 1.00 | 0.00 | C |
| ATOM | 368 | N | PRO | L | 52 | −9.797 | −26.799 | 12.499 | 1.00 | 0.00 | N |
| ATOM | 369 | CA | PRO | L | 52 | −8.818 | −26.678 | 11.427 | 1.00 | 0.00 | C |
| ATOM | 370 | C | PRO | L | 52 | −8.028 | −25.377 | 11.428 | 1.00 | 0.00 | C |
| ATOM | 371 | O | PRO | L | 52 | −6.825 | −25.388 | 11.203 | 1.00 | 0.00 | O |
| ATOM | 372 | CB | PRO | L | 52 | −9.592 | −26.833 | 10.125 | 1.00 | 0.00 | C |
| ATOM | 373 | CG | PRO | L | 52 | −10.863 | −27.542 | 10.527 | 1.00 | 0.00 | C |
| ATOM | 374 | CD | PRO | L | 52 | −11.104 | −27.123 | 11.962 | 1.00 | 0.00 | C |
| ATOM | 375 | N | PHE | L | 53 | −8.777 | −24.222 | 11.638 | 1.00 | 0.00 | N |
| ATOM | 376 | CA | PHE | L | 53 | −8.158 | −22.904 | 11.575 | 1.00 | 0.00 | C |

TABLE 4-continued

| | | | | | | | | | | |
|---|---|---|---|---|---|---|---|---|---|---|
| ATOM | 377 | C | PHE | L | 53 | −7.070 | −22.835 | 12.640 | 1.00 | 0.00 | C |
| ATOM | 378 | O | PHE | L | 53 | −5.919 | −22.563 | 12.328 | 1.00 | 0.00 | O |
| ATOM | 379 | CB | PHE | L | 53 | −9.165 | −21.749 | 11.710 | 1.00 | 0.00 | C |
| ATOM | 380 | CG | PHE | L | 53 | −8.486 | −20.406 | 11.576 | 1.00 | 0.00 | C |
| ATOM | 381 | CD1 | PHE | L | 53 | −8.068 | −19.938 | 10.308 | 1.00 | 0.00 | C |
| ATOM | 382 | CD2 | PHE | L | 53 | −8.232 | −19.601 | 12.715 | 1.00 | 0.00 | C |
| ATOM | 383 | CE1 | PHE | L | 53 | −7.415 | −18.699 | 10.186 | 1.00 | 0.00 | C |
| ATOM | 384 | CE2 | PHE | L | 53 | −7.598 | −18.352 | 12.585 | 1.00 | 0.00 | C |
| ATOM | 385 | CZ | PHE | L | 53 | −7.185 | −17.903 | 11.320 | 1.00 | 0.00 | C |
| ATOM | 386 | N | PHE | L | 54 | −7.493 | −23.069 | 13.942 | 1.00 | 0.00 | N |
| ATOM | 387 | CA | PHE | L | 54 | −6.624 | −22.780 | 15.082 | 1.00 | 0.00 | C |
| ATOM | 388 | C | PHE | L | 54 | −5.283 | −23.500 | 14.934 | 1.00 | 0.00 | C |
| ATOM | 389 | O | PHE | L | 54 | −4.238 | −22.899 | 15.149 | 1.00 | 0.00 | O |
| ATOM | 390 | CB | PHE | L | 54 | −7.258 | −23.112 | 16.446 | 1.00 | 0.00 | C |
| ATOM | 391 | CG | PHE | L | 54 | −8.520 | −22.346 | 16.780 | 1.00 | 0.00 | C |
| ATOM | 392 | CD1 | PHE | L | 54 | −8.627 | −20.946 | 16.577 | 1.00 | 0.00 | C |
| ATOM | 393 | CD2 | PHE | L | 54 | −9.626 | −23.027 | 17.347 | 1.00 | 0.00 | C |
| ATOM | 394 | CE1 | PHE | L | 54 | −9.810 | −20.260 | 16.905 | 1.00 | 0.00 | C |
| ATOM | 395 | CE2 | PHE | L | 54 | −10.796 | −22.330 | 17.701 | 1.00 | 0.00 | C |
| ATOM | 396 | CZ | PHE | L | 54 | −10.892 | −20.948 | 17.473 | 1.00 | 0.00 | C |
| ATOM | 397 | N | ILE | L | 55 | −5.352 | −24.850 | 14.595 | 1.00 | 0.00 | N |
| ATOM | 398 | CA | ILE | L | 55 | −4.139 | −25.666 | 14.492 | 1.00 | 0.00 | C |
| ATOM | 399 | C | ILE | L | 55 | −3.201 | −25.129 | 13.402 | 1.00 | 0.00 | C |
| ATOM | 400 | O | ILE | L | 55 | −2.003 | −25.002 | 13.627 | 1.00 | 0.00 | O |
| ATOM | 401 | CB | ILE | L | 55 | −4.402 | −27.198 | 14.419 | 1.00 | 0.00 | C |
| ATOM | 402 | CG1 | ILE | L | 55 | −3.088 | −27.977 | 14.635 | 1.00 | 0.00 | C |
| ATOM | 403 | CG2 | ILE | L | 55 | −5.106 | −27.651 | 13.136 | 1.00 | 0.00 | C |
| ATOM | 404 | CD1 | ILE | L | 55 | −3.303 | −29.446 | 14.966 | 1.00 | 0.00 | C |
| ATOM | 405 | N | THR | L | 56 | −3.789 | −24.860 | 12.169 | 1.00 | 0.00 | N |
| ATOM | 406 | CA | THR | L | 56 | −2.977 | −24.541 | 10.996 | 1.00 | 0.00 | C |
| ATOM | 407 | C | THR | L | 56 | −2.190 | −23.229 | 11.131 | 1.00 | 0.00 | C |
| ATOM | 408 | O | THR | L | 56 | −1.166 | −23.089 | 10.475 | 1.00 | 0.00 | O |
| ATOM | 409 | CB | THR | L | 56 | −3.767 | −24.642 | 9.664 | 1.00 | 0.00 | C |
| ATOM | 410 | OG1 | THR | L | 56 | −2.866 | −24.908 | 8.586 | 1.00 | 0.00 | O |
| ATOM | 411 | CG2 | THR | L | 56 | −4.606 | −23.421 | 9.294 | 1.00 | 0.00 | C |
| ATOM | 412 | N | VAL | L | 57 | −2.720 | −22.244 | 11.970 | 1.00 | 0.00 | N |
| ATOM | 413 | CA | VAL | L | 57 | −2.067 | −20.936 | 12.149 | 1.00 | 0.00 | C |
| ATOM | 414 | C | VAL | L | 57 | −0.599 | −21.186 | 12.511 | 1.00 | 0.00 | C |
| ATOM | 415 | O | VAL | L | 57 | 0.303 | −20.738 | 11.815 | 1.00 | 0.00 | O |
| ATOM | 416 | CB | VAL | L | 57 | −2.746 | −20.000 | 13.195 | 1.00 | 0.00 | C |
| ATOM | 417 | CG1 | VAL | L | 57 | −1.993 | −18.675 | 13.324 | 1.00 | 0.00 | C |
| ATOM | 418 | CG2 | VAL | L | 57 | −4.196 | −19.681 | 12.839 | 1.00 | 0.00 | C |
| ATOM | 419 | N | GLY | L | 58 | −0.405 | −21.929 | 13.671 | 1.00 | 0.00 | N |
| ATOM | 420 | CA | GLY | L | 58 | 0.911 | −22.161 | 14.239 | 1.00 | 0.00 | C |
| ATOM | 421 | C | GLY | L | 58 | 1.842 | −22.808 | 13.236 | 1.00 | 0.00 | C |
| ATOM | 422 | O | GLY | L | 58 | 2.952 | −22.341 | 13.023 | 1.00 | 0.00 | O |
| ATOM | 423 | N | LEU | L | 59 | 1.332 | −23.958 | 12.645 | 1.00 | 0.00 | N |
| ATOM | 424 | CA | LEU | L | 59 | 2.136 | −24.819 | 11.776 | 1.00 | 0.00 | C |
| ATOM | 425 | C | LEU | L | 59 | 2.757 | −24.020 | 10.627 | 1.00 | 0.00 | C |
| ATOM | 426 | O | LEU | L | 59 | 3.950 | −24.127 | 10.374 | 1.00 | 0.00 | O |
| ATOM | 427 | CB | LEU | L | 59 | 1.344 | −26.017 | 11.210 | 1.00 | 0.00 | C |
| ATOM | 428 | CG | LEU | L | 59 | 0.863 | −27.034 | 12.268 | 1.00 | 0.00 | C |
| ATOM | 429 | CD1 | LEU | L | 59 | −0.081 | −28.045 | 11.621 | 1.00 | 0.00 | C |
| ATOM | 430 | CD2 | LEU | L | 59 | 2.027 | −27.772 | 12.932 | 1.00 | 0.00 | C |
| ATOM | 431 | N | VAL | L | 60 | 1.872 | −23.244 | 9.886 | 1.00 | 0.00 | N |
| ATOM | 432 | CA | VAL | L | 60 | 2.291 | −22.521 | 8.680 | 1.00 | 0.00 | C |
| ATOM | 433 | C | VAL | L | 60 | 3.333 | −21.474 | 9.071 | 1.00 | 0.00 | C |
| ATOM | 434 | O | VAL | L | 60 | 4.419 | −21.440 | 8.507 | 1.00 | 0.00 | O |
| ATOM | 435 | CB | VAL | L | 60 | 1.098 | −21.909 | 7.895 | 1.00 | 0.00 | C |
| ATOM | 436 | CG1 | VAL | L | 60 | 1.551 | −20.964 | 6.776 | 1.00 | 0.00 | C |
| ATOM | 437 | CG2 | VAL | L | 60 | 0.246 | −23.017 | 7.273 | 1.00 | 0.00 | C |
| ATOM | 438 | N | GLU | L | 61 | 2.931 | −20.563 | 10.039 | 1.00 | 0.00 | N |
| ATOM | 439 | CA | GLU | L | 61 | 3.735 | −19.381 | 10.357 | 1.00 | 0.00 | C |
| ATOM | 440 | C | GLU | L | 61 | 5.107 | −19.722 | 10.949 | 1.00 | 0.00 | C |
| ATOM | 441 | O | GLU | L | 61 | 6.043 | −18.942 | 10.816 | 1.00 | 0.00 | O |
| ATOM | 442 | CB | GLU | L | 61 | 2.988 | −18.378 | 11.246 | 1.00 | 0.00 | C |
| ATOM | 443 | CG | GLU | L | 61 | 1.789 | −17.773 | 10.507 | 1.00 | 0.00 | C |
| ATOM | 444 | CD | GLU | L | 61 | 1.165 | −16.637 | 11.308 | 1.00 | 0.00 | C |
| ATOM | 445 | OE1 | GLU | L | 61 | 0.658 | −16.959 | 12.417 | 1.00 | 0.00 | O |
| ATOM | 446 | OE2 | GLU | L | 61 | 1.212 | −15.497 | 10.769 | 1.00 | 0.00 | O |
| ATOM | 447 | N | ALA | L | 62 | 5.207 | −20.935 | 11.625 | 1.00 | 0.00 | N |
| ATOM | 448 | CA | ALA | L | 62 | 6.476 | −21.443 | 12.148 | 1.00 | 0.00 | C |
| ATOM | 449 | C | ALA | L | 62 | 7.593 | −21.430 | 11.110 | 1.00 | 0.00 | C |
| ATOM | 450 | O | ALA | L | 62 | 8.733 | −21.152 | 11.454 | 1.00 | 0.00 | O |
| ATOM | 451 | CB | ALA | L | 62 | 6.351 | −22.844 | 12.734 | 1.00 | 0.00 | C |
| ATOM | 452 | N | ALA | L | 63 | 7.235 | −21.777 | 9.810 | 1.00 | 0.00 | N |
| ATOM | 453 | CA | ALA | L | 63 | 8.205 | −21.820 | 8.714 | 1.00 | 0.00 | C |
| ATOM | 454 | C | ALA | L | 63 | 9.043 | −20.543 | 8.636 | 1.00 | 0.00 | C |
| ATOM | 455 | O | ALA | L | 63 | 10.257 | −20.607 | 8.499 | 1.00 | 0.00 | O |
| ATOM | 456 | CB | ALA | L | 63 | 7.547 | −22.083 | 7.362 | 1.00 | 0.00 | C |

TABLE 4-continued

| | | | | | | | | | | |
|---|---|---|---|---|---|---|---|---|---|---|
| ATOM | 457 | N | TYR | L | 64 | 8.333 | −19.349 | 8.701 | 1.00 | 0.00 | N |
| ATOM | 458 | CA | TYR | L | 64 | 9.006 | −18.049 | 8.621 | 1.00 | 0.00 | C |
| ATOM | 459 | C | TYR | L | 64 | 10.000 | −17.881 | 9.768 | 1.00 | 0.00 | C |
| ATOM | 460 | O | TYR | L | 64 | 11.097 | −17.379 | 9.562 | 1.00 | 0.00 | O |
| ATOM | 461 | CB | TYR | L | 64 | 8.042 | −16.849 | 8.590 | 1.00 | 0.00 | C |
| ATOM | 462 | CG | TYR | L | 64 | 7.194 | −16.820 | 7.341 | 1.00 | 0.00 | C |
| ATOM | 463 | CD1 | TYR | L | 64 | 7.770 | −16.499 | 6.085 | 1.00 | 0.00 | C |
| ATOM | 464 | CD2 | TYR | L | 64 | 5.811 | −17.118 | 7.404 | 1.00 | 0.00 | C |
| ATOM | 465 | CE1 | TYR | L | 64 | 6.990 | −16.502 | 4.914 | 1.00 | 0.00 | C |
| ATOM | 466 | CE2 | TYR | L | 64 | 5.024 | −17.125 | 6.238 | 1.00 | 0.00 | C |
| ATOM | 467 | CZ | TYR | L | 64 | 5.615 | −16.821 | 4.997 | 1.00 | 0.00 | C |
| ATOM | 468 | OH | TYR | L | 64 | 4.807 | −16.847 | 3.870 | 1.00 | 0.00 | O |
| ATOM | 469 | N | PHE | L | 65 | 9.571 | −18.285 | 11.026 | 1.00 | 0.00 | N |
| ATOM | 470 | CA | PHE | L | 65 | 10.456 | −18.198 | 12.188 | 1.00 | 0.00 | C |
| ATOM | 471 | C | PHE | L | 65 | 11.751 | −19.001 | 11.982 | 1.00 | 0.00 | C |
| ATOM | 472 | O | PHE | L | 65 | 12.807 | −18.572 | 12.428 | 1.00 | 0.00 | O |
| ATOM | 473 | CB | PHE | L | 65 | 9.751 | −18.584 | 13.503 | 1.00 | 0.00 | C |
| ATOM | 474 | CG | PHE | L | 65 | 10.605 | −18.264 | 14.707 | 1.00 | 0.00 | C |
| ATOM | 475 | CD1 | PHE | L | 65 | 10.790 | −16.921 | 15.123 | 1.00 | 0.00 | C |
| ATOM | 476 | CE1 | PHE | L | 65 | 11.649 | −16.616 | 16.194 | 1.00 | 0.00 | C |
| ATOM | 477 | CZ | PHE | L | 65 | 12.328 | −17.647 | 16.867 | 1.00 | 0.00 | C |
| ATOM | 478 | CE2 | PHE | L | 65 | 12.135 | 18.985 | 16.481 | 1.00 | 0.00 | C |
| ATOM | 479 | CD2 | PHE | L | 65 | 11.277 | −19.295 | 15.410 | 1.00 | 0.00 | C |
| ATOM | 480 | N | ILE | L | 66 | 11.648 | −20.219 | 11.314 | 1.00 | 0.00 | N |
| ATOM | 481 | CA | ILE | L | 66 | 12.834 | −21.039 | 11.020 | 1.00 | 0.00 | C |
| ATOM | 482 | C | ILE | L | 66 | 13.831 | −20.203 | 10.207 | 1.00 | 0.00 | C |
| ATOM | 483 | O | ILE | L | 66 | 15.012 | −20.185 | 10.527 | 1.00 | 0.00 | O |
| ATOM | 484 | CB | ILE | L | 66 | 12.536 | −22.402 | 10.326 | 1.00 | 0.00 | C |
| ATOM | 485 | CG1 | ILE | L | 66 | 11.537 | −23.293 | 11.099 | 1.00 | 0.00 | C |
| ATOM | 486 | CG2 | ILE | L | 66 | 13.824 | −23.190 | 10.054 | 1.00 | 0.00 | C |
| ATOM | 487 | CD1 | ILE | L | 66 | 11.915 | −23.605 | 12.541 | 1.00 | 0.00 | C |
| ATOM | 488 | N | ASN | L | 67 | 13.319 | −19.523 | 9.103 | 1.00 | 0.00 | N |
| ATOM | 489 | CA | ASN | L | 67 | 14.170 | −18.671 | 8.257 | 1.00 | 0.00 | C |
| ATOM | 490 | C | ASN | L | 67 | 14.893 | −17.621 | 9.100 | 1.00 | 0.00 | C |
| ATOM | 491 | O | ASN | L | 67 | 16.086 | −17.414 | 8.918 | 1.00 | 0.00 | O |
| ATOM | 492 | CB | ASN | L | 67 | 13.433 | −17.956 | 7.109 | 1.00 | 0.00 | C |
| ATOM | 493 | CG | ASN | L | 67 | 12.966 | −18.928 | 6.045 | 1.00 | 0.00 | C |
| ATOM | 494 | OD1 | ASN | L | 67 | 11.854 | −19.433 | 6.070 | 1.00 | 0.00 | O |
| ATOM | 495 | ND2 | ASN | L | 67 | 13.914 | −19.210 | 5.086 | 1.00 | 0.00 | N |
| ATOM | 496 | N | LEU | L | 68 | 14.100 | −16.932 | 10.018 | 1.00 | 0.00 | N |
| ATOM | 497 | CA | LEU | L | 68 | 14.623 | −15.890 | 10.911 | 1.00 | 0.00 | C |
| ATOM | 498 | C | LEU | L | 68 | 15.848 | −16.461 | 11.624 | 1.00 | 0.00 | C |
| ATOM | 499 | O | LEU | L | 68 | 16.945 | −15.935 | 11.495 | 1.00 | 0.00 | O |
| ATOM | 500 | CB | LEU | L | 68 | 13.567 | −15.371 | 11.923 | 1.00 | 0.00 | C |
| ATOM | 501 | CG | LEU | L | 68 | 13.797 | −13.942 | 12.458 | 1.00 | 0.00 | C |
| ATOM | 502 | CD1 | LEU | L | 68 | 12.687 | −13.579 | 13.446 | 1.00 | 0.00 | C |
| ATOM | 503 | CD2 | LEU | L | 68 | 15.146 | −13.745 | 13.146 | 1.00 | 0.00 | C |
| ATOM | 504 | N | ALA | L | 69 | 15.599 | −17.586 | 12.403 | 1.00 | 0.00 | N |
| ATOM | 505 | CA | ALA | L | 69 | 16.590 | −18.175 | 13.295 | 1.00 | 0.00 | C |
| ATOM | 506 | C | ALA | L | 69 | 17.875 | −18.501 | 12.545 | 1.00 | 0.00 | C |
| ATOM | 507 | O | ALA | L | 69 | 18.956 | −18.146 | 12.993 | 1.00 | 0.00 | O |
| ATOM | 508 | CB | ALA | L | 69 | 16.062 | −19.423 | 13.999 | 1.00 | 0.00 | C |
| ATOM | 509 | N | SER | M | 199 | −10.235 | −24.828 | 20.448 | 1.00 | 0.00 | N |
| ATOM | 510 | CA | SER | M | 199 | −10.460 | −26.277 | 20.457 | 1.00 | 0.00 | C |
| ATOM | 511 | C | SER | M | 199 | −9.383 | −26.909 | 21.342 | 1.00 | 0.00 | C |
| ATOM | 512 | O | SER | M | 199 | −8.255 | −26.439 | 21.436 | 1.00 | 0.00 | O |
| ATOM | 513 | CB | SER | M | 199 | −10.426 | −26.831 | 19.028 | 1.00 | 0.00 | C |
| ATOM | 514 | OG | SER | M | 199 | −10.782 | −28.211 | 19.040 | 1.00 | 0.00 | O |
| ATOM | 515 | N | ALA | M | 202 | −6.359 | −28.395 | 19.399 | 1.00 | 0.00 | N |
| ATOM | 516 | CA | ALA | M | 202 | −5.624 | −27.448 | 18.568 | 1.00 | 0.00 | C |
| ATOM | 517 | C | ALA | M | 202 | −4.672 | −26.589 | 19.389 | 1.00 | 0.00 | C |
| ATOM | 518 | O | ALA | M | 202 | −3.496 | −26.490 | 19.067 | 1.00 | 0.00 | O |
| ATOM | 519 | CB | ALA | M | 202 | −6.548 | −26.552 | 17.752 | 1.00 | 0.00 | C |
| ATOM | 520 | N | LYS | M | 203 | −5.259 | −25.887 | 20.436 | 1.00 | 0.00 | N |
| ATOM | 521 | CA | LYS | M | 203 | −4.565 | −24.776 | 21.085 | 1.00 | 0.00 | C |
| ATOM | 522 | C | LYS | M | 203 | −3.211 | −25.173 | 21.673 | 1.00 | 0.00 | C |
| ATOM | 523 | O | LYS | M | 203 | −2.244 | −24.472 | 21.408 | 1.00 | 0.00 | O |
| ATOM | 524 | CB | LYS | M | 203 | −5.421 | −24.006 | 22.104 | 1.00 | 0.00 | C |
| ATOM | 525 | CG | LYS | M | 203 | −6.351 | −23.021 | 21.397 | 1.00 | 0.00 | C |
| ATOM | 526 | CD | LYS | M | 203 | −7.207 | −22.239 | 22.391 | 1.00 | 0.00 | C |
| ATOM | 527 | CE | LYS | M | 203 | −7.942 | −21.073 | 21.731 | 1.00 | 0.00 | C |
| ATOM | 528 | NZ | LYS | M | 203 | −8.880 | −21.518 | 20.704 | 1.00 | 0.00 | N |
| ATOM | 529 | N | PRO | M | 204 | −3.121 | −26.287 | 22.520 | 1.00 | 0.00 | N |
| ATOM | 530 | CA | PRO | M | 204 | −1.857 | −26.688 | 23.113 | 1.00 | 0.00 | C |
| ATOM | 531 | C | PRO | M | 204 | −0.698 | −26.719 | 22.124 | 1.00 | 0.00 | C |
| ATOM | 532 | O | PRO | M | 204 | 0.311 | −26.064 | 22.348 | 1.00 | 0.00 | O |
| ATOM | 533 | CB | PRO | M | 204 | −2.120 | −28.029 | 23.781 | 1.00 | 0.00 | C |
| ATOM | 534 | CG | PRO | M | 204 | −3.599 | −27.984 | 24.098 | 1.00 | 0.00 | C |
| ATOM | 535 | CD | PRO | M | 204 | −4.203 | −27.116 | 23.010 | 1.00 | 0.00 | C |
| ATOM | 536 | N | ILE | M | 205 | −0.871 | −27.523 | 21.001 | 1.00 | 0.00 | N |

TABLE 4-continued

| | | | | | | | | | | |
|---|---|---|---|---|---|---|---|---|---|---|
| ATOM | 537 | CA | ILE | M | 205 | 0.201 | −27.693 | 20.012 | 1.00 | 0.00 | C |
| ATOM | 538 | C | ILE | M | 205 | 0.518 | −26.340 | 19.365 | 1.00 | 0.00 | C |
| ATOM | 539 | O | ILE | M | 205 | 1.669 | −25.924 | 19.342 | 1.00 | 0.00 | O |
| ATOM | 540 | CB | ILE | M | 205 | −0.021 | −28.884 | 19.030 | 1.00 | 0.00 | C |
| ATOM | 541 | CG1 | ILE | M | 205 | 1.238 | −29.236 | 18.204 | 1.00 | 0.00 | C |
| ATOM | 542 | CG2 | ILE | M | 205 | −1.273 | −28.799 | 18.151 | 1.00 | 0.00 | C |
| ATOM | 543 | CD1 | ILE | M | 205 | 1.490 | −28.405 | 16.949 | 1.00 | 0.00 | C |
| ATOM | 544 | N | SER | M | 206 | −0.566 | −25.670 | 18.816 | 1.00 | 0.00 | N |
| ATOM | 545 | CA | SER | M | 206 | −0.425 | −24.504 | 17.945 | 1.00 | 0.00 | C |
| ATOM | 546 | C | SER | M | 206 | 0.370 | −23.401 | 18.645 | 1.00 | 0.00 | C |
| ATOM | 547 | O | SER | M | 206 | 1.352 | −22.898 | 18.114 | 1.00 | 0.00 | O |
| ATOM | 548 | CB | SER | M | 206 | −1.797 | −24.005 | 17.472 | 1.00 | 0.00 | C |
| ATOM | 549 | OG | SER | M | 206 | −1.651 | −23.006 | 16.468 | 1.00 | 0.00 | O |
| ATOM | 550 | N | LEU | M | 207 | −0.143 | −23.008 | 19.874 | 1.00 | 0.00 | N |
| ATOM | 551 | CA | LEU | M | 207 | 0.392 | −21.871 | 20.615 | 1.00 | 0.00 | C |
| ATOM | 552 | C | LEU | M | 207 | 1.815 | −22.188 | 21.070 | 1.00 | 0.00 | C |
| ATOM | 553 | O | LEU | M | 207 | 2.709 | −21.379 | 20.864 | 1.00 | 0.00 | O |
| ATOM | 554 | CB | LEU | M | 207 | −0.487 | −21.463 | 21.816 | 1.00 | 0.00 | C |
| ATOM | 555 | CG | LEU | M | 207 | −1.681 | −20.526 | 21.513 | 1.00 | 0.00 | C |
| ATOM | 556 | CD1 | LEU | M | 207 | −1.223 | −19.102 | 21.205 | 1.00 | 0.00 | C |
| ATOM | 557 | CD2 | LEU | M | 207 | −2.610 | −21.034 | 20.412 | 1.00 | 0.00 | C |
| ATOM | 558 | N | SER | M | 208 | 1.997 | −23.392 | 21.748 | 1.00 | 0.00 | N |
| ATOM | 559 | CA | SER | M | 208 | 3.280 | −23.736 | 22.372 | 1.00 | 0.00 | C |
| ATOM | 560 | C | SER | M | 208 | 4.455 | −23.617 | 21.403 | 1.00 | 0.00 | C |
| ATOM | 561 | O | SER | M | 208 | 5.522 | −23.154 | 21.783 | 1.00 | 0.00 | O |
| ATOM | 562 | CB | SER | M | 208 | 3.290 | −25.118 | 23.033 | 1.00 | 0.00 | C |
| ATOM | 563 | OG | SER | M | 208 | 3.107 | −26.159 | 22.078 | 1.00 | 0.00 | O |
| ATOM | 564 | N | LEU | M | 209 | 4.216 | −24.105 | 20.122 | 1.00 | 0.00 | N |
| ATOM | 565 | CA | LEU | M | 209 | 5.240 | −24.173 | 19.081 | 1.00 | 0.00 | C |
| ATOM | 566 | C | LEU | M | 209 | 6.054 | −22.878 | 19.001 | 1.00 | 0.00 | C |
| ATOM | 567 | O | LEU | M | 209 | 7.275 | −22.927 | 18.919 | 1.00 | 0.00 | O |
| ATOM | 568 | CB | LEU | M | 209 | 4.615 | −24.547 | 17.722 | 1.00 | 0.00 | C |
| ATOM | 569 | CG | LEU | M | 209 | 5.609 | −24.789 | 16.570 | 1.00 | 0.00 | C |
| ATOM | 570 | CD1 | LEU | M | 209 | 6.590 | −25.923 | 16.871 | 1.00 | 0.00 | C |
| ATOM | 571 | CD2 | LEU | M | 209 | 4.831 | −25.116 | 15.295 | 1.00 | 0.00 | C |
| ATOM | 572 | N | ARG | M | 210 | 5.314 | −21.695 | 19.000 | 1.00 | 0.00 | N |
| ATOM | 573 | CA | ARG | M | 210 | 5.938 | −20.386 | 18.796 | 1.00 | 0.00 | C |
| ATOM | 574 | C | ARG | M | 210 | 7.094 | −20.160 | 19.780 | 1.00 | 0.00 | C |
| ATOM | 575 | O | ARG | M | 210 | 8.194 | −19.788 | 19.390 | 1.00 | 0.00 | O |
| ATOM | 576 | CB | ARG | M | 210 | 4.919 | −19.217 | 18.766 | 1.00 | 0.00 | C |
| ATOM | 577 | CG | ARG | M | 210 | 4.539 | −18.617 | 20.123 | 1.00 | 0.00 | C |
| ATOM | 578 | CD | ARG | M | 210 | 3.368 | −17.645 | 20.037 | 1.00 | 0.00 | C |
| ATOM | 579 | NE | ARG | M | 210 | 3.204 | −16.963 | 21.336 | 1.00 | 0.00 | N |
| ATOM | 580 | CZ | ARG | M | 210 | 2.675 | −17.521 | 22.478 | 1.00 | 0.00 | C |
| ATOM | 581 | NH1 | ARG | M | 210 | 2.108 | −18.771 | 22.534 | 1.00 | 0.00 | N |
| ATOM | 582 | NH2 | ARG | M | 210 | 2.702 | −16.823 | 23.658 | 1.00 | 0.00 | N |
| ATOM | 583 | N | LEU | M | 211 | 6.766 | −20.348 | 21.118 | 1.00 | 0.00 | N |
| ATOM | 584 | CA | LEU | M | 211 | 7.668 | −19.970 | 22.201 | 1.00 | 0.00 | C |
| ATOM | 585 | C | LEU | M | 211 | 8.744 | −21.017 | 22.457 | 1.00 | 0.00 | C |
| ATOM | 586 | O | LEU | M | 211 | 9.830 | −20.675 | 22.903 | 1.00 | 0.00 | O |
| ATOM | 587 | CB | LEU | M | 211 | 6.921 | −19.556 | 23.477 | 1.00 | 0.00 | C |
| ATOM | 588 | CG | LEU | M | 211 | 6.253 | −20.691 | 24.283 | 1.00 | 0.00 | C |
| ATOM | 589 | CD1 | LEU | M | 211 | 7.071 | −21.031 | 25.529 | 1.00 | 0.00 | C |
| ATOM | 590 | CD2 | LEU | M | 211 | 4.828 | −20.304 | 24.668 | 1.00 | 0.00 | C |
| ATOM | 591 | N | PHE | M | 212 | 8.395 | −22.335 | 22.194 | 1.00 | 0.00 | N |
| ATOM | 592 | CA | PHE | M | 212 | 9.343 | −23.437 | 22.323 | 1.00 | 0.00 | C |
| ATOM | 593 | C | PHE | M | 212 | 10.537 | −23.177 | 21.400 | 1.00 | 0.00 | C |
| ATOM | 594 | O | PHE | M | 212 | 11.684 | −23.308 | 21.810 | 1.00 | 0.00 | O |
| ATOM | 595 | CB | PHE | M | 212 | 8.657 | −24.790 | 22.053 | 1.00 | 0.00 | C |
| ATOM | 596 | CG | PHE | M | 212 | 9.531 | −26.001 | 22.266 | 1.00 | 0.00 | C |
| ATOM | 597 | CD1 | PHE | M | 212 | 9.585 | −27.015 | 21.279 | 1.00 | 0.00 | C |
| ATOM | 598 | CD2 | PHE | M | 212 | 10.273 | −26.176 | 23.463 | 1.00 | 0.00 | C |
| ATOM | 599 | CE1 | PHE | M | 212 | 10.360 | −28.171 | 21.483 | 1.00 | 0.00 | C |
| ATOM | 600 | CE2 | PHE | M | 212 | 11.054 | −27.328 | 23.659 | 1.00 | 0.00 | C |
| ATOM | 601 | CZ | PHE | M | 212 | 11.095 | −28.324 | 22.671 | 1.00 | 0.00 | C |
| ATOM | 602 | N | GLY | M | 213 | 10.213 | −22.782 | 20.106 | 1.00 | 0.00 | N |
| ATOM | 603 | CA | GLY | M | 213 | 11.222 | −22.358 | 19.149 | 1.00 | 0.00 | C |
| ATOM | 604 | C | GLY | M | 213 | 12.077 | −21.244 | 19.726 | 1.00 | 0.00 | C |
| ATOM | 605 | O | GLY | M | 213 | 13.296 | −21.353 | 19.773 | 1.00 | 0.00 | O |
| ATOM | 606 | N | ASN | M | 214 | 11.360 | −20.130 | 20.149 | 1.00 | 0.00 | N |
| ATOM | 607 | CA | ASN | M | 214 | 12.007 | −18.898 | 20.604 | 1.00 | 0.00 | C |
| ATOM | 608 | C | ASN | M | 214 | 13.063 | −19.144 | 21.674 | 1.00 | 0.00 | C |
| ATOM | 609 | O | ASN | M | 214 | 14.176 | −18.654 | 21.546 | 1.00 | 0.00 | O |
| ATOM | 610 | CB | ASN | M | 214 | 11.001 | −17.841 | 21.083 | 1.00 | 0.00 | C |
| ATOM | 611 | CG | ASN | M | 214 | 11.704 | −16.606 | 21.615 | 1.00 | 0.00 | C |
| ATOM | 612 | OD1 | ASN | M | 214 | 11.859 | −16.419 | 22.813 | 1.00 | 0.00 | O |
| ATOM | 613 | ND2 | ASN | M | 214 | 12.177 | −15.754 | 20.643 | 1.00 | 0.00 | N |
| ATOM | 614 | N | GLN | M | 252 | 6.092 | −15.258 | 27.574 | 1.00 | 0.00 | N |
| ATOM | 615 | CA | GLN | M | 252 | 5.399 | −15.988 | 26.508 | 1.00 | 0.00 | C |
| ATOM | 616 | C | GLN | M | 252 | 4.487 | −17.062 | 27.109 | 1.00 | 0.00 | C |

TABLE 4-continued

| ATOM | 617 | O | GLN | M | 252 | 3.343 | −17.209 | 26.701 | 1.00 | 0.00 | O |
|---|---|---|---|---|---|---|---|---|---|---|---|
| ATOM | 618 | CB | GLN | M | 252 | 6.348 | −16.641 | 25.488 | 1.00 | 0.00 | C |
| ATOM | 619 | CG | GLN | M | 252 | 7.165 | −15.662 | 24.639 | 1.00 | 0.00 | C |
| ATOM | 620 | CD | GLN | M | 252 | 6.294 | −14.812 | 23.745 | 1.00 | 0.00 | C |
| ATOM | 621 | OE1 | GLN | M | 252 | 5.949 | −13.685 | 24.069 | 1.00 | 0.00 | O |
| ATOM | 622 | NE2 | GLN | M | 252 | 5.911 | −15.431 | 22.578 | 1.00 | 0.00 | N |
| ATOM | 623 | N | ILE | M | 255 | 1.315 | −15.654 | 28.673 | 1.00 | 0.00 | N |
| ATOM | 624 | CA | ILE | M | 255 | 0.314 | −15.323 | 27.648 | 1.00 | 0.00 | C |
| ATOM | 625 | C | ILE | M | 255 | −0.456 | −16.594 | 27.270 | 1.00 | 0.00 | C |
| ATOM | 626 | O | ILE | M | 255 | −1.677 | −16.562 | 27.206 | 1.00 | 0.00 | O |
| ATOM | 627 | CB | ILE | M | 255 | 0.899 | −14.600 | 26.397 | 1.00 | 0.00 | C |
| ATOM | 628 | CG1 | ILE | M | 255 | 1.511 | −13.217 | 26.721 | 1.00 | 0.00 | C |
| ATOM | 629 | CG2 | ILE | M | 255 | −0.132 | −14.462 | 25.269 | 1.00 | 0.00 | C |
| ATOM | 630 | CD1 | ILE | M | 255 | 0.539 | −12.178 | 27.265 | 1.00 | 0.00 | C |
| ATOM | 631 | N | PHE | M | 256 | 0.309 | −17.724 | 26.987 | 1.00 | 0.00 | N |
| ATOM | 632 | CA | PHE | M | 256 | −0.300 | −19.014 | 26.640 | 1.00 | 0.00 | C |
| ATOM | 633 | C | PHE | M | 256 | −1.370 | −19.377 | 27.673 | 1.00 | 0.00 | C |
| ATOM | 634 | O | PHE | M | 256 | −2.501 | −19.676 | 27.309 | 1.00 | 0.00 | O |
| ATOM | 635 | CB | PHE | M | 256 | 0.741 | −20.143 | 26.468 | 1.00 | 0.00 | C |
| ATOM | 636 | CG | PHE | M | 256 | 0.139 | −21.530 | 26.434 | 1.00 | 0.00 | C |
| ATOM | 637 | CD1 | PHE | M | 256 | 0.410 | −22.456 | 27.472 | 1.00 | 0.00 | C |
| ATOM | 638 | CD2 | PHE | M | 256 | −0.735 | −21.920 | 25.391 | 1.00 | 0.00 | C |
| ATOM | 639 | CE1 | PHE | M | 256 | −0.169 | −23.740 | 27.459 | 1.00 | 0.00 | C |
| ATOM | 640 | CE2 | PHE | M | 256 | −1.314 | −23.203 | 25.379 | 1.00 | 0.00 | C |
| ATOM | 641 | CZ | PHE | M | 256 | −1.029 | −24.114 | 26.412 | 1.00 | 0.00 | C |
| ATOM | 642 | N | LEU | M | 259 | −4.533 | −17.251 | 27.581 | 1.00 | 0.00 | N |
| ATOM | 643 | CA | LEU | M | 259 | −5.286 | −17.370 | 26.332 | 1.00 | 0.00 | C |
| ATOM | 644 | C | LEU | M | 259 | −6.190 | −18.597 | 26.384 | 1.00 | 0.00 | C |
| ATOM | 645 | O | LEU | M | 259 | −7.382 | −18.501 | 26.120 | 1.00 | 0.00 | O |
| ATOM | 646 | CB | LEU | M | 259 | −4.356 | −17.357 | 25.099 | 1.00 | 0.00 | C |
| ATOM | 647 | CG | LEU | M | 259 | −5.088 | −17.225 | 23.745 | 1.00 | 0.00 | C |
| ATOM | 648 | CD1 | LEU | M | 259 | −4.218 | −16.458 | 22.749 | 1.00 | 0.00 | C |
| ATOM | 649 | CD2 | LEU | M | 259 | −5.448 | −18.586 | 23.146 | 1.00 | 0.00 | C |

TABLE 5

| ATOM | 1 | N | ALA | A | 21 | 5.881 | −12.842 | −1.403 | 1.00 | 0.00 | N |
|---|---|---|---|---|---|---|---|---|---|---|---|
| ATOM | 2 | CA | ALA | A | 21 | 5.032 | −12.962 | −0.219 | 1.00 | 0.00 | C |
| ATOM | 3 | C | ALA | A | 21 | 3.724 | −12.190 | −0.393 | 1.00 | 0.00 | C |
| ATOM | 4 | O | ALA | A | 21 | 2.644 | −12.753 | −0.261 | 1.00 | 0.00 | O |
| ATOM | 5 | CB | ALA | A | 21 | 5.743 | −12.524 | 1.061 | 1.00 | 0.00 | C |
| ATOM | 6 | N | ILE | A | 22 | 3.865 | −10.830 | −0.654 | 1.00 | 0.00 | N |
| ATOM | 7 | CA | ILE | A | 22 | 2.696 | −9.942 | −0.707 | 1.00 | 0.00 | C |
| ATOM | 8 | C | ILE | A | 22 | 1.780 | −10.304 | −1.877 | 1.00 | 0.00 | C |
| ATOM | 9 | O | ILE | A | 22 | 0.564 | −10.249 | −1.742 | 1.00 | 0.00 | O |
| ATOM | 10 | CB | ILE | A | 22 | 3.012 | −8.420 | −0.634 | 1.00 | 0.00 | C |
| ATOM | 11 | CG1 | ILE | A | 22 | 3.808 | −7.845 | −1.829 | 1.00 | 0.00 | C |
| ATOM | 12 | CG2 | ILE | A | 22 | 3.732 | −8.094 | 0.679 | 1.00 | 0.00 | C |
| ATOM | 13 | CD1 | ILE | A | 22 | 2.917 | −7.216 | −2.890 | 1.00 | 0.00 | C |
| ATOM | 14 | N | ALA | A | 24 | 1.317 | −13.263 | −3.458 | 1.00 | 0.00 | N |
| ATOM | 15 | CA | ALA | A | 24 | 0.563 | −14.470 | −3.134 | 1.00 | 0.00 | C |
| ATOM | 16 | C | ALA | A | 24 | −0.656 | −14.135 | −2.280 | 1.00 | 0.00 | C |
| ATOM | 17 | O | ALA | A | 24 | −1.754 | −14.581 | −2.580 | 1.00 | 0.00 | O |
| ATOM | 18 | CB | ALA | A | 24 | 1.423 | −15.525 | −2.443 | 1.00 | 0.00 | C |
| ATOM | 19 | N | GLY | A | 25 | −0.414 | 13.331 | −1.171 | 1.00 | 0.00 | N |
| ATOM | 20 | CA | GLY | A | 25 | −1.450 | −12.972 | −0.212 | 1.00 | 0.00 | C |
| ATOM | 21 | C | GLY | A | 25 | −2.689 | −12.390 | −0.872 | 1.00 | 0.00 | C |
| ATOM | 22 | O | GLY | A | 25 | −3.799 | −12.857 | −0.647 | 1.00 | 0.00 | O |
| ATOM | 23 | N | LEU | A | 59 | −1.069 | −19.335 | −3.710 | 1.00 | 0.00 | N |
| ATOM | 24 | CA | LEU | A | 59 | −0.138 | −19.537 | −2.599 | 1.00 | 0.00 | C |
| ATOM | 25 | C | LEU | A | 59 | 1.257 | −19.890 | −3.118 | 1.00 | 0.00 | C |
| ATOM | 26 | O | LEU | A | 59 | 2.236 | −19.287 | −2.700 | 1.00 | 0.00 | O |
| ATOM | 27 | CB | LEU | A | 59 | −0.654 | −20.593 | −1.599 | 1.00 | 0.00 | C |
| ATOM | 28 | CG | LEU | A | 59 | 0.253 | −20.834 | −0.375 | 1.00 | 0.00 | C |
| ATOM | 29 | CD1 | LEU | A | 59 | 0.412 | −19.583 | 0.489 | 1.00 | 0.00 | C |
| ATOM | 30 | CD2 | LEU | A | 59 | −0.317 | −21.972 | 0.469 | 1.00 | 0.00 | C |
| ATOM | 31 | N | ILE | K | 16 | 10.647 | −2.985 | 11.484 | 1.00 | 0.00 | N |
| ATOM | 32 | CA | ILE | K | 16 | 9.949 | −4.131 | 12.078 | 1.00 | 0.00 | C |
| ATOM | 33 | C | ILE | K | 16 | 8.633 | −3.639 | 12.688 | 1.00 | 0.00 | C |
| ATOM | 34 | O | ILE | K | 16 | 7.578 | −4.192 | 12.405 | 1.00 | 0.00 | O |
| ATOM | 35 | CB | ILE | K | 16 | 10.839 | −4.911 | 13.092 | 1.00 | 0.00 | C |
| ATOM | 36 | CG1 | ILE | K | 16 | 11.982 | −5.650 | 12.360 | 1.00 | 0.00 | C |
| ATOM | 37 | CG2 | ILE | K | 16 | 10.028 | −5.918 | 13.915 | 1.00 | 0.00 | C |
| ATOM | 38 | CD1 | ILE | K | 16 | 13.158 | −5.961 | 13.274 | 1.00 | 0.00 | C |
| ATOM | 39 | N | GLY | K | 19 | 5.970 | −2.022 | 10.048 | 1.00 | 0.00 | N |
| ATOM | 40 | CA | GLY | K | 19 | 5.412 | −3.072 | 9.210 | 1.00 | 0.00 | C |
| ATOM | 41 | C | GLY | K | 19 | 4.400 | −3.910 | 9.967 | 1.00 | 0.00 | C |

TABLE 5-continued

| | | | | | | | | | | | |
|---|---|---|---|---|---|---|---|---|---|---|---|
| ATOM | 42 | O | GLY | K | 19 | 3.291 | −4.135 | 9.498 | 1.00 | 0.00 | O |
| ATOM | 43 | N | GLY | K | 20 | 4.855 | −4.394 | 11.185 | 1.00 | 0.00 | N |
| ATOM | 44 | CA | GLY | K | 20 | 4.029 | −5.189 | 12.076 | 1.00 | 0.00 | C |
| ATOM | 45 | C | GLY | K | 20 | 2.705 | −4.513 | 12.381 | 1.00 | 0.00 | C |
| ATOM | 46 | O | GLY | K | 20 | 1.655 | −5.133 | 12.286 | 1.00 | 0.00 | O |
| ATOM | 47 | N | ALA | K | 21 | 2.813 | −3.195 | 12.802 | 1.00 | 0.00 | N |
| ATOM | 48 | CA | ALA | K | 21 | 1.674 | −2.403 | 13.259 | 1.00 | 0.00 | C |
| ATOM | 49 | C | ALA | K | 21 | 0.573 | −2.358 | 12.210 | 1.00 | 0.00 | C |
| ATOM | 50 | O | ALA | K | 21 | −0.571 | −2.687 | 12.496 | 1.00 | 0.00 | O |
| ATOM | 51 | CB | ALA | K | 21 | 2.069 | −0.980 | 13.646 | 1.00 | 0.00 | C |
| ATOM | 52 | N | ILE | K | 22 | 0.959 | −1.866 | 10.968 | 1.00 | 0.00 | N |
| ATOM | 53 | CA | ILE | K | 22 | −0.022 | −1.644 | 9.902 | 1.00 | 0.00 | C |
| ATOM | 54 | C | ILE | K | 22 | −0.648 | −2.967 | 9.462 | 1.00 | 0.00 | C |
| ATOM | 55 | O | ILE | K | 22 | −1.839 | −3.017 | 9.187 | 1.00 | 0.00 | O |
| ATOM | 56 | CB | ILE | K | 22 | 0.471 | −0.759 | 8.721 | 1.00 | 0.00 | C |
| ATOM | 57 | CG1 | ILE | K | 22 | 1.645 | −1.331 | 7.895 | 1.00 | 0.00 | C |
| ATOM | 58 | CG2 | ILE | K | 22 | 0.838 | 0.636 | 9.238 | 1.00 | 0.00 | C |
| ATOM | 59 | CD1 | ILE | K | 22 | 1.196 | −2.128 | 6.680 | 1.00 | 0.00 | C |
| ATOM | 60 | N | GLY | K | 23 | 0.209 | −4.060 | 9.392 | 1.00 | 0.00 | N |
| ATOM | 61 | CA | GLY | K | 23 | −0.252 | −5.389 | 9.028 | 1.00 | 0.00 | C |
| ATOM | 62 | C | GLY | K | 23 | −1.370 | −5.851 | 9.940 | 1.00 | 0.00 | C |
| ATOM | 63 | O | GLY | K | 23 | −2.445 | −6.210 | 9.480 | 1.00 | 0.00 | O |
| ATOM | 64 | N | ALA | K | 24 | −1.045 | −5.828 | 11.290 | 1.00 | 0.00 | N |
| ATOM | 65 | CA | ALA | K | 24 | −1.970 | −6.229 | 12.347 | 1.00 | 0.00 | C |
| ATOM | 66 | C | ALA | K | 24 | −3.298 | −5.486 | 12.227 | 1.00 | 0.00 | C |
| ATOM | 67 | O | ALA | K | 24 | −4.355 | −6.101 | 12.268 | 1.00 | 0.00 | O |
| ATOM | 68 | CB | ALA | K | 24 | −1.374 | −6.022 | 13.737 | 1.00 | 0.00 | C |
| ATOM | 69 | N | GLY | K | 25 | −3.201 | −4.105 | 12.103 | 1.00 | 0.00 | N |
| ATOM | 70 | CA | GLY | K | 25 | −4.358 | −3.224 | 12.066 | 1.00 | 0.00 | C |
| ATOM | 71 | C | GLY | K | 25 | −5.345 | −3.604 | 10.977 | 1.00 | 0.00 | C |
| ATOM | 72 | O | GLY | K | 25 | −6.530 | −3.776 | 11.233 | 1.00 | 0.00 | O |
| ATOM | 73 | N | GLY | K | 27 | −5.390 | −6.420 | 9.296 | 1.00 | 0.00 | N |
| ATOM | 74 | CA | GLY | K | 27 | −5.822 | −7.781 | 9.578 | 1.00 | 0.00 | C |
| ATOM | 75 | C | GLY | K | 27 | −7.102 | −7.831 | 10.391 | 1.00 | 0.00 | C |
| ATOM | 76 | O | GLY | K | 27 | −8.060 | −8.484 | 9.997 | 1.00 | 0.00 | O |
| ATOM | 77 | N | ASP | K | 28 | −7.068 | −7.107 | 11.579 | 1.00 | 0.00 | N |
| ATOM | 78 | CA | ASP | K | 28 | −8.213 | −7.027 | 12.494 | 1.00 | 0.00 | C |
| ATOM | 79 | C | ASP | K | 28 | −9.473 | −6.650 | 11.728 | 1.00 | 0.00 | C |
| ATOM | 80 | O | ASP | K | 28 | −10.504 | −7.289 | 11.892 | 1.00 | 0.00 | O |
| ATOM | 81 | CB | ASP | K | 28 | −8.029 | −6.024 | 13.647 | 1.00 | 0.00 | C |
| ATOM | 82 | CG | ASP | K | 28 | −7.176 | −6.602 | 14.743 | 1.00 | 0.00 | C |
| ATOM | 83 | OD1 | ASP | K | 28 | −5.961 | −6.498 | 14.817 | 1.00 | 0.00 | O |
| ATOM | 84 | OD2 | ASP | K | 28 | −7.934 | −7.314 | 15.613 | 1.00 | 0.00 | O |
| ATOM | 85 | N | ALA | K | 31 | −10.360 | −9.341 | 8.254 | 1.00 | 0.00 | N |
| ATOM | 86 | CA | ALA | K | 31 | −10.695 | −10.710 | 8.645 | 1.00 | 0.00 | C |
| ATOM | 87 | C | ALA | K | 31 | −11.886 | −10.733 | 9.598 | 1.00 | 0.00 | C |
| ATOM | 88 | O | ALA | K | 31 | −12.791 | −11.543 | 9.438 | 1.00 | 0.00 | O |
| ATOM | 89 | CB | ALA | K | 31 | −9.513 | −11.450 | 9.262 | 1.00 | 0.00 | C |
| ATOM | 90 | N | PHE | K | 53 | −11.251 | −14.828 | 19.330 | 1.00 | 0.00 | N |
| ATOM | 91 | CA | PHE | K | 53 | −10.086 | −15.610 | 18.910 | 1.00 | 0.00 | C |
| ATOM | 92 | C | PHE | K | 53 | −9.416 | −14.919 | 17.715 | 1.00 | 0.00 | C |
| ATOM | 93 | O | PHE | K | 53 | −8.214 | −14.687 | 17.727 | 1.00 | 0.00 | O |
| ATOM | 94 | CB | PHE | K | 53 | −10.413 | −17.088 | 18.615 | 1.00 | 0.00 | C |
| ATOM | 95 | CG | PHE | K | 53 | −9.168 | −17.944 | 18.656 | 1.00 | 0.00 | C |
| ATOM | 96 | CD1 | PHE | K | 53 | −8.363 | −18.116 | 17.502 | 1.00 | 0.00 | C |
| ATOM | 97 | CD2 | PHE | K | 53 | −8.769 | −18.572 | 19.864 | 1.00 | 0.00 | C |
| ATOM | 98 | CE1 | PHE | K | 53 | −7.177 | −18.871 | 17.564 | 1.00 | 0.00 | C |
| ATOM | 99 | CE2 | PHE | K | 53 | −7.587 | −19.335 | 19.920 | 1.00 | 0.00 | C |
| ATOM | 100 | CZ | PHE | K | 53 | −6.787 | −19.478 | 18.772 | 1.00 | 0.00 | C |
| ATOM | 101 | N | PHE | K | 54 | −10.253 | −14.602 | 16.650 | 1.00 | 0.00 | N |
| ATOM | 102 | CA | PHE | K | 54 | −9.754 | −13.946 | 15.437 | 1.00 | 0.00 | C |
| ATOM | 103 | C | PHE | K | 54 | −9.027 | −12.653 | 15.816 | 1.00 | 0.00 | C |
| ATOM | 104 | O | PHE | K | 54 | −7.868 | −12.465 | 15.469 | 1.00 | 0.00 | O |
| ATOM | 105 | CB | PHE | K | 54 | −10.857 | −13.644 | 14.396 | 1.00 | 0.00 | C |
| ATOM | 106 | CG | PHE | K | 54 | −11.031 | −14.732 | 13.363 | 1.00 | 0.00 | C |
| ATOM | 107 | CD1 | PHE | K | 54 | −10.657 | −14.497 | 12.014 | 1.00 | 0.00 | C |
| ATOM | 108 | CD2 | PHE | K | 54 | −11.600 | −15.986 | 13.699 | 1.00 | 0.00 | C |
| ATOM | 109 | CE1 | PHE | K | 54 | −10.855 | −15.483 | 11.030 | 1.00 | 0.00 | C |
| ATOM | 110 | CE2 | PHE | K | 54 | −11.796 | −16.971 | 12.711 | 1.00 | 0.00 | C |
| ATOM | 111 | CZ | PHE | K | 54 | −11.427 | −16.719 | 11.377 | 1.00 | 0.00 | C |
| ATOM | 112 | N | ILE | K | 55 | −9.789 | −11.720 | 16.511 | 1.00 | 0.00 | N |
| ATOM | 113 | CA | ILE | K | 55 | −9.296 | −10.359 | 16.735 | 1.00 | 0.00 | C |
| ATOM | 114 | C | ILE | K | 55 | −8.075 | −10.305 | 17.655 | 1.00 | 0.00 | C |
| ATOM | 115 | O | ILE | K | 55 | −7.239 | −9.431 | 17.475 | 1.00 | 0.00 | O |
| ATOM | 116 | CB | ILE | K | 55 | −10.374 | −9.314 | 17.141 | 1.00 | 0.00 | C |
| ATOM | 117 | CG1 | ILE | K | 55 | −11.066 | −9.614 | 18.484 | 1.00 | 0.00 | C |
| ATOM | 118 | CG2 | ILE | K | 55 | −11.397 | −9.148 | 16.011 | 1.00 | 0.00 | C |
| ATOM | 119 | CD1 | ILE | K | 55 | −11.876 | −8.446 | 19.024 | 1.00 | 0.00 | C |
| ATOM | 120 | N | THR | K | 56 | −8.005 | −11.228 | 18.695 | 1.00 | 0.00 | N |
| ATOM | 121 | CA | THR | K | 56 | −6.877 | −11.241 | 19.628 | 1.00 | 0.00 | C |

TABLE 5-continued

| | | | | | | | | | | |
|---|---|---|---|---|---|---|---|---|---|---|
| ATOM | 122 | C | THR | K | 56 | −5.591 | −11.653 | 18.909 | 1.00 | 0.00 | C |
| ATOM | 123 | O | THR | K | 56 | −4.545 | −11.076 | 19.169 | 1.00 | 0.00 | O |
| ATOM | 124 | CB | THR | K | 56 | −7.142 | −12.025 | 20.940 | 1.00 | 0.00 | C |
| ATOM | 125 | OG1 | THR | K | 56 | −6.232 | −11.582 | 21.949 | 1.00 | 0.00 | O |
| ATOM | 126 | CG2 | THR | K | 56 | −6.997 | −13.539 | 20.848 | 1.00 | 0.00 | C |
| ATOM | 127 | N | VAL | K | 57 | −5.684 | −12.700 | 17.993 | 1.00 | 0.00 | N |
| ATOM | 128 | CA | VAL | K | 57 | −4.525 | −13.128 | 17.197 | 1.00 | 0.00 | C |
| ATOM | 129 | C | VAL | K | 57 | −4.015 | −11.905 | 16.430 | 1.00 | 0.00 | C |
| ATOM | 130 | O | VAL | K | 57 | −2.835 | −11.585 | 16.495 | 1.00 | 0.00 | O |
| ATOM | 131 | CB | VAL | K | 57 | −4.821 | −14.346 | 16.278 | 1.00 | 0.00 | C |
| ATOM | 132 | CG1 | VAL | K | 57 | −3.708 | −14.594 | 15.256 | 1.00 | 0.00 | C |
| ATOM | 133 | CG2 | VAL | K | 57 | −5.001 | −15.618 | 17.111 | 1.00 | 0.00 | C |
| ATOM | 134 | N | GLY | K | 58 | −4.974 | −11.224 | 15.688 | 1.00 | 0.00 | N |
| ATOM | 135 | CA | GLY | K | 58 | −4.665 | −10.040 | 14.902 | 1.00 | 0.00 | C |
| ATOM | 136 | C | GLY | K | 58 | −3.915 | −8.999 | 15.716 | 1.00 | 0.00 | C |
| ATOM | 137 | O | GLY | K | 58 | −2.837 | −8.566 | 15.338 | 1.00 | 0.00 | O |
| ATOM | 138 | N | LEU | K | 59 | −4.569 | −8.588 | 16.866 | 1.00 | 0.00 | N |
| ATOM | 139 | CA | LEU | K | 59 | −4.102 | −7.488 | 17.709 | 1.00 | 0.00 | C |
| ATOM | 140 | C | LEU | K | 59 | −2.696 | −7.785 | 18.219 | 1.00 | 0.00 | C |
| ATOM | 141 | O | LEU | K | 59 | −1.786 | −6.994 | 18.011 | 1.00 | 0.00 | O |
| ATOM | 142 | CB | LEU | K | 59 | −5.084 | −7.200 | 18.866 | 1.00 | 0.00 | C |
| ATOM | 143 | CG | LEU | K | 59 | −4.667 | −6.055 | 19.810 | 1.00 | 0.00 | C |
| ATOM | 144 | CD1 | LEU | K | 59 | −4.617 | −4.705 | 19.094 | 1.00 | 0.00 | C |
| ATOM | 145 | CD2 | LEU | K | 59 | −5.640 | −5.983 | 20.985 | 1.00 | 0.00 | C |
| ATOM | 146 | N | VAL | K | 60 | −2.575 | −8.958 | 18.956 | 1.00 | 0.00 | N |
| ATOM | 147 | CA | VAL | K | 60 | −1.376 | −9.313 | 19.723 | 1.00 | 0.00 | C |
| ATOM | 148 | C | VAL | K | 60 | −0.172 | −9.621 | 18.808 | 1.00 | 0.00 | C |
| ATOM | 149 | O | VAL | K | 60 | 0.965 | −9.587 | 19.262 | 1.00 | 0.00 | O |
| ATOM | 150 | CB | VAL | K | 60 | −1.666 | −10.425 | 20.774 | 1.00 | 0.00 | C |
| ATOM | 151 | CG1 | VAL | K | 60 | −0.436 | −10.797 | 21.603 | 1.00 | 0.00 | C |
| ATOM | 152 | CG2 | VAL | K | 60 | −2.756 | −9.980 | 21.761 | 1.00 | 0.00 | C |
| ATOM | 153 | N | GLU | K | 61 | −0.439 | −9.875 | 17.464 | 1.00 | 0.00 | N |
| ATOM | 154 | CA | GLU | K | 61 | 0.617 | −9.928 | 16.448 | 1.00 | 0.00 | C |
| ATOM | 155 | C | GLU | K | 61 | 1.600 | −8.765 | 16.629 | 1.00 | 0.00 | C |
| ATOM | 156 | O | GLU | K | 61 | 2.806 | −8.976 | 16.643 | 1.00 | 0.00 | O |
| ATOM | 157 | CB | GLU | K | 61 | 0.048 | −9.957 | 15.018 | 1.00 | 0.00 | C |
| ATOM | 158 | CG | GLU | K | 61 | 1.116 | −10.204 | 13.955 | 1.00 | 0.00 | C |
| ATOM | 159 | CD | GLU | K | 61 | 0.480 | −10.239 | 12.589 | 1.00 | 0.00 | C |
| ATOM | 160 | OE1 | GLU | K | 61 | 0.270 | −9.258 | 11.891 | 1.00 | 0.00 | O |
| ATOM | 161 | OE2 | GLU | K | 61 | 0.106 | −11.500 | 12.255 | 1.00 | 0.00 | O |
| ATOM | 162 | N | ALA | K | 62 | 1.026 | −7.499 | 16.735 | 1.00 | 0.00 | N |
| ATOM | 163 | CA | ALA | K | 62 | 1.838 | −6.288 | 16.832 | 1.00 | 0.00 | C |
| ATOM | 164 | C | ALA | K | 62 | 2.817 | −6.381 | 18.011 | 1.00 | 0.00 | C |
| ATOM | 165 | O | ALA | K | 62 | 4.014 | −6.325 | 17.766 | 1.00 | 0.00 | O |
| ATOM | 166 | CB | ALA | K | 62 | 1.026 | −4.994 | 16.802 | 1.00 | 0.00 | C |
| ATOM | 167 | N | TYR | K | 64 | 4.143 | −8.947 | 19.533 | 1.00 | 0.00 | N |
| ATOM | 168 | CA | TYR | K | 64 | 5.238 | −9.901 | 19.299 | 1.00 | 0.00 | C |
| ATOM | 169 | C | TYR | K | 64 | 6.411 | −9.187 | 18.617 | 1.00 | 0.00 | C |
| ATOM | 170 | O | TYR | K | 64 | 7.549 | −9.293 | 19.057 | 1.00 | 0.00 | O |
| ATOM | 171 | CB | TYR | K | 64 | 4.859 | −11.158 | 18.485 | 1.00 | 0.00 | C |
| ATOM | 172 | CG | TYR | K | 64 | 3.743 | −12.009 | 19.045 | 1.00 | 0.00 | C |
| ATOM | 173 | CD1 | TYR | K | 64 | 3.591 | −12.248 | 20.436 | 1.00 | 0.00 | C |
| ATOM | 174 | CD2 | TYR | K | 64 | 2.826 | −12.617 | 18.151 | 1.00 | 0.00 | C |
| ATOM | 175 | CE1 | TYR | K | 64 | 2.524 | −13.026 | 20.919 | 1.00 | 0.00 | C |
| ATOM | 176 | CE2 | TYR | K | 64 | 1.754 | −13.394 | 18.625 | 1.00 | 0.00 | C |
| ATOM | 177 | CZ | TYR | K | 64 | 1.603 | −13.582 | 20.014 | 1.00 | 0.00 | C |
| ATOM | 178 | OH | TYR | K | 64 | 0.533 | −14.296 | 20.528 | 1.00 | 0.00 | O |
| ATOM | 179 | N | PHE | K | 65 | 6.092 | −8.473 | 17.468 | 1.00 | 0.00 | N |
| ATOM | 180 | CA | PHE | K | 65 | 7.112 | −7.764 | 16.688 | 1.00 | 0.00 | C |
| ATOM | 181 | C | PHE | K | 65 | 7.701 | −6.560 | 17.423 | 1.00 | 0.00 | C |
| ATOM | 182 | O | PHE | K | 65 | 8.869 | −6.250 | 17.232 | 1.00 | 0.00 | O |
| ATOM | 183 | CB | PHE | K | 65 | 6.605 | −7.346 | 15.295 | 1.00 | 0.00 | C |
| ATOM | 184 | CG | PHE | K | 65 | 6.399 | −8.550 | 14.405 | 1.00 | 0.00 | C |
| ATOM | 185 | CD1 | PHE | K | 65 | 7.512 | −9.293 | 13.931 | 1.00 | 0.00 | C |
| ATOM | 186 | CE1 | PHE | K | 65 | 7.321 | −10.463 | 13.174 | 1.00 | 0.00 | C |
| ATOM | 187 | CZ | PHE | K | 65 | 6.021 | −10.897 | 12.868 | 1.00 | 0.00 | C |
| ATOM | 188 | CE2 | PHE | K | 65 | 4.911 | −10.153 | 13.301 | 1.00 | 0.00 | C |
| ATOM | 189 | CD2 | PHE | K | 65 | 5.096 | −8.983 | 14.061 | 1.00 | 0.00 | C |
| ATOM | 190 | N | ILE | K | 66 | 6.849 | −5.852 | 18.262 | 1.00 | 0.00 | N |
| ATOM | 191 | CA | ILE | K | 66 | 7.323 | −4.737 | 19.093 | 1.00 | 0.00 | C |
| ATOM | 192 | C | ILE | K | 66 | 8.436 | −5.275 | 19.995 | 1.00 | 0.00 | C |
| ATOM | 193 | O | ILE | K | 66 | 9.510 | −4.692 | 20.045 | 1.00 | 0.00 | O |
| ATOM | 194 | CB | ILE | K | 66 | 6.205 | −4.010 | 19.896 | 1.00 | 0.00 | C |
| ATOM | 195 | CG1 | ILE | K | 66 | 5.194 | −3.331 | 18.944 | 1.00 | 0.00 | C |
| ATOM | 196 | CG2 | ILE | K | 66 | 6.795 | −2.959 | 20.847 | 1.00 | 0.00 | C |
| ATOM | 197 | CD1 | ILE | K | 66 | 3.915 | −2.888 | 19.641 | 1.00 | 0.00 | C |
| ATOM | 198 | N | ASN | K | 67 | 8.135 | −6.412 | 20.737 | 1.00 | 0.00 | N |
| ATOM | 199 | CA | ASN | K | 67 | 9.101 | −7.043 | 21.643 | 1.00 | 0.00 | C |
| ATOM | 200 | C | ASN | K | 67 | 10.396 | −7.398 | 20.922 | 1.00 | 0.00 | C |
| ATOM | 201 | O | ASN | K | 67 | 11.470 | −7.186 | 21.466 | 1.00 | 0.00 | O |

TABLE 5-continued

| | | | | | | | | | | | |
|---|---|---|---|---|---|---|---|---|---|---|---|
| ATOM | 202 | CB | ASN | K | 67 | 8.561 | −8.295 | 22.359 | 1.00 | 0.00 | C |
| ATOM | 203 | CG | ASN | K | 67 | 7.789 | −7.913 | 23.607 | 1.00 | 0.00 | C |
| ATOM | 204 | OD1 | ASN | K | 67 | 6.585 | −7.703 | 23.596 | 1.00 | 0.00 | O |
| ATOM | 205 | ND2 | ASN | K | 67 | 8.574 | −7.784 | 24.731 | 1.00 | 0.00 | N |
| ATOM | 206 | N | LEU | K | 68 | 10.265 | −8.000 | 19.676 | 1.00 | 0.00 | N |
| ATOM | 207 | CA | LEU | K | 68 | 11.425 | −8.412 | 18.874 | 1.00 | 0.00 | C |
| ATOM | 208 | C | LEU | K | 68 | 12.356 | −7.211 | 18.673 | 1.00 | 0.00 | C |
| ATOM | 209 | O | LEU | K | 68 | 13.544 | −7.283 | 18.962 | 1.00 | 0.00 | O |
| ATOM | 210 | CB | LEU | K | 68 | 11.000 | −9.085 | 17.550 | 1.00 | 0.00 | C |
| ATOM | 211 | CG | LEU | K | 68 | 12.106 | −9.924 | 16.872 | 1.00 | 0.00 | C |
| ATOM | 212 | CD1 | LEU | K | 68 | 11.478 | −11.029 | 16.022 | 1.00 | 0.00 | C |
| ATOM | 213 | CD2 | LEU | K | 68 | 13.020 | −9.082 | 15.983 | 1.00 | 0.00 | C |
| ATOM | 214 | N | GLY | L | 14 | 15.198 | −8.074 | 9.311 | 1.00 | 0.00 | N |
| ATOM | 215 | CA | GLY | L | 14 | 14.066 | −7.197 | 9.559 | 1.00 | 0.00 | C |
| ATOM | 216 | C | GLY | L | 14 | 12.995 | −7.318 | 8.489 | 1.00 | 0.00 | C |
| ATOM | 217 | O | GLY | L | 14 | 11.827 | −7.504 | 8.800 | 1.00 | 0.00 | O |
| ATOM | 218 | N | ILE | L | 16 | 12.564 | −9.668 | 6.039 | 1.00 | 0.00 | N |
| ATOM | 219 | CA | ILE | L | 16 | 11.972 | −10.997 | 5.849 | 1.00 | 0.00 | C |
| ATOM | 220 | C | ILE | L | 16 | 10.872 | −11.230 | 6.896 | 1.00 | 0.00 | C |
| ATOM | 221 | O | ILE | L | 16 | 9.821 | −11.769 | 6.579 | 1.00 | 0.00 | O |
| ATOM | 222 | CB | ILE | L | 16 | 13.034 | −12.140 | 5.737 | 1.00 | 0.00 | C |
| ATOM | 223 | CG1 | ILE | L | 16 | 12.723 | −13.142 | 4.605 | 1.00 | 0.00 | C |
| ATOM | 224 | CG2 | ILE | L | 16 | 13.344 | −12.873 | 7.046 | 1.00 | 0.00 | C |
| ATOM | 225 | CD1 | ILE | L | 16 | 11.458 | −13.971 | 4.775 | 1.00 | 0.00 | C |
| ATOM | 226 | N | MET | L | 17 | 11.163 | −10.818 | 8.193 | 1.00 | 0.00 | N |
| ATOM | 227 | CA | MET | L | 17 | 10.196 | −10.952 | 9.281 | 1.00 | 0.00 | C |
| ATOM | 228 | C | MET | L | 17 | 8.956 | −10.129 | 8.951 | 1.00 | 0.00 | C |
| ATOM | 229 | O | MET | L | 17 | 7.865 | −10.675 | 8.862 | 1.00 | 0.00 | O |
| ATOM | 230 | CB | MET | L | 17 | 10.759 | −10.564 | 10.663 | 1.00 | 0.00 | C |
| ATOM | 231 | CG | MET | L | 17 | 11.766 | −11.566 | 11.230 | 1.00 | 0.00 | C |
| ATOM | 232 | SD | MET | L | 17 | 10.949 | −13.111 | 11.753 | 1.00 | 0.00 | S |
| ATOM | 233 | CE | MET | L | 17 | 11.549 | −14.216 | 10.448 | 1.00 | 0.00 | C |
| ATOM | 234 | N | ALA | L | 18 | 9.158 | −8.765 | 8.795 | 1.00 | 0.00 | N |
| ATOM | 235 | CA | ALA | L | 18 | 8.046 | −7.822 | 8.702 | 1.00 | 0.00 | C |
| ATOM | 236 | C | ALA | L | 18 | 7.152 | −8.180 | 7.521 | 1.00 | 0.00 | C |
| ATOM | 237 | O | ALA | L | 18 | 5.979 | −8.477 | 7.692 | 1.00 | 0.00 | O |
| ATOM | 238 | CB | ALA | L | 18 | 8.510 | −6.370 | 8.625 | 1.00 | 0.00 | C |
| ATOM | 239 | N | GLY | L | 19 | 7.766 | −8.127 | 6.279 | 1.00 | 0.00 | N |
| ATOM | 240 | CA | GLY | L | 19 | 7.039 | −8.324 | 5.037 | 1.00 | 0.00 | C |
| ATOM | 241 | C | GLY | L | 19 | 6.426 | −9.707 | 4.980 | 1.00 | 0.00 | C |
| ATOM | 242 | O | GLY | L | 19 | 5.227 | −9.857 | 4.788 | 1.00 | 0.00 | O |
| ATOM | 243 | N | GLY | L | 20 | 7.342 | −10.737 | 5.121 | 1.00 | 0.00 | N |
| ATOM | 244 | CA | GLY | L | 20 | 7.000 | −12.131 | 4.906 | 1.00 | 0.00 | C |
| ATOM | 245 | C | GLY | L | 20 | 5.877 | −12.608 | 5.802 | 1.00 | 0.00 | C |
| ATOM | 246 | O | GLY | L | 20 | 4.881 | −13.136 | 5.327 | 1.00 | 0.00 | O |
| ATOM | 247 | N | ALA | L | 21 | 6.105 | −12.439 | 7.161 | 1.00 | 0.00 | N |
| ATOM | 248 | CA | ALA | L | 21 | 5.177 | −12.957 | 8.167 | 1.00 | 0.00 | C |
| ATOM | 249 | C | ALA | L | 21 | 3.795 | −12.317 | 8.072 | 1.00 | 0.00 | C |
| ATOM | 250 | O | ALA | L | 21 | 2.795 | −12.996 | 8.255 | 1.00 | 0.00 | O |
| ATOM | 251 | CB | ALA | L | 21 | 5.700 | −12.806 | 9.589 | 1.00 | 0.00 | C |
| ATOM | 252 | N | ILE | L | 22 | 3.756 | −10.947 | 7.836 | 1.00 | 0.00 | N |
| ATOM | 253 | CA | ILE | L | 22 | 2.476 | −10.243 | 7.663 | 1.00 | 0.00 | C |
| ATOM | 254 | C | ILE | L | 22 | 1.766 | −10.786 | 6.419 | 1.00 | 0.00 | C |
| ATOM | 255 | O | ILE | L | 22 | 0.554 | −10.946 | 6.440 | 1.00 | 0.00 | O |
| ATOM | 256 | CB | ILE | L | 22 | 2.626 | −8.694 | 7.709 | 1.00 | 0.00 | C |
| ATOM | 257 | CG1 | ILE | L | 22 | 2.574 | −8.158 | 9.161 | 1.00 | 0.00 | C |
| ATOM | 258 | CG2 | ILE | L | 22 | 1.550 | −7.959 | 6.902 | 1.00 | 0.00 | C |
| ATOM | 259 | CD1 | ILE | L | 22 | 3.547 | −8.791 | 10.144 | 1.00 | 0.00 | C |
| ATOM | 260 | N | GLY | L | 23 | 2.556 | −11.065 | 5.313 | 1.00 | 0.00 | N |
| ATOM | 261 | CA | GLY | L | 23 | 2.039 | −11.727 | 4.122 | 1.00 | 0.00 | C |
| ATOM | 262 | C | GLY | L | 23 | 1.274 | −12.998 | 4.463 | 1.00 | 0.00 | C |
| ATOM | 263 | O | GLY | L | 23 | 0.151 | −13.189 | 4.016 | 1.00 | 0.00 | O |
| ATOM | 264 | N | ALA | L | 24 | 1.957 | −13.889 | 5.281 | 1.00 | 0.00 | N |
| ATOM | 265 | CA | ALA | L | 24 | 1.364 | −15.139 | 5.762 | 1.00 | 0.00 | C |
| ATOM | 266 | C | ALA | L | 24 | 0.049 | −14.890 | 6.499 | 1.00 | 0.00 | C |
| ATOM | 267 | O | ALA | L | 24 | −0.925 | −15.594 | 6.275 | 1.00 | 0.00 | O |
| ATOM | 268 | CB | ALA | L | 24 | 2.317 | −15.935 | 6.650 | 1.00 | 0.00 | C |
| ATOM | 269 | N | GLY | L | 25 | 0.070 | −13.864 | 7.434 | 1.00 | 0.00 | N |
| ATOM | 270 | CA | GLY | L | 25 | −1.089 | −13.467 | 8.219 | 1.00 | 0.00 | C |
| ATOM | 271 | C | GLY | L | 25 | −2.292 | −13.111 | 7.362 | 1.00 | 0.00 | C |
| ATOM | 272 | O | GLY | L | 25 | −3.397 | −13.566 | 7.623 | 1.00 | 0.00 | O |
| ATOM | 273 | N | ILE | L | 26 | −2.031 | −12.218 | 6.329 | 1.00 | 0.00 | N |
| ATOM | 274 | CA | ILE | L | 26 | −3.054 | −11.761 | 5.381 | 1.00 | 0.00 | C |
| ATOM | 275 | C | ILE | L | 26 | −3.674 | −13.003 | 4.743 | 1.00 | 0.00 | C |
| ATOM | 276 | O | ILE | L | 26 | −4.889 | −13.145 | 4.749 | 1.00 | 0.00 | O |
| ATOM | 277 | CB | ILE | L | 26 | −2.514 | −10.752 | 4.324 | 1.00 | 0.00 | C |
| ATOM | 278 | CG1 | ILE | L | 26 | −2.147 | −9.409 | 4.994 | 1.00 | 0.00 | C |
| ATOM | 279 | CG2 | ILE | L | 26 | −3.535 | −10.506 | 3.201 | 1.00 | 0.00 | C |
| ATOM | 280 | CD1 | ILE | L | 26 | −1.217 | −8.554 | 4.146 | 1.00 | 0.00 | C |
| ATOM | 281 | N | GLY | L | 27 | −2.774 | −13.896 | 4.170 | 1.00 | 0.00 | N |

TABLE 5-continued

| | | | | | | | | | | |
|---|---|---|---|---|---|---|---|---|---|---|
| ATOM | 282 | CA | GLY | L | 27 | −3.181 | −15.110 | 3.481 | 1.00 | 0.00 | C |
| ATOM | 283 | C | GLY | L | 27 | −4.140 | −15.936 | 4.316 | 1.00 | 0.00 | C |
| ATOM | 284 | O | GLY | L | 27 | −5.230 | −16.267 | 3.870 | 1.00 | 0.00 | O |
| ATOM | 285 | N | ASP | L | 28 | −3.663 | −16.268 | 5.578 | 1.00 | 0.00 | N |
| ATOM | 286 | CA | ASP | L | 28 | −4.426 | −17.067 | 6.539 | 1.00 | 0.00 | C |
| ATOM | 287 | C | ASP | L | 28 | −5.824 | −16.490 | 6.730 | 1.00 | 0.00 | C |
| ATOM | 288 | O | ASP | L | 28 | −6.793 | −17.235 | 6.725 | 1.00 | 0.00 | O |
| ATOM | 289 | CB | ASP | L | 28 | −3.714 | −17.205 | 7.894 | 1.00 | 0.00 | C |
| ATOM | 290 | CG | ASP | L | 28 | −4.554 | −17.995 | 8.870 | 1.00 | 0.00 | C |
| ATOM | 291 | OD1 | ASP | L | 28 | −5.304 | −17.502 | 9.701 | 1.00 | 0.00 | O |
| ATOM | 292 | OD2 | ASP | L | 28 | −4.426 | −19.331 | 8.666 | 1.00 | 0.00 | O |
| ATOM | 293 | N | GLY | L | 29 | −5.891 | −15.120 | 6.948 | 1.00 | 0.00 | N |
| ATOM | 294 | CA | GLY | L | 29 | −7.140 | −14.419 | 7.187 | 1.00 | 0.00 | C |
| ATOM | 295 | C | GLY | L | 29 | −8.116 | −14.632 | 6.046 | 1.00 | 0.00 | C |
| ATOM | 296 | O | GLY | L | 29 | −9.157 | −15.251 | 6.219 | 1.00 | 0.00 | O |
| ATOM | 297 | N | VAL | L | 30 | −7.724 | −14.059 | 4.844 | 1.00 | 0.00 | N |
| ATOM | 298 | CA | VAL | L | 30 | −8.629 | −13.949 | 3.692 | 1.00 | 0.00 | C |
| ATOM | 299 | C | VAL | L | 30 | −9.094 | −15.327 | 3.208 | 1.00 | 0.00 | C |
| ATOM | 300 | O | VAL | L | 30 | −10.279 | −15.543 | 2.987 | 1.00 | 0.00 | O |
| ATOM | 301 | CB | VAL | L | 30 | −8.106 | −13.054 | 2.531 | 1.00 | 0.00 | C |
| ATOM | 302 | CG1 | VAL | L | 30 | −7.924 | −11.606 | 2.995 | 1.00 | 0.00 | C |
| ATOM | 303 | CG2 | VAL | L | 30 | −6.817 | −13.548 | 1.866 | 1.00 | 0.00 | C |
| ATOM | 304 | N | ALA | L | 31 | −8.091 | −16.272 | 3.023 | 1.00 | 0.00 | N |
| ATOM | 305 | CA | ALA | L | 31 | −8.388 | −17.640 | 2.597 | 1.00 | 0.00 | C |
| ATOM | 306 | C | ALA | L | 31 | −9.244 | −18.351 | 3.642 | 1.00 | 0.00 | C |
| ATOM | 307 | O | ALA | L | 31 | −10.141 | −19.108 | 3.299 | 1.00 | 0.00 | O |
| ATOM | 308 | CB | ALA | L | 31 | −7.130 | −18.455 | 2.312 | 1.00 | 0.00 | C |
| ATOM | 309 | N | GLY | L | 32 | −8.904 | −18.097 | 4.963 | 1.00 | 0.00 | N |
| ATOM | 310 | CA | GLY | L | 32 | −9.633 | −18.628 | 6.099 | 1.00 | 0.00 | C |
| ATOM | 311 | C | GLY | L | 32 | −11.116 | −18.323 | 6.071 | 1.00 | 0.00 | C |
| ATOM | 312 | O | GLY | L | 32 | −11.909 | −19.166 | 6.460 | 1.00 | 0.00 | O |
| ATOM | 313 | N | PHE | L | 53 | −8.496 | −25.187 | 12.274 | 1.00 | 0.00 | N |
| ATOM | 314 | CA | PHE | L | 53 | −8.171 | −23.763 | 12.130 | 1.00 | 0.00 | C |
| ATOM | 315 | C | PHE | L | 53 | −6.890 | −23.457 | 12.911 | 1.00 | 0.00 | C |
| ATOM | 316 | O | PHE | L | 53 | −5.962 | −22.867 | 12.377 | 1.00 | 0.00 | O |
| ATOM | 317 | CB | PHE | L | 53 | −9.326 | −22.816 | 12.515 | 1.00 | 0.00 | C |
| ATOM | 318 | CG | PHE | L | 53 | −8.993 | −21.357 | 12.292 | 1.00 | 0.00 | C |
| ATOM | 319 | CD1 | PHE | L | 53 | −8.825 | −20.842 | 10.980 | 1.00 | 0.00 | C |
| ATOM | 320 | CD2 | PHE | L | 53 | −8.839 | −20.476 | 13.391 | 1.00 | 0.00 | C |
| ATOM | 321 | CE1 | PHE | L | 53 | −8.485 | −19.490 | 10.779 | 1.00 | 0.00 | C |
| ATOM | 322 | CE2 | PHE | L | 53 | −8.500 | −19.125 | 13.186 | 1.00 | 0.00 | C |
| ATOM | 323 | CZ | PHE | L | 53 | −8.317 | −18.634 | 11.882 | 1.00 | 0.00 | C |
| ATOM | 324 | N | PHE | L | 54 | −6.879 | −23.863 | 14.237 | 1.00 | 0.00 | N |
| ATOM | 325 | CA | PHE | L | 54 | −5.791 | −23.484 | 15.142 | 1.00 | 0.00 | C |
| ATOM | 326 | C | PHE | L | 54 | −4.446 | −24.003 | 14.630 | 1.00 | 0.00 | C |
| ATOM | 327 | O | PHE | L | 54 | −3.462 | −23.274 | 14.628 | 1.00 | 0.00 | O |
| ATOM | 328 | CB | PHE | L | 54 | −6.001 | −23.941 | 16.598 | 1.00 | 0.00 | C |
| ATOM | 329 | CG | PHE | L | 54 | −7.288 | −23.500 | 17.265 | 1.00 | 0.00 | C |
| ATOM | 330 | CD1 | PHE | L | 54 | −7.981 | −22.312 | 16.907 | 1.00 | 0.00 | C |
| ATOM | 331 | CD2 | PHE | L | 54 | −7.828 | −24.299 | 18.301 | 1.00 | 0.00 | C |
| ATOM | 332 | CE1 | PHE | L | 54 | −9.188 | −21.961 | 17.539 | 1.00 | 0.00 | C |
| ATOM | 333 | CE2 | PHE | L | 54 | −9.027 | −23.943 | 18.937 | 1.00 | 0.00 | C |
| ATOM | 334 | CZ | PHE | L | 54 | −9.708 | −22.777 | 18.557 | 1.00 | 0.00 | C |
| ATOM | 335 | N | ILE | L | 55 | −4.415 | −25.339 | 14.241 | 1.00 | 0.00 | N |
| ATOM | 336 | CA | ILE | L | 55 | −3.169 | −25.944 | 13.764 | 1.00 | 0.00 | C |
| ATOM | 337 | C | ILE | L | 55 | −2.708 | −25.302 | 12.450 | 1.00 | 0.00 | C |
| ATOM | 338 | O | ILE | L | 55 | −1.515 | −25.103 | 12.267 | 1.00 | 0.00 | O |
| ATOM | 339 | CB | ILE | L | 55 | −3.180 | −27.498 | 13.738 | 1.00 | 0.00 | C |
| ATOM | 340 | CG1 | ILE | L | 55 | −1.738 | −28.049 | 13.695 | 1.00 | 0.00 | C |
| ATOM | 341 | CG2 | ILE | L | 55 | −4.026 | −28.078 | 12.602 | 1.00 | 0.00 | C |
| ATOM | 342 | CD1 | ILE | L | 55 | −1.648 | −29.541 | 13.981 | 1.00 | 0.00 | C |
| ATOM | 343 | N | THR | L | 56 | −3.685 | −25.022 | 11.495 | 1.00 | 0.00 | N |
| ATOM | 344 | CA | THR | L | 56 | −3.324 | −24.487 | 10.182 | 1.00 | 0.00 | C |
| ATOM | 345 | C | THR | L | 56 | −2.776 | −23.057 | 10.234 | 1.00 | 0.00 | C |
| ATOM | 346 | O | THR | L | 56 | −2.032 | −22.682 | 9.339 | 1.00 | 0.00 | O |
| ATOM | 347 | CB | THR | L | 56 | −4.411 | −24.676 | 9.094 | 1.00 | 0.00 | C |
| ATOM | 348 | OG1 | THR | L | 56 | −3.794 | −24.763 | 7.805 | 1.00 | 0.00 | O |
| ATOM | 349 | CG2 | THR | L | 56 | −5.482 | −23.591 | 9.035 | 1.00 | 0.00 | C |
| ATOM | 350 | N | VAL | L | 57 | −3.164 | −22.246 | 11.299 | 1.00 | 0.00 | N |
| ATOM | 351 | CA | VAL | L | 57 | −2.504 | −20.955 | 11.560 | 1.00 | 0.00 | C |
| ATOM | 352 | C | VAL | L | 57 | −0.999 | −21.238 | 11.646 | 1.00 | 0.00 | C |
| ATOM | 353 | O | VAL | L | 57 | −0.210 | −20.630 | 10.934 | 1.00 | 0.00 | O |
| ATOM | 354 | CB | VAL | L | 57 | −3.046 | −20.209 | 12.813 | 1.00 | 0.00 | C |
| ATOM | 355 | CG1 | VAL | L | 57 | −2.177 | −19.007 | 13.193 | 1.00 | 0.00 | C |
| ATOM | 356 | CG2 | VAL | L | 57 | −4.475 | −19.712 | 12.588 | 1.00 | 0.00 | C |
| ATOM | 357 | N | GLY | L | 58 | −0.638 | −22.227 | 12.555 | 1.00 | 0.00 | N |
| ATOM | 358 | CA | GLY | L | 58 | 0.734 | −22.669 | 12.735 | 1.00 | 0.00 | C |
| ATOM | 359 | C | GLY | L | 58 | 1.405 | −23.027 | 11.420 | 1.00 | 0.00 | C |
| ATOM | 360 | O | GLY | L | 58 | 2.484 | −22.536 | 11.126 | 1.00 | 0.00 | O |
| ATOM | 361 | N | LEU | L | 59 | 0.728 | −23.952 | 10.636 | 1.00 | 0.00 | N |

TABLE 5-continued

| ATOM | 362 | CA | LEU | L | 59 | 1.280 | −24.490 | 9.384 | 1.00 | 0.00 | C |
| --- | --- | --- | --- | --- | --- | --- | --- | --- | --- | --- | --- |
| ATOM | 363 | C | LEU | L | 59 | 1.613 | −23.390 | 8.370 | 1.00 | 0.00 | C |
| ATOM | 364 | O | LEU | L | 59 | 2.651 | −23.446 | 7.725 | 1.00 | 0.00 | O |
| ATOM | 365 | CB | LEU | L | 59 | 0.366 | −25.532 | 8.706 | 1.00 | 0.00 | C |
| ATOM | 366 | CG | LEU | L | 59 | 0.194 | −26.846 | 9.498 | 1.00 | 0.00 | C |
| ATOM | 367 | CD1 | LEU | L | 59 | −0.918 | −27.689 | 8.875 | 1.00 | 0.00 | C |
| ATOM | 368 | CD2 | LEU | L | 59 | 1.486 | −27.663 | 9.541 | 1.00 | 0.00 | C |
| ATOM | 369 | N | VAL | L | 60 | 0.655 | −22.399 | 8.202 | 1.00 | 0.00 | N |
| ATOM | 370 | CA | VAL | L | 60 | 0.818 | −21.290 | 7.253 | 1.00 | 0.00 | C |
| ATOM | 371 | C | VAL | L | 60 | 2.049 | −20.455 | 7.640 | 1.00 | 0.00 | C |
| ATOM | 372 | O | VAL | L | 60 | 2.832 | −20.078 | 6.778 | 1.00 | 0.00 | O |
| ATOM | 373 | CB | VAL | L | 60 | −0.480 | −20.445 | 7.107 | 1.00 | 0.00 | C |
| ATOM | 374 | CG1 | VAL | L | 60 | −0.256 | −19.131 | 6.358 | 1.00 | 0.00 | C |
| ATOM | 375 | CG2 | VAL | L | 60 | −1.560 | −21.237 | 6.361 | 1.00 | 0.00 | C |
| ATOM | 376 | N | GLU | L | 61 | 2.172 | −20.129 | 8.986 | 1.00 | 0.00 | N |
| ATOM | 377 | CA | GLU | L | 61 | 3.337 | −19.405 | 9.510 | 1.00 | 0.00 | C |
| ATOM | 378 | C | GLU | L | 61 | 4.651 | −20.199 | 9.436 | 1.00 | 0.00 | C |
| ATOM | 379 | O | GLU | L | 61 | 5.716 | −19.596 | 9.419 | 1.00 | 0.00 | O |
| ATOM | 380 | CB | GLU | L | 61 | 3.138 | −18.941 | 10.962 | 1.00 | 0.00 | C |
| ATOM | 381 | CG | GLU | L | 61 | 2.061 | −17.864 | 11.090 | 1.00 | 0.00 | C |
| ATOM | 382 | CD | GLU | L | 61 | 2.006 | −17.374 | 12.535 | 1.00 | 0.00 | C |
| ATOM | 383 | OE1 | GLU | L | 61 | 1.291 | −18.073 | 13.310 | 1.00 | 0.00 | O |
| ATOM | 384 | OE2 | GLU | L | 61 | 2.715 | −16.364 | 12.786 | 1.00 | 0.00 | O |
| ATOM | 385 | N | ALA | L | 62 | 4.558 | −21.588 | 9.464 | 1.00 | 0.00 | N |
| ATOM | 386 | CA | ALA | L | 62 | 5.692 | −22.469 | 9.740 | 1.00 | 0.00 | C |
| ATOM | 387 | C | ALA | L | 62 | 6.978 | −22.140 | 8.986 | 1.00 | 0.00 | C |
| ATOM | 388 | O | ALA | L | 62 | 8.021 | −22.108 | 9.623 | 1.00 | 0.00 | O |
| ATOM | 389 | CB | ALA | L | 62 | 5.366 | −23.956 | 9.613 | 1.00 | 0.00 | C |
| ATOM | 390 | N | TYR | L | 64 | 8.184 | −19.301 | 7.912 | 1.00 | 0.00 | N |
| ATOM | 391 | CA | TYR | L | 64 | 8.775 | −18.086 | 8.479 | 1.00 | 0.00 | C |
| ATOM | 392 | C | TYR | L | 64 | 9.317 | −18.325 | 9.892 | 1.00 | 0.00 | C |
| ATOM | 393 | O | TYR | L | 64 | 10.332 | −17.753 | 10.266 | 1.00 | 0.00 | O |
| ATOM | 394 | CB | TYR | L | 64 | 7.803 | −16.892 | 8.449 | 1.00 | 0.00 | C |
| ATOM | 395 | CG | TYR | L | 64 | 7.396 | −16.567 | 7.028 | 1.00 | 0.00 | C |
| ATOM | 396 | CD1 | TYR | L | 64 | 8.268 | −15.834 | 6.184 | 1.00 | 0.00 | C |
| ATOM | 397 | CD2 | TYR | L | 64 | 6.169 | −17.040 | 6.496 | 1.00 | 0.00 | C |
| ATOM | 398 | CE1 | TYR | L | 64 | 7.935 | −15.597 | 4.837 | 1.00 | 0.00 | C |
| ATOM | 399 | CE2 | TYR | L | 64 | 5.833 | −16.808 | 5.148 | 1.00 | 0.00 | C |
| ATOM | 400 | CZ | TYR | L | 64 | 6.713 | −16.085 | 4.325 | 1.00 | 0.00 | C |
| ATOM | 401 | OH | TYR | L | 64 | 6.340 | −15.867 | 3.006 | 1.00 | 0.00 | O |
| ATOM | 402 | N | PHE | L | 65 | 8.591 | −19.196 | 10.695 | 1.00 | 0.00 | N |
| ATOM | 403 | CA | PHE | L | 65 | 9.106 | −19.699 | 11.977 | 1.00 | 0.00 | C |
| ATOM | 404 | C | PHE | L | 65 | 10.500 | −20.313 | 11.766 | 1.00 | 0.00 | C |
| ATOM | 405 | O | PHE | L | 65 | 11.435 | −19.983 | 12.486 | 1.00 | 0.00 | O |
| ATOM | 406 | CB | PHE | L | 65 | 8.086 | −20.622 | 12.690 | 1.00 | 0.00 | C |
| ATOM | 407 | CG | PHE | L | 65 | 8.660 | −21.781 | 13.471 | 1.00 | 0.00 | C |
| ATOM | 408 | CD1 | PHE | L | 65 | 9.445 | −21.570 | 14.632 | 1.00 | 0.00 | C |
| ATOM | 409 | CE1 | PHE | L | 65 | 9.992 | −22.664 | 15.330 | 1.00 | 0.00 | C |
| ATOM | 410 | CZ | PHE | L | 65 | 9.742 | −23.979 | 14.897 | 1.00 | 0.00 | C |
| ATOM | 411 | CE2 | PHE | L | 65 | 8.951 | −24.200 | 13.758 | 1.00 | 0.00 | C |
| ATOM | 412 | CD2 | PHE | L | 65 | 8.417 | −23.111 | 13.045 | 1.00 | 0.00 | C |
| ATOM | 413 | N | ILE | L | 66 | 10.602 | −21.255 | 10.746 | 1.00 | 0.00 | N |
| ATOM | 414 | CA | ILE | L | 66 | 11.863 | −21.934 | 10.436 | 1.00 | 0.00 | C |
| ATOM | 415 | C | ILE | L | 66 | 12.921 | −20.880 | 10.109 | 1.00 | 0.00 | C |
| ATOM | 416 | O | ILE | L | 66 | 14.024 | −20.969 | 10.629 | 1.00 | 0.00 | O |
| ATOM | 417 | CB | ILE | L | 66 | 11.743 | −23.027 | 9.333 | 1.00 | 0.00 | C |
| ATOM | 418 | CG1 | ILE | L | 66 | 10.834 | −24.206 | 9.754 | 1.00 | 0.00 | C |
| ATOM | 419 | CG2 | ILE | L | 66 | 13.112 | −23.552 | 8.880 | 1.00 | 0.00 | C |
| ATOM | 420 | CD1 | ILE | L | 66 | 11.332 | −25.031 | 10.935 | 1.00 | 0.00 | C |
| ATOM | 421 | N | ASN | L | 67 | 12.568 | −19.878 | 9.205 | 1.00 | 0.00 | N |
| ATOM | 422 | CA | ASN | L | 67 | 13.514 | −18.826 | 8.807 | 1.00 | 0.00 | C |
| ATOM | 423 | C | ASN | L | 67 | 14.165 | −18.202 | 10.035 | 1.00 | 0.00 | C |
| ATOM | 424 | O | ASN | L | 67 | 15.379 | −18.068 | 10.066 | 1.00 | 0.00 | O |
| ATOM | 425 | CB | ASN | L | 67 | 12.928 | −17.686 | 7.946 | 1.00 | 0.00 | C |
| ATOM | 426 | CG | ASN | L | 67 | 12.679 | −18.089 | 6.508 | 1.00 | 0.00 | C |
| ATOM | 427 | OD1 | ASN | L | 67 | 11.560 | −18.310 | 6.072 | 1.00 | 0.00 | O |
| ATOM | 428 | ND2 | ASN | L | 67 | 13.821 | −18.186 | 5.747 | 1.00 | 0.00 | N |
| ATOM | 429 | N | LEU | L | 68 | 13.303 | −17.783 | 11.044 | 1.00 | 0.00 | N |
| ATOM | 430 | CA | LEU | L | 68 | 13.771 | −17.078 | 12.243 | 1.00 | 0.00 | C |
| ATOM | 431 | C | LEU | L | 68 | 14.883 | −17.907 | 12.894 | 1.00 | 0.00 | C |
| ATOM | 432 | O | LEU | L | 68 | 16.014 | −17.453 | 13.016 | 1.00 | 0.00 | O |
| ATOM | 433 | CB | LEU | L | 68 | 12.610 | −16.759 | 13.216 | 1.00 | 0.00 | C |
| ATOM | 434 | CG | LEU | L | 68 | 12.886 | −15.638 | 14.239 | 1.00 | 0.00 | C |
| ATOM | 435 | CD1 | LEU | L | 68 | 11.590 | −15.292 | 14.973 | 1.00 | 0.00 | C |
| ATOM | 436 | CD2 | LEU | L | 68 | 13.950 | −16.005 | 15.272 | 1.00 | 0.00 | C |
| ATOM | 437 | N | ALA | L | 69 | 14.497 | −19.171 | 13.327 | 1.00 | 0.00 | N |
| ATOM | 438 | CA | ALA | L | 69 | 15.382 | −20.029 | 14.117 | 1.00 | 0.00 | C |
| ATOM | 439 | C | ALA | L | 69 | 16.671 | −20.348 | 13.360 | 1.00 | 0.00 | C |
| ATOM | 440 | O | ALA | L | 69 | 17.761 | −20.262 | 13.911 | 1.00 | 0.00 | O |
| ATOM | 441 | CB | ALA | L | 69 | 14.694 | −21.321 | 14.552 | 1.00 | 0.00 | C |

TABLE 5-continued

| | | | | | | | | | | |
|---|---|---|---|---|---|---|---|---|---|---|
| ATOM | 442 | N | PRO | K | 63 | 2.328 | −6.569 | 19.314 | 1.00 | 0.00 | N |
| ATOM | 443 | CA | PRO | K | 63 | 3.195 | −6.836 | 20.450 | 1.00 | 0.00 | C |
| ATOM | 444 | C | PRO | K | 63 | 4.365 | −7.788 | 20.267 | 1.00 | 0.00 | C |
| ATOM | 445 | O | PRO | K | 63 | 5.439 | −7.509 | 20.781 | 1.00 | 0.00 | O |
| ATOM | 446 | CB | PRO | K | 63 | 2.260 | −7.282 | 21.557 | 1.00 | 0.00 | C |
| ATOM | 447 | CG | PRO | K | 63 | 0.996 | −6.494 | 21.282 | 1.00 | 0.00 | C |
| ATOM | 448 | CD | PRO | K | 63 | 0.991 | −6.259 | 19.780 | 1.00 | 0.00 | C |
| ATOM | 449 | N | PRO | L | 63 | 6.948 | −21.920 | 7.602 | 1.00 | 0.00 | N |
| ATOM | 450 | CA | PRO | L | 63 | 8.151 | −21.540 | 6.873 | 1.00 | 0.00 | C |
| ATOM | 451 | C | PRO | L | 63 | 8.940 | −20.389 | 7.501 | 1.00 | 0.00 | C |
| ATOM | 452 | O | PRO | L | 63 | 10.158 | −20.447 | 7.588 | 1.00 | 0.00 | O |
| ATOM | 453 | CB | PRO | L | 63 | 7.683 | −21.204 | 5.464 | 1.00 | 0.00 | C |
| ATOM | 454 | CG | PRO | L | 63 | 6.402 | −21.994 | 5.304 | 1.00 | 0.00 | C |
| ATOM | 455 | CD | PRO | L | 63 | 5.820 | −22.071 | 6.701 | 1.00 | 0.00 | C |
| ATOM | 456 | N | SER | M | 206 | −1.465 | −25.569 | 20.193 | 1.00 | 0.00 | N |
| ATOM | 457 | CA | SER | M | 206 | −1.251 | −24.467 | 19.250 | 1.00 | 0.00 | C |
| ATOM | 458 | C | SER | M | 206 | −0.394 | −23.364 | 19.890 | 1.00 | 0.00 | C |
| ATOM | 459 | O | SER | M | 206 | 0.590 | −22.924 | 19.311 | 1.00 | 0.00 | O |
| ATOM | 460 | CB | SER | M | 206 | −2.578 | −23.921 | 18.704 | 1.00 | 0.00 | C |
| ATOM | 461 | OG | SER | M | 206 | −2.343 | −22.955 | 17.679 | 1.00 | 0.00 | O |
| ATOM | 462 | N | LEU | M | 207 | −0.835 | −22.896 | 21.123 | 1.00 | 0.00 | N |
| ATOM | 463 | CA | LEU | M | 207 | −0.188 | −21.775 | 21.816 | 1.00 | 0.00 | C |
| ATOM | 464 | C | LEU | M | 207 | 1.276 | −22.088 | 22.145 | 1.00 | 0.00 | C |
| ATOM | 465 | O | LEU | M | 207 | 2.137 | −21.226 | 22.019 | 1.00 | 0.00 | O |
| ATOM | 466 | CB | LEU | M | 207 | −0.942 | −21.337 | 23.093 | 1.00 | 0.00 | C |
| ATOM | 467 | CG | LEU | M | 207 | −2.049 | −20.274 | 22.888 | 1.00 | 0.00 | C |
| ATOM | 468 | CD1 | LEU | M | 207 | −1.457 | −18.899 | 22.585 | 1.00 | 0.00 | C |
| ATOM | 469 | CD2 | LEU | M | 207 | −3.097 | −20.644 | 21.838 | 1.00 | 0.00 | C |
| ATOM | 470 | N | LEU | M | 209 | 3.398 | −23.907 | 20.563 | 1.00 | 0.00 | N |
| ATOM | 471 | CA | LEU | M | 209 | 4.255 | −23.926 | 19.376 | 1.00 | 0.00 | C |
| ATOM | 472 | C | LEU | M | 209 | 5.088 | −22.645 | 19.269 | 1.00 | 0.00 | C |
| ATOM | 473 | O | LEU | M | 209 | 6.295 | −22.716 | 19.078 | 1.00 | 0.00 | O |
| ATOM | 474 | CB | LEU | M | 209 | 3.458 | −24.190 | 18.082 | 1.00 | 0.00 | C |
| ATOM | 475 | CG | LEU | M | 209 | 4.307 | −24.350 | 16.802 | 1.00 | 0.00 | C |
| ATOM | 476 | CD1 | LEU | M | 209 | 5.264 | −25.541 | 16.875 | 1.00 | 0.00 | C |
| ATOM | 477 | CD2 | LEU | M | 209 | 3.386 | −24.506 | 15.593 | 1.00 | 0.00 | C |
| ATOM | 478 | N | ARG | M | 210 | 4.395 | −21.436 | 19.334 | 1.00 | 0.00 | N |
| ATOM | 479 | CA | ARG | M | 210 | 5.121 | −20.192 | 19.071 | 1.00 | 0.00 | C |
| ATOM | 480 | C | ARG | M | 210 | 6.175 | −19.896 | 20.142 | 1.00 | 0.00 | C |
| ATOM | 481 | O | ARG | M | 210 | 7.276 | −19.473 | 19.811 | 1.00 | 0.00 | O |
| ATOM | 482 | CB | ARG | M | 210 | 4.268 | −18.971 | 18.667 | 1.00 | 0.00 | C |
| ATOM | 483 | CG | ARG | M | 210 | 3.638 | −18.112 | 19.768 | 1.00 | 0.00 | C |
| ATOM | 484 | CD | ARG | M | 210 | 2.158 | −18.393 | 20.003 | 1.00 | 0.00 | C |
| ATOM | 485 | NE | ARG | M | 210 | 1.604 | −17.342 | 20.877 | 1.00 | 0.00 | N |
| ATOM | 486 | CZ | ARG | M | 210 | 1.731 | −17.257 | 22.245 | 1.00 | 0.00 | C |
| ATOM | 487 | NH1 | ARG | M | 210 | 2.289 | −18.232 | 23.037 | 1.00 | 0.00 | N |
| ATOM | 488 | NH2 | ARG | M | 210 | 1.286 | −16.136 | 22.899 | 1.00 | 0.00 | N |
| ATOM | 489 | N | LEU | M | 211 | 5.795 | −20.083 | 21.471 | 1.00 | 0.00 | N |
| ATOM | 490 | CA | LEU | M | 211 | 6.734 | −19.803 | 22.567 | 1.00 | 0.00 | C |
| ATOM | 491 | C | LEU | M | 211 | 7.939 | −20.746 | 22.556 | 1.00 | 0.00 | C |
| ATOM | 492 | O | LEU | M | 211 | 9.039 | −20.338 | 22.899 | 1.00 | 0.00 | O |
| ATOM | 493 | CB | LEU | M | 211 | 6.067 | −19.645 | 23.947 | 1.00 | 0.00 | C |
| ATOM | 494 | CG | LEU | M | 211 | 5.526 | −20.909 | 24.642 | 1.00 | 0.00 | C |
| ATOM | 495 | CD1 | LEU | M | 211 | 6.600 | −21.602 | 25.484 | 1.00 | 0.00 | C |
| ATOM | 496 | CD2 | LEU | M | 211 | 4.341 | −20.550 | 25.539 | 1.00 | 0.00 | C |
| ATOM | 497 | N | PHE | M | 212 | 7.680 | −22.052 | 22.157 | 1.00 | 0.00 | N |
| ATOM | 498 | CA | PHE | M | 212 | 8.707 | −23.084 | 21.988 | 1.00 | 0.00 | C |
| ATOM | 499 | C | PHE | M | 212 | 9.819 | −22.550 | 21.076 | 1.00 | 0.00 | C |
| ATOM | 500 | O | PHE | M | 212 | 10.996 | −22.649 | 21.401 | 1.00 | 0.00 | O |
| ATOM | 501 | CB | PHE | M | 212 | 8.068 | −24.391 | 21.469 | 1.00 | 0.00 | C |
| ATOM | 502 | CG | PHE | M | 212 | 9.004 | −25.542 | 21.220 | 1.00 | 0.00 | C |
| ATOM | 503 | CD1 | PHE | M | 212 | 9.208 | −26.025 | 19.902 | 1.00 | 0.00 | C |
| ATOM | 504 | CD2 | PHE | M | 212 | 9.628 | −26.211 | 22.299 | 1.00 | 0.00 | C |
| ATOM | 505 | CE1 | PHE | M | 212 | 10.009 | −27.158 | 19.672 | 1.00 | 0.00 | C |
| ATOM | 506 | CE2 | PHE | M | 212 | 10.431 | −27.339 | 22.062 | 1.00 | 0.00 | C |
| ATOM | 507 | CZ | PHE | M | 212 | 10.625 | −27.813 | 20.752 | 1.00 | 0.00 | C |
| ATOM | 508 | N | GLY | M | 213 | 9.388 | −21.965 | 19.891 | 1.00 | 0.00 | N |
| ATOM | 509 | CA | GLY | M | 213 | 10.301 | −21.336 | 18.951 | 1.00 | 0.00 | C |
| ATOM | 510 | C | GLY | M | 213 | 11.123 | −20.232 | 19.597 | 1.00 | 0.00 | C |
| ATOM | 511 | O | GLY | M | 213 | 12.347 | −20.250 | 19.546 | 1.00 | 0.00 | O |
| ATOM | 512 | N | ASN | M | 214 | 10.364 | −19.229 | 20.191 | 1.00 | 0.00 | N |
| ATOM | 513 | CA | ASN | M | 214 | 10.951 | −17.998 | 20.736 | 1.00 | 0.00 | C |
| ATOM | 514 | C | ASN | M | 214 | 12.113 | −18.295 | 21.676 | 1.00 | 0.00 | C |
| ATOM | 515 | O | ASN | M | 214 | 13.171 | −17.697 | 21.543 | 1.00 | 0.00 | O |
| ATOM | 516 | CB | ASN | M | 214 | 9.942 | −17.090 | 21.468 | 1.00 | 0.00 | C |
| ATOM | 517 | CG | ASN | M | 214 | 9.292 | −16.100 | 20.522 | 1.00 | 0.00 | C |
| ATOM | 518 | OD1 | ASN | M | 214 | 9.826 | −15.042 | 20.224 | 1.00 | 0.00 | O |
| ATOM | 519 | ND2 | ASN | M | 214 | 8.080 | −16.508 | 20.015 | 1.00 | 0.00 | N |
| ATOM | 520 | N | GLN | M | 252 | 5.809 | −14.680 | 27.293 | 1.00 | 0.00 | N |
| ATOM | 521 | CA | GLN | M | 252 | 4.947 | −15.475 | 26.417 | 1.00 | 0.00 | C |

TABLE 5-continued

| ATOM | 522 | C | GLN | M | 252 | 3.965 | −16.318 | 27.234 | 1.00 | 0.00 | C |
| --- | --- | --- | --- | --- | --- | --- | --- | --- | --- | --- | --- |
| ATOM | 523 | O | GLN | M | 252 | 2.796 | −16.423 | 26.885 | 1.00 | 0.00 | O |
| ATOM | 524 | CB | GLN | M | 252 | 5.729 | −16.384 | 25.460 | 1.00 | 0.00 | C |
| ATOM | 525 | CG | GLN | M | 252 | 6.493 | −15.632 | 24.365 | 1.00 | 0.00 | C |
| ATOM | 526 | CD | GLN | M | 252 | 5.558 | −14.976 | 23.366 | 1.00 | 0.00 | C |
| ATOM | 527 | OE1 | GLN | M | 252 | 5.266 | −13.790 | 23.431 | 1.00 | 0.00 | O |
| ATOM | 528 | NE2 | GLN | M | 252 | 5.051 | −15.838 | 22.419 | 1.00 | 0.00 | N |
| ATOM | 529 | N | ILE | M | 255 | 0.964 | −14.328 | 28.520 | 1.00 | 0.00 | N |
| ATOM | 530 | CA | ILE | M | 255 | −0.102 | −14.190 | 27.516 | 1.00 | 0.00 | C |
| ATOM | 531 | C | ILE | M | 255 | −0.955 | −15.467 | 27.497 | 1.00 | 0.00 | C |
| ATOM | 532 | O | ILE | M | 255 | −2.176 | −15.390 | 27.471 | 1.00 | 0.00 | O |
| ATOM | 533 | CB | ILE | M | 255 | 0.417 | −13.804 | 26.101 | 1.00 | 0.00 | C |
| ATOM | 534 | CG1 | ILE | M | 255 | 1.209 | −12.476 | 26.083 | 1.00 | 0.00 | C |
| ATOM | 535 | CG2 | ILE | M | 255 | −0.717 | −13.748 | 25.070 | 1.00 | 0.00 | C |
| ATOM | 536 | CD1 | ILE | M | 255 | 0.452 | −11.258 | 26.598 | 1.00 | 0.00 | C |
| ATOM | 537 | N | PHE | M | 256 | −0.261 | −16.672 | 27.484 | 1.00 | 0.00 | N |
| ATOM | 538 | CA | PHE | M | 256 | −0.946 | −17.970 | 27.541 | 1.00 | 0.00 | C |
| ATOM | 539 | C | PHE | M | 256 | −1.898 | −18.032 | 28.747 | 1.00 | 0.00 | C |
| ATOM | 540 | O | PHE | M | 256 | −3.034 | −18.468 | 28.616 | 1.00 | 0.00 | O |
| ATOM | 541 | CB | PHE | M | 256 | 0.059 | −19.141 | 27.510 | 1.00 | 0.00 | C |
| ATOM | 542 | CG | PHE | M | 256 | −0.534 | −20.518 | 27.696 | 1.00 | 0.00 | C |
| ATOM | 543 | CD1 | PHE | M | 256 | −0.013 | −21.386 | 28.689 | 1.00 | 0.00 | C |
| ATOM | 544 | CD2 | PHE | M | 256 | −1.597 | −20.985 | 26.882 | 1.00 | 0.00 | C |
| ATOM | 545 | CE1 | PHE | M | 256 | −0.539 | −22.680 | 28.863 | 1.00 | 0.00 | C |
| ATOM | 546 | CE2 | PHE | M | 256 | −2.128 | −22.276 | 27.065 | 1.00 | 0.00 | C |
| ATOM | 547 | CZ | PHE | M | 256 | −1.597 | −23.125 | 28.052 | 1.00 | 0.00 | C |
| ATOM | 548 | N | LEU | M | 259 | −5.058 | −16.050 | 28.251 | 1.00 | 0.00 | N |
| ATOM | 549 | CA | LEU | M | 259 | −5.940 | −16.735 | 27.308 | 1.00 | 0.00 | C |
| ATOM | 550 | C | LEU | M | 259 | −6.805 | −17.754 | 28.046 | 1.00 | 0.00 | C |
| ATOM | 551 | O | LEU | M | 259 | −8.018 | −17.761 | 27.887 | 1.00 | 0.00 | O |
| ATOM | 552 | CB | LEU | M | 259 | −5.159 | −17.348 | 26.128 | 1.00 | 0.00 | C |
| ATOM | 553 | CG | LEU | M | 259 | −6.050 | −17.856 | 24.974 | 1.00 | 0.00 | C |
| ATOM | 554 | CD1 | LEU | M | 259 | −5.327 | −17.681 | 23.640 | 1.00 | 0.00 | C |
| ATOM | 555 | CD2 | LEU | M | 259 | −6.433 | −19.328 | 25.144 | 1.00 | 0.00 | C |
| ATOM | 556 | N | ILE | M | 205 | −1.811 | −26.903 | 22.691 | 1.00 | 0.00 | N |
| ATOM | 557 | CA | ILE | M | 205 | −0.778 | −27.375 | 21.760 | 1.00 | 0.00 | C |
| ATOM | 558 | C | ILE | M | 205 | −0.407 | −26.242 | 20.791 | 1.00 | 0.00 | C |
| ATOM | 559 | O | ILE | M | 205 | 0.770 | −25.964 | 20.598 | 1.00 | 0.00 | O |
| ATOM | 560 | CB | ILE | M | 205 | −1.070 | −28.769 | 21.130 | 1.00 | 0.00 | C |
| ATOM | 561 | CG1 | ILE | M | 205 | 0.183 | −29.444 | 20.526 | 1.00 | 0.00 | C |
| ATOM | 562 | CG2 | ILE | M | 205 | −2.263 | −28.819 | 20.179 | 1.00 | 0.00 | C |
| ATOM | 563 | CD1 | ILE | M | 205 | 0.576 | −29.023 | 19.115 | 1.00 | 0.00 | C |
| ATOM | 564 | N | SER | M | 208 | 1.542 | −23.361 | 22.633 | 1.00 | 0.00 | N |
| ATOM | 565 | CA | SER | M | 208 | 2.900 | −23.765 | 22.998 | 1.00 | 0.00 | C |
| ATOM | 566 | C | SER | M | 208 | 3.883 | −23.597 | 21.833 | 1.00 | 0.00 | C |
| ATOM | 567 | O | SER | M | 208 | 5.032 | −23.247 | 22.054 | 1.00 | 0.00 | O |
| ATOM | 568 | CB | SER | M | 208 | 2.985 | −25.173 | 23.602 | 1.00 | 0.00 | C |
| ATOM | 569 | OG | SER | M | 208 | 2.785 | −26.197 | 22.634 | 1.00 | 0.00 | O |

TABLE 6

| ATOM | 1 | N | ILE | K | 5 | 27.058 | −0.783 | 12.427 | 1.00 | 0.00 | N |
| --- | --- | --- | --- | --- | --- | --- | --- | --- | --- | --- | --- |
| ATOM | 2 | CA | ILE | K | 5 | 26.005 | −1.691 | 12.91 | 1.00 | 0.00 | C |
| ATOM | 3 | C | ILE | K | 5 | 24.924 | −0.881 | 13.636 | 1.00 | 0.00 | C |
| ATOM | 4 | O | ILE | K | 5 | 23.769 | −1.281 | 13.67 | 1.00 | 0.00 | O |
| ATOM | 5 | CB | ILE | K | 5 | 26.579 | −2.844 | 13.786 | 1.00 | 0.00 | C |
| ATOM | 6 | CG1 | ILE | K | 5 | 25.508 | −3.932 | 14.021 | 1.00 | 0.00 | C |
| ATOM | 7 | CG2 | ILE | K | 5 | 27.182 | −2.353 | 15.11 | 1.00 | 0.00 | C |
| ATOM | 8 | CD1 | ILE | K | 5 | 26.069 | −5.224 | 14.594 | 1.00 | 0.00 | C |
| ATOM | 21 | N | ALA | K | 6 | 25.369 | 0.283 | 14.253 | 1.00 | 0.00 | N |
| ATOM | 22 | CA | ALA | K | 6 | 24.511 | 1.128 | 15.082 | 1.00 | 0.00 | C |
| ATOM | 23 | C | ALA | K | 6 | 23.265 | 1.544 | 14.305 | 1.00 | 0.00 | C |
| ATOM | 24 | O | ALA | K | 6 | 22.147 | 1.344 | 14.761 | 1.00 | 0.00 | O |
| ATOM | 25 | CB | ALA | K | 6 | 25.244 | 2.356 | 15.619 | 1.00 | 0.00 | C |
| ATOM | 31 | N | ALA | K | 7 | 23.517 | 2.156 | 13.081 | 1.00 | 0.00 | N |
| ATOM | 32 | CA | ALA | K | 7 | 22.441 | 2.61 | 12.201 | 1.00 | 0.00 | C |
| ATOM | 33 | C | ALA | K | 7 | 21.495 | 1.458 | 11.876 | 1.00 | 0.00 | C |
| ATOM | 34 | O | ALA | K | 7 | 20.285 | 1.619 | 11.95 | 1.00 | 0.00 | O |
| ATOM | 35 | CB | ALA | K | 7 | 22.963 | 3.241 | 10.913 | 1.00 | 0.00 | C |
| ATOM | 41 | N | GLY | K | 8 | 22.114 | 0.275 | 11.484 | 1.00 | 0.00 | N |
| ATOM | 42 | CA | GLY | K | 8 | 21.387 | −0.928 | 11.111 | 1.00 | 0.00 | C |
| ATOM | 43 | C | GLY | K | 8 | 20.361 | −1.344 | 12.15 | 1.00 | 0.00 | C |
| ATOM | 44 | O | GLY | K | 8 | 19.223 | −1.636 | 11.812 | 1.00 | 0.00 | O |
| ATOM | 48 | N | ALA | K | 9 | 20.834 | −1.403 | 13.453 | 1.00 | 0.00 | N |
| ATOM | 49 | CA | ALA | K | 9 | 19.997 | −1.824 | 14.574 | 1.00 | 0.00 | C |
| ATOM | 50 | C | ALA | K | 9 | 18.758 | −0.942 | 14.691 | 1.00 | 0.00 | C |
| ATOM | 51 | O | ALA | K | 9 | 17.646 | −1.449 | 14.766 | 1.00 | 0.00 | O |

TABLE 6-continued

| | | | | | | | | | | |
|---|---|---|---|---|---|---|---|---|---|---|
| ATOM | 52 | CB | ALA | K | 9 | 20.76 | −1.855 | 15.898 | 1.00 | 0.00 | C |
| ATOM | 58 | N | LEU | K | 10 | 18.999 | 0.426 | 14.75 | 1.00 | 0.00 | N |
| ATOM | 59 | CA | LEU | K | 10 | 17.924 | 1.389 | 15 | 1.00 | 0.00 | C |
| ATOM | 60 | C | LEU | K | 10 | 16.887 | 1.33 | 13.879 | 1.00 | 0.00 | C |
| ATOM | 61 | O | LEU | K | 10 | 15.7 | 1.191 | 14.146 | 1.00 | 0.00 | O |
| ATOM | 62 | CB | LEU | K | 10 | 18.423 | 2.836 | 15.198 | 1.00 | 0.00 | C |
| ATOM | 63 | CG | LEU | K | 10 | 18.696 | 3.198 | 16.672 | 1.00 | 0.00 | C |
| ATOM | 64 | CD1 | LEU | K | 10 | 19.859 | 2.414 | 17.278 | 1.00 | 0.00 | C |
| ATOM | 65 | CD2 | LEU | K | 10 | 18.969 | 4.695 | 16.798 | 1.00 | 0.00 | C |
| ATOM | 77 | N | ILE | K | 11 | 17.378 | 1.5 | 12.587 | 1.00 | 0.00 | N |
| ATOM | 78 | CA | ILE | K | 11 | 16.48 | 1.562 | 11.429 | 1.00 | 0.00 | C |
| ATOM | 79 | C | ILE | K | 11 | 15.7 | 0.252 | 11.263 | 1.00 | 0.00 | C |
| ATOM | 80 | O | ILE | K | 11 | 14.534 | 0.274 | 10.896 | 1.00 | 0.00 | O |
| ATOM | 81 | CB | ILE | K | 11 | 17.176 | 2.041 | 10.122 | 1.00 | 0.00 | C |
| ATOM | 82 | CG1 | ILE | K | 11 | 16.131 | 2.575 | 9.12 | 1.00 | 0.00 | C |
| ATOM | 83 | CG2 | ILE | K | 11 | 18.055 | 0.966 | 9.473 | 1.00 | 0.00 | C |
| ATOM | 84 | CD1 | ILE | K | 11 | 16.741 | 3.382 | 7.984 | 1.00 | 0.00 | C |
| ATOM | 96 | N | GLY | K | 12 | 16.41 | −0.914 | 11.531 | 1.00 | 0.00 | N |
| ATOM | 97 | CA | GLY | K | 12 | 15.813 | −2.237 | 11.499 | 1.00 | 0.00 | C |
| ATOM | 98 | C | GLY | K | 12 | 14.611 | −2.303 | 12.416 | 1.00 | 0.00 | C |
| ATOM | 99 | O | GLY | K | 12 | 13.536 | −2.709 | 12 | 1.00 | 0.00 | O |
| ATOM | 103 | N | GLY | K | 13 | 14.846 | −1.88 | 13.717 | 1.00 | 0.00 | N |
| ATOM | 104 | CA | GLY | K | 13 | 13.807 | −1.823 | 14.732 | 1.00 | 0.00 | C |
| ATOM | 105 | C | GLY | K | 13 | 12.578 | −1.072 | 14.253 | 1.00 | 0.00 | C |
| ATOM | 106 | O | GLY | K | 13 | 11.46 | −1.551 | 14.387 | 1.00 | 0.00 | O |
| ATOM | 110 | N | GLY | K | 14 | 12.838 | 0.172 | 13.697 | 1.00 | 0.00 | N |
| ATOM | 111 | CA | GLY | K | 14 | 11.798 | 1.03 | 13.153 | 1.00 | 0.00 | C |
| ATOM | 112 | C | GLY | K | 14 | 10.931 | 0.316 | 12.128 | 1.00 | 0.00 | C |
| ATOM | 113 | O | GLY | K | 14 | 9.712 | 0.341 | 12.22 | 1.00 | 0.00 | O |
| ATOM | 117 | N | LEU | K | 15 | 11.635 | −0.303 | 11.102 | 1.00 | 0.00 | N |
| ATOM | 118 | CA | LEU | K | 15 | 10.993 | −1.025 | 9.999 | 1.00 | 0.00 | C |
| ATOM | 119 | C | LEU | K | 15 | 10.067 | −2.105 | 10.557 | 1.00 | 0.00 | C |
| ATOM | 120 | O | LEU | K | 15 | 8.915 | −2.197 | 10.152 | 1.00 | 0.00 | O |
| ATOM | 121 | CB | LEU | K | 15 | 12.035 | −1.587 | 9.004 | 1.00 | 0.00 | C |
| ATOM | 122 | CG | LEU | K | 15 | 11.445 | −2.194 | 7.711 | 1.00 | 0.00 | C |
| ATOM | 123 | CD1 | LEU | K | 15 | 12.428 | −2.021 | 6.554 | 1.00 | 0.00 | C |
| ATOM | 124 | CD2 | LEU | K | 15 | 11.123 | −3.683 | 7.861 | 1.00 | 0.00 | C |
| ATOM | 136 | N | ILE | K | 16 | 10.642 | −2.954 | 11.496 | 1.00 | 0.00 | N |
| ATOM | 137 | CA | ILE | K | 16 | 9.942 | −4.097 | 12.092 | 1.00 | 0.00 | C |
| ATOM | 138 | C | ILE | K | 16 | 8.626 | −3.603 | 12.7 | 1.00 | 0.00 | C |
| ATOM | 139 | O | ILE | K | 16 | 7.571 | −4.156 | 12.418 | 1.00 | 0.00 | O |
| ATOM | 140 | CB | ILE | K | 16 | 10.83 | −4.875 | 13.109 | 1.00 | 0.00 | C |
| ATOM | 141 | CG1 | ILE | K | 16 | 11.973 | −5.618 | 12.381 | 1.00 | 0.00 | C |
| ATOM | 142 | CG2 | ILE | K | 16 | 10.018 | −5.879 | 13.935 | 1.00 | 0.00 | C |
| ATOM | 143 | CD1 | ILE | K | 16 | 13.148 | −5.927 | 13.297 | 1.00 | 0.00 | C |
| ATOM | 155 | N | MET | K | 17 | 8.739 | −2.545 | 13.594 | 1.00 | 0.00 | N |
| ATOM | 156 | CA | MET | K | 17 | 7.591 | −2.019 | 14.334 | 1.00 | 0.00 | C |
| ATOM | 157 | C | MET | K | 17 | 6.504 | −1.535 | 13.381 | 1.00 | 0.00 | C |
| ATOM | 158 | O | MET | K | 17 | 5.348 | −1.902 | 13.537 | 1.00 | 0.00 | O |
| ATOM | 159 | CB | MET | K | 17 | 7.962 | −0.901 | 15.322 | 1.00 | 0.00 | C |
| ATOM | 160 | CG | MET | K | 17 | 8.601 | −1.47 | 16.585 | 1.00 | 0.00 | C |
| ATOM | 161 | SD | MET | K | 17 | 8.93 | −0.146 | 17.788 | 1.00 | 0.00 | S |
| ATOM | 162 | CE | MET | K | 17 | 10.614 | 0.288 | 17.282 | 1.00 | 0.00 | C |
| ATOM | 172 | N | ALA | K | 18 | 6.911 | −0.636 | 12.403 | 1.00 | 0.00 | N |
| ATOM | 173 | CA | ALA | K | 18 | 5.964 | 0.011 | 11.493 | 1.00 | 0.00 | C |
| ATOM | 174 | C | ALA | K | 18 | 5.188 | −1.023 | 10.677 | 1.00 | 0.00 | C |
| ATOM | 175 | O | ALA | K | 18 | 3.97 | −0.95 | 10.578 | 1.00 | 0.00 | O |
| ATOM | 176 | CB | ALA | K | 18 | 6.641 | 1.021 | 10.569 | 1.00 | 0.00 | C |
| ATOM | 182 | N | GLY | K | 19 | 5.967 | −1.991 | 10.054 | 1.00 | 0.00 | N |
| ATOM | 183 | CA | GLY | K | 19 | 5.408 | −3.043 | 9.218 | 1.00 | 0.00 | C |
| ATOM | 184 | C | GLY | K | 19 | 4.394 | −3.878 | 9.977 | 1.00 | 0.00 | C |
| ATOM | 185 | O | GLY | K | 19 | 3.286 | −4.103 | 9.508 | 1.00 | 0.00 | O |
| ATOM | 189 | N | GLY | K | 20 | 4.848 | −4.359 | 11.197 | 1.00 | 0.00 | N |
| ATOM | 190 | CA | GLY | K | 20 | 4.021 | −5.15 | 12.09 | 1.00 | 0.00 | C |
| ATOM | 191 | C | GLY | K | 20 | 2.697 | −4.472 | 12.392 | 1.00 | 0.00 | C |
| ATOM | 192 | O | GLY | K | 20 | 1.647 | −5.091 | 12.298 | 1.00 | 0.00 | O |
| ATOM | 196 | N | ALA | K | 21 | 2.806 | −3.152 | 12.809 | 1.00 | 0.00 | N |
| ATOM | 197 | CA | ALA | K | 21 | 1.667 | −2.358 | 13.263 | 1.00 | 0.00 | C |
| ATOM | 198 | C | ALA | K | 21 | 0.567 | −2.315 | 12.213 | 1.00 | 0.00 | C |
| ATOM | 199 | O | ALA | K | 21 | −0.577 | −2.642 | 12.5 | 1.00 | 0.00 | O |
| ATOM | 200 | CB | ALA | K | 21 | 2.064 | −0.934 | 13.646 | 1.00 | 0.00 | C |
| ATOM | 206 | N | ILE | K | 22 | 0.955 | −1.827 | 10.97 | 1.00 | 0.00 | N |
| ATOM | 207 | CA | ILE | K | 22 | −0.025 | −1.608 | 9.903 | 1.00 | 0.00 | C |
| ATOM | 208 | C | ILE | K | 22 | −0.652 | −2.932 | 9.466 | 1.00 | 0.00 | C |
| ATOM | 209 | O | ILE | K | 22 | −1.843 | −2.981 | 9.19 | 1.00 | 0.00 | O |
| ATOM | 210 | CB | ILE | K | 22 | 0.469 | −0.726 | 8.719 | 1.00 | 0.00 | C |
| ATOM | 211 | CG1 | ILE | K | 22 | 1.644 | −1.303 | 7.896 | 1.00 | 0.00 | C |
| ATOM | 212 | CG2 | ILE | K | 22 | 0.837 | 0.67 | 9.233 | 1.00 | 0.00 | C |
| ATOM | 213 | CD1 | ILE | K | 22 | 1.194 | −2.103 | 6.683 | 1.00 | 0.00 | C |
| ATOM | 225 | N | GLY | K | 23 | 0.203 | −4.026 | 9.4 | 1.00 | 0.00 | N |

TABLE 6-continued

| | | | | | | | | | | |
|---|---|---|---|---|---|---|---|---|---|---|
| ATOM | 226 | CA | GLY | K | 23 | −0.258 | −5.356 | 9.039 | 1.00 | 0.00 | C |
| ATOM | 227 | C | GLY | K | 23 | −1.377 | −5.813 | 9.952 | 1.00 | 0.00 | C |
| ATOM | 228 | O | GLY | K | 23 | −2.452 | −6.173 | 9.493 | 1.00 | 0.00 | O |
| ATOM | 232 | N | ALA | K | 24 | −1.053 | −5.787 | 11.302 | 1.00 | 0.00 | N |
| ATOM | 233 | CA | ALA | K | 24 | −1.98 | −6.184 | 12.36 | 1.00 | 0.00 | C |
| ATOM | 234 | C | ALA | K | 24 | −3.307 | −5.44 | 12.237 | 1.00 | 0.00 | C |
| ATOM | 235 | O | ALA | K | 24 | −4.364 | −6.054 | 12.279 | 1.00 | 0.00 | O |
| ATOM | 236 | CB | ALA | K | 24 | −1.384 | −5.973 | 13.75 | 1.00 | 0.00 | C |
| ATOM | 242 | N | GLY | K | 25 | −3.208 | −4.059 | 12.109 | 1.00 | 0.00 | N |
| ATOM | 243 | CA | GLY | K | 25 | −4.364 | −3.177 | 12.068 | 1.00 | 0.00 | C |
| ATOM | 244 | C | GLY | K | 25 | −5.351 | −3.56 | 10.98 | 1.00 | 0.00 | C |
| ATOM | 245 | O | GLY | K | 25 | −6.536 | −3.73 | 11.236 | 1.00 | 0.00 | O |
| ATOM | 249 | N | ILE | K | 26 | −4.796 | −3.657 | 9.709 | 1.00 | 0.00 | N |
| ATOM | 250 | CA | ILE | K | 26 | −5.591 | −4.032 | 8.536 | 1.00 | 0.00 | C |
| ATOM | 251 | C | ILE | K | 26 | −6.235 | −5.396 | 8.795 | 1.00 | 0.00 | C |
| ATOM | 252 | O | ILE | K | 26 | −7.416 | −5.566 | 8.528 | 1.00 | 0.00 | O |
| ATOM | 253 | CB | ILE | K | 26 | −4.783 | −4 | 7.206 | 1.00 | 0.00 | C |
| ATOM | 254 | CG1 | ILE | K | 26 | −4.292 | −2.579 | 6.838 | 1.00 | 0.00 | C |
| ATOM | 255 | CG2 | ILE | K | 26 | −5.561 | −4.608 | 6.032 | 1.00 | 0.00 | C |
| ATOM | 256 | CD1 | ILE | K | 26 | −5.385 | −1.554 | 6.559 | 1.00 | 0.00 | C |
| ATOM | 268 | N | GLY | K | 27 | −5.397 | −6.38 | 9.307 | 1.00 | 0.00 | N |
| ATOM | 269 | CA | GLY | K | 27 | −5.83 | −7.74 | 9.594 | 1.00 | 0.00 | C |
| ATOM | 270 | C | GLY | K | 27 | −7.112 | −7.787 | 10.405 | 1.00 | 0.00 | C |
| ATOM | 271 | O | GLY | K | 27 | −8.07 | −8.439 | 10.013 | 1.00 | 0.00 | O |
| ATOM | 275 | N | ASP | K | 28 | −7.077 | −7.058 | 11.591 | 1.00 | 0.00 | N |
| ATOM | 276 | CA | ASP | K | 28 | −8.223 | −6.975 | 12.505 | 1.00 | 0.00 | C |
| ATOM | 277 | C | ASP | K | 28 | −9.482 | −6.599 | 11.738 | 1.00 | 0.00 | C |
| ATOM | 278 | O | ASP | K | 28 | −10.514 | −7.236 | 11.903 | 1.00 | 0.00 | O |
| ATOM | 279 | CB | ASP | K | 28 | −8.039 | −5.969 | 13.656 | 1.00 | 0.00 | C |
| ATOM | 280 | CG | ASP | K | 28 | −7.187 | −6.544 | 14.754 | 1.00 | 0.00 | C |
| ATOM | 281 | OD1 | ASP | K | 28 | −5.972 | −6.441 | 14.829 | 1.00 | 0.00 | O |
| ATOM | 282 | OD2 | ASP | K | 28 | −7.946 | −7.253 | 15.625 | 1.00 | 0.00 | O |
| ATOM | 288 | N | GLY | K | 29 | −9.359 | −5.492 | 10.907 | 1.00 | 0.00 | N |
| ATOM | 289 | CA | GLY | K | 29 | −10.461 | −4.983 | 10.114 | 1.00 | 0.00 | C |
| ATOM | 290 | C | GLY | K | 29 | −11.002 | −6.071 | 9.208 | 1.00 | 0.00 | C |
| ATOM | 291 | O | GLY | K | 29 | −12.083 | −6.597 | 9.429 | 1.00 | 0.00 | O |
| ATOM | 295 | N | VAL | K | 30 | −10.178 | −6.399 | 8.143 | 1.00 | 0.00 | N |
| ATOM | 296 | CA | VAL | K | 30 | −10.67 | −7.186 | 7.009 | 1.00 | 0.00 | C |
| ATOM | 297 | C | VAL | K | 30 | −11.213 | −8.543 | 7.465 | 1.00 | 0.00 | C |
| ATOM | 298 | O | VAL | K | 30 | −12.315 | −8.919 | 7.092 | 1.00 | 0.00 | O |
| ATOM | 299 | CB | VAL | K | 30 | −9.698 | −7.303 | 5.8 | 1.00 | 0.00 | C |
| ATOM | 300 | CG1 | VAL | K | 30 | −9.406 | −5.926 | 5.198 | 1.00 | 0.00 | C |
| ATOM | 301 | CG2 | VAL | K | 30 | −8.382 | −8.03 | 6.091 | 1.00 | 0.00 | C |
| ATOM | 311 | N | ALA | K | 31 | −10.37 | −9.299 | 8.271 | 1.00 | 0.00 | N |
| ATOM | 312 | CA | ALA | K | 31 | −10.706 | −10.667 | 8.665 | 1.00 | 0.00 | C |
| ATOM | 313 | C | ALA | K | 31 | −11.898 | −10.686 | 9.618 | 1.00 | 0.00 | C |
| ATOM | 314 | O | ALA | K | 31 | −12.803 | −11.495 | 9.46 | 1.00 | 0.00 | O |
| ATOM | 315 | CB | ALA | K | 31 | −9.525 | −11.407 | 9.286 | 1.00 | 0.00 | C |
| ATOM | 321 | N | GLY | K | 32 | −11.834 | −9.779 | 10.669 | 1.00 | 0.00 | N |
| ATOM | 322 | CA | GLY | K | 32 | −12.843 | −9.719 | 11.713 | 1.00 | 0.00 | C |
| ATOM | 323 | C | GLY | K | 32 | −14.212 | −9.398 | 11.15 | 1.00 | 0.00 | C |
| ATOM | 324 | O | GLY | K | 32 | −15.182 | −10.089 | 11.427 | 1.00 | 0.00 | O |
| ATOM | 328 | N | ASN | K | 33 | −14.267 | −8.257 | 10.363 | 1.00 | 0.00 | N |
| ATOM | 329 | CA | ASN | K | 33 | −15.523 | −7.785 | 9.783 | 1.00 | 0.00 | C |
| ATOM | 330 | C | ASN | K | 33 | −16.1 | −8.775 | 8.775 | 1.00 | 0.00 | C |
| ATOM | 331 | O | ASN | K | 33 | −17.312 | −8.902 | 8.669 | 1.00 | 0.00 | O |
| ATOM | 332 | CB | ASN | K | 33 | −15.438 | −6.39 | 9.141 | 1.00 | 0.00 | C |
| ATOM | 333 | CG | ASN | K | 33 | −15.197 | −5.297 | 10.168 | 1.00 | 0.00 | C |
| ATOM | 334 | OD1 | ASN | K | 33 | −14.133 | −4.701 | 10.251 | 1.00 | 0.00 | O |
| ATOM | 335 | ND2 | ASN | K | 33 | −16.269 | −5.042 | 10.995 | 1.00 | 0.00 | N |
| ATOM | 342 | N | ALA | K | 34 | −15.199 | −9.465 | 7.974 | 1.00 | 0.00 | N |
| ATOM | 343 | CA | ALA | K | 34 | −15.658 | −10.508 | 7.052 | 1.00 | 0.00 | C |
| ATOM | 344 | C | ALA | K | 34 | −16.41 | −11.608 | 7.806 | 1.00 | 0.00 | C |
| ATOM | 345 | O | ALA | K | 34 | −17.483 | −12.02 | 7.386 | 1.00 | 0.00 | O |
| ATOM | 346 | CB | ALA | K | 34 | −14.527 | −11.101 | 6.219 | 1.00 | 0.00 | C |
| ATOM | 352 | N | LEU | K | 35 | −15.783 | −12.094 | 8.95 | 1.00 | 0.00 | N |
| ATOM | 353 | CA | LEU | K | 35 | −16.377 | −13.139 | 9.789 | 1.00 | 0.00 | C |
| ATOM | 354 | C | LEU | K | 35 | −17.768 | −12.695 | 10.244 | 1.00 | 0.00 | C |
| ATOM | 355 | O | LEU | K | 35 | −18.742 | −13.411 | 10.043 | 1.00 | 0.00 | O |
| ATOM | 356 | CB | LEU | K | 35 | −15.479 | −13.513 | 10.99 | 1.00 | 0.00 | C |
| ATOM | 357 | CG | LEU | K | 35 | −16.052 | −14.618 | 11.902 | 1.00 | 0.00 | C |
| ATOM | 358 | CD1 | LEU | K | 35 | −16.009 | −15.99 | 11.23 | 1.00 | 0.00 | C |
| ATOM | 359 | CD2 | LEU | K | 35 | −15.276 | −14.658 | 13.216 | 1.00 | 0.00 | C |
| ATOM | 371 | N | ILE | K | 36 | −17.815 | −11.478 | 10.924 | 1.00 | 0.00 | N |
| ATOM | 372 | CA | ILE | K | 36 | −19.036 | −11.013 | 11.585 | 1.00 | 0.00 | C |
| ATOM | 373 | C | ILE | K | 36 | −20.189 | −10.855 | 10.589 | 1.00 | 0.00 | C |
| ATOM | 374 | O | ILE | K | 36 | −21.332 | −11.098 | 10.941 | 1.00 | 0.00 | O |
| ATOM | 375 | CB | ILE | K | 36 | −18.824 | −9.757 | 12.487 | 1.00 | 0.00 | C |
| ATOM | 376 | CG1 | ILE | K | 36 | −19.806 | −9.719 | 13.676 | 1.00 | 0.00 | C |
| ATOM | 377 | CG2 | ILE | K | 36 | −18.929 | −8.435 | 11.725 | 1.00 | 0.00 | C |

TABLE 6-continued

| | | | | | | | | | | |
|---|---|---|---|---|---|---|---|---|---|---|
| ATOM | 378 | CD1 | ILE | K | 36 | −19.42 | −10.675 | 14.794 | 1.00 | 0.00 | C |
| ATOM | 390 | N | SER | K | 37 | −19.865 | −10.405 | 9.312 | 1.00 | 0.00 | N |
| ATOM | 391 | CA | SER | K | 37 | −20.884 | −10.186 | 8.284 | 1.00 | 0.00 | C |
| ATOM | 392 | C | SER | K | 37 | −21.815 | −11.397 | 8.16 | 1.00 | 0.00 | C |
| ATOM | 393 | O | SER | K | 37 | −23.023 | −11.239 | 8.041 | 1.00 | 0.00 | O |
| ATOM | 394 | CB | SER | K | 37 | −20.287 | −9.841 | 6.914 | 1.00 | 0.00 | C |
| ATOM | 395 | OG | SER | K | 37 | −19.614 | −8.584 | 6.969 | 1.00 | 0.00 | O |
| ATOM | 401 | N | GLY | K | 38 | −21.186 | −12.637 | 8.153 | 1.00 | 0.00 | N |
| ATOM | 402 | CA | GLY | K | 38 | −21.939 | −13.876 | 8.213 | 1.00 | 0.00 | C |
| ATOM | 403 | C | GLY | K | 38 | −22.605 | −14.037 | 9.569 | 1.00 | 0.00 | C |
| ATOM | 404 | O | GLY | K | 38 | −23.824 | −14.017 | 9.682 | 1.00 | 0.00 | O |
| ATOM | 408 | N | VAL | K | 39 | −21.718 | −14.263 | 10.616 | 1.00 | 0.00 | N |
| ATOM | 409 | CA | VAL | K | 39 | −22.168 | −14.679 | 11.946 | 1.00 | 0.00 | C |
| ATOM | 410 | C | VAL | K | 39 | −22.563 | −13.39 | 12.682 | 1.00 | 0.00 | C |
| ATOM | 411 | O | VAL | K | 39 | −21.756 | −12.748 | 13.341 | 1.00 | 0.00 | O |
| ATOM | 412 | CB | VAL | K | 39 | −21.084 | −15.481 | 12.719 | 1.00 | 0.00 | C |
| ATOM | 413 | CG1 | VAL | K | 39 | −21.656 | −16.043 | 14.02 | 1.00 | 0.00 | C |
| ATOM | 414 | CG2 | VAL | K | 39 | −20.526 | −16.646 | 11.894 | 1.00 | 0.00 | C |
| ATOM | 424 | N | ALA | K | 40 | −23.894 | −13.035 | 12.506 | 1.00 | 0.00 | N |
| ATOM | 425 | CA | ALA | K | 40 | −24.463 | −11.774 | 13.006 | 1.00 | 0.00 | C |
| ATOM | 426 | C | ALA | K | 40 | −25.936 | −11.94 | 13.362 | 1.00 | 0.00 | C |
| ATOM | 427 | O | ALA | K | 40 | −26.358 | −11.554 | 14.443 | 1.00 | 0.00 | O |
| ATOM | 428 | CB | ALA | K | 40 | −24.298 | −10.61 | 12.033 | 1.00 | 0.00 | C |
| ATOM | 434 | N | ARG | K | 41 | −26.737 | −12.496 | 12.37 | 1.00 | 0.00 | N |
| ATOM | 435 | CA | ARG | K | 41 | −28.114 | −12.909 | 12.642 | 1.00 | 0.00 | C |
| ATOM | 436 | C | ARG | K | 41 | −28.115 | −14.033 | 13.684 | 1.00 | 0.00 | C |
| ATOM | 437 | O | ARG | K | 41 | −28.983 | −14.075 | 14.545 | 1.00 | 0.00 | O |
| ATOM | 438 | CB | ARG | K | 41 | −28.899 | −13.343 | 11.39 | 1.00 | 0.00 | C |
| ATOM | 439 | CG | ARG | K | 41 | −29.26 | −12.176 | 10.458 | 1.00 | 0.00 | C |
| ATOM | 440 | CD | ARG | K | 41 | −28.242 | −11.958 | 9.338 | 1.00 | 0.00 | C |
| ATOM | 441 | NE | ARG | K | 41 | −28.568 | −10.728 | 8.596 | 1.00 | 0.00 | N |
| ATOM | 442 | CZ | ARG | K | 41 | −28.108 | −9.468 | 8.913 | 1.00 | 0.00 | C |
| ATOM | 443 | NH1 | ARG | K | 41 | −27.365 | −9.179 | 10.037 | 1.00 | 0.00 | N |
| ATOM | 444 | NH2 | ARG | K | 41 | −28.387 | −8.41 | 8.087 | 1.00 | 0.00 | N |
| ATOM | 457 | N | GLN | K | 42 | −27.106 | −14.986 | 13.554 | 1.00 | 0.00 | N |
| ATOM | 458 | CA | GLN | K | 42 | −26.838 | −15.971 | 14.603 | 1.00 | 0.00 | C |
| ATOM | 459 | C | GLN | K | 42 | −26.427 | −15.168 | 15.845 | 1.00 | 0.00 | C |
| ATOM | 460 | O | GLN | K | 42 | −25.66 | −14.219 | 15.736 | 1.00 | 0.00 | O |
| ATOM | 461 | CB | GLN | K | 42 | −25.692 | −16.926 | 14.241 | 1.00 | 0.00 | C |
| ATOM | 462 | CG | GLN | K | 42 | −26.038 | −17.841 | 13.067 | 1.00 | 0.00 | C |
| ATOM | 463 | CD | GLN | K | 42 | −24.858 | −18.734 | 12.753 | 1.00 | 0.00 | C |
| ATOM | 464 | OE1 | GLN | K | 42 | −23.974 | −18.394 | 11.98 | 1.00 | 0.00 | O |
| ATOM | 465 | NE2 | GLN | K | 42 | −24.852 | −19.924 | 13.446 | 1.00 | 0.00 | N |
| ATOM | 474 | N | PRO | K | 43 | −26.929 | −15.616 | 17.076 | 1.00 | 0.00 | N |
| ATOM | 475 | CA | PRO | K | 43 | −26.718 | −14.888 | 18.317 | 1.00 | 0.00 | C |
| ATOM | 476 | C | PRO | K | 43 | −25.257 | −14.537 | 18.565 | 1.00 | 0.00 | C |
| ATOM | 477 | O | PRO | K | 43 | −24.341 | −15.313 | 18.304 | 1.00 | 0.00 | O |
| ATOM | 478 | CB | PRO | K | 43 | −27.219 | −15.818 | 19.412 | 1.00 | 0.00 | C |
| ATOM | 479 | CG | PRO | K | 43 | −28.251 | −16.685 | 18.727 | 1.00 | 0.00 | C |
| ATOM | 480 | CD | PRO | K | 43 | −27.812 | −16.751 | 17.277 | 1.00 | 0.00 | C |
| ATOM | 488 | N | GLU | K | 44 | −25.104 | −13.304 | 19.191 | 1.00 | 0.00 | N |
| ATOM | 489 | CA | GLU | K | 44 | −23.821 | −12.843 | 19.719 | 1.00 | 0.00 | C |
| ATOM | 490 | C | GLU | K | 44 | −23.618 | −13.555 | 21.061 | 1.00 | 0.00 | C |
| ATOM | 491 | O | GLU | K | 44 | −23.904 | −13.05 | 22.137 | 1.00 | 0.00 | O |
| ATOM | 492 | CB | GLU | K | 44 | −23.689 | −11.309 | 19.801 | 1.00 | 0.00 | C |
| ATOM | 493 | CG | GLU | K | 44 | −24.829 | −10.561 | 20.501 | 1.00 | 0.00 | C |
| ATOM | 494 | CD | GLU | K | 44 | −24.464 | −9.106 | 20.633 | 1.00 | 0.00 | C |
| ATOM | 495 | OE1 | GLU | K | 44 | −24.639 | −8.26 | 19.768 | 1.00 | 0.00 | O |
| ATOM | 496 | OE2 | GLU | K | 44 | −23.844 | −8.861 | 21.816 | 1.00 | 0.00 | O |
| ATOM | 504 | N | ALA | K | 45 | −23.108 | −14.832 | 20.905 | 1.00 | 0.00 | N |
| ATOM | 505 | CA | ALA | K | 45 | −22.829 | −15.746 | 22.006 | 1.00 | 0.00 | C |
| ATOM | 506 | C | ALA | K | 45 | −21.818 | −16.757 | 21.467 | 1.00 | 0.00 | C |
| ATOM | 507 | O | ALA | K | 45 | −20.672 | −16.776 | 21.891 | 1.00 | 0.00 | O |
| ATOM | 508 | CB | ALA | K | 45 | −24.083 | −16.4 | 22.583 | 1.00 | 0.00 | C |
| ATOM | 514 | N | GLN | K | 46 | −22.284 | −17.575 | 20.441 | 1.00 | 0.00 | N |
| ATOM | 515 | CA | GLN | K | 46 | −21.387 | −18.407 | 19.636 | 1.00 | 0.00 | C |
| ATOM | 516 | C | GLN | K | 46 | −20.471 | −17.482 | 18.834 | 1.00 | 0.00 | C |
| ATOM | 517 | O | GLN | K | 46 | −19.257 | −17.639 | 18.851 | 1.00 | 0.00 | O |
| ATOM | 518 | CB | GLN | K | 46 | −22.133 | −19.373 | 18.697 | 1.00 | 0.00 | C |
| ATOM | 519 | CG | GLN | K | 46 | −22.759 | −20.568 | 19.422 | 1.00 | 0.00 | C |
| ATOM | 520 | CD | GLN | K | 46 | −23.88 | −20.164 | 20.364 | 1.00 | 0.00 | C |
| ATOM | 521 | OE1 | GLN | K | 46 | −24.797 | −19.434 | 20.015 | 1.00 | 0.00 | O |
| ATOM | 522 | NE2 | GLN | K | 46 | −23.776 | −20.701 | 21.628 | 1.00 | 0.00 | N |
| ATOM | 531 | N | GLY | K | 47 | −21.113 | −16.481 | 18.113 | 1.00 | 0.00 | N |
| ATOM | 532 | CA | GLY | K | 47 | −20.379 | −15.473 | 17.363 | 1.00 | 0.00 | C |
| ATOM | 533 | C | GLY | K | 47 | −19.364 | −14.732 | 18.212 | 1.00 | 0.00 | C |
| ATOM | 534 | O | GLY | K | 47 | −18.227 | −14.543 | 17.801 | 1.00 | 0.00 | O |
| ATOM | 538 | N | ARG | K | 48 | −19.851 | −14.254 | 19.419 | 1.00 | 0.00 | N |
| ATOM | 539 | CA | ARG | K | 48 | −19.045 | −13.46 | 20.342 | 1.00 | 0.00 | C |
| ATOM | 540 | C | ARG | K | 48 | −17.993 | −14.261 | 21.128 | 1.00 | 0.00 | C |

TABLE 6-continued

| | | | | | | | | | | |
|---|---|---|---|---|---|---|---|---|---|---|
| ATOM | 541 | O | ARG | K | 48 | −17.214 | −13.663 | 21.854 | 1.00 | 0.00 | O |
| ATOM | 542 | CB | ARG | K | 48 | −19.954 | −12.677 | 21.313 | 1.00 | 0.00 | C |
| ATOM | 543 | CG | ARG | K | 48 | −19.359 | −11.324 | 21.726 | 1.00 | 0.00 | C |
| ATOM | 544 | CD | ARG | K | 48 | −20.308 | −10.519 | 22.607 | 1.00 | 0.00 | C |
| ATOM | 545 | NE | ARG | K | 48 | −20.356 | −11.117 | 23.953 | 1.00 | 0.00 | N |
| ATOM | 546 | CZ | ARG | K | 48 | −21.46 | −11.2 | 24.769 | 1.00 | 0.00 | C |
| ATOM | 547 | NH1 | ARG | K | 48 | −22.727 | −10.788 | 24.417 | 1.00 | 0.00 | N |
| ATOM | 548 | NH2 | ARG | K | 48 | −21.325 | −11.724 | 26.032 | 1.00 | 0.00 | N |
| ATOM | 561 | N | LEU | K | 49 | −17.971 | −15.646 | 20.987 | 1.00 | 0.00 | N |
| ATOM | 562 | CA | LEU | K | 49 | −16.83 | −16.458 | 21.424 | 1.00 | 0.00 | C |
| ATOM | 563 | C | LEU | K | 49 | −15.744 | −16.45 | 20.342 | 1.00 | 0.00 | C |
| ATOM | 564 | O | LEU | K | 49 | −14.582 | −16.192 | 20.63 | 1.00 | 0.00 | O |
| ATOM | 565 | CB | LEU | K | 49 | −17.252 | −17.894 | 21.798 | 1.00 | 0.00 | C |
| ATOM | 566 | CG | LEU | K | 49 | −16.109 | −18.79 | 22.321 | 1.00 | 0.00 | C |
| ATOM | 567 | CD1 | LEU | K | 49 | −15.498 | −18.26 | 23.619 | 1.00 | 0.00 | C |
| ATOM | 568 | CD2 | LEU | K | 49 | −16.627 | −20.209 | 22.542 | 1.00 | 0.00 | C |
| ATOM | 580 | N | PHE | K | 50 | −16.16 | −16.818 | 19.064 | 1.00 | 0.00 | N |
| ATOM | 581 | CA | PHE | K | 50 | −15.203 | −17.015 | 17.967 | 1.00 | 0.00 | C |
| ATOM | 582 | C | PHE | K | 50 | −14.483 | −15.701 | 17.636 | 1.00 | 0.00 | C |
| ATOM | 583 | O | PHE | K | 50 | −13.28 | −15.693 | 17.411 | 1.00 | 0.00 | O |
| ATOM | 584 | CB | PHE | K | 50 | −15.847 | −17.62 | 16.692 | 1.00 | 0.00 | C |
| ATOM | 585 | CG | PHE | K | 50 | −15.074 | −18.773 | 16.077 | 1.00 | 0.00 | C |
| ATOM | 586 | CD1 | PHE | K | 50 | −13.675 | −18.707 | 15.835 | 1.00 | 0.00 | C |
| ATOM | 587 | CE1 | PHE | K | 50 | −12.985 | −19.792 | 15.262 | 1.00 | 0.00 | C |
| ATOM | 588 | CZ | PHE | K | 50 | −13.679 | −20.958 | 14.898 | 1.00 | 0.00 | C |
| ATOM | 589 | CE2 | PHE | K | 50 | −15.066 | −21.038 | 15.111 | 1.00 | 0.00 | C |
| ATOM | 590 | CD2 | PHE | K | 50 | −15.757 | −19.958 | 15.696 | 1.00 | 0.00 | C |
| ATOM | 600 | N | THR | K | 51 | −15.291 | −14.571 | 17.559 | 1.00 | 0.00 | N |
| ATOM | 601 | CA | THR | K | 51 | −14.79 | −13.258 | 17.147 | 1.00 | 0.00 | C |
| ATOM | 602 | C | THR | K | 51 | −13.543 | −12.867 | 17.958 | 1.00 | 0.00 | C |
| ATOM | 603 | O | THR | K | 51 | −12.534 | −12.554 | 17.343 | 1.00 | 0.00 | O |
| ATOM | 604 | CB | THR | K | 51 | −15.891 | −12.173 | 17.107 | 1.00 | 0.00 | C |
| ATOM | 605 | OG1 | THR | K | 51 | −16.873 | −12.559 | 16.143 | 1.00 | 0.00 | O |
| ATOM | 606 | CG2 | THR | K | 51 | −15.364 | −10.808 | 16.678 | 1.00 | 0.00 | C |
| ATOM | 614 | N | PRO | K | 52 | −13.59 | −12.897 | 19.362 | 1.00 | 0.00 | N |
| ATOM | 615 | CA | PRO | K | 52 | −12.407 | −12.708 | 20.183 | 1.00 | 0.00 | C |
| ATOM | 616 | C | PRO | K | 52 | −11.143 | −13.421 | 19.738 | 1.00 | 0.00 | C |
| ATOM | 617 | O | PRO | K | 52 | −10.081 | −12.818 | 19.762 | 1.00 | 0.00 | O |
| ATOM | 618 | CB | PRO | K | 52 | −12.818 | −13.12 | 21.581 | 1.00 | 0.00 | C |
| ATOM | 619 | CG | PRO | K | 52 | −14.286 | −12.768 | 21.63 | 1.00 | 0.00 | C |
| ATOM | 620 | CD | PRO | K | 52 | −14.776 | −12.857 | 20.191 | 1.00 | 0.00 | C |
| ATOM | 628 | N | PHE | K | 53 | −11.273 | −14.753 | 19.362 | 1.00 | 0.00 | N |
| ATOM | 629 | CA | PHE | K | 53 | −10.108 | −15.537 | 18.945 | 1.00 | 0.00 | C |
| ATOM | 630 | C | PHE | K | 53 | −9.437 | −14.85 | 17.749 | 1.00 | 0.00 | C |
| ATOM | 631 | O | PHE | K | 53 | −8.235 | −14.619 | 17.761 | 1.00 | 0.00 | O |
| ATOM | 632 | CB | PHE | K | 53 | −10.436 | −17.016 | 18.655 | 1.00 | 0.00 | C |
| ATOM | 633 | CG | PHE | K | 53 | −9.193 | −17.873 | 18.699 | 1.00 | 0.00 | C |
| ATOM | 634 | CD1 | PHE | K | 53 | −8.387 | −18.048 | 17.547 | 1.00 | 0.00 | C |
| ATOM | 635 | CD2 | PHE | K | 53 | −8.795 | −18.497 | 19.91 | 1.00 | 0.00 | C |
| ATOM | 636 | CE1 | PHE | K | 53 | −7.202 | −18.805 | 17.612 | 1.00 | 0.00 | C |
| ATOM | 637 | CE2 | PHE | K | 53 | −7.613 | 19.261 | 19.968 | 1.00 | 0.00 | C |
| ATOM | 638 | CZ | PHE | K | 53 | −6.813 | −19.409 | 18.822 | 1.00 | 0.00 | C |
| ATOM | 648 | N | PHE | K | 54 | −10.273 | −14.535 | 16.683 | 1.00 | 0.00 | N |
| ATOM | 649 | CA | PHE | K | 54 | −9.772 | −13.883 | 15.468 | 1.00 | 0.00 | C |
| ATOM | 650 | C | PHE | K | 54 | −9.045 | −12.59 | 15.844 | 1.00 | 0.00 | C |
| ATOM | 651 | O | PHE | K | 54 | −7.885 | −12.404 | 15.497 | 1.00 | 0.00 | O |
| ATOM | 652 | CB | PHE | K | 54 | −10.875 | −13.584 | 14.425 | 1.00 | 0.00 | C |
| ATOM | 653 | CG | PHE | K | 54 | −11.049 | −14.675 | 13.395 | 1.00 | 0.00 | C |
| ATOM | 654 | CD1 | PHE | K | 54 | −10.674 | −14.445 | 12.046 | 1.00 | 0.00 | C |
| ATOM | 655 | CD2 | PHE | K | 54 | −11.619 | −15.927 | 13.735 | 1.00 | 0.00 | C |
| ATOM | 656 | CE1 | PHE | K | 54 | −10.872 | −15.433 | 11.064 | 1.00 | 0.00 | C |
| ATOM | 657 | CE2 | PHE | K | 54 | −11.815 | −16.915 | 12.749 | 1.00 | 0.00 | C |
| ATOM | 658 | CZ | PHE | K | 54 | −11.446 | −16.668 | 11.415 | 1.00 | 0.00 | C |
| ATOM | 668 | N | ILE | K | 55 | −9.806 | −11.654 | 16.535 | 1.00 | 0.00 | N |
| ATOM | 669 | CA | ILE | K | 55 | −9.312 | −10.293 | 16.755 | 1.00 | 0.00 | C |
| ATOM | 670 | C | ILE | K | 55 | −8.091 | −10.238 | 17.676 | 1.00 | 0.00 | C |
| ATOM | 671 | O | ILE | K | 55 | −7.254 | −9.365 | 17.494 | 1.00 | 0.00 | O |
| ATOM | 672 | CB | ILE | K | 55 | −10.389 | −9.246 | 17.158 | 1.00 | 0.00 | C |
| ATOM | 673 | CG1 | ILE | K | 55 | −11.082 | −9.542 | 18.501 | 1.00 | 0.00 | C |
| ATOM | 674 | CG2 | ILE | K | 55 | −11.412 | −9.083 | 16.026 | 1.00 | 0.00 | C |
| ATOM | 675 | CD1 | ILE | K | 55 | −11.891 | −8.371 | 19.037 | 1.00 | 0.00 | C |
| ATOM | 687 | N | THR | K | 56 | −8.023 | −11.158 | 18.719 | 1.00 | 0.00 | N |
| ATOM | 688 | CA | THR | K | 56 | −6.895 | −11.169 | 19.652 | 1.00 | 0.00 | C |
| ATOM | 689 | C | THR | K | 56 | −5.609 | −11.585 | 18.936 | 1.00 | 0.00 | C |
| ATOM | 690 | O | THR | K | 56 | −4.563 | −11.008 | 19.195 | 1.00 | 0.00 | O |
| ATOM | 691 | CB | THR | K | 56 | −7.163 | −11.948 | 20.967 | 1.00 | 0.00 | C |
| ATOM | 692 | OG1 | THR | K | 56 | −6.253 | −11.504 | 21.975 | 1.00 | 0.00 | O |
| ATOM | 693 | CG2 | THR | K | 56 | −7.019 | −13.463 | 20.88 | 1.00 | 0.00 | C |
| ATOM | 701 | N | VAL | K | 57 | −5.703 | −12.634 | 18.023 | 1.00 | 0.00 | N |
| ATOM | 702 | CA | VAL | K | 57 | −4.544 | −13.065 | 17.229 | 1.00 | 0.00 | C |

TABLE 6-continued

| | | | | | | | | | | |
|---|---|---|---|---|---|---|---|---|---|---|
| ATOM | 703 | C | VAL | K | 57 | −4.032 | −11.845 | 16.459 | 1.00 | 0.00 | C |
| ATOM | 704 | O | VAL | K | 57 | −2.852 | −11.526 | 16.523 | 1.00 | 0.00 | O |
| ATOM | 705 | CB | VAL | K | 57 | −4.84 | −14.286 | 16.314 | 1.00 | 0.00 | C |
| ATOM | 706 | CG1 | VAL | K | 57 | −3.727 | −14.538 | 15.293 | 1.00 | 0.00 | C |
| ATOM | 707 | CG2 | VAL | K | 57 | −5.023 | −15.555 | 17.15 | 1.00 | 0.00 | C |
| ATOM | 717 | N | GLY | K | 58 | −4.99 | −11.166 | 15.714 | 1.00 | 0.00 | N |
| ATOM | 718 | CA | GLY | K | 58 | −4.679 | −9.985 | 14.925 | 1.00 | 0.00 | C |
| ATOM | 719 | C | GLY | K | 58 | −3.929 | −8.942 | 15.735 | 1.00 | 0.00 | C |
| ATOM | 720 | O | GLY | K | 58 | −2.85 | −8.511 | 15.357 | 1.00 | 0.00 | O |
| ATOM | 724 | N | LEU | K | 59 | −4.583 | −8.526 | 16.885 | 1.00 | 0.00 | N |
| ATOM | 725 | CA | LEU | K | 59 | −4.116 | −7.424 | 17.724 | 1.00 | 0.00 | C |
| ATOM | 726 | C | LEU | K | 59 | −2.71 | −7.721 | 18.236 | 1.00 | 0.00 | C |
| ATOM | 727 | O | LEU | K | 59 | −1.8 | −6.932 | 18.027 | 1.00 | 0.00 | O |
| ATOM | 728 | CB | LEU | K | 59 | −5.098 | −7.132 | 18.879 | 1.00 | 0.00 | C |
| ATOM | 729 | CG | LEU | K | 59 | −4.681 | −5.985 | 19.821 | 1.00 | 0.00 | C |
| ATOM | 730 | CD1 | LEU | K | 59 | −4.63 | −4.637 | 19.101 | 1.00 | 0.00 | C |
| ATOM | 731 | CD2 | LEU | K | 59 | −5.655 | −5.908 | 20.995 | 1.00 | 0.00 | C |
| ATOM | 743 | N | VAL | K | 60 | −2.591 | −8.892 | 18.977 | 1.00 | 0.00 | N |
| ATOM | 744 | CA | VAL | K | 60 | −1.393 | −9.246 | 19.745 | 1.00 | 0.00 | C |
| ATOM | 745 | C | VAL | K | 60 | −0.188 | −9.558 | 18.832 | 1.00 | 0.00 | C |
| ATOM | 746 | O | VAL | K | 60 | 0.948 | −9.523 | 19.287 | 1.00 | 0.00 | O |
| ATOM | 747 | CB | VAL | K | 60 | −1.685 | −10.355 | 20.8 | 1.00 | 0.00 | C |
| ATOM | 748 | CG1 | VAL | K | 60 | −0.456 | −10.725 | 21.631 | 1.00 | 0.00 | C |
| ATOM | 749 | CG2 | VAL | K | 60 | −2.775 | −9.905 | 21.784 | 1.00 | 0.00 | C |
| ATOM | 759 | N | GLU | K | 61 | −0.455 | −9.815 | 17.489 | 1.00 | 0.00 | N |
| ATOM | 760 | CA | GLU | K | 61 | 0.601 | −9.873 | 16.474 | 1.00 | 0.00 | C |
| ATOM | 761 | C | GLU | K | 61 | 1.585 | −8.71 | 16.652 | 1.00 | 0.00 | C |
| ATOM | 762 | O | GLU | K | 61 | 2.791 | −8.922 | 16.668 | 1.00 | 0.00 | O |
| ATOM | 763 | CB | GLU | K | 61 | 0.034 | −9.906 | 15.044 | 1.00 | 0.00 | C |
| ATOM | 764 | CG | GLU | K | 61 | 1.102 | −10.157 | 13.982 | 1.00 | 0.00 | C |
| ATOM | 765 | CD | GLU | K | 61 | 0.467 | −10.196 | 12.615 | 1.00 | 0.00 | C |
| ATOM | 766 | OE1 | GLU | K | 61 | 0.258 | −9.216 | 11.914 | 1.00 | 0.00 | O |
| ATOM | 767 | OE2 | GLU | K | 61 | 0.092 | −11.457 | 12.285 | 1.00 | 0.00 | O |
| ATOM | 775 | N | ALA | K | 62 | 1.013 | −7.443 | 16.754 | 1.00 | 0.00 | N |
| ATOM | 776 | CA | ALA | K | 62 | 1.826 | −6.232 | 16.847 | 1.00 | 0.00 | C |
| ATOM | 777 | C | ALA | K | 62 | 2.804 | −6.324 | 18.027 | 1.00 | 0.00 | C |
| ATOM | 778 | O | ALA | K | 62 | 4.001 | −6.269 | 17.784 | 1.00 | 0.00 | O |
| ATOM | 779 | CB | ALA | K | 62 | 1.015 | −4.938 | 16.813 | 1.00 | 0.00 | C |
| ATOM | 785 | N | TYR | K | 64 | 4.126 | −8.886 | 19.558 | 1.00 | 0.00 | N |
| ATOM | 786 | CA | TYR | K | 64 | 5.22 | −9.841 | 19.328 | 1.00 | 0.00 | C |
| ATOM | 787 | C | TYR | K | 64 | 6.395 | −9.131 | 18.644 | 1.00 | 0.00 | C |
| ATOM | 788 | O | TYR | K | 64 | 7.533 | −9.237 | 19.085 | 1.00 | 0.00 | O |
| ATOM | 789 | CB | TYR | K | 64 | 4.841 | −11.101 | 18.517 | 1.00 | 0.00 | C |
| ATOM | 790 | CG | TYR | K | 64 | 3.724 | −11.949 | 19.079 | 1.00 | 0.00 | C |
| ATOM | 791 | CD1 | TYR | K | 64 | 3.57 | −12.184 | 20.471 | 1.00 | 0.00 | C |
| ATOM | 792 | CD2 | TYR | K | 64 | 2.807 | −12.559 | 18.186 | 1.00 | 0.00 | C |
| ATOM | 793 | CE1 | TYR | K | 64 | 2.502 | −12.959 | 20.955 | 1.00 | 0.00 | C |
| ATOM | 794 | CE2 | TYR | K | 64 | 1.734 | −13.333 | 18.662 | 1.00 | 0.00 | C |
| ATOM | 795 | CZ | TYR | K | 64 | 1.582 | −13.517 | 20.051 | 1.00 | 0.00 | C |
| ATOM | 796 | OH | TYR | K | 64 | 0.51 | −14.228 | 20.567 | 1.00 | 0.00 | O |
| ATOM | 806 | N | PHE | K | 65 | 6.078 | −8.42 | 17.493 | 1.00 | 0.00 | N |
| ATOM | 807 | CA | PHE | K | 65 | 7.098 | −7.715 | 16.711 | 1.00 | 0.00 | C |
| ATOM | 808 | C | PHE | K | 65 | 7.688 | −6.509 | 17.443 | 1.00 | 0.00 | C |
| ATOM | 809 | O | PHE | K | 65 | 8.857 | −6.2 | 17.252 | 1.00 | 0.00 | O |
| ATOM | 810 | CB | PHE | K | 65 | 6.592 | −7.299 | 15.317 | 1.00 | 0.00 | C |
| ATOM | 811 | CG | PHE | K | 65 | 6.386 | −8.506 | 14.431 | 1.00 | 0.00 | C |
| ATOM | 812 | CD1 | PHE | K | 65 | 7.499 | −9.252 | 13.959 | 1.00 | 0.00 | C |
| ATOM | 813 | CE1 | PHE | K | 65 | 7.307 | −10.424 | 13.206 | 1.00 | 0.00 | C |
| ATOM | 814 | CZ | PHE | K | 65 | 6.007 | −10.858 | 12.9 | 1.00 | 0.00 | C |
| ATOM | 815 | CE2 | PHE | K | 65 | 4.898 | −10.111 | 13.33 | 1.00 | 0.00 | C |
| ATOM | 816 | CD2 | PHE | K | 65 | 5.083 | −8.939 | 14.087 | 1.00 | 0.00 | C |
| ATOM | 826 | N | ILE | K | 66 | 6.836 | −5.797 | 18.28 | 1.00 | 0.00 | N |
| ATOM | 827 | CA | ILE | K | 66 | 7.311 | −4.68 | 19.108 | 1.00 | 0.00 | C |
| ATOM | 828 | C | ILE | K | 66 | 8.423 | −5.216 | 20.012 | 1.00 | 0.00 | C |
| ATOM | 829 | O | ILE | K | 66 | 9.497 | −4.635 | 20.061 | 1.00 | 0.00 | O |
| ATOM | 830 | CB | ILE | K | 66 | 6.193 | −3.949 | 19.908 | 1.00 | 0.00 | C |
| ATOM | 831 | CG1 | ILE | K | 66 | 5.183 | −3.272 | 18.953 | 1.00 | 0.00 | C |
| ATOM | 832 | CG2 | ILE | K | 66 | 6.784 | −2.897 | 20.856 | 1.00 | 0.00 | C |
| ATOM | 833 | CD1 | ILE | K | 66 | 3.904 | −2.827 | 19.648 | 1.00 | 0.00 | C |
| ATOM | 845 | N | ASN | K | 67 | 8.12 | −6.351 | 20.758 | 1.00 | 0.00 | N |
| ATOM | 846 | CA | ASN | K | 67 | 9.084 | −6.98 | 21.666 | 1.00 | 0.00 | C |
| ATOM | 847 | C | ASN | K | 67 | 10.38 | −7.338 | 20.946 | 1.00 | 0.00 | C |
| ATOM | 848 | O | ASN | K | 67 | 11.454 | −7.126 | 21.491 | 1.00 | 0.00 | O |
| ATOM | 849 | CB | ASN | K | 67 | 8.543 | −8.23 | 22.385 | 1.00 | 0.00 | C |
| ATOM | 850 | CG | ASN | K | 67 | 7.77 | −7.843 | 23.631 | 1.00 | 0.00 | C |
| ATOM | 851 | OD1 | ASN | K | 67 | 6.567 | −7.632 | 23.619 | 1.00 | 0.00 | O |
| ATOM | 852 | ND2 | ASN | K | 67 | 8.555 | −7.711 | 24.756 | 1.00 | 0.00 | N |
| ATOM | 859 | N | LEU | K | 68 | 10.249 | −7.945 | 19.702 | 1.00 | 0.00 | N |
| ATOM | 860 | CA | LEU | K | 68 | 11.409 | −8.36 | 18.903 | 1.00 | 0.00 | C |
| ATOM | 861 | C | LEU | K | 68 | 12.342 | −7.161 | 18.698 | 1.00 | 0.00 | C |

TABLE 6-continued

| ATOM | 862 | O | LEU | K | 68 | 13.529 | −7.233 | 18.988 | 1.00 | 0.00 | O |
|---|---|---|---|---|---|---|---|---|---|---|---|
| ATOM | 863 | CB | LEU | K | 68 | 10.985 | −9.036 | 17.579 | 1.00 | 0.00 | C |
| ATOM | 864 | CG | LEU | K | 68 | 12.09 | −9.878 | 16.906 | 1.00 | 0.00 | C |
| ATOM | 865 | CD1 | LEU | K | 68 | 11.462 | −10.985 | 16.058 | 1.00 | 0.00 | C |
| ATOM | 866 | CD2 | LEU | K | 68 | 13.006 | −9.04 | 16.015 | 1.00 | 0.00 | C |
| ATOM | 878 | N | ALA | K | 69 | 11.744 | −6.024 | 18.167 | 1.00 | 0.00 | N |
| ATOM | 879 | CA | ALA | K | 69 | 12.484 | −4.781 | 17.934 | 1.00 | 0.00 | C |
| ATOM | 880 | C | ALA | K | 69 | 13.125 | −4.241 | 19.216 | 1.00 | 0.00 | C |
| ATOM | 881 | O | ALA | K | 69 | 14.252 | −3.764 | 19.191 | 1.00 | 0.00 | O |
| ATOM | 882 | CB | ALA | K | 69 | 11.606 | −3.701 | 17.312 | 1.00 | 0.00 | C |
| ATOM | 888 | N | PHE | K | 70 | 12.328 | −4.3 | 20.354 | 1.00 | 0.00 | N |
| ATOM | 889 | CA | PHE | K | 70 | 12.764 | −3.853 | 21.679 | 1.00 | 0.00 | C |
| ATOM | 890 | C | PHE | K | 70 | 14.099 | −4.515 | 22.02 | 1.00 | 0.00 | C |
| ATOM | 891 | O | PHE | K | 70 | 15.029 | −3.848 | 22.445 | 1.00 | 0.00 | O |
| ATOM | 892 | CB | PHE | K | 70 | 11.724 | −4.153 | 22.791 | 1.00 | 0.00 | C |
| ATOM | 893 | CG | PHE | K | 70 | 11.511 | −3.023 | 23.769 | 1.00 | 0.00 | C |
| ATOM | 894 | CD1 | PHE | K | 70 | 10.227 | −2.434 | 23.901 | 1.00 | 0.00 | C |
| ATOM | 895 | CE1 | PHE | K | 70 | 10.001 | −1.403 | 24.831 | 1.00 | 0.00 | C |
| ATOM | 896 | CZ | PHE | K | 70 | 11.054 | −0.936 | 25.635 | 1.00 | 0.00 | C |
| ATOM | 897 | CE2 | PHE | K | 70 | 12.332 | −1.512 | 25.521 | 1.00 | 0.00 | C |
| ATOM | 898 | CD2 | PHE | K | 70 | 12.559 | −2.555 | 24.602 | 1.00 | 0.00 | C |
| ATOM | 908 | N | MET | K | 71 | 14.144 | −5.895 | 21.855 | 1.00 | 0.00 | N |
| ATOM | 909 | CA | MET | K | 71 | 15.311 | −6.702 | 22.213 | 1.00 | 0.00 | C |
| ATOM | 910 | C | MET | K | 71 | 16.54 | −6.268 | 21.42 | 1.00 | 0.00 | C |
| ATOM | 911 | O | MET | K | 71 | 17.617 | −6.161 | 21.989 | 1.00 | 0.00 | O |
| ATOM | 912 | CB | MET | K | 71 | 15.074 | −8.211 | 22.043 | 1.00 | 0.00 | C |
| ATOM | 913 | CG | MET | K | 71 | 14.1 | −8.744 | 23.094 | 1.00 | 0.00 | C |
| ATOM | 914 | SD | MET | K | 71 | 13.617 | −10.446 | 22.689 | 1.00 | 0.00 | S |
| ATOM | 915 | CE | MET | K | 71 | 12.287 | −10.632 | 23.901 | 1.00 | 0.00 | C |
| ATOM | 925 | N | ALA | K | 72 | 16.354 | −6.05 | 20.057 | 1.00 | 0.00 | N |
| ATOM | 926 | CA | ALA | K | 72 | 17.447 | −5.605 | 19.185 | 1.00 | 0.00 | C |
| ATOM | 927 | C | ALA | K | 72 | 18.091 | −4.323 | 19.72 | 1.00 | 0.00 | C |
| ATOM | 928 | O | ALA | K | 72 | 19.307 | −4.229 | 19.831 | 1.00 | 0.00 | O |
| ATOM | 929 | CB | ALA | K | 72 | 17.003 | −5.411 | 17.736 | 1.00 | 0.00 | C |
| ATOM | 935 | N | LEU | K | 73 | 17.199 | −3.304 | 20.035 | 1.00 | 0.00 | N |
| ATOM | 936 | CA | LEU | K | 73 | 17.624 | −2.018 | 20.597 | 1.00 | 0.00 | C |
| ATOM | 937 | C | LEU | K | 73 | 18.403 | −2.272 | 21.888 | 1.00 | 0.00 | C |
| ATOM | 938 | O | LEU | K | 73 | 19.485 | −1.735 | 22.075 | 1.00 | 0.00 | O |
| ATOM | 939 | CB | LEU | K | 73 | 16.417 | −1.069 | 20.8 | 1.00 | 0.00 | C |
| ATOM | 940 | CG | LEU | K | 73 | 16.695 | 0.393 | 21.215 | 1.00 | 0.00 | C |
| ATOM | 941 | CD1 | LEU | K | 73 | 17.026 | 0.557 | 22.699 | 1.00 | 0.00 | C |
| ATOM | 942 | CD2 | LEU | K | 73 | 17.744 | 1.075 | 20.34 | 1.00 | 0.00 | C |
| ATOM | 954 | N | PHE | K | 74 | 17.774 | −3.097 | 22.81 | 1.00 | 0.00 | N |
| ATOM | 955 | CA | PHE | K | 74 | 18.26 | −3.297 | 24.171 | 1.00 | 0.00 | C |
| ATOM | 956 | C | PHE | K | 74 | 19.694 | −3.832 | 24.176 | 1.00 | 0.00 | C |
| ATOM | 957 | O | PHE | K | 74 | 20.534 | −3.302 | 24.891 | 1.00 | 0.00 | O |
| ATOM | 958 | CB | PHE | K | 74 | 17.307 | −4.194 | 24.987 | 1.00 | 0.00 | C |
| ATOM | 959 | CG | PHE | K | 74 | 17.521 | −4.114 | 26.478 | 1.00 | 0.00 | C |
| ATOM | 960 | CD1 | PHE | K | 74 | 17.967 | −5.242 | 27.209 | 1.00 | 0.00 | C |
| ATOM | 961 | CE1 | PHE | K | 74 | 18.105 | −5.172 | 28.609 | 1.00 | 0.00 | C |
| ATOM | 962 | CZ | PHE | K | 74 | 17.815 | −3.979 | 29.293 | 1.00 | 0.00 | C |
| ATOM | 963 | CE2 | PHE | K | 74 | 17.377 | −2.851 | 28.579 | 1.00 | 0.00 | C |
| ATOM | 964 | CD2 | PHE | K | 74 | 17.224 | −2.918 | 27.182 | 1.00 | 0.00 | C |
| ATOM | 974 | N | VAL | K | 75 | 19.946 | −4.946 | 23.371 | 1.00 | 0.00 | N |
| ATOM | 975 | CA | VAL | K | 75 | 21.272 | −5.585 | 23.333 | 1.00 | 0.00 | C |
| ATOM | 976 | C | VAL | K | 75 | 22.348 | −4.601 | 22.861 | 1.00 | 0.00 | C |
| ATOM | 977 | O | VAL | K | 75 | 23.447 | −4.59 | 23.401 | 1.00 | 0.00 | O |
| ATOM | 978 | CB | VAL | K | 75 | 21.372 | −6.94 | 22.573 | 1.00 | 0.00 | C |
| ATOM | 979 | CG1 | VAL | K | 75 | 20.544 | −8.024 | 23.262 | 1.00 | 0.00 | C |
| ATOM | 980 | CG2 | VAL | K | 75 | 21.017 | −6.882 | 21.086 | 1.00 | 0.00 | C |
| ATOM | 990 | N | PHE | K | 76 | 21.997 | −3.787 | 21.789 | 1.00 | 0.00 | N |
| ATOM | 991 | CA | PHE | K | 76 | 22.881 | −2.742 | 21.272 | 1.00 | 0.00 | C |
| ATOM | 992 | C | PHE | K | 76 | 23.25 | −1.789 | 22.416 | 1.00 | 0.00 | C |
| ATOM | 993 | O | PHE | K | 76 | 24.423 | −1.544 | 22.664 | 1.00 | 0.00 | O |
| ATOM | 994 | CB | PHE | K | 76 | 22.268 | −2.031 | 20.042 | 1.00 | 0.00 | C |
| ATOM | 995 | CG | PHE | K | 76 | 22.877 | −0.685 | 19.729 | 1.00 | 0.00 | C |
| ATOM | 996 | CD1 | PHE | K | 76 | 22.154 | 0.501 | 20.013 | 1.00 | 0.00 | C |
| ATOM | 997 | CD2 | PHE | K | 76 | 24.174 | −0.578 | 19.171 | 1.00 | 0.00 | C |
| ATOM | 998 | CE1 | PHE | K | 76 | 22.718 | 1.764 | 19.756 | 1.00 | 0.00 | C |
| ATOM | 999 | CE2 | PHE | K | 76 | 24.736 | 0.689 | 18.92 | 1.00 | 0.00 | C |
| ATOM | 1000 | CZ | PHE | K | 76 | 24.01 | 1.858 | 19.211 | 1.00 | 0.00 | C |
| ATOM | 1010 | N | ALA | K | 77 | 22.172 | −1.217 | 23.081 | 1.00 | 0.00 | N |
| ATOM | 1011 | CA | ALA | K | 77 | 22.328 | −0.136 | 24.048 | 1.00 | 0.00 | C |
| ATOM | 1012 | C | ALA | K | 77 | 23.234 | −0.547 | 25.206 | 1.00 | 0.00 | C |
| ATOM | 1013 | O | ALA | K | 77 | 24.165 | 0.171 | 25.545 | 1.00 | 0.00 | O |
| ATOM | 1014 | CB | ALA | K | 77 | 20.987 | 0.377 | 24.569 | 1.00 | 0.00 | C |
| ATOM | 1020 | N | THR | K | 78 | 22.88 | −1.727 | 25.855 | 1.00 | 0.00 | N |
| ATOM | 1021 | CA | THR | K | 78 | 23.625 | −2.223 | 27.009 | 1.00 | 0.00 | C |
| ATOM | 1022 | C | THR | K | 78 | 24.987 | −2.674 | 26.515 | 1.00 | 0.00 | C |
| ATOM | 1023 | O | THR | K | 78 | 25.974 | −2.7 | 27.236 | 1.00 | 0.00 | O |

TABLE 6-continued

| ATOM | 1024 | CB | THR | K | 78 | 22.881 | −3.339 | 27.78 | 1.00 | 0.00 | C |
|---|---|---|---|---|---|---|---|---|---|---|---|
| ATOM | 1025 | OG1 | THR | K | 78 | 23.43 | −3.473 | 29.094 | 1.00 | 0.00 | O |
| ATOM | 1026 | CG2 | THR | K | 78 | 22.894 | −4.71 | 27.107 | 1.00 | 0.00 | C |
| ATOM | 1035 | N | PRO | K | 63 | 2.314 | −6.507 | 19.331 | 1.00 | 0.00 | N |
| ATOM | 1036 | CA | PRO | K | 63 | 3.18 | −6.771 | 20.468 | 1.00 | 0.00 | C |
| ATOM | 1038 | C | PRO | K | 63 | 4.349 | −7.725 | 20.289 | 1.00 | 0.00 | C |
| ATOM | 1039 | O | PRO | K | 63 | 5.423 | −7.445 | 20.802 | 1.00 | 0.00 | O |
| ATOM | 1040 | CB | PRO | K | 63 | 2.244 | −7.213 | 21.576 | 1.00 | 0.00 | C |
| ATOM | 1043 | CG | PRO | K | 63 | 0.981 | −6.425 | 21.298 | 1.00 | 0.00 | C |
| ATOM | 1046 | CD | PRO | K | 63 | 0.977 | −6.194 | 19.795 | 1.00 | 0.00 | C |

TABLE 7

| ATOM | 1 | N | ILE | K | 5 | 28.121 | −7.663 | 2.389 | 1.00 | 0.00 | N |
|---|---|---|---|---|---|---|---|---|---|---|---|
| ATOM | 2 | CA | ILE | K | 5 | 27.537 | −8.933 | 2.847 | 1.00 | 0.00 | C |
| ATOM | 3 | C | ILE | K | 5 | 26.933 | −8.728 | 4.240 | 1.00 | 0.00 | C |
| ATOM | 4 | O | ILE | K | 5 | 25.896 | −9.292 | 4.558 | 1.00 | 0.00 | O |
| ATOM | 5 | CB | ILE | K | 5 | 28.544 | −10.118 | 2.780 | 1.00 | 0.00 | C |
| ATOM | 6 | CG1 | ILE | K | 5 | 27.845 | −11.446 | 3.142 | 1.00 | 0.00 | C |
| ATOM | 7 | CG2 | ILE | K | 5 | 29.809 | −9.894 | 3.618 | 1.00 | 0.00 | C |
| ATOM | 8 | CD1 | ILE | K | 5 | 28.630 | −12.682 | 2.730 | 1.00 | 0.00 | C |
| ATOM | 9 | N | ALA | K | 6 | 27.652 | −7.885 | 5.078 | 1.00 | 0.00 | N |
| ATOM | 10 | CA | ALA | K | 6 | 27.188 | −7.544 | 6.421 | 1.00 | 0.00 | C |
| ATOM | 11 | C | ALA | K | 6 | 25.850 | −6.821 | 6.317 | 1.00 | 0.00 | C |
| ATOM | 12 | O | ALA | K | 6 | 24.876 | −7.223 | 6.940 | 1.00 | 0.00 | O |
| ATOM | 13 | CB | ALA | K | 6 | 28.205 | −6.721 | 7.207 | 1.00 | 0.00 | C |
| ATOM | 14 | N | ALA | K | 7 | 25.842 | −5.715 | 5.472 | 1.00 | 0.00 | N |
| ATOM | 15 | CA | ALA | K | 7 | 24.627 | −4.946 | 5.207 | 1.00 | 0.00 | C |
| ATOM | 16 | C | ALA | K | 7 | 23.504 | −5.870 | 4.742 | 1.00 | 0.00 | C |
| ATOM | 17 | O | ALA | K | 7 | 22.387 | −5.777 | 5.234 | 1.00 | 0.00 | O |
| ATOM | 18 | CB | ALA | K | 7 | 24.850 | −3.832 | 4.187 | 1.00 | 0.00 | C |
| ATOM | 19 | N | GLY | K | 8 | 23.861 | −6.771 | 3.743 | 1.00 | 0.00 | N |
| ATOM | 20 | CA | GLY | K | 8 | 22.942 | −7.733 | 3.159 | 1.00 | 0.00 | C |
| ATOM | 21 | C | GLY | K | 8 | 22.190 | −8.547 | 4.197 | 1.00 | 0.00 | C |
| ATOM | 22 | O | GLY | K | 8 | 20.981 | −8.701 | 4.105 | 1.00 | 0.00 | O |
| ATOM | 23 | N | ALA | K | 9 | 22.983 | −9.120 | 5.181 | 1.00 | 0.00 | N |
| ATOM | 24 | CA | ALA | K | 9 | 22.435 | −9.985 | 6.224 | 1.00 | 0.00 | C |
| ATOM | 25 | C | ALA | K | 9 | 21.368 | −9.263 | 7.040 | 1.00 | 0.00 | C |
| ATOM | 26 | O | ALA | K | 9 | 20.289 | −9.802 | 7.254 | 1.00 | 0.00 | O |
| ATOM | 27 | CB | ALA | K | 9 | 23.515 | −10.557 | 7.140 | 1.00 | 0.00 | C |
| ATOM | 28 | N | LEU | K | 10 | 21.734 | −8.017 | 7.538 | 1.00 | 0.00 | N |
| ATOM | 29 | CA | LEU | K | 10 | 20.857 | −7.260 | 8.435 | 1.00 | 0.00 | C |
| ATOM | 30 | C | LEU | K | 10 | 19.538 | −6.964 | 7.722 | 1.00 | 0.00 | C |
| ATOM | 31 | O | LEU | K | 10 | 18.472 | −7.283 | 8.235 | 1.00 | 0.00 | O |
| ATOM | 32 | CB | LEU | K | 10 | 21.475 | −5.951 | 8.973 | 1.00 | 0.00 | C |
| ATOM | 33 | CG | LEU | K | 10 | 22.328 | −6.133 | 10.246 | 1.00 | 0.00 | C |
| ATOM | 34 | CD1 | LEU | K | 10 | 23.675 | −6.796 | 9.973 | 1.00 | 0.00 | C |
| ATOM | 35 | CD2 | LEU | K | 10 | 22.563 | −4.777 | 10.912 | 1.00 | 0.00 | C |
| ATOM | 36 | N | ILE | K | 11 | 19.650 | −6.281 | 6.514 | 1.00 | 0.00 | N |
| ATOM | 37 | CA | ILE | K | 11 | 18.467 | −5.824 | 5.777 | 1.00 | 0.00 | C |
| ATOM | 38 | C | ILE | K | 11 | 17.578 | −7.005 | 5.372 | 1.00 | 0.00 | C |
| ATOM | 39 | O | ILE | K | 11 | 16.360 | −6.901 | 5.425 | 1.00 | 0.00 | O |
| ATOM | 40 | CB | ILE | K | 11 | 18.795 | −4.856 | 4.606 | 1.00 | 0.00 | C |
| ATOM | 41 | CG1 | ILE | K | 11 | 17.524 | −4.109 | 4.147 | 1.00 | 0.00 | C |
| ATOM | 42 | CG2 | ILE | K | 11 | 19.480 | −5.544 | 3.421 | 1.00 | 0.00 | C |
| ATOM | 43 | CD1 | ILE | K | 11 | 17.822 | −2.876 | 3.306 | 1.00 | 0.00 | C |
| ATOM | 44 | N | GLY | K | 12 | 18.241 | −8.146 | 4.933 | 1.00 | 0.00 | N |
| ATOM | 45 | CA | GLY | K | 12 | 17.555 | −9.364 | 4.535 | 1.00 | 0.00 | C |
| ATOM | 46 | C | GLY | K | 12 | 16.642 | −9.865 | 5.635 | 1.00 | 0.00 | C |
| ATOM | 47 | O | GLY | K | 12 | 15.472 | −10.131 | 5.399 | 1.00 | 0.00 | O |
| ATOM | 48 | N | GLY | K | 13 | 17.246 | −10.004 | 6.877 | 1.00 | 0.00 | N |
| ATOM | 49 | CA | GLY | K | 13 | 16.527 | −10.463 | 8.054 | 1.00 | 0.00 | C |
| ATOM | 50 | C | GLY | K | 13 | 15.268 | −9.650 | 8.300 | 1.00 | 0.00 | C |
| ATOM | 51 | O | GLY | K | 13 | 14.189 | −10.202 | 8.473 | 1.00 | 0.00 | O |
| ATOM | 52 | N | GLY | K | 14 | 15.468 | −8.276 | 8.332 | 1.00 | 0.00 | N |
| ATOM | 53 | CA | GLY | K | 14 | 14.388 | −7.324 | 8.544 | 1.00 | 0.00 | C |
| ATOM | 54 | C | GLY | K | 14 | 13.234 | −7.535 | 7.579 | 1.00 | 0.00 | C |
| ATOM | 55 | O | GLY | K | 14 | 12.086 | −7.620 | 7.992 | 1.00 | 0.00 | O |
| ATOM | 56 | N | LEU | K | 15 | 13.605 | −7.585 | 6.240 | 1.00 | 0.00 | N |
| ATOM | 57 | CA | LEU | K | 15 | 12.661 | −7.745 | 5.129 | 1.00 | 0.00 | C |
| ATOM | 58 | C | LEU | K | 15 | 11.777 | −8.963 | 5.401 | 1.00 | 0.00 | C |
| ATOM | 59 | O | LEU | K | 15 | 10.558 | −8.853 | 5.398 | 1.00 | 0.00 | O |
| ATOM | 60 | CB | LEU | K | 15 | 13.400 | −7.824 | 3.771 | 1.00 | 0.00 | C |
| ATOM | 61 | CG | LEU | K | 15 | 12.529 | −7.641 | 2.510 | 1.00 | 0.00 | C |
| ATOM | 62 | CD1 | LEU | K | 15 | 13.428 | −7.309 | 1.318 | 1.00 | 0.00 | C |
| ATOM | 63 | CD2 | LEU | K | 15 | 11.700 | −8.879 | 2.169 | 1.00 | 0.00 | C |
| ATOM | 64 | N | ILE | K | 16 | 12.463 | −10.153 | 5.628 | 1.00 | 0.00 | N |

TABLE 7-continued

| | | | | | | | | | | |
|---|---|---|---|---|---|---|---|---|---|---|
| ATOM | 65 | CA | ILE | K | 16 | 11.799 | −11.454 | 5.776 | 1.00 | 0.00 | C |
| ATOM | 66 | C | ILE | K | 16 | 10.735 | −11.338 | 6.868 | 1.00 | 0.00 | C |
| ATOM | 67 | O | ILE | K | 16 | 9.582 | −11.680 | 6.643 | 1.00 | 0.00 | O |
| ATOM | 68 | CB | ILE | K | 16 | 12.803 | −12.619 | 6.039 | 1.00 | 0.00 | C |
| ATOM | 69 | CG1 | ILE | K | 16 | 13.659 | −12.895 | 4.782 | 1.00 | 0.00 | C |
| ATOM | 70 | CG2 | ILE | K | 16 | 12.086 | −13.909 | 6.458 | 1.00 | 0.00 | C |
| ATOM | 71 | CD1 | ILE | K | 16 | 14.930 | −13.674 | 5.089 | 1.00 | 0.00 | C |
| ATOM | 72 | N | MET | K | 17 | 11.186 | −10.883 | 8.101 | 1.00 | 0.00 | N |
| ATOM | 73 | CA | MET | K | 17 | 10.325 | −10.873 | 9.285 | 1.00 | 0.00 | C |
| ATOM | 74 | C | MET | K | 17 | 9.112 | −9.969 | 9.083 | 1.00 | 0.00 | C |
| ATOM | 75 | O | MET | K | 17 | 7.992 | −10.376 | 9.358 | 1.00 | 0.00 | O |
| ATOM | 76 | CB | MET | K | 17 | 11.072 | −10.480 | 10.569 | 1.00 | 0.00 | C |
| ATOM | 77 | CG | MET | K | 17 | 11.965 | −11.617 | 11.063 | 1.00 | 0.00 | C |
| ATOM | 78 | SD | MET | K | 17 | 12.781 | −11.152 | 12.622 | 1.00 | 0.00 | S |
| ATOM | 79 | CE | MET | K | 17 | 14.229 | −10.299 | 11.947 | 1.00 | 0.00 | C |
| ATOM | 80 | N | ALA | K | 18 | 9.381 | −8.681 | 8.641 | 1.00 | 0.00 | N |
| ATOM | 81 | CA | ALA | K | 18 | 8.335 | −7.661 | 8.530 | 1.00 | 0.00 | C |
| ATOM | 82 | C | ALA | K | 18 | 7.251 | −8.073 | 7.536 | 1.00 | 0.00 | C |
| ATOM | 83 | O | ALA | K | 18 | 6.066 | −7.978 | 7.829 | 1.00 | 0.00 | O |
| ATOM | 84 | CB | ALA | K | 18 | 8.898 | −6.297 | 8.153 | 1.00 | 0.00 | C |
| ATOM | 85 | N | GLY | K | 19 | 7.717 | −8.515 | 6.304 | 1.00 | 0.00 | N |
| ATOM | 86 | CA | GLY | K | 19 | 6.829 | −9.005 | 5.260 | 1.00 | 0.00 | C |
| ATOM | 87 | C | GLY | K | 19 | 5.987 | −10.160 | 5.767 | 1.00 | 0.00 | C |
| ATOM | 88 | O | GLY | K | 19 | 4.781 | −10.204 | 5.565 | 1.00 | 0.00 | O |
| ATOM | 89 | N | GLY | K | 20 | 6.707 | −11.134 | 6.437 | 1.00 | 0.00 | N |
| ATOM | 90 | CA | GLY | K | 20 | 6.099 | −12.302 | 7.039 | 1.00 | 0.00 | C |
| ATOM | 91 | C | GLY | K | 20 | 4.913 | −11.965 | 7.916 | 1.00 | 0.00 | C |
| ATOM | 92 | O | GLY | K | 20 | 3.864 | −12.584 | 7.803 | 1.00 | 0.00 | O |
| ATOM | 93 | N | ALA | K | 21 | 5.151 | −10.963 | 8.844 | 1.00 | 0.00 | N |
| ATOM | 94 | CA | ALA | K | 21 | 4.174 | −10.565 | 9.849 | 1.00 | 0.00 | C |
| ATOM | 95 | C | ALA | K | 21 | 2.837 | −10.204 | 9.219 | 1.00 | 0.00 | C |
| ATOM | 96 | O | ALA | K | 21 | 1.807 | −10.745 | 9.602 | 1.00 | 0.00 | O |
| ATOM | 97 | CB | ALA | K | 21 | 4.669 | −9.411 | 10.713 | 1.00 | 0.00 | C |
| ATOM | 98 | N | ILE | K | 22 | 2.887 | −9.210 | 8.246 | 1.00 | 0.00 | N |
| ATOM | 99 | CA | ILE | K | 22 | 1.657 | −8.691 | 7.639 | 1.00 | 0.00 | C |
| ATOM | 100 | C | ILE | K | 22 | 0.932 | −9.798 | 6.872 | 1.00 | 0.00 | C |
| ATOM | 101 | O | ILE | K | 22 | −0.288 | −9.878 | 6.917 | 1.00 | 0.00 | O |
| ATOM | 102 | CB | ILE | K | 22 | 1.811 | −7.360 | 6.845 | 1.00 | 0.00 | C |
| ATOM | 103 | CG1 | ILE | K | 22 | 2.660 | −7.427 | 5.557 | 1.00 | 0.00 | C |
| ATOM | 104 | CG2 | ILE | K | 22 | 2.377 | −6.274 | 7.765 | 1.00 | 0.00 | C |
| ATOM | 105 | CD1 | ILE | K | 22 | 1.848 | −7.745 | 4.310 | 1.00 | 0.00 | C |
| ATOM | 106 | N | GLY | K | 23 | 1.741 | −10.663 | 6.142 | 1.00 | 0.00 | N |
| ATOM | 107 | CA | GLY | K | 23 | 1.204 | −11.765 | 5.363 | 1.00 | 0.00 | C |
| ATOM | 108 | C | GLY | K | 23 | 0.376 | −12.709 | 6.211 | 1.00 | 0.00 | C |
| ATOM | 109 | O | GLY | K | 23 | −0.767 | −13.004 | 5.889 | 1.00 | 0.00 | O |
| ATOM | 110 | N | ALA | K | 24 | 1.042 | −13.206 | 7.322 | 1.00 | 0.00 | N |
| ATOM | 111 | CA | ALA | K | 24 | 0.432 | −14.149 | 8.256 | 1.00 | 0.00 | C |
| ATOM | 112 | C | ALA | K | 24 | −0.867 | −13.592 | 8.834 | 1.00 | 0.00 | C |
| ATOM | 113 | O | ALA | K | 24 | −1.841 | −14.320 | 8.961 | 1.00 | 0.00 | O |
| ATOM | 114 | CB | ALA | K | 24 | 1.385 | −14.552 | 9.378 | 1.00 | 0.00 | C |
| ATOM | 115 | N | GLY | K | 25 | −0.837 | −12.253 | 9.209 | 1.00 | 0.00 | N |
| ATOM | 116 | CA | GLY | K | 25 | −1.989 | −11.554 | 9.762 | 1.00 | 0.00 | C |
| ATOM | 117 | C | GLY | K | 25 | −3.224 | −11.712 | 8.896 | 1.00 | 0.00 | C |
| ATOM | 118 | O | GLY | K | 25 | −4.270 | −12.142 | 9.367 | 1.00 | 0.00 | O |
| ATOM | 119 | N | ILE | K | 26 | −3.049 | −11.314 | 7.575 | 1.00 | 0.00 | N |
| ATOM | 120 | CA | ILE | K | 26 | −4.123 | −11.406 | 6.580 | 1.00 | 0.00 | C |
| ATOM | 121 | C | ILE | K | 26 | −4.608 | −12.856 | 6.541 | 1.00 | 0.00 | C |
| ATOM | 122 | O | ILE | K | 26 | −5.800 | −13.101 | 6.670 | 1.00 | 0.00 | O |
| ATOM | 123 | CB | ILE | K | 26 | −3.723 | −10.885 | 5.167 | 1.00 | 0.00 | C |
| ATOM | 124 | CG1 | ILE | K | 26 | −3.329 | −9.390 | 5.154 | 1.00 | 0.00 | C |
| ATOM | 125 | CG2 | ILE | K | 26 | −4.818 | −11.147 | 4.125 | 1.00 | 0.00 | C |
| ATOM | 126 | CD1 | ILE | K | 26 | −4.410 | −8.423 | 5.617 | 1.00 | 0.00 | C |
| ATOM | 127 | N | GLY | K | 27 | −3.622 | −13.815 | 6.331 | 1.00 | 0.00 | N |
| ATOM | 128 | CA | GLY | K | 27 | −3.902 | −15.227 | 6.118 | 1.00 | 0.00 | C |
| ATOM | 129 | C | GLY | K | 27 | −4.862 | −15.800 | 7.143 | 1.00 | 0.00 | C |
| ATOM | 130 | O | GLY | K | 27 | −5.885 | −16.369 | 6.784 | 1.00 | 0.00 | O |
| ATOM | 131 | N | ASP | K | 28 | −4.461 | −15.632 | 8.465 | 1.00 | 0.00 | N |
| ATOM | 132 | CA | ASP | K | 28 | −5.235 | −16.133 | 9.607 | 1.00 | 0.00 | C |
| ATOM | 133 | C | ASP | K | 28 | −6.691 | −15.707 | 9.464 | 1.00 | 0.00 | C |
| ATOM | 134 | O | ASP | K | 28 | −7.587 | −16.541 | 9.509 | 1.00 | 0.00 | O |
| ATOM | 135 | CB | ASP | K | 28 | −4.707 | −15.657 | 10.975 | 1.00 | 0.00 | C |
| ATOM | 136 | CG | ASP | K | 28 | −3.539 | −16.488 | 11.442 | 1.00 | 0.00 | C |
| ATOM | 137 | OD1 | ASP | K | 28 | −2.373 | −16.308 | 11.122 | 1.00 | 0.00 | O |
| ATOM | 138 | OD2 | ASP | K | 28 | −3.957 | −17.506 | 12.234 | 1.00 | 0.00 | O |
| ATOM | 139 | N | GLY | K | 29 | −6.886 | −14.338 | 9.315 | 1.00 | 0.00 | N |
| ATOM | 140 | CA | GLY | K | 29 | −8.205 | −13.736 | 9.279 | 1.00 | 0.00 | C |
| ATOM | 141 | C | GLY | K | 29 | −9.036 | −14.339 | 8.166 | 1.00 | 0.00 | C |
| ATOM | 142 | O | GLY | K | 29 | −10.008 | −15.041 | 8.410 | 1.00 | 0.00 | O |
| ATOM | 143 | N | VAL | K | 30 | −8.603 | −14.009 | 6.889 | 1.00 | 0.00 | N |
| ATOM | 144 | CA | VAL | K | 30 | −9.444 | −14.243 | 5.714 | 1.00 | 0.00 | C |

TABLE 7-continued

| | | | | | | | | | | |
|---|---|---|---|---|---|---|---|---|---|---|
| ATOM | 145 | C | VAL | K | 30 | −9.809 | −15.722 | 5.590 | 1.00 | 0.00 | C |
| ATOM | 146 | O | VAL | K | 30 | −10.974 | −16.055 | 5.423 | 1.00 | 0.00 | O |
| ATOM | 147 | CB | VAL | K | 30 | −8.921 | −13.639 | 4.378 | 1.00 | 0.00 | C |
| ATOM | 148 | CG1 | VAL | K | 30 | −8.803 | −12.116 | 4.474 | 1.00 | 0.00 | C |
| ATOM | 149 | CG2 | VAL | K | 30 | −7.604 | −14.230 | 3.864 | 1.00 | 0.00 | C |
| ATOM | 150 | N | ALA | K | 31 | −8.745 | −16.616 | 5.628 | 1.00 | 0.00 | N |
| ATOM | 151 | CA | ALA | K | 31 | −8.927 | −18.027 | 5.299 | 1.00 | 0.00 | C |
| ATOM | 152 | C | ALA | K | 31 | −9.775 | −18.719 | 6.360 | 1.00 | 0.00 | C |
| ATOM | 153 | O | ALA | K | 31 | −10.740 | −19.402 | 6.043 | 1.00 | 0.00 | O |
| ATOM | 154 | CB | ALA | K | 31 | −7.605 | −18.761 | 5.097 | 1.00 | 0.00 | C |
| ATOM | 155 | N | GLY | K | 32 | −9.344 | −18.541 | 7.669 | 1.00 | 0.00 | N |
| ATOM | 156 | CA | GLY | K | 32 | −9.973 | −19.223 | 8.786 | 1.00 | 0.00 | C |
| ATOM | 157 | C | GLY | K | 32 | −11.448 | −18.886 | 8.852 | 1.00 | 0.00 | C |
| ATOM | 158 | O | GLY | K | 32 | −12.311 | −19.748 | 8.739 | 1.00 | 0.00 | O |
| ATOM | 159 | N | ASN | K | 33 | −11.697 | −17.540 | 9.067 | 1.00 | 0.00 | N |
| ATOM | 160 | CA | ASN | K | 33 | −13.041 | −17.042 | 9.353 | 1.00 | 0.00 | C |
| ATOM | 161 | C | ASN | K | 33 | −14.030 | −17.338 | 8.237 | 1.00 | 0.00 | C |
| ATOM | 162 | O | ASN | K | 33 | −15.195 | −17.586 | 8.518 | 1.00 | 0.00 | O |
| ATOM | 163 | CB | ASN | K | 33 | −13.082 | −15.548 | 9.682 | 1.00 | 0.00 | C |
| ATOM | 164 | CG | ASN | K | 33 | −12.429 | −15.313 | 11.027 | 1.00 | 0.00 | C |
| ATOM | 165 | OD1 | ASN | K | 33 | −11.228 | −15.123 | 11.150 | 1.00 | 0.00 | O |
| ATOM | 166 | ND2 | ASN | K | 33 | −13.304 | −15.391 | 12.084 | 1.00 | 0.00 | N |
| ATOM | 167 | N | ALA | K | 34 | −13.550 | −17.251 | 6.936 | 1.00 | 0.00 | N |
| ATOM | 168 | CA | ALA | K | 34 | −14.421 | −17.507 | 5.790 | 1.00 | 0.00 | C |
| ATOM | 169 | C | ALA | K | 34 | −15.122 | −18.859 | 5.907 | 1.00 | 0.00 | C |
| ATOM | 170 | O | ALA | K | 34 | −16.319 | −18.947 | 5.666 | 1.00 | 0.00 | O |
| ATOM | 171 | CB | ALA | K | 34 | −13.694 | −17.415 | 4.452 | 1.00 | 0.00 | C |
| ATOM | 172 | N | LEU | K | 35 | −14.314 | −19.944 | 6.241 | 1.00 | 0.00 | N |
| ATOM | 173 | CA | LEU | K | 35 | −14.846 | −21.307 | 6.228 | 1.00 | 0.00 | C |
| ATOM | 174 | C | LEU | K | 35 | −15.971 | −21.436 | 7.251 | 1.00 | 0.00 | C |
| ATOM | 175 | O | LEU | K | 35 | −17.069 | −21.845 | 6.903 | 1.00 | 0.00 | O |
| ATOM | 176 | CB | LEU | K | 35 | −13.772 | −22.394 | 6.421 | 1.00 | 0.00 | C |
| ATOM | 177 | CG | LEU | K | 35 | 14.300 | −23.840 | 6.297 | 1.00 | 0.00 | C |
| ATOM | 178 | CD1 | LEU | K | 35 | −15.047 | −24.085 | 4.985 | 1.00 | 0.00 | C |
| ATOM | 179 | CD2 | LEU | K | 35 | −13.141 | −24.824 | 6.390 | 1.00 | 0.00 | C |
| ATOM | 180 | N | ILE | K | 36 | −15.638 | −21.099 | 8.558 | 1.00 | 0.00 | N |
| ATOM | 181 | CA | ILE | K | 36 | −16.600 | −21.255 | 9.659 | 1.00 | 0.00 | C |
| ATOM | 182 | C | ILE | K | 36 | −17.882 | −20.429 | 9.441 | 1.00 | 0.00 | C |
| ATOM | 183 | O | ILE | K | 36 | −18.949 | −20.824 | 9.886 | 1.00 | 0.00 | O |
| ATOM | 184 | CB | ILE | K | 36 | −15.962 | −21.030 | 11.062 | 1.00 | 0.00 | C |
| ATOM | 185 | CG1 | ILE | K | 36 | −16.871 | −21.445 | 12.238 | 1.00 | 0.00 | C |
| ATOM | 186 | CG2 | ILE | K | 36 | −15.510 | −19.587 | 11.273 | 1.00 | 0.00 | C |
| ATOM | 187 | CD1 | ILE | K | 36 | −17.169 | −22.935 | 12.277 | 1.00 | 0.00 | C |
| ATOM | 188 | N | SER | K | 37 | −17.738 | −19.213 | 8.783 | 1.00 | 0.00 | N |
| ATOM | 189 | CA | SER | K | 37 | −18.885 | −18.361 | 8.470 | 1.00 | 0.00 | C |
| ATOM | 190 | C | SER | K | 37 | −19.842 | −19.064 | 7.503 | 1.00 | 0.00 | C |
| ATOM | 191 | O | SER | K | 37 | −21.048 | −19.060 | 7.714 | 1.00 | 0.00 | O |
| ATOM | 192 | CB | SER | K | 37 | −18.468 | −16.998 | 7.904 | 1.00 | 0.00 | C |
| ATOM | 193 | OG | SER | K | 37 | −17.726 | −16.273 | 8.882 | 1.00 | 0.00 | O |
| ATOM | 194 | N | GLY | K | 38 | −19.250 | −19.608 | 6.368 | 1.00 | 0.00 | N |
| ATOM | 195 | CA | GLY | K | 38 | −20.018 | −20.200 | 5.286 | 1.00 | 0.00 | C |
| ATOM | 196 | C | GLY | K | 38 | −20.674 | −21.495 | 5.719 | 1.00 | 0.00 | C |
| ATOM | 197 | O | GLY | K | 38 | −21.892 | −21.595 | 5.801 | 1.00 | 0.00 | O |
| ATOM | 198 | N | VAL | K | 39 | −19.771 | −22.524 | 5.962 | 1.00 | 0.00 | N |
| ATOM | 199 | CA | VAL | K | 39 | −20.202 | −23.854 | 6.388 | 1.00 | 0.00 | C |
| ATOM | 200 | C | VAL | K | 39 | −20.585 | −23.634 | 7.851 | 1.00 | 0.00 | C |
| ATOM | 201 | O | VAL | K | 39 | −19.755 | −23.371 | 8.710 | 1.00 | 0.00 | O |
| ATOM | 202 | CB | VAL | K | 39 | −19.109 | −24.938 | 6.216 | 1.00 | 0.00 | C |
| ATOM | 203 | CG1 | VAL | K | 39 | −19.600 | −26.295 | 6.726 | 1.00 | 0.00 | C |
| ATOM | 204 | CG2 | VAL | K | 39 | −18.706 | −25.084 | 4.746 | 1.00 | 0.00 | C |
| ATOM | 205 | N | ALA | K | 40 | −21.950 | −23.720 | 8.052 | 1.00 | 0.00 | N |
| ATOM | 206 | CA | ALA | K | 40 | −22.661 | −23.216 | 9.225 | 1.00 | 0.00 | C |
| ATOM | 207 | C | ALA | K | 40 | −24.147 | −23.511 | 9.031 | 1.00 | 0.00 | C |
| ATOM | 208 | O | ALA | K | 40 | −24.767 | −24.137 | 9.880 | 1.00 | 0.00 | O |
| ATOM | 209 | CB | ALA | K | 40 | −22.458 | −21.723 | 9.480 | 1.00 | 0.00 | C |
| ATOM | 210 | N | ARG | K | 41 | −24.700 | −23.008 | 7.852 | 1.00 | 0.00 | N |
| ATOM | 211 | CA | ARG | K | 41 | −26.085 | −23.274 | 7.460 | 1.00 | 0.00 | C |
| ATOM | 212 | C | ARG | K | 41 | −26.211 | −24.778 | 7.215 | 1.00 | 0.00 | C |
| ATOM | 213 | O | ARG | K | 41 | −27.000 | −25.451 | 7.864 | 1.00 | 0.00 | O |
| ATOM | 214 | CB | ARG | K | 41 | −26.570 | −22.473 | 6.234 | 1.00 | 0.00 | C |
| ATOM | 215 | CG | ARG | K | 41 | −26.713 | −20.966 | 6.485 | 1.00 | 0.00 | C |
| ATOM | 216 | CD | ARG | K | 41 | −25.452 | −20.174 | 6.135 | 1.00 | 0.00 | C |
| ATOM | 217 | NE | ARG | K | 41 | −25.678 | −18.741 | 6.386 | 1.00 | 0.00 | N |
| ATOM | 218 | CZ | ARG | K | 41 | −25.452 | −18.101 | 7.583 | 1.00 | 0.00 | C |
| ATOM | 219 | NH1 | ARG | K | 41 | −25.060 | −18.741 | 8.738 | 1.00 | 0.00 | N |
| ATOM | 220 | NH2 | ARG | K | 41 | −25.621 | −16.742 | 7.672 | 1.00 | 0.00 | N |
| ATOM | 221 | N | GLN | K | 42 | −25.370 | −25.293 | 6.231 | 1.00 | 0.00 | N |
| ATOM | 222 | CA | GLN | K | 42 | −25.068 | −26.723 | 6.170 | 1.00 | 0.00 | C |
| ATOM | 223 | C | GLN | K | 42 | −24.106 | −26.908 | 7.346 | 1.00 | 0.00 | C |
| ATOM | 224 | O | GLN | K | 42 | −23.120 | −26.187 | 7.425 | 1.00 | 0.00 | O |

TABLE 7-continued

| | | | | | | | | | | |
|---|---|---|---|---|---|---|---|---|---|---|
| ATOM | 225 | CB | GLN | K | 42 | −24.378 | −27.132 | 4.861 | 1.00 | 0.00 | C |
| ATOM | 226 | CG | GLN | K | 42 | −25.309 | −26.988 | 3.656 | 1.00 | 0.00 | C |
| ATOM | 227 | CD | GLN | K | 42 | −24.569 | −27.351 | 2.387 | 1.00 | 0.00 | C |
| ATOM | 228 | OE1 | GLN | K | 42 | −23.890 | −26.535 | 1.781 | 1.00 | 0.00 | O |
| ATOM | 229 | NE2 | GLN | K | 42 | −24.697 | −28.671 | 2.018 | 1.00 | 0.00 | N |
| ATOM | 230 | N | PRO | K | 43 | −24.423 | −27.890 | 8.291 | 1.00 | 0.00 | N |
| ATOM | 231 | CA | PRO | K | 43 | −23.884 | −27.878 | 9.642 | 1.00 | 0.00 | C |
| ATOM | 232 | C | PRO | K | 43 | −22.377 | −27.648 | 9.717 | 1.00 | 0.00 | C |
| ATOM | 233 | O | PRO | K | 43 | −21.587 | −28.264 | 9.010 | 1.00 | 0.00 | O |
| ATOM | 234 | CB | PRO | K | 43 | −24.244 | −29.240 | 10.215 | 1.00 | 0.00 | C |
| ATOM | 235 | CG | PRO | K | 43 | −25.513 | −29.627 | 9.485 | 1.00 | 0.00 | C |
| ATOM | 236 | CD | PRO | K | 43 | −25.436 | −28.920 | 8.145 | 1.00 | 0.00 | C |
| ATOM | 237 | N | GLU | K | 44 | −22.018 | −26.729 | 10.698 | 1.00 | 0.00 | N |
| ATOM | 238 | CA | GLU | K | 44 | −20.630 | −26.532 | 11.109 | 1.00 | 0.00 | C |
| ATOM | 239 | C | GLU | K | 44 | −20.263 | −27.787 | 11.901 | 1.00 | 0.00 | C |
| ATOM | 240 | O | GLU | K | 44 | −20.648 | −27.973 | 13.047 | 1.00 | 0.00 | O |
| ATOM | 241 | CB | GLU | K | 44 | −20.357 | −25.222 | 11.885 | 1.00 | 0.00 | C |
| ATOM | 242 | CG | GLU | K | 44 | −21.282 | −24.897 | 13.065 | 1.00 | 0.00 | C |
| ATOM | 243 | CD | GLU | K | 44 | −20.874 | −23.584 | 13.689 | 1.00 | 0.00 | C |
| ATOM | 244 | OE1 | GLU | K | 44 | −21.169 | −22.482 | 13.249 | 1.00 | 0.00 | O |
| ATOM | 245 | OE2 | GLU | K | 44 | −20.084 | −23.772 | 14.778 | 1.00 | 0.00 | O |
| ATOM | 246 | N | ALA | K | 45 | −19.503 | −28.690 | 11.171 | 1.00 | 0.00 | N |
| ATOM | 247 | CA | ALA | K | 45 | −19.111 | −29.993 | 11.700 | 1.00 | 0.00 | C |
| ATOM | 248 | C | ALA | K | 45 | −17.820 | −30.392 | 10.992 | 1.00 | 0.00 | C |
| ATOM | 249 | O | ALA | K | 45 | −16.751 | −30.343 | 11.586 | 1.00 | 0.00 | O |
| ATOM | 250 | CB | ALA | K | 45 | −20.221 | −31.038 | 11.595 | 1.00 | 0.00 | C |
| ATOM | 251 | N | GLN | K | 46 | −17.945 | −30.742 | 9.651 | 1.00 | 0.00 | N |
| ATOM | 252 | CA | GLN | K | 46 | −16.777 | −31.025 | 8.812 | 1.00 | 0.00 | C |
| ATOM | 253 | C | GLN | K | 46 | −15.948 | −29.747 | 8.696 | 1.00 | 0.00 | C |
| ATOM | 254 | O | GLN | K | 46 | −14.745 | −29.762 | 8.923 | 1.00 | 0.00 | O |
| ATOM | 255 | CB | GLN | K | 46 | −17.123 | −31.555 | 7.408 | 1.00 | 0.00 | C |
| ATOM | 256 | CG | GLN | K | 46 | −17.621 | −33.004 | 7.392 | 1.00 | 0.00 | C |
| ATOM | 257 | CD | GLN | K | 46 | −19.006 | −33.186 | 7.986 | 1.00 | 0.00 | C |
| ATOM | 258 | OE1 | GLN | K | 46 | −19.859 | −32.308 | 7.971 | 1.00 | 0.00 | O |
| ATOM | 259 | NE2 | GLN | K | 46 | −19.226 | −34.446 | 8.491 | 1.00 | 0.00 | N |
| ATOM | 260 | N | GLY | K | 47 | −16.657 | −28.614 | 8.311 | 1.00 | 0.00 | N |
| ATOM | 261 | CA | GLY | K | 47 | −16.039 | −27.303 | 8.201 | 1.00 | 0.00 | C |
| ATOM | 262 | C | GLY | K | 47 | −15.338 | −26.879 | 9.479 | 1.00 | 0.00 | C |
| ATOM | 263 | O | GLY | K | 47 | −14.240 | −26.342 | 9.441 | 1.00 | 0.00 | O |
| ATOM | 264 | N | ARG | K | 48 | −16.061 | −27.090 | 10.644 | 1.00 | 0.00 | N |
| ATOM | 265 | CA | ARG | K | 48 | −15.555 | −26.706 | 11.960 | 1.00 | 0.00 | C |
| ATOM | 266 | C | ARG | K | 48 | −14.231 | −27.405 | 12.262 | 1.00 | 0.00 | C |
| ATOM | 267 | O | ARG | K | 48 | −13.287 | −26.756 | 12.689 | 1.00 | 0.00 | O |
| ATOM | 268 | CB | ARG | K | 48 | −16.597 | −26.944 | 13.061 | 1.00 | 0.00 | C |
| ATOM | 269 | CG | ARG | K | 48 | −16.186 | −26.354 | 14.413 | 1.00 | 0.00 | C |
| ATOM | 270 | CD | ARG | K | 48 | −17.369 | −26.238 | 15.367 | 1.00 | 0.00 | C |
| ATOM | 271 | NE | ARG | K | 48 | −17.915 | −27.575 | 15.655 | 1.00 | 0.00 | N |
| ATOM | 272 | CZ | ARG | K | 48 | −19.183 | −27.822 | 16.126 | 1.00 | 0.00 | C |
| ATOM | 273 | NH1 | ARG | K | 48 | −20.102 | −26.840 | 16.422 | 1.00 | 0.00 | N |
| ATOM | 274 | NH2 | ARG | K | 48 | −19.592 | −29.116 | 16.330 | 1.00 | 0.00 | N |
| ATOM | 275 | N | LEU | K | 49 | −14.204 | −28.779 | 12.049 | 1.00 | 0.00 | N |
| ATOM | 276 | CA | LEU | K | 49 | −13.005 | −29.597 | 12.271 | 1.00 | 0.00 | C |
| ATOM | 277 | C | LEU | K | 49 | −11.827 | −29.081 | 11.437 | 1.00 | 0.00 | C |
| ATOM | 278 | O | LEU | K | 49 | −10.702 | −29.027 | 11.916 | 1.00 | 0.00 | O |
| ATOM | 279 | CB | LEU | K | 49 | −13.275 | −31.090 | 11.982 | 1.00 | 0.00 | C |
| ATOM | 280 | CG | LEU | K | 49 | −12.083 | −32.036 | 12.236 | 1.00 | 0.00 | C |
| ATOM | 281 | CD1 | LEU | K | 49 | −11.677 | −32.080 | 13.709 | 1.00 | 0.00 | C |
| ATOM | 282 | CD2 | LEU | K | 49 | −12.425 | −33.444 | 11.754 | 1.00 | 0.00 | C |
| ATOM | 283 | N | PHE | K | 50 | −12.130 | −28.759 | 10.121 | 1.00 | 0.00 | N |
| ATOM | 284 | CA | PHE | K | 50 | −11.132 | −28.301 | 9.155 | 1.00 | 0.00 | C |
| ATOM | 285 | C | PHE | K | 50 | −10.455 | −27.011 | 9.641 | 1.00 | 0.00 | C |
| ATOM | 286 | O | PHE | K | 50 | −9.236 | −26.909 | 9.608 | 1.00 | 0.00 | O |
| ATOM | 287 | CB | PHE | K | 50 | −11.767 | −28.116 | 7.763 | 1.00 | 0.00 | C |
| ATOM | 288 | CG | PHE | K | 50 | −10.777 | −28.053 | 6.628 | 1.00 | 0.00 | C |
| ATOM | 289 | CD1 | PHE | K | 50 | −10.020 | −26.882 | 6.371 | 1.00 | 0.00 | C |
| ATOM | 290 | CE1 | PHE | K | 50 | −9.135 | −26.833 | 5.279 | 1.00 | 0.00 | C |
| ATOM | 291 | CZ | PHE | K | 50 | −9.016 | −27.936 | 4.421 | 1.00 | 0.00 | C |
| ATOM | 292 | CE2 | PHE | K | 50 | −9.753 | −29.103 | 4.664 | 1.00 | 0.00 | C |
| ATOM | 293 | CD2 | PHE | K | 50 | −10.628 | −29.162 | 5.761 | 1.00 | 0.00 | C |
| ATOM | 294 | N | THR | K | 51 | −11.316 | −25.991 | 10.042 | 1.00 | 0.00 | N |
| ATOM | 295 | CA | THR | K | 51 | −10.914 | −24.586 | 10.190 | 1.00 | 0.00 | C |
| ATOM | 296 | C | THR | K | 51 | −9.594 | −24.387 | 10.960 | 1.00 | 0.00 | C |
| ATOM | 297 | O | THR | K | 51 | −8.750 | −23.638 | 10.482 | 1.00 | 0.00 | O |
| ATOM | 298 | CB | THR | K | 51 | −12.056 | −23.684 | 10.725 | 1.00 | 0.00 | C |
| ATOM | 299 | OG1 | THR | K | 51 | −13.156 | −23.711 | 9.813 | 1.00 | 0.00 | O |
| ATOM | 300 | CG2 | THR | K | 51 | −11.641 | −22.223 | 10.839 | 1.00 | 0.00 | C |
| ATOM | 301 | N | PRO | K | 52 | −9.405 | −25.041 | 12.190 | 1.00 | 0.00 | N |
| ATOM | 302 | CA | PRO | K | 52 | −8.158 | −24.960 | 12.932 | 1.00 | 0.00 | C |
| ATOM | 303 | C | PRO | K | 52 | −6.858 | −25.075 | 12.146 | 1.00 | 0.00 | C |
| ATOM | 304 | O | PRO | K | 52 | −5.885 | −24.428 | 12.506 | 1.00 | 0.00 | O |

TABLE 7-continued

| | | | | | | | | | | |
|---|---|---|---|---|---|---|---|---|---|---|
| ATOM | 305 | CB | PRO | K | 52 | −8.261 | −26.043 | 13.991 | 1.00 | 0.00 | C |
| ATOM | 306 | CG | PRO | K | 52 | −9.743 | −26.108 | 14.284 | 1.00 | 0.00 | C |
| ATOM | 307 | CD | PRO | K | 52 | −10.411 | −25.728 | 12.977 | 1.00 | 0.00 | C |
| ATOM | 308 | N | PHE | K | 53 | −6.854 | −25.955 | 11.068 | 1.00 | 0.00 | N |
| ATOM | 309 | CA | PHE | K | 53 | −5.670 | −26.171 | 10.235 | 1.00 | 0.00 | C |
| ATOM | 310 | C | PHE | K | 53 | −5.125 | −24.829 | 9.739 | 1.00 | 0.00 | C |
| ATOM | 311 | O | PHE | K | 53 | −3.942 | −24.556 | 9.891 | 1.00 | 0.00 | O |
| ATOM | 312 | CB | PHE | K | 53 | −5.936 | −27.142 | 9.069 | 1.00 | 0.00 | C |
| ATOM | 313 | CG | PHE | K | 53 | −4.673 | −27.523 | 8.331 | 1.00 | 0.00 | C |
| ATOM | 314 | CD1 | PHE | K | 53 | −4.287 | −26.835 | 7.153 | 1.00 | 0.00 | C |
| ATOM | 315 | CD2 | PHE | K | 53 | −3.860 | −28.588 | 8.795 | 1.00 | 0.00 | C |
| ATOM | 316 | CE1 | PHE | K | 53 | −3.117 | −27.201 | 6.460 | 1.00 | 0.00 | C |
| ATOM | 317 | CE2 | PHE | K | 53 | −2.693 | −28.953 | 8.097 | 1.00 | 0.00 | C |
| ATOM | 318 | CZ | PHE | K | 53 | −2.322 | −28.262 | 6.930 | 1.00 | 0.00 | C |
| ATOM | 319 | N | PHE | K | 54 | −6.042 | −23.989 | 9.109 | 1.00 | 0.00 | N |
| ATOM | 320 | CA | PHE | K | 54 | −5.632 | −22.714 | 8.512 | 1.00 | 0.00 | C |
| ATOM | 321 | C | PHE | K | 54 | −4.879 | −21.890 | 9.557 | 1.00 | 0.00 | C |
| ATOM | 322 | O | PHE | K | 54 | −3.748 | −21.476 | 9.337 | 1.00 | 0.00 | O |
| ATOM | 323 | CB | PHE | K | 54 | −6.794 | −21.857 | 7.962 | 1.00 | 0.00 | C |
| ATOM | 324 | CG | PHE | K | 54 | −7.478 | −22.388 | 6.726 | 1.00 | 0.00 | C |
| ATOM | 325 | CD1 | PHE | K | 54 | −6.776 | −22.516 | 5.501 | 1.00 | 0.00 | C |
| ATOM | 326 | CD2 | PHE | K | 54 | −8.868 | −22.667 | 6.744 | 1.00 | 0.00 | C |
| ATOM | 327 | CE1 | PHE | K | 54 | −7.453 | −22.895 | 4.325 | 1.00 | 0.00 | C |
| ATOM | 328 | CE2 | PHE | K | 54 | −9.540 | −23.037 | 5.565 | 1.00 | 0.00 | C |
| ATOM | 329 | CZ | PHE | K | 54 | −8.835 | −23.146 | 4.354 | 1.00 | 0.00 | C |
| ATOM | 330 | N | ILE | K | 55 | −5.602 | −21.616 | 10.711 | 1.00 | 0.00 | N |
| ATOM | 331 | CA | ILE | K | 55 | −5.139 | −20.632 | 11.690 | 1.00 | 0.00 | C |
| ATOM | 332 | C | ILE | K | 55 | −3.881 | −21.077 | 12.435 | 1.00 | 0.00 | C |
| ATOM | 333 | O | ILE | K | 55 | −3.018 | −20.252 | 12.706 | 1.00 | 0.00 | O |
| ATOM | 334 | CB | ILE | K | 55 | −6.240 | −20.109 | 12.653 | 1.00 | 0.00 | C |
| ATOM | 335 | CG1 | ILE | K | 55 | −6.944 | −21.221 | 13.459 | 1.00 | 0.00 | C |
| ATOM | 336 | CG2 | ILE | K | 55 | −7.249 | −19.271 | 11.863 | 1.00 | 0.00 | C |
| ATOM | 337 | CD1 | ILE | K | 55 | −7.916 | −20.694 | 14.499 | 1.00 | 0.00 | C |
| ATOM | 338 | N | THR | K | 56 | −3.815 | −22.415 | 12.811 | 1.00 | 0.00 | N |
| ATOM | 339 | CA | THR | K | 56 | −2.675 | −22.938 | 13.561 | 1.00 | 0.00 | C |
| ATOM | 340 | C | THR | K | 56 | −1.407 | −22.838 | 12.711 | 1.00 | 0.00 | C |
| ATOM | 341 | O | THR | K | 56 | −0.371 | −22.417 | 13.208 | 1.00 | 0.00 | O |
| ATOM | 342 | CB | THR | K | 56 | −2.921 | −24.337 | 14.185 | 1.00 | 0.00 | C |
| ATOM | 343 | OG1 | THR | K | 56 | −1.991 | −24.550 | 15.248 | 1.00 | 0.00 | O |
| ATOM | 344 | CG2 | THR | K | 56 | −2.789 | −25.522 | 13.234 | 1.00 | 0.00 | C |
| ATOM | 345 | N | VAL | K | 57 | −1.512 | −23.258 | 11.387 | 1.00 | 0.00 | N |
| ATOM | 346 | CA | VAL | K | 57 | −0.372 | −23.191 | 10.471 | 1.00 | 0.00 | C |
| ATOM | 347 | C | VAL | K | 57 | 0.068 | −21.732 | 10.327 | 1.00 | 0.00 | C |
| ATOM | 348 | O | VAL | K | 57 | 1.259 | −21.469 | 10.285 | 1.00 | 0.00 | O |
| ATOM | 349 | CB | VAL | K | 57 | −0.628 | −23.887 | 9.109 | 1.00 | 0.00 | C |
| ATOM | 350 | CG1 | VAL | K | 57 | 0.515 | −23.659 | 8.115 | 1.00 | 0.00 | C |
| ATOM | 351 | CG2 | VAL | K | 57 | −0.791 | −25.399 | 9.300 | 1.00 | 0.00 | C |
| ATOM | 352 | N | GLY | K | 58 | −0.931 | −20.773 | 10.232 | 1.00 | 0.00 | N |
| ATOM | 353 | CA | GLY | K | 58 | −0.646 | −19.343 | 10.177 | 1.00 | 0.00 | C |
| ATOM | 354 | C | GLY | K | 58 | 0.245 | −18.856 | 11.314 | 1.00 | 0.00 | C |
| ATOM | 355 | O | GLY | K | 58 | 1.223 | −18.154 | 11.094 | 1.00 | 0.00 | O |
| ATOM | 356 | N | LEU | K | 59 | −0.170 | −19.229 | 12.585 | 1.00 | 0.00 | N |
| ATOM | 357 | CA | LEU | K | 59 | 0.563 | −18.847 | 13.797 | 1.00 | 0.00 | C |
| ATOM | 358 | C | LEU | K | 59 | 1.995 | −19.390 | 13.755 | 1.00 | 0.00 | C |
| ATOM | 359 | O | LEU | K | 59 | 2.950 | −18.680 | 14.037 | 1.00 | 0.00 | O |
| ATOM | 360 | CB | LEU | K | 59 | −0.175 | −19.306 | 15.071 | 1.00 | 0.00 | C |
| ATOM | 361 | CG | LEU | K | 59 | 0.460 | −18.836 | 16.396 | 1.00 | 0.00 | C |
| ATOM | 362 | CD1 | LEU | K | 59 | 0.454 | −17.314 | 16.532 | 1.00 | 0.00 | C |
| ATOM | 363 | CD2 | LEU | K | 59 | −0.280 | −19.457 | 17.578 | 1.00 | 0.00 | C |
| ATOM | 364 | N | VAL | K | 60 | 2.103 | −20.735 | 13.437 | 1.00 | 0.00 | N |
| ATOM | 365 | CA | VAL | K | 60 | 3.383 | −21.445 | 13.401 | 1.00 | 0.00 | C |
| ATOM | 366 | C | VAL | K | 60 | 4.304 | −20.826 | 12.329 | 1.00 | 0.00 | C |
| ATOM | 367 | O | VAL | K | 60 | 5.497 | −20.677 | 12.556 | 1.00 | 0.00 | O |
| ATOM | 368 | CB | VAL | K | 60 | 3.168 | −22.974 | 13.243 | 1.00 | 0.00 | C |
| ATOM | 369 | CG1 | VAL | K | 60 | 4.467 | −23.717 | 12.973 | 1.00 | 0.00 | C |
| ATOM | 370 | CG2 | VAL | K | 60 | 2.530 | −23.575 | 14.502 | 1.00 | 0.00 | C |
| ATOM | 371 | N | GLU | K | 61 | 3.707 | −20.485 | 11.121 | 1.00 | 0.00 | N |
| ATOM | 372 | CA | GLU | K | 61 | 4.409 | −19.828 | 10.011 | 1.00 | 0.00 | C |
| ATOM | 373 | C | GLU | K | 61 | 5.144 | −18.585 | 10.515 | 1.00 | 0.00 | C |
| ATOM | 374 | O | GLU | K | 61 | 6.304 | −18.381 | 10.182 | 1.00 | 0.00 | O |
| ATOM | 375 | CB | GLU | K | 61 | 3.458 | −19.496 | 8.840 | 1.00 | 0.00 | C |
| ATOM | 376 | CG | GLU | K | 61 | 4.128 | −18.695 | 7.725 | 1.00 | 0.00 | C |
| ATOM | 377 | CD | GLU | K | 61 | 3.185 | −18.379 | 6.589 | 1.00 | 0.00 | C |
| ATOM | 378 | OE1 | GLU | K | 61 | 1.978 | −18.211 | 6.690 | 1.00 | 0.00 | O |
| ATOM | 379 | OE2 | GLU | K | 61 | 3.875 | −18.199 | 5.434 | 1.00 | 0.00 | O |
| ATOM | 380 | N | ALA | K | 62 | 4.398 | −17.723 | 11.310 | 1.00 | 0.00 | N |
| ATOM | 381 | CA | ALA | K | 62 | 4.961 | −16.490 | 11.858 | 1.00 | 0.00 | C |
| ATOM | 382 | C | ALA | K | 62 | 6.272 | −16.759 | 12.595 | 1.00 | 0.00 | C |
| ATOM | 383 | O | ALA | K | 62 | 7.268 | −16.086 | 12.362 | 1.00 | 0.00 | O |
| ATOM | 384 | CB | ALA | K | 62 | 3.985 | −15.755 | 12.765 | 1.00 | 0.00 | C |

TABLE 7-continued

| | | | | | | | | | | |
|---|---|---|---|---|---|---|---|---|---|---|
| ATOM | 385 | N | ALA | K | 63 | 6.222 | −17.786 | 13.532 | 1.00 | 0.00 | N |
| ATOM | 386 | CA | ALA | K | 63 | 7.397 | −18.184 | 14.304 | 1.00 | 0.00 | C |
| ATOM | 387 | C | ALA | K | 63 | 8.559 | −18.562 | 13.385 | 1.00 | 0.00 | C |
| ATOM | 388 | O | ALA | K | 63 | 9.683 | −18.139 | 13.615 | 1.00 | 0.00 | O |
| ATOM | 389 | CB | ALA | K | 63 | 7.109 | −19.317 | 15.286 | 1.00 | 0.00 | C |
| ATOM | 390 | N | TYR | K | 64 | 8.256 | −19.413 | 12.328 | 1.00 | 0.00 | N |
| ATOM | 391 | CA | TYR | K | 64 | 9.285 | −19.912 | 11.410 | 1.00 | 0.00 | C |
| ATOM | 392 | C | TYR | K | 64 | 10.073 | −18.796 | 10.731 | 1.00 | 0.00 | C |
| ATOM | 393 | O | TYR | K | 64 | 11.269 | −18.949 | 10.526 | 1.00 | 0.00 | O |
| ATOM | 394 | CB | TYR | K | 64 | 8.751 | −20.857 | 10.318 | 1.00 | 0.00 | C |
| ATOM | 395 | CG | TYR | K | 64 | 8.211 | −22.195 | 10.773 | 1.00 | 0.00 | C |
| ATOM | 396 | CD1 | TYR | K | 64 | 8.685 | −22.868 | 11.933 | 1.00 | 0.00 | C |
| ATOM | 397 | CD2 | TYR | K | 64 | 7.247 | −22.847 | 9.964 | 1.00 | 0.00 | C |
| ATOM | 398 | CE1 | TYR | K | 64 | 8.206 | −24.146 | 12.270 | 1.00 | 0.00 | C |
| ATOM | 399 | CE2 | TYR | K | 64 | 6.796 | −24.141 | 10.271 | 1.00 | 0.00 | C |
| ATOM | 400 | CZ | TYR | K | 64 | 7.279 | −24.784 | 11.431 | 1.00 | 0.00 | C |
| ATOM | 401 | OH | TYR | K | 64 | 6.844 | −26.049 | 11.786 | 1.00 | 0.00 | O |
| ATOM | 402 | N | PHE | K | 65 | 9.364 | −17.669 | 10.325 | 1.00 | 0.00 | N |
| ATOM | 403 | CA | PHE | K | 65 | 10.059 | −16.531 | 9.710 | 1.00 | 0.00 | C |
| ATOM | 404 | C | PHE | K | 65 | 11.164 | −16.015 | 10.631 | 1.00 | 0.00 | C |
| ATOM | 405 | O | PHE | K | 65 | 12.265 | −15.736 | 10.172 | 1.00 | 0.00 | O |
| ATOM | 406 | CB | PHE | K | 65 | 9.145 | −15.353 | 9.328 | 1.00 | 0.00 | C |
| ATOM | 407 | CG | PHE | K | 65 | 8.256 | −15.625 | 8.140 | 1.00 | 0.00 | C |
| ATOM | 408 | CD1 | PHE | K | 65 | 6.850 | −15.558 | 8.269 | 1.00 | 0.00 | C |
| ATOM | 409 | CE1 | PHE | K | 65 | 6.019 | −15.722 | 7.147 | 1.00 | 0.00 | C |
| ATOM | 410 | CZ | PHE | K | 65 | 6.578 | −15.970 | 5.883 | 1.00 | 0.00 | C |
| ATOM | 411 | CE2 | PHE | K | 65 | 7.973 | −16.052 | 5.738 | 1.00 | 0.00 | C |
| ATOM | 412 | CD2 | PHE | K | 65 | 8.808 | −15.877 | 6.858 | 1.00 | 0.00 | C |
| ATOM | 413 | N | ILE | K | 66 | 10.810 | −15.851 | 11.967 | 1.00 | 0.00 | N |
| ATOM | 414 | CA | ILE | K | 66 | 11.764 | −15.375 | 12.973 | 1.00 | 0.00 | C |
| ATOM | 415 | C | ILE | K | 66 | 12.951 | −16.337 | 13.006 | 1.00 | 0.00 | C |
| ATOM | 416 | O | ILE | K | 66 | 14.086 | −15.893 | 12.915 | 1.00 | 0.00 | O |
| ATOM | 417 | CB | ILE | K | 66 | 11.140 | −15.149 | 14.379 | 1.00 | 0.00 | C |
| ATOM | 418 | CG1 | ILE | K | 66 | 10.099 | −14.011 | 14.323 | 1.00 | 0.00 | C |
| ATOM | 419 | CG2 | ILE | K | 66 | 12.227 | −14.831 | 15.415 | 1.00 | 0.00 | C |
| ATOM | 420 | CD1 | ILE | K | 66 | 9.228 | −13.930 | 15.564 | 1.00 | 0.00 | C |
| ATOM | 421 | N | ASN | K | 67 | 12.652 | −17.685 | 13.180 | 1.00 | 0.00 | N |
| ATOM | 422 | CA | ASN | K | 67 | 13.703 | −18.702 | 13.320 | 1.00 | 0.00 | C |
| ATOM | 423 | C | ASN | K | 67 | 14.701 | −18.596 | 12.170 | 1.00 | 0.00 | C |
| ATOM | 424 | O | ASN | K | 67 | 15.900 | −18.535 | 12.401 | 1.00 | 0.00 | O |
| ATOM | 425 | CB | ASN | K | 67 | 13.186 | −20.151 | 13.395 | 1.00 | 0.00 | C |
| ATOM | 426 | CG | ASN | K | 67 | 12.499 | −20.446 | 14.713 | 1.00 | 0.00 | C |
| ATOM | 427 | OD1 | ASN | K | 67 | 11.286 | −20.373 | 14.846 | 1.00 | 0.00 | O |
| ATOM | 428 | ND2 | ASN | K | 67 | 13.361 | −20.767 | 15.738 | 1.00 | 0.00 | N |
| ATOM | 429 | N | LEU | K | 68 | 14.148 | −18.617 | 10.895 | 1.00 | 0.00 | N |
| ATOM | 430 | CA | LEU | K | 68 | 14.952 | −18.648 | 9.672 | 1.00 | 0.00 | C |
| ATOM | 431 | C | LEU | K | 68 | 15.897 | −17.447 | 9.657 | 1.00 | 0.00 | C |
| ATOM | 432 | O | LEU | K | 68 | 17.102 | −17.606 | 9.507 | 1.00 | 0.00 | O |
| ATOM | 433 | CB | LEU | K | 68 | 14.060 | −18.741 | 8.415 | 1.00 | 0.00 | C |
| ATOM | 434 | CG | LEU | K | 68 | 14.812 | −19.062 | 7.106 | 1.00 | 0.00 | C |
| ATOM | 435 | CD1 | LEU | K | 68 | 13.884 | −19.801 | 6.142 | 1.00 | 0.00 | C |
| ATOM | 436 | CD2 | LEU | K | 68 | 15.348 | −17.806 | 6.416 | 1.00 | 0.00 | C |
| ATOM | 437 | N | ALA | K | 69 | 15.280 | −16.209 | 9.799 | 1.00 | 0.00 | N |
| ATOM | 438 | CA | ALA | K | 69 | 16.020 | −14.950 | 9.727 | 1.00 | 0.00 | C |
| ATOM | 439 | C | ALA | K | 69 | 17.139 | −14.903 | 10.766 | 1.00 | 0.00 | C |
| ATOM | 440 | O | ALA | K | 69 | 18.266 | −14.546 | 10.449 | 1.00 | 0.00 | O |
| ATOM | 441 | CB | ALA | K | 69 | 15.107 | −13.737 | 9.887 | 1.00 | 0.00 | C |
| ATOM | 442 | N | PHE | K | 70 | 16.758 | −15.243 | 12.059 | 1.00 | 0.00 | N |
| ATOM | 443 | CA | PHE | K | 70 | 17.670 | −15.188 | 13.199 | 1.00 | 0.00 | C |
| ATOM | 444 | C | PHE | K | 70 | 18.884 | −16.072 | 12.927 | 1.00 | 0.00 | C |
| ATOM | 445 | O | PHE | K | 70 | 20.011 | −15.631 | 13.104 | 1.00 | 0.00 | O |
| ATOM | 446 | CB | PHE | K | 70 | 16.975 | −15.568 | 14.523 | 1.00 | 0.00 | C |
| ATOM | 447 | CG | PHE | K | 70 | 17.885 | −15.411 | 15.718 | 1.00 | 0.00 | C |
| ATOM | 448 | CD1 | PHE | K | 70 | 18.073 | −14.141 | 16.317 | 1.00 | 0.00 | C |
| ATOM | 449 | CE1 | PHE | K | 70 | 18.941 | −13.990 | 17.415 | 1.00 | 0.00 | C |
| ATOM | 450 | CZ | PHE | K | 70 | 19.631 | −15.104 | 17.928 | 1.00 | 0.00 | C |
| ATOM | 451 | CE2 | PHE | K | 70 | 19.449 | −16.372 | 17.346 | 1.00 | 0.00 | C |
| ATOM | 452 | CD2 | PHE | K | 70 | 18.578 | −16.527 | 16.251 | 1.00 | 0.00 | C |
| ATOM | 453 | N | MET | K | 71 | 18.608 | −17.374 | 12.522 | 1.00 | 0.00 | N |
| ATOM | 454 | CA | MET | K | 71 | 19.663 | −18.364 | 12.302 | 1.00 | 0.00 | C |
| ATOM | 455 | C | MET | K | 71 | 20.669 | −17.820 | 11.295 | 1.00 | 0.00 | C |
| ATOM | 456 | O | MET | K | 71 | 21.861 | −17.837 | 11.565 | 1.00 | 0.00 | O |
| ATOM | 457 | CB | MET | K | 71 | 19.144 | −19.738 | 11.845 | 1.00 | 0.00 | C |
| ATOM | 458 | CG | MET | K | 71 | 18.539 | −20.532 | 13.001 | 1.00 | 0.00 | C |
| ATOM | 459 | SD | MET | K | 71 | 17.840 | −22.089 | 12.369 | 1.00 | 0.00 | S |
| ATOM | 460 | CE | MET | K | 71 | 17.151 | −22.720 | 13.919 | 1.00 | 0.00 | C |
| ATOM | 461 | N | ALA | K | 72 | 20.140 | −17.350 | 10.096 | 1.00 | 0.00 | N |
| ATOM | 462 | CA | ALA | K | 72 | 20.987 | −16.868 | 9.002 | 1.00 | 0.00 | C |
| ATOM | 463 | C | ALA | K | 72 | 21.948 | −15.778 | 9.479 | 1.00 | 0.00 | C |
| ATOM | 464 | O | ALA | K | 72 | 23.143 | −15.836 | 9.214 | 1.00 | 0.00 | O |

TABLE 7-continued

| | | | | | | | | | | |
|---|---|---|---|---|---|---|---|---|---|---|
| ATOM | 465 | CB | ALA | K | 72 | 20.171 | −16.371 | 7.810 | 1.00 | 0.00 | C |
| ATOM | 466 | N | LEU | K | 73 | 21.352 | −14.740 | 10.188 | 1.00 | 0.00 | N |
| ATOM | 467 | CA | LEU | K | 73 | 22.105 | −13.603 | 10.723 | 1.00 | 0.00 | C |
| ATOM | 468 | C | LEU | K | 73 | 23.219 | −14.134 | 11.625 | 1.00 | 0.00 | C |
| ATOM | 469 | O | LEU | K | 73 | 24.380 | −13.793 | 11.445 | 1.00 | 0.00 | O |
| ATOM | 470 | CB | LEU | K | 73 | 21.168 | −12.597 | 11.435 | 1.00 | 0.00 | C |
| ATOM | 471 | CG | LEU | K | 73 | 21.770 | −11.268 | 11.940 | 1.00 | 0.00 | C |
| ATOM | 472 | CD1 | LEU | K | 73 | 22.598 | −11.416 | 13.216 | 1.00 | 0.00 | C |
| ATOM | 473 | CD2 | LEU | K | 73 | 22.551 | −10.518 | 10.865 | 1.00 | 0.00 | C |
| ATOM | 474 | N | PHE | K | 74 | 22.798 | −14.976 | 12.647 | 1.00 | 0.00 | N |
| ATOM | 475 | CA | PHE | K | 74 | 23.673 | −15.420 | 13.728 | 1.00 | 0.00 | C |
| ATOM | 476 | C | PHE | K | 74 | 24.905 | −16.131 | 13.168 | 1.00 | 0.00 | C |
| ATOM | 477 | O | PHE | K | 74 | 26.020 | −15.816 | 13.560 | 1.00 | 0.00 | O |
| ATOM | 478 | CB | PHE | K | 74 | 22.924 | −16.299 | 14.751 | 1.00 | 0.00 | C |
| ATOM | 479 | CG | PHE | K | 74 | 23.732 | −16.543 | 16.002 | 1.00 | 0.00 | C |
| ATOM | 480 | CD1 | PHE | K | 74 | 24.581 | −17.672 | 16.106 | 1.00 | 0.00 | C |
| ATOM | 481 | CE1 | PHE | K | 74 | 25.344 | −17.887 | 17.269 | 1.00 | 0.00 | C |
| ATOM | 482 | CZ | PHE | K | 74 | 25.264 | −16.982 | 18.342 | 1.00 | 0.00 | C |
| ATOM | 483 | CE2 | PHE | K | 74 | 24.421 | −15.860 | 18.254 | 1.00 | 0.00 | C |
| ATOM | 484 | CD2 | PHE | K | 74 | 23.658 | −15.640 | 17.091 | 1.00 | 0.00 | C |
| ATOM | 485 | N | VAL | K | 75 | 24.659 | −17.162 | 12.265 | 1.00 | 0.00 | N |
| ATOM | 486 | CA | VAL | K | 75 | 25.740 | −18.022 | 11.768 | 1.00 | 0.00 | C |
| ATOM | 487 | C | VAL | K | 75 | 26.806 | −17.217 | 11.023 | 1.00 | 0.00 | C |
| ATOM | 488 | O | VAL | K | 75 | 27.988 | −17.509 | 11.151 | 1.00 | 0.00 | O |
| ATOM | 489 | CB | VAL | K | 75 | 25.296 | −19.270 | 10.961 | 1.00 | 0.00 | C |
| ATOM | 490 | CG1 | VAL | K | 75 | 24.498 | −20.225 | 11.849 | 1.00 | 0.00 | C |
| ATOM | 491 | CG2 | VAL | K | 75 | 24.524 | −18.965 | 9.677 | 1.00 | 0.00 | C |
| ATOM | 492 | N | PHE | K | 76 | 26.338 | −16.197 | 10.199 | 1.00 | 0.00 | N |
| ATOM | 493 | CA | PHE | K | 76 | 27.254 | −15.284 | 9.518 | 1.00 | 0.00 | C |
| ATOM | 494 | C | PHE | K | 76 | 28.106 | −14.562 | 10.570 | 1.00 | 0.00 | C |
| ATOM | 495 | O | PHE | K | 76 | 29.327 | −14.567 | 10.485 | 1.00 | 0.00 | O |
| ATOM | 496 | CB | PHE | K | 76 | 26.514 | −14.307 | 8.577 | 1.00 | 0.00 | C |
| ATOM | 497 | CG | PHE | K | 76 | 27.428 | −13.236 | 8.034 | 1.00 | 0.00 | C |
| ATOM | 498 | CD1 | PHE | K | 76 | 27.372 | −11.920 | 8.557 | 1.00 | 0.00 | C |
| ATOM | 499 | CD2 | PHE | K | 76 | 28.398 | −13.540 | 7.048 | 1.00 | 0.00 | C |
| ATOM | 500 | CE1 | PHE | K | 76 | 28.293 | −10.945 | 8.136 | 1.00 | 0.00 | C |
| ATOM | 501 | CE2 | PHE | K | 76 | 29.317 | −12.561 | 6.628 | 1.00 | 0.00 | C |
| ATOM | 502 | CZ | PHE | K | 76 | 29.271 | −11.268 | 7.180 | 1.00 | 0.00 | C |
| ATOM | 503 | N | ALA | K | 77 | 27.390 | −13.889 | 11.554 | 1.00 | 0.00 | N |
| ATOM | 504 | CA | ALA | K | 77 | 28.022 | −12.981 | 12.509 | 1.00 | 0.00 | C |
| ATOM | 505 | C | ALA | K | 77 | 29.158 | −13.664 | 13.265 | 1.00 | 0.00 | C |
| ATOM | 506 | O | ALA | K | 77 | 30.255 | −13.126 | 13.348 | 1.00 | 0.00 | O |
| ATOM | 507 | CB | ALA | K | 77 | 27.020 | −12.372 | 13.488 | 1.00 | 0.00 | C |
| ATOM | 508 | N | THR | K | 78 | 28.833 | −14.872 | 13.873 | 1.00 | 0.00 | N |
| ATOM | 509 | CA | THR | K | 78 | 29.831 | −15.665 | 14.586 | 1.00 | 0.00 | C |
| ATOM | 510 | C | THR | K | 78 | 30.768 | −16.240 | 13.544 | 1.00 | 0.00 | C |
| ATOM | 511 | O | THR | K | 78 | 31.932 | −16.523 | 13.791 | 1.00 | 0.00 | O |
| ATOM | 512 | CB | THR | K | 78 | 29.211 | −16.756 | 15.490 | 1.00 | 0.00 | C |
| ATOM | 513 | OG1 | THR | K | 78 | 30.185 | −17.218 | 16.432 | 1.00 | 0.00 | O |
| ATOM | 514 | CG2 | THR | K | 78 | 28.636 | −17.966 | 14.756 | 1.00 | 0.00 | C |

What is claimed is:

1. An isolated nucleic acid sequence comprising a nucleotide sequence encoding an isolated mutant atpE protein selected from the group consisting of:
   (a) a protein identical to SEQ ID NO:1 except for at least one point mutation located in any one of amino acids 14 to 34 or of amino acids 54 to 69; and
   (b) a protein identical to SEQ ID NO:3 except for at least one point mutation located in any one of amino acids 18 to 38 or of amino acids 58 to 73;
   wherein said protein induces antimicrobial resistance in a host cell.

2. A vector comprising the nucleic acid sequence according to claim 1.

3. A host cell carrying the vector according to claim 2.

4. A method to identify whether a test compound binds to an isolated atpE protein, said method comprising:
   a) contacting cells expressing an atpE protein wherein such cells do not normally express said atpE protein, with the test compound in the presence and absence of a compound known to bind the atpE protein,
   b) determine the binding of the test compound to the atpE protein using the compound known to bind to the atpE protein as a reference, wherein step a) consists of contacting a cellular composition comprising an atpE protein, with the test compound in the presence and absence of a compound known to bind the atpE protein,
   wherein the cellular composition consists of a membrane preparation obtained from a host cell comprising an isolated nucleic acid encoding an isolated mutant atpE protein wherein the mutation consists of at least one point mutation located in any one of amino acids 20 to 40 or of amino acids 60 to 75 as shown in the sequence alignment of FIG. 2.

5. The method according to claim 4, wherein the mutation in the mutant atpE protein consists of at least one point mutation located in any one of amino acids 30 to 40 or 62 to 73 as shown in the sequence alignment of FIG. 2.

* * * * *

SEQUENCE LISTING

<160> NUMBER OF SEQ ID NOS: 28

<210> SEQ ID NO 1
<211> LENGTH: 81
<212> TYPE: PRT
<213> ORGANISM: Mycobacterium tuberculosis

<400> SEQUENCE: 1

Met Asp Pro Thr Ile Ala Ala Gly Ala Leu Ile Gly Gly Leu Ile
1               5                   10                  15

Met Ala Gly Gly Ala Ile Gly Ala Gly Ile Gly Asp Gly Val Ala Gly
                20                  25                  30

Asn Ala Leu Ile Ser Gly Val Ala Arg Gln Pro Glu Ala Gln Gly Arg
            35                  40                  45

Leu Phe Thr Pro Phe Phe Ile Thr Val Gly Leu Val Glu Ala Ala Tyr
        50                  55                  60

```
Phe Ile Asn Leu Ala Phe Met Ala Leu Phe Val Phe Ala Thr Pro Val
 65                  70                  75                  80

Lys

<210> SEQ ID NO 2
<211> LENGTH: 81
<212> TYPE: PRT
<213> ORGANISM: Mycobacterium tuberculosis

<400> SEQUENCE: 2

Met Asp Pro Thr Ile Ala Ala Gly Ala Leu Ile Gly Gly Leu Ile
 1               5                  10                  15

Met Ala Gly Gly Ala Ile Gly Ala Gly Ile Gly Asp Gly Val Ala Gly
                20                  25                  30

Asn Ala Leu Ile Ser Gly Val Ala Arg Gln Pro Glu Ala Gln Gly Arg
             35                  40                  45

Leu Phe Thr Pro Phe Phe Ile Thr Val Gly Leu Val Glu Ala Pro Tyr
         50                  55                  60

Phe Ile Asn Leu Ala Phe Met Ala Leu Phe Val Phe Ala Thr Pro Val
 65                  70                  75                  80

Lys

<210> SEQ ID NO 3
<211> LENGTH: 86
<212> TYPE: PRT
<213> ORGANISM: Mycobacterium smegmatis

<400> SEQUENCE: 3

Met Asp Leu Asp Pro Asn Ala Ile Ile Thr Ala Gly Ala Leu Ile Gly
 1               5                  10                  15

Gly Gly Leu Ile Met Gly Gly Gly Ala Ile Gly Ala Gly Ile Gly Asp
                20                  25                  30

Gly Ile Ala Gly Asn Ala Leu Ile Ser Gly Ile Ala Arg Gln Pro Glu
             35                  40                  45

Ala Gln Gly Arg Leu Phe Thr Pro Phe Phe Ile Thr Val Gly Leu Val
         50                  55                  60

Glu Ala Ala Tyr Phe Ile Asn Leu Ala Phe Met Ala Leu Phe Val Phe
 65                  70                  75                  80

Ala Thr Pro Gly Leu Gln
                85

<210> SEQ ID NO 4
<211> LENGTH: 86
<212> TYPE: PRT
<213> ORGANISM: Mycobacterium smegmatis

<400> SEQUENCE: 4

Met Asp Leu Asp Pro Asn Ala Ile Ile Thr Ala Gly Ala Leu Ile Gly
 1               5                  10                  15

Gly Gly Leu Ile Met Gly Gly Gly Ala Ile Gly Ala Gly Ile Gly Val
                20                  25                  30

Gly Ile Ala Gly Asn Ala Leu Ile Ser Gly Ile Ala Arg Gln Pro Glu
             35                  40                  45

Ala Gln Gly Arg Leu Phe Thr Pro Phe Phe Ile Thr Val Gly Leu Val
         50                  55                  60

Glu Ala Ala Tyr Phe Ile Asn Leu Ala Phe Met Ala Leu Phe Val Phe
 65                  70                  75                  80

Ala Thr Pro Gly Leu Gln
```

<210> SEQ ID NO 5
<211> LENGTH: 86
<212> TYPE: PRT
<213> ORGANISM: Mycobacterium smegmatis

<400> SEQUENCE: 5

```
Met Asp Leu Asp Pro Asn Ala Ile Ile Thr Ala Gly Ala Leu Ile Gly
1               5                   10                  15
Gly Gly Leu Ile Met Gly Gly Gly Ala Ile Gly Ala Gly Ile Gly Val
            20                  25                  30
Gly Ile Ala Gly Asn Ala Leu Ile Ser Gly Ile Ala Arg Gln Pro Glu
        35                  40                  45
Ala Gln Gly Arg Leu Phe Thr Pro Phe Phe Ile Thr Val Gly Leu Val
    50                  55                  60
Glu Ala Ala Tyr Phe Ile Asn Leu Ala Phe Met Ala Leu Phe Val Phe
65                  70                  75                  80
Ala Thr Pro Gly Leu Gln
                85
```

<210> SEQ ID NO 6
<211> LENGTH: 246
<212> TYPE: DNA
<213> ORGANISM: Mycobacterium tuberculosis

<400> SEQUENCE: 6

```
atggacccca ctatcgctgc cggcgccctc atcggcggtg gactgatcat ggccggtggc    60
gccatcggcg ccggtatcgg tgacggtgtc gccggtaacg cgcttatctc cggtgtcgcc   120
cggcaacccg aggcgcaagg gcggctgttc acaccgttct tcatcaccgt cggtttggtt   180
gaggcggcat acttcatcaa cctggcgttt atggcgctgt tcgtcttcgc tacacccgtc   240
aagtaa                                                               246
```

<210> SEQ ID NO 7
<211> LENGTH: 246
<212> TYPE: DNA
<213> ORGANISM: Mycobacterium tuberculosis

<400> SEQUENCE: 7

```
atggacccca ctatcgctgc cggcgccctc atcggcggtg gactgatcat ggccggtggc    60
gccatcggcg ccggtatcgg tgacggtgtc gccggtaacg cgcttatctc cggtgtcgcc   120
cggcaacccg aggcgcaagg gcggctgttc acaccgttct tcatcaccgt cggtttggtt   180
gaggcgccat acttcatcaa cctggcgttt atggcgctgt tcgtcttcgc tacacccgtc   240
aagtaa                                                               246
```

<210> SEQ ID NO 8
<211> LENGTH: 261
<212> TYPE: DNA
<213> ORGANISM: Mycobacterium smegmatis

<400> SEQUENCE: 8

```
atggatctcg atcccaacgc catcatcacg gccggcgccc tgatcggcgg tggattgatc    60
atgggtggcg gcgccatcgg tgccggtatc ggcgacggta tcgcgggtaa cgcgctgatc   120
tcgggtatcg cccgtcagcc cgaggcccag ggcggctgt tcacccgtt cttcatcacc    180 gtcggtctgg tggaagccgc gtacttcatc aacctggcct tcatggcgct gttcgtcttc   240
```

```
gccactcctg gccttcagta a                                              261
```

<210> SEQ ID NO 9
<211> LENGTH: 261
<212> TYPE: DNA
<213> ORGANISM: Mycobacterium smegmatis

<400> SEQUENCE: 9

```
atggatctcg atcccaacgc catcatcacg gccggcgccc tgatcggcgg tggattgatc    60
atgggtggcg gcgccatcgg tgccggtatc ggcgtcggta tcgcgggtaa cgcgctgatc   120
tcgggtatcg cccgtcagcc cgaggcccag ggccggctgt tcaccccgtt cttcatcacc   180
gtcggtctgg tggaagccgc gtacttcatc aacctggcct tcatggcgct gttcgtcttc   240
gccactcctg gccttcagta a                                              261
```

<210> SEQ ID NO 10
<211> LENGTH: 261
<212> TYPE: DNA
<213> ORGANISM: Mycobacterium smegmatis

<400> SEQUENCE: 10

```
atggatctcg atcccaacgc catcatcacg gccggcgccc tgatcggcgg tggattgatc    60
atgggtggcg gcgccatcgg tgccggtatc ggcgtcggta tcgcgggtaa cgcgctgatc   120
tcgggtatcg cccgtcagcc cgaggcccag ggccggctgt tcaccccgtt cttcatcacc   180
gtcggtctgg tggaagccgc gtacttcatc aacctggcct tcatggcgct gttcgtcttc   240
gccactcctg gccttcagta a                                              261
```

<210> SEQ ID NO 11
<211> LENGTH: 753
<212> TYPE: DNA
<213> ORGANISM: Mycobacterium tuberculosis

<400> SEQUENCE: 11

```
atgactgaga ccatcctggc cgcccaaatc gaggtcggcg agcaccacac ggccacctgg    60
ctcggtatga cggtcaacac cgacaccgtg ttgtcgacgg cgatcgccgg gttgatcgtg   120
atcgcgttgg ccttttacct gcgcgccaaa gtgacttcga cggatgtgcc aggcggggtg   180
cagttgtttt ttgaggcgat caccattcag atgcgcaatc aggtcgaaag cgccatcggg   240
atgcggatcg caccccttcgt gctgccgctg gcggtgacca tcttcgtgtt catcctgatc   300
tccaactggc tggcagtcct cccggtgcag tacaccgata acacgggca caccaccgag   360
ttgctcaaat cggcagcagc ggacatcaat tacgtgctgg cgctggcgct tttcgtgttc   420
gtctgctacc acacggccgg tatttggcgg cgcggtattg tcgacacccc gatcaagttg   480
ctgaaagggc acgtgacgct cctcgcgccg atcaaccttg tcgaagaagt cgccaagcca   540
atctcgttgt cgctccgact tttcggcaac attttcgccg gcggcattct ggtcgcactg   600
atcgcgctct ttccccccta catcatgtgg gcgcccaatg cgatctggaa agcatttgac   660
ctgttcgtcg gcgcaatcca ggccttcatt tttgcgctgc tgacaatttt gtacttcagc   720
caagcgatgg agctcgaaga ggaacaccac tag                                753
```

<210> SEQ ID NO 12
<211> LENGTH: 250
<212> TYPE: PRT
<213> ORGANISM: Mycobacterium tuberculosis

<400> SEQUENCE: 12

```
Met Thr Glu Thr Ile Leu Ala Ala Gln Ile Glu Val Gly Glu His His
1               5                   10                  15

Thr Ala Thr Trp Leu Gly Met Thr Val Asn Thr Asp Thr Val Leu Ser
                20                  25                  30

Thr Ala Ile Ala Gly Leu Ile Val Ile Ala Leu Ala Phe Tyr Leu Arg
            35                  40                  45

Ala Lys Val Thr Ser Thr Asp Val Pro Gly Val Gln Leu Phe Phe
50                  55                  60

Glu Ala Ile Thr Ile Gln Met Arg Asn Gln Val Gly Ser Ala Ile Gly
65                  70                  75                  80

Met Arg Ile Ala Pro Phe Val Leu Pro Leu Ala Val Thr Ile Phe Val
                85                  90                  95

Phe Ile Leu Ile Ser Asn Trp Leu Ala Val Leu Pro Val Gln Tyr Thr
            100                 105                 110

Asp Lys His Gly His Thr Thr Glu Leu Leu Lys Ser Ala Ala Ala Asp
        115                 120                 125

Ile Asn Tyr Val Leu Ala Leu Ala Leu Phe Val Phe Val Cys Tyr His
    130                 135                 140

Thr Ala Gly Ile Trp Arg Arg Gly Ile Val Gly His Pro Ile Lys Leu
145                 150                 155                 160

Leu Lys Gly His Val Thr Leu Leu Ala Pro Ile Asn Leu Val Glu Glu
                165                 170                 175

Val Ala Lys Pro Ile Ser Leu Ser Leu Arg Leu Phe Gly Asn Ile Phe
            180                 185                 190

Ala Gly Gly Ile Leu Val Ala Leu Ile Ala Leu Phe Pro Pro Tyr Ile
        195                 200                 205

Met Trp Ala Pro Asn Ala Ile Trp Lys Ala Phe Asp Leu Phe Val Gly
    210                 215                 220

Ala Ile Gln Ala Phe Ile Phe Ala Leu Leu Thr Ile Leu Tyr Phe Ser
225                 230                 235                 240

Gln Ala Met Glu Leu Glu Glu His His
                245                 250

<210> SEQ ID NO 13
<211> LENGTH: 77
<212> TYPE: PRT
<213> ORGANISM: Homo sapiens

<400> SEQUENCE: 13

Ser Arg Asp Ile Asp Thr Ala Lys Phe Ile Gly Ala Gly Ala Ala
1               5                   10                  15

Thr Val Gly Val Ala Gly Ser Gly Ala Gly Ile Gly Thr Val Phe Gly
                20                  25                  30

Ser Leu Ile Ile Gly Tyr Ala Arg Asn Pro Ser Leu Lys Gln Gln Leu
            35                  40                  45

Phe Ser Tyr Ala Ile Leu Gly Phe Ala Leu Ser Glu Ala Met Gly Leu
        50                  55                  60

Phe Cys Leu Met Val Ala Phe Leu Ile Leu Phe Ala Met
65                  70                  75

<210> SEQ ID NO 14
<211> LENGTH: 11
<212> TYPE: PRT
<213> ORGANISM: Mycobacterium tuberculosis

<400> SEQUENCE: 14

Gly Gly Ala Ile Gly Ala Gly Ile Gly Asp Gly
```

```
<210> SEQ ID NO 15
<211> LENGTH: 10
<212> TYPE: PRT
<213> ORGANISM: Mycobacterium tuberculosis

<400> SEQUENCE: 15

Thr Val Gly Leu Val Glu Ala Ala Tyr Phe
1               5                   10

<210> SEQ ID NO 16
<211> LENGTH: 9
<212> TYPE: PRT
<213> ORGANISM: Mycobacterium tuberculosis

<400> SEQUENCE: 16

Ala Ile Gly Ala Gly Ile Gly Asp Gly
1               5

<210> SEQ ID NO 17
<211> LENGTH: 14
<212> TYPE: PRT
<213> ORGANISM: Mycobacterium tuberculosis

<400> SEQUENCE: 17

Gly Gly Ala Ile Gly Ala Gly Ile Gly Asp Gly Val Ala Gly
1               5                   10

<210> SEQ ID NO 18
<211> LENGTH: 12
<212> TYPE: PRT
<213> ORGANISM: Mycobacterium tuberculosis

<400> SEQUENCE: 18

Phe Phe Ile Thr Val Gly Val Glu Ala Ala Tyr Phe
1               5                   10

<210> SEQ ID NO 19
<211> LENGTH: 17
<212> TYPE: PRT
<213> ORGANISM: Mycobacterium tuberculosis

<400> SEQUENCE: 19

Ile Met Ala Gly Gly Ala Ile Gly Ala Gly Ile Gly Asp Gly Val Ala
1               5                   10                  15

Gly

<210> SEQ ID NO 20
<211> LENGTH: 19
<212> TYPE: PRT
<213> ORGANISM: Mycobacterium tuberculosis

<400> SEQUENCE: 20

Thr Pro Phe Phe Ile Thr Val Gly Leu Val Glu Ala Ala Tyr Phe Ile
1               5                   10                  15

Asn Leu Ala
```

<210> SEQ ID NO 21
<211> LENGTH: 13
<212> TYPE: PRT
<213> ORGANISM: Mycobacterium tuberculosis

<400> SEQUENCE: 21

Ala Lys Pro Ile Ser Leu Ser Leu Arg Leu Phe Gly Asn
1               5                   10

<210> SEQ ID NO 22
<211> LENGTH: 7
<212> TYPE: PRT
<213> ORGANISM: Mycobacterium tuberculosis

<400> SEQUENCE: 22

Gly Gly Ala Ile Gly Ala Gly
1               5

<210> SEQ ID NO 23
<211> LENGTH: 10
<212> TYPE: PRT
<213> ORGANISM: Mycobacterium tuberculosis

<400> SEQUENCE: 23

Phe Phe Ile Thr Val Gly Leu Val Glu Ala
1               5                   10

<210> SEQ ID NO 24
<211> LENGTH: 5
<212> TYPE: PRT
<213> ORGANISM: Mycobacterium tuberculosis

<400> SEQUENCE: 24

Tyr Phe Ile Asn Leu
1               5

<210> SEQ ID NO 25
<211> LENGTH: 17
<212> TYPE: PRT
<213> ORGANISM: Mycobacterium tuberculosis

<400> SEQUENCE: 25

Ile Met Ala Gly Gly Ala Ile Gly Ala Gly Ile Gly Asp Gly Val Ala
1               5                   10                  15

Gly

<210> SEQ ID NO 26
<211> LENGTH: 10
<212> TYPE: PRT
<213> ORGANISM: Mycobacterium tuberculosis

<400> SEQUENCE: 26

Phe Phe Ile Thr Val Gly Leu Val Glu Ala
1               5                   10

<210> SEQ ID NO 27
<211> LENGTH: 6
<212> TYPE: PRT
<213> ORGANISM: Mycobacterium tuberculosis

<400> SEQUENCE: 27

Tyr Phe Ile Asn Leu Ala
1               5

<210> SEQ ID NO 28

```
<211> LENGTH: 6
<212> TYPE: PRT
<213> ORGANISM: Mycobacterium tuberculosis

<400> SEQUENCE: 28

Leu Arg Leu Phe Gly Asn
1               5
```